United States Patent
Sagara et al.

(10) Patent No.: US 7,834,019 B2
(45) Date of Patent: Nov. 16, 2010

(54) SUBSTITUTED PYRAZOLO[3,4-D]PYRIMIDINONE DERIVATIVES

(75) Inventors: Takeshi Sagara, Tsukuba (JP); Sachie Otsuki, Tsukuba (JP); Satoshi Sunami, Toride (JP); Toshihiro Sakamoto, Moriya (JP); Kenji Niiyama, Tsuchiura (JP); Fuyuki Yamamoto, Tsukuba (JP); Takashi Yoshizumi, Ushiku (JP); Hidetomo Furuyama, Tsukuba (JP); Yasuhiro Goto, Tsukuba (JP); Makoto Bamba, Tsukuba (JP); Keiji Takahashi, Tsukuba (JP); Hiroshi Hirai, Tsukuba (JP); Toshihide Nishibata, Tsukuba (JP)

(73) Assignee: Banyu Pharmaceutical Co., Ltd., Chiyoda-Ku, Tokyo (JP)

( * ) Notice: Subject to any disclaimer, the term of this patent is extended or adjusted under 35 U.S.C. 154(b) by 654 days.

(21) Appl. No.: 11/789,548

(22) Filed: Apr. 25, 2007

(65) Prior Publication Data
US 2007/0254892 A1 Nov. 1, 2007

Related U.S. Application Data

(60) Provisional application No. 60/800,096, filed on May 12, 2006.

(51) Int. Cl.
*A61K 31/519* (2006.01)
*A61K 31/497* (2006.01)
*C07D 487/04* (2006.01)
*A61P 35/00* (2006.01)

(52) U.S. Cl. .............................. 514/252.16; 514/234.5; 514/262.1; 544/262; 544/117

(58) Field of Classification Search ................ 544/262; 514/262.1
See application file for complete search history.

(56) References Cited

FOREIGN PATENT DOCUMENTS

| WO | WO0043394 | 7/2000 |
|---|---|---|
| WO | WO 2004/056786 | 7/2004 |
| WO | WO 2005/021532 | 3/2005 |
| WO | WO2006074985 | 7/2006 |
| WO | WO 2006/091737 | 8/2006 |
| WO | WO2007126122 | 11/2007 |

*Primary Examiner*—James O Wilson
*Assistant Examiner*—Susanna Moore
(74) *Attorney, Agent, or Firm*—Nicole M. Beeler

(57) ABSTRACT

The invention relates to compounds of a general formula (I):

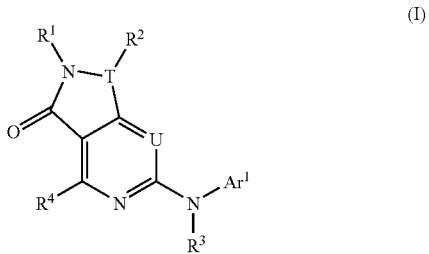

wherein $Ar^1$ is an optionally-substituted aryl or heteroaromatic group; $R^1$ is an optionally-substituted lower alkyl, lower alkenyl, lower alkynyl or cyclo-lower alkyl group, or is an aryl, aralkyl or heteroaromatic group optionally having a substituent; $R^2$ is a hydrogen atom, a lower alkyl group, a lower alkenyl group or a lower alkynyl group, or is an aryl, aralkyl or heteroaromatic group optionally having a substituent; $R^3$ is a hydrogen atom or a lower alkyl group; $R^4$ is a hydrogen atom, a halogen atom, a hydroxyl group, a lower alkyl group or a group of —N($R^{1k}$)$R^{1m}$; T and U are a nitrogen atom or a methine group, etc.

The compounds of the invention have excellent Wee1 kinase-inhibitory effect and are therefore useful in the field of medicines, especially treatment of various cancers.

15 Claims, No Drawings

SUBSTITUTED PYRAZOLO[3,4-D]PYRIMIDINONE DERIVATIVES

PRIORITY CLAIM

This application claims priority from U.S. Provisional Application Ser. No. 60/800,096 filed on May 12, 2006, which claims priority from Japanese Provisional Application Serial No. 2006-124,208, filed on Apr. 27, 2006.

TECHNICAL FIELD

The present invention is useful in the field of medicine. More precisely, the dihydropyrazolopyrimidinone derivatives of the invention are useful in the field of treatment of various cancers as a kinase inhibitor, especially as a Weel kinase inhibitor.

BACKGROUND ART

Cells have a checkpoint mechanism of such that, when the DNA therein is damaged, then the cells temporarily stop the cell cycle and repair the damaged DNA (*Cell Proliferation*, Vol. 33, pp. 261-274). In about a half of human cancers, a cancer-suppressor gene, p53 is mutated or depleted and the cells thereby have lost the G1 checkpoint function thereof. However, such cancer cells still keep the G2 checkpoint function remaining therein, which is considered to be one factor of lowering the sensitivity of the cells to DNA-active anticancer agents and to radiations.

A Weel kinase is a tyrosine kinase that participates in the G2 checkpoint of a cell cycle. Weel phosphorylates Cdc2 (Cdk1) tyrosine 15 that participates in the progress to the M stage from the G2 stage in a cell cycle, thereby inactivating Cdc2 and temporarily stopping the cell cycle at the G2 stage (*The EMBO Journal*, Vol. 12, pp. 75-85). Accordingly, in cancer cells having lost the p53 function therein, it is considered that the G2 checkpoint function by Weel is important for repairing the damaged DNA so as to evade the cell death. Heretofore, it has been reported that the Weel expression reduction by RNA interference or the Weel inhibition by compounds may increase the sensitivity of cancer cells to adriamycin, X ray and gamma ray (*Cancer Biology & Therapy*, Vol. 3, pp. 305-313; *Cancer Research*, Vol. 61, pp. 8211-8217). From the above, it is considered that a Weel inhibitor may inhibit the G2 checkpoint function of p53-depleted cancer cells, thereby enhancing the sensitivity of the cells to DNA-active anticancer agents and to radiations.

As a low-molecular Weel kinase inhibitor, for example, known are compounds described in US Application 2005/0250836, WO2003/091255, *Cancer Research*, Vol. 61, pp. 8211-8217, or *Bioorg & Med. Chem. Lett.*, Vol. 15, pp. 1931-1935. However, the compounds described in these references quite differ from the compounds of the invention in point of their structures.

On the other hand, WO2004/056786 or WO2005/021532 or WO2006/091737 disclose various compounds such as dihydropyrazolopyridines that are relatively similar to the compounds of the invention in point of their skeletons. However, these references do neither concretely disclose nor suggest any Weel kinase-inhibitory effect of those compounds as well as the compounds of the invention.

DISCLOSURE OF INVENTION

An object of the invention is to provide a novel anticancer agent having a kinase-inhibitory effect, especially a Weel kinase-inhibitory effect.

As a result of assiduous studies, the present inventors have found that compounds of the following general formula (I) have an excellent kinase-inhibitory effect, especially an excellent Weel kinase-inhibitory effect, and have completed the present invention:

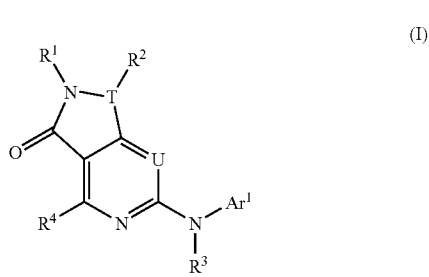

wherein;

$Ar^1$ is an aryl group or a heteroaromatic group, which may have a substituent selected from a group consisting of a halogen atom, a lower alkyl group, a halo-lower alkyl group, a hydroxy-lower alkyl group, a lower alkoxy group, a lower alkanoyl group, a hydroxy-lower alkylamino group, a carbamoyl group, a hydroxy-lower alkylcarbamoyl group, a heteroaromatic group optionally substituted by a lower alkyl group, and a group of $-Q^1-A^1-Q^2-A^2(R^{1a})R^{1b}$;

$A^1$ is a single bond, an oxygen atom or a sulfur atom, or is an imino group optionally substituted by a lower alkyl group;

$A^2$ is a nitrogen atom, or is a methine or 1-vinyl-2-ylidene group optionally substituted by a hydroxyl group, a lower alkyl group or a hydroxy-lower alkyl group;

$Q^1$ is a single bond, a carbonyl group, or a methylene group optionally substituted by a lower alkyl group;

$Q^2$ is a single bond, or an ethylene group optionally substituted by a lower alkyl group;

$R^{1a}$ and $R^{1b}$ are independently a hydrogen atom, a lower alkyl group or a hydroxy-lower alkyl group, or together form a lower alkylene group wherein one or two or more methylene groups constituting the lower alkylene group may be independently replaced by an oxygen atom, a sulfur atom, a sulfinyl group, a sulfonyl group, a carbonyl group, a vinylene group or a group of $-N(R^{1c})-$, and/or substituted by a hydroxyl group or a lower alkyl group;

$R^{1c}$ is a hydrogen atom, a lower alkenyl group or a group of $Q^3-A^3(R^{1d})R^{1e}$;

$A^3$ is a nitrogen atom, or is a methine or 1-vinyl-2-ylidene group optionally substituted by a hydroxyl group, a lower alkyl group or a hydroxy-lower alkyl group;

$Q^3$ is a single bond or a lower alkylene group, wherein one or two or more methylene groups constituting the lower alkylene group may be independently replaced by an oxygen atom, a sulfur atom, a carbonyl group, a sulfinyl group or a sulfonyl group, and/or substituted by a halogen atom, a cyano group, a hydroxyl group or a lower alkyl group;

$R^{1d}$ and $R^{1e}$ are independently a hydrogen atom, a halogen atom, a cyano group, a hydroxyl group, a lower alkyl group or a hydroxy-lower alkyl group, or together form a lower alkylene group wherein one or two or more methylene groups constituting the lower alkylene group may be independently replaced by an oxygen atom, a sulfur atom, a sulfinyl group, a sulfonyl group, a carbonyl group, a vinylene group or a group of —N($R^{1f}$)—, and/or substituted by a hydroxyl group or a lower alkyl group;

$R^{1f}$ is a hydrogen atom, a lower alkyl group, a halo-lower alkyl group, a lower alkenyl group or a lower alkanoyl group;

$R^1$ is a lower alkyl group, a lower alkenyl group, a lower alkynyl group or a cyclo-lower alkyl group optionally substituted by a halogen atom, or is an aryl group, an aralkyl group or a heteroaromatic group optionally having a substituent selected from a group consisting of a halogen atom, a cyano group, an amino group and a lower alkyl group;

$R^2$ is a hydrogen atom, a lower alkyl group, a lower alkenyl group or a lower alkynyl group, or is an aryl group, an aralkyl group or a heteroaromatic group optionally having a substituent selected from a group consisting of a halogen atom, a cyano group, a nitro group, a carboxyl group, a group of -$Q^4$-$A^4$($R^{1g}$)$R^{1h}$ and a group of -$Q^5$-$Ar^a$, wherein one or two or more methylene groups constituting the lower alkyl group, the lower alkenyl group or the lower alkynyl group may be independently replaced by an oxygen atom, a sulfur atom, a sulfinyl group, a sulfonyl group, a carbonyl group or a group of —N($R^{1j}$)—, and/or substituted by a halogen atom;

$A^4$ is a nitrogen atom, or is a methine group optionally substituted by a halogen atom, a hydroxyl group, a lower alkyl group or a hydroxy-lower alkyl group;

$Ar^a$ is an aryl group or a heteroaromatic group, which may have a substituent selected from a group consisting of a halogen atom, a lower alkyl group, a halo-lower alkyl group, a hydroxy-lower alkyl group and a lower alkoxy group;

$Q^4$ is a single bond or a lower alkylene group, wherein one or two or more methylene groups constituting the lower alkylene group may be independently replaced by an oxygen atom or a carbonyl group, and/or substituted by a lower alkyl group;

$Q^5$ is a single bond, an oxygen atom, a sulfur atom, a carbonyl group or a lower alkylene group, wherein one or two or more methylene groups constituting the lower alkylene group may be independently replaced by an oxygen atom, a sulfur atom or a carbonyl group, and/or substituted by a halogen atom or a lower alkyl group;

$R^{1g}$ and $R^{1h}$ are independently a hydrogen atom, a halogen atom, a cyano group, a hydroxyl group, a lower alkyl group, a lower alkoxy-lower alkyl group, a lower alkanoyl group, a lower alkoxycarbonyl group or a lower alkylsulfonyl group, or together form a lower alkylene group, wherein one or two or more methylene groups constituting the lower alkylene group may be independently replaced by an oxygen atom, a sulfur atom, a sulfinyl group, a sulfonyl group, a carbonyl group or a group of —N($R^{1i}$)—, and/or substituted by a halogen atom or a lower alkyl group;

$R^{1i}$ is a hydrogen atom, a lower alkyl group or a halo-lower alkyl group;

$R^{1j}$ is a hydrogen atom or a lower alkyl group;

$R^3$ is a hydrogen atom or a lower alkyl group;

$R^4$ is a hydrogen atom, a halogen atom, a hydroxyl group, a lower alkyl group or a group of —N($R^{1k}$)$R^{1m}$;

$R^{1k}$ and $R^{1m}$ are independently a hydrogen atom or a lower alkyl group;

T and U are independently a nitrogen atom or a methine group, provided that the compounds wherein $R^1$ is a methyl group and $R^2$ is an unsubstituted phenyl group are excluded.

The compounds (I) of the invention have a kinase-inhibitory effect, especially a Wee1 kinase-inhibitory effect, and are therefore useful as remedies for various cancers such as brain cancer, cervicocerebral cancer, esophageal cancer, thyroid cancer, small cell cancer, non-small cell cancer, breast cancer, lung cancer, stomach cancer, gallbladder/bile duct cancer, liver cancer, pancreatic cancer, colon cancer, rectal cancer, ovarian cancer, choriocarcinoma, uterus body cancer, uterocervical cancer, renal pelvis/ureter cancer, bladder cancer, prostate cancer, penis cancer, testicles cancer, fetal cancer, Wilms' cancer, skin cancer, malignant melanoma, neuroblastoma, osteosarcoma, Ewing's tumor, soft part sarcoma, acute leukemia, chronic lymphatic leukemia, chronic myelocytic leukemia, Hodgkin's lymphoma.

In particular, the compounds (I) of the invention are useful as remedies, for example, for breast cancer, lung cancer, pancreatic cancer, colon cancer, ovarian cancer, acute leukemia, chronic lymphatic leukemia, chronic myelocytic leukemia, Hodgkin's lymphoma.

The invention relates to the compounds of formula (I), their salts and esters, as well as to their production methods and their use.

The meanings of the terms used in this description are described below, and the invention is described in more detail hereinunder.

"Halogen atom" means a fluorine atom, a chlorine atom, a bromine atom and an iodine atom.

"Lower alkyl group" means a linear or branched alkyl group having from 1 to 6 carbon atoms, including, for example, a methyl group, an ethyl group, a propyl group, an isopropyl group, a butyl group, an isobutyl group, a sec-butyl group, a tert-butyl group, a pentyl group, an isopentyl group, a hexyl group, an isohexyl group.

"Halo-lower alkyl group" means the above-mentioned lower alkyl group in which any substitutable position is substituted by one or two or more, preferably from 1 to 3, the same or different, above-mentioned halogen atoms, including, for example, a fluoromethyl group, a difluoromethyl group, a trifluoromethyl group, a 2-fluoroethyl group, a 1,2-difluoroethyl group, a chloromethyl group, a 2-chloroethyl group, a 1,2-dichloroethyl group, a bromomethyl group, an iodomethyl group.

"Hydroxy-lower alkyl group" means the above-mentioned lower alkyl group in which any substitutable position is substituted by one or two or more, preferably 1 or 2 hydroxyl groups, including, for example, a hydroxymethyl group, a 2-hydroxyethyl group, a 1-hydroxy-1-methylethyl group, a 1,2-dihydroxyethyl group, a 3-hydroxypropyl group.

"Lower alkoxy group" means a linear or branched alkoxy group having from 1 to 6 carbon atoms, including, for example, a methoxy group, an ethoxy group, a propoxy group, an isopropoxy group, a butoxy group, a sec-butoxy group, an isobutoxy group, a tert-butoxy group, a pentyloxy group, an isopentyloxy group, a hexyloxy group, an isohexyloxy group.

"Lower alkanoyl group" means an alkanoyl group having the above-mentioned lower alkyl group, or that is, an alkanoyl group having from 2 to 7 carbon atoms, including, for example, an acetyl group, a propionyl group, a butyryl group, an isobutyryl group, a valeryl group, an isovaleryl group, a pivaloyl group.

"Hydroxy-lower alkylamino group" means an amino group mono- or di-substituted, preferably mono-substituted by the above-mentioned hydroxy-lower alkyl group, including, for example, a hydroxymethylamino group, a 2-hydroxyethylamino group, a 1-hydroxy-1-methylethylamino group, a 1,2-dihydroxyethylamino group, a 3-hydroxypropylamino group.

"Hydroxy-lower alkylcarbamoyl group" means a carbamoyl group mono- or di-substituted, preferably mono-substituted by the above-mentioned hydroxy-lower alkyl group, including, for example, a hydroxymethylcarbamoyl group, a 2-hydroxyethylcarbamoyl group, a 1-hydroxy-1-methylethylcarbamoyl group, a 1,2-dihydroxyethylcarbamoyl group, a 3-hydroxypropylcarbamoyl group.

"Aryl group" includes, for example, a phenyl group, a naphthyl group.

"Heteroaromatic group" means a 5-membered or 6-membered monocyclic aromatic heterocyclic group having one or two or more, preferably from 1 to 3, the same or different hetero atoms selected from a group consisting of an oxygen atom, a nitrogen atom and a sulfur atom; or a condensed cyclic aromatic heterocyclic group formed through condensation of that monocyclic aromatic heterocyclic group and the above-mentioned aryl group, or through condensation of the same or different such monocyclic aromatic heterocyclic groups; and it includes, for example, a pyrrolyl group, a furyl group, a thienyl group, an imidazolyl group, a pyrazolyl group, a thiazolyl group, an isothiazolyl group, an oxazolyl group, an isoxazolyl group, a triazolyl group, a tetrazolyl group, an oxadiazolyl group, a 1,2,3-thiadiazolyl group, a 1,2,4-thiadiazolyl group, a 1,3,4-thiadiazolyl group, a pyridyl group, a pyrazinyl group, a pyrimidinyl group, a pyridazinyl group, a 1,2,4-triazinyl group, a 1,3,5-triazinyl group, an indolyl group, a benzofuranyl group, a benzothienyl group, a benzimidazolyl group, a benzoxazolyl group, a benzisoxazolyl group, a benzothiazolyl group, a benzisothiazolyl group, an indazolyl group, a purinyl group, a quinolyl group, an isoquinolyl group, a phthalazinyl group, a naphthyridinyl group, a quinoxalinyl group, a quinazolinyl group, a cinnolinyl group, a pteridinyl group, a pyrido[3,2-b]pyridyl group.

"Lower alkylene group" means a linear or branched alkylene group having from 1 to 6 carbon atoms, including, for example, a methylene group, an ethylene group, a trimethylene group, a tetramethylene group, a pentamethylene group, a hexamethylene group.

"Lower alkenyl group" means a linear or branched alkenyl group having from 2 to 6 carbon atoms, including, for example, a vinyl group, a 1-propenyl group, an allyl group, an isopropenyl group, a 3-butenyl group, a 2-butenyl group, a 1-butenyl group, a 1-methyl-2-propenyl group, a 1-methyl-1-propenyl group, a 1-ethyl-1-ethenyl group, a 2-methyl-2-propenyl group, a 2-methyl-1-propenyl group, a 3-methyl-2-butenyl group, a 4-pentenyl group.

"Lower alkynyl group" means a linear or branched alkynyl group having from 2 to 6 carbon atoms, including, for example, an ethynyl group, a 1-propynyl group, a 2-propynyl group, a 3-butynyl group, a 2-butynyl group, a 1-butynyl group, a 1-methyl-2-propynyl group, a 1-ethyl-2-propynyl group, a 1-methyl-2-butynyl group, a 4-pentynyl group.

"Cyclo-lower alkyl group" means a cycloalkyl group having from 3 to 6 carbon atoms, including, for example, a cyclopropyl group, a cyclobutyl group, a cyclopentyl group, a cyclohexyl group.

"Aralkyl group" means the above-mentioned alkyl group in which any substitutable position is substituted by one or two or more, preferably one, above-mentioned aryl groups, including, for example, a benzyl group, a 1-phenylethyl group, a phenethyl group, a 1-naphthylmethyl group, a 2-naphthylmethyl group.

"Lower alkoxy-lower alkyl group" means the above-mentioned lower alkyl group in which any substitutable position is substituted by one or two or more, preferably 1 or 2, the same or different, above-mentioned lower alkoxy groups, including, for example, a methoxymethyl group, an ethoxymethyl group, a 2-methoxyethyl group, a 2-ethoxyethyl group, a 1-methoxy-1-methylethyl group, a 1,2-dimethoxyethyl group, a 3-methoxypropyl group.

"Lower alkoxycarbonyl group" means an alkoxycarbonyl group having the above-mentioned lower alkoxy group, or that is, an alkoxycarbonyl group having from 2 to 7 carbon atoms, including, for example, a methoxycarbonyl group, an ethoxycarbonyl group, a propoxycarbonyl group, an isopropoxycarbonyl group, a butoxycarbonyl group, an isobutoxycarbonyl group, a tert-butoxycarbonyl group, a pentyloxycarbonyl group.

"Lower alkylsulfonyl group" means a linear or branched alkylsulfonyl group having from 1 to 6 carbon atoms, including, for example, a methylsulfonyl group, an ethylsulfonyl group, a propylsulfonyl group, an isopropylsulfonyl group, a butylsulfonyl group, a sec-butylsulfonyl group, an isobutylsulfonyl group, a tert-butylsulfonyl group, a pentylsulfonyl group, an isopentylsulfonyl group, a hexylsulfonyl group, an isohexylsulfonyl group.

"Salts" of the compounds of the invention mean ordinary, pharmaceutically-acceptable salts. For example, when the compounds have a carboxyl group, a hydroxyl group, or an acidic heterocyclic group such as a tetrazolyl group, then they may form base-addition salts at the carboxyl group, the hydroxyl group or the acidic heterocyclic group; or when the compounds have an amino group or a basic heterocyclic group, then they may form acid-addition salts at the amino group or the basic heterocyclic group.

The base-addition salts include, for example, alkali metal salts such as sodium salts, potassium salts; alkaline earth metal salts such as calcium salts, magnesium salts; ammonium salts; and organic amine salts such as trimethylamine salts, triethylamine salts, dicyclohexylamine salts, ethanolamine salts, diethanolamine salts, triethanolamine salts, procaine salts, N,N'-dibenzylethylenediamine salts.

The acid-addition salts include, for example, inorganic acid salts such as hydrochlorides, sulfates, nitrates, phosphates, perchlorates; organic acid salts such as maleates, fumarates, tartrates, citrates, ascorbates, trifluoroacetates; and sulfonates such as methanesulfonates, isethionates, benzenesulfonates, p-toluenesulfonates.

"Esters" of the compounds of the invention means ordinary pharmaceutically-acceptable esters at the carboxyl group, if any, of the compounds. They include, for example, esters with a lower alkyl group such as a methyl group, an ethyl group, a propyl group, an isopropyl group, a butyl group, a sec-butyl group, a tert-butyl group, a pentyl group, an isopentyl group, a neopentyl group, a cyclopropyl group, a cyclobutyl group, a cyclopentyl group; esters with an aralkyl group such as a benzyl group, a phenethyl group; esters with a lower alkenyl group such as an allyl group, a 2-butenyl group; esters with a lower alkoxy-lower alkyl group such as a methoxymethyl group, a 2-methoxyethyl group, a 2-ethoxyethyl group; esters with a lower alkanoyloxy-lower alkyl group such as an acetoxymethyl group, a pivaloyloxymethyl group, a 1-pivaloyloxyethyl group; esters with a lower alkoxycarbonyl-lower alkyl group such as a methoxycarbonylmethyl group, an isopropoxycarbonylmethyl group; esters with a carboxy-lower alkyl group such as a carboxymethyl group; esters with a lower alkoxycarbonyloxy-lower alkyl group such as a 1-(ethoxycarbonyloxy)ethyl group, a 1-(cyclohexyloxycarbonyloxy)ethyl group; esters with a carbamoyloxy-lower alkyl group such as a carbamoyloxymethyl group; esters with a phthalidyl group; esters with a (5-substituted-2-oxo-1,3-dioxol-4-yl)methyl group such as a (5-methyl-2-oxo-1,3-dioxol-4-yl)methyl group.

For illustrating the compounds of the invention more concretely, preferred examples of the symbols used in formula (I) and others are described below in more detail.

$Ar^1$ is an aryl group or a heteroaromatic group, which may have a substituent selected from a group consisting of a halogen atom, a lower alkyl group, a halo-lower alkyl group, a hydroxy-lower alkyl group, a lower alkoxy group, a lower alkanoyl group, a hydroxy-lower alkylamino group, a carbamoyl group, a hydroxy-lower alkylcarbamoyl group, a heteroaromatic group optionally substituted by a lower alkyl group, and a group of $-Q^1-A^1-Q^2-A^2(R^{1a})R^{1b}$.

"An aryl group or a heteroaromatic group, which may have a substituent selected from a group consisting of a halogen atom, a lower alkyl group, a halo-lower alkyl group, a hydroxy-lower alkyl group, a lower alkoxy group, a lower alkanoyl group, a hydroxy-lower alkylamino group, a carbamoyl group, a hydroxy-lower alkylcarbamoyl group, a heteroaromatic group optionally substituted by a lower alkyl group, and a group of $-Q^1-A^1-Q^2-A^2(R^{1a})R^{1b}$" means the above-mentioned unsubstituted aryl group or heteroaromatic group, or the above-mentioned aryl group or heteroaromatic group which has a substituent at any substitutable position thereof and in which the substituent may be one or two or more, preferably 1 or 2, the same or different substituents selected from a group consisting of a halogen atom, a lower alkyl group, a halo-lower alkyl group, a hydroxy-lower alkyl group, a lower alkoxy group, a lower alkanoyl group, a hydroxy-lower alkylamino group, a carbamoyl group, a hydroxy-lower alkylcarbamoyl group, a heteroaromatic group optionally substituted by a lower alkyl group, and a group of $-Q^1-A^1-Q^2-A^2(R^{1a})R^{1b}$.

The halogen atom for the substituent is, for example, preferably a fluorine atom, a chlorine atom.

The lower alkyl group for the substituent is, for example, preferably a methyl group, ethyl group.

The halo-lower alkyl group for the substituent is, for example, preferably a fluoromethyl group, a difluoromethyl group, a trifluoromethyl group.

The hydroxy-lower alkyl group for the substituent is, for example, preferably a hydroxymethyl group, a 2-hydroxyethyl group.

The lower alkoxy group for the substituent is, for example, preferably a methoxy group, an ethoxy group.

The lower alkanoyl group for the substituent is, for example, preferably an acetyl group.

The hydroxy-lower alkylamino group for the substituent is, for example, preferably a hydroxymethylamino group, a 2-hydroxyethylamino group.

The hydroxy-lower alkylcarbamoyl group for the substituent is, for example, preferably a hydroxymethylcarbamoyl group, a 2-hydroxyethylcarbamoyl group.

The "heteroaromatic group optionally substituted by a lower alkyl group" for the substituent means the above-mentioned unsubstituted heteroaromatic group, or the above-mentioned heteroaromatic group having one or two or more, preferably one or two, the above-mentioned lower alkyl groups at any substitutable positions therein, and is, for example, preferably a 4-methyl-1-imidazolyl group, a 1-methyl-4-pyrazolyl group.

In the group of $-Q^1-A^1-Q^2-A^2(R^{1a})R^{1b}$ for the substituent, $A^1$ is a single bond, an oxygen atom or a sulfur atom, or is an imino group optionally substituted by a lower alkyl group; $A^2$ is a nitrogen atom, or is a methine or 1-vinyl-2-ylidene group optionally substituted by a hydroxyl group, a lower alkyl group or a hydroxy-lower alkyl group; $Q^1$ is a single bond, a carbonyl group, or a methylene group optionally substituted by a lower alkyl group; $Q^2$ is a single bond, or an ethylene group optionally substituted by a lower alkyl group; $R^{1a}$ and $R^{1b}$ are independently a hydrogen atom, a lower alkyl group or a hydroxy-lower alkyl group, or together form a lower alkylene group wherein one or two or more methylene groups constituting the lower alkylene group may be independently replaced by an oxygen atom, a sulfur atom, a sulfinyl group, a sulfonyl group, a carbonyl group, a vinylene group or a group of $-N(R^{1c})-$, and/or substituted by a hydroxyl group or a lower alkyl group.

The "imino group optionally substituted by a lower alkyl group" for $A^1$ means an unsubstituted imino group, or an imino group substituted by the above-mentioned lower alkyl group, in which the lower alkyl group for the substituent is, for example, preferably a methyl group, ethyl group.

The "methine or 1-vinyl-2-ylidene group optionally substituted by a hydroxyl group, a lower alkyl group or a hydroxy-lower alkyl group" for $A^2$ means an unsubstituted methine or 1-vinyl-2-ylidene group, or a methine or 1-vinyl-2-ylidene group having a substituent selected from a group consisting of a hydroxyl group, a lower alkyl group and a hydroxy-lower alkyl group.

The lower alkyl group for the substituent is, for example, preferably a methyl group, an ethyl group.

The hydroxy-lower alkyl group for the substituent is, for example, preferably a hydroxymethyl group, a 2-hydroxyethyl group.

The substituent is, for example, preferably a hydroxyl group.

The "methylene group optionally substituted by a lower alkyl group" for $Q^1$ means an unsubstituted methylene group, or a methylene group substituted by the same or different, one or two, above-mentioned lower alkyl groups.

The lower alkyl group for the substituent is preferably a methyl group.

The "ethylene group optionally substituted by a lower alkyl group" for $Q^2$ means an unsubstituted ethylene group, or an ethylene group substituted by the same or different, one or two or more, preferably 1 or 2, above-mentioned lower alkyl groups at any substitutable position therein.

The lower alkyl group for the substituent is preferably a methyl group.

The lower alkyl group for $R^{1a}$ or $R^{1b}$ is, for example, preferably a methyl group, an ethyl group, a propyl group, an isopropyl group.

The hydroxy-lower alkyl group for $R^{1a}$ or $R^{1b}$ is, for example, preferably a hydroxymethyl group, a 2-hydroxyethyl group.

The lower alkylene group that $R^{1a}$ and $R^{1b}$ together form is, for example, preferably a trimethylene group, a tetramethylene group, a pentamethylene group, a hexamethylene group. When "$A^2$" to which they bond is a nitrogen atom, then they form, along with the nitrogen atom, a 1-azetidinyl group, a 1-pyrrolidinyl group, a piperidino group, a perhydro-1H-azepin-1-yl group. When "$A^2$" is a methine group, then they form, along with the methine group, a cyclobutyl group, a cyclopentyl group, a cyclohexyl group, a cycloheptyl group. When "$A^2$" is a 1-vinyl-2-ylidene group, then they form, along with the 1-vinyl-2-ylidene group, a 1-cyclopentenyl group, a 1-cyclohexenyl group, a 1-cycloheptenyl group, a 1-cyclooctenyl group. Above all, more preferred are a 1-pyrrolidinyl group, a piperidino group, a perhydro-1H-azepin-1-yl group, a cyclobutyl group, a cyclohexyl group, a 1-cyclohexenyl group.

One or two or more methylene groups constituting the lower alkylene group may be independently replaced by an oxygen atom, a sulfur atom, a sulfinyl group, a sulfonyl group, a carbonyl group, a vinylene group or a group of —N($R^{1c}$)—, and/or substituted by a hydroxyl group or a lower alkyl group. Examples of the replaced or substituted groups are preferably selected from the following formula (aa1):

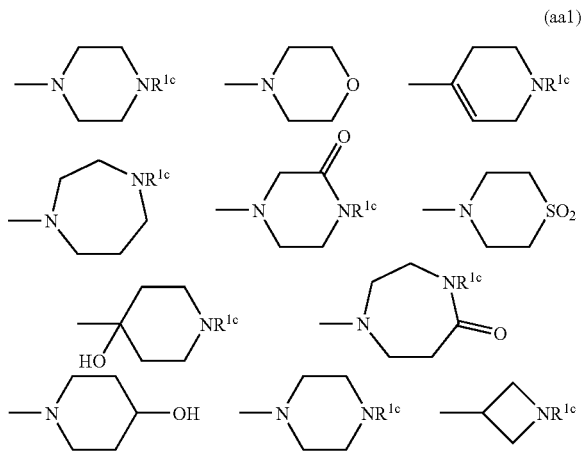

Above all, examples of the groups are more preferably selected from the following formula (aa1'):

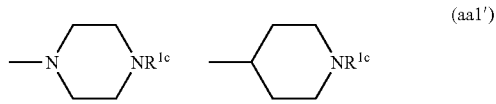

$R^{1c}$ in the group of —N($R^{1c}$)— is a hydrogen atom, a lower alkenyl group or a group of -$Q^3$-$A^3$($R^{1d}$)$R^{1e}$.

The lower alkenyl group for $R^{1c}$ is, for example, preferably a vinyl group, an allyl group.

In the group of -$Q^3$-$A^3$($R^{1d}$)$R^{1e}$ for $R^{1c}$, $A^3$ is a nitrogen atom, or is a methine or 1-vinyl-2-ylidene group optionally substituted by a hydroxyl group, a lower alkyl group or a hydroxy-lower alkyl group; $Q^3$ is a single bond or a lower alkylene group, wherein one or two or more methylene groups constituting the lower alkylene group may be independently replaced by an oxygen atom, a sulfur atom, a carbonyl group, a sulfinyl group or a sulfonyl group, and/or substituted by a halogen atom, a cyano group, a hydroxyl group or a lower alkyl group; $R^{1d}$ and $R^{1e}$ are independently a hydrogen atom, a halogen atom, a cyano group, a hydroxyl group, a lower alkyl group or a hydroxy-lower alkyl group, or together form a lower alkylene group wherein one or two or more methylene groups constituting the lower alkylene group may be independently replaced by an oxygen atom, a sulfur atom, a sulfinyl group, a sulfonyl group, a carbonyl group, a vinylene group or a group of —N($R^{1f}$)—, and/or substituted by a hydroxyl group or a lower alkyl group.

The "methine or 1-vinyl-2-ylidene group optionally substituted by a hydroxyl group, a lower alkyl group or a hydroxy-lower alkyl group" for $A^3$ means an unsubstituted methine or 1-vinyl-2-ylidene group, or a methine or 1-vinyl-2-ylidene group having a substituent selected from a group consisting of a hydroxyl group, a lower alkyl group and a hydroxy-lower alkyl group.

The lower alkyl group for the substituent is, for example, preferably a methyl group, an ethyl group.

The hydroxy-lower alkyl group for the substituent is, for example, preferably a hydroxymethyl group, a 2-hydroxyethyl group, a 2-hydroxypropyl group, a 2-methyl-2-hydroxypropyl group.

The substituent is preferably a hydroxyl group, a lower alkyl group.

The lower alkylene group for $Q^3$ is, for example, preferably a methylene group, an ethylene group, a trimethylene group.

One or two or more methylene groups constituting the lower alkylene group for $Q^3$ may be independently replaced by an oxygen atom, a sulfur atom, a carbonyl group, a sulfinyl group or a sulfonyl group, and/or substituted by a halogen atom, a cyano group, a hydroxyl group or a lower alkyl group. Examples of the replaced or substituted groups are preferably selected from the following formula (aa2):

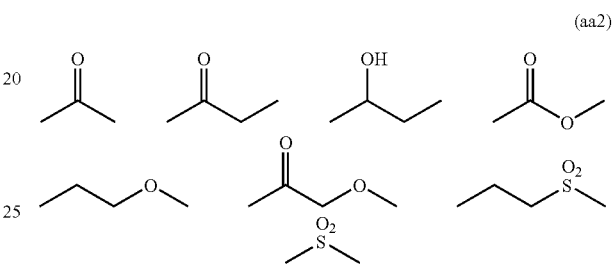

The halogen atom for $R^{1d}$ or $R^{1e}$ is, for example, preferably a fluorine atom, a chlorine atom.

The lower alkyl for $R^{1d}$ or $R^{1e}$ is, for example, preferably a methyl group, an ethyl group.

The hydroxy-lower alkyl group for $R^{1d}$ or $R^{1e}$ is, for example, preferably a hydroxymethyl group, a 2-hydroxyethyl group.

The lower alkylene group which for $R^{1d}$ and $R^{1e}$ together form is, for example, preferably an ethylene group, a trimethylene group, a tetramethylene group. When "$A^3$" to which they bond is a nitrogen atom, then they form along with the nitrogen atom, a 1-aziridinyl group, a 1-azetidinyl group, a 1-pyrrolidinyl group; when "$A^3$" is a methine group, they form along with the methine group, a cyclopropyl group, a cyclobutyl group, a cyclopentyl group; when "$A^3$" is a 1-vinyl-2-ylidene group, then they form along with the 1-vinyl-2-ylidene group, a 1-cyclobutenyl group, a 1-cyclopentenyl group, a 1-cyclohexenyl group. Above all, more preferred are a cyclopropyl group, a cyclobutyl group, a cyclopentyl group.

One or two or more methylene groups constituting the above-mentioned lower alkylene group may be independently replaced by an oxygen atom, a sulfur atom, a sulfinyl group or a sulfonyl group, a carbonyl group, a vinylene group or a group of —N($R^{1f}$)—, and/or substituted by a hydroxyl group or a lower alkyl group. Examples of the replaced or substituted groups are preferably selected from the following formula (aa3):

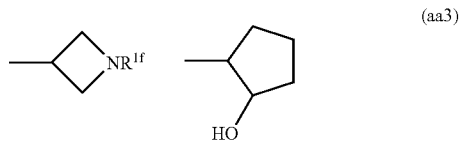

$R^{1f}$ in the group of —N($R^{1f}$)— is a hydrogen atom, a lower alkyl group, a halo-lower alkyl group, a lower alkenyl group or a lower alkanoyl group.

The lower alkyl group for $R^{1f}$ is, for example, preferably a methyl group, an ethyl group.

The halo-lower alkyl group for $R^{1f}$ is, for example, preferably a fluoromethyl group, a difluoromethyl group.

The lower alkenyl group for $R^{1f}$ is, for example, preferably an allyl group.

The lower alkanoyl group for $R^{1f}$ is, for example, preferably an acetyl group.

Preferred embodiments of the group of $-Q^3-A^3(R^{1d})R^{1e}$ are, for example, as follows:

(i) $A^3$ is a methine group optionally substituted by a hydroxyl group or a lower alkyl group, $Q^3$ is a single bond, and $R^{1d}$ and $R^{1e}$ are independently a hydrogen atom or a lower alkyl group, (ii) $A^3$ is a methine group, $Q^3$ is a single bond or a lower alkylene group, and $R^{1d}$ and $R^{1e}$ together form a lower alkylene group wherein one methylene group constituting the lower alkylene group may be replaced by a group of $-N(R^{1f})-$, (iii) $A^3$ is a methine group optionally substituted by a hydroxyl group or a lower alkyl group, $Q^3$ is a lower alkylene group wherein one or two methylene groups constituting the lower alkylene group may be independently replaced by an oxygen atom, a carbonyl group or a sulfonyl group, and/or substituted by a hydroxyl group, and $R^{1d}$ and $R^{1e}$ are independently a hydrogen atom, a halogen atom, a cyano group or a lower alkyl group;

(iv) $A^3$ is a nitrogen atom, $Q^3$ is a lower alkylene group wherein one methylene group constituting the lower alkylene group is replaced by a carbonyl group, and $R^{1d}$ and $R^{1e}$ are independently a hydrogen atom or a lower alkyl group; more preferably above (i).

More concretely, the group of $-Q^3-A^3(R^{1d})R^{1e}$ is, for example, preferably a methyl group, an ethyl group, a propyl group, an isopropyl group, a tert-butyl group, a hydroxymethyl group, a 1-hydroxy-1-methylethyl group, a cyclopropyl group, a cyclobutyl group, a cyclopropylmethyl group, a 1-acetyl-3-azetidinyl group, a cyclopentyl group, a 2-hydroxycyclopentyl group, a 2-hydroxyethyl group, a 2-cyanoethyl group, a 2-methoxyethyl group, a 2-ethoxyethyl group, a 2-hydroxy-2-methylpropyl group, a 3-fluoro-2-hydroxypropyl group, an acetyl group, a propionyl group, a 2-methoxyacetyl group, a tert-butoxycarbonyl group, a methylsulfonyl group, a 2-(methylsulfonyl)ethyl group, a dimethylcarbamoyl group, a dimethylcarbamoylmethyl group, a 2-(dimethylamino)acetyl group; more preferably a methyl group, an ethyl group, a tert-butyl group, a 2-hydroxyethyl group, a 2-methoxyethyl group, an acetyl group; more preferably a methyl group.

$R^{1c}$ is preferably a hydrogen atom or a group of $-Q^3-A^3(R^{1d})R^{1e}$, more preferably a group of $-Q^3-A^3(R^{1d})R^{1e}$.

Preferred embodiments of the group of $-Q^1-A^1-Q^2-A^2(R^{1a})R^{1b}$ are, for example, as follows:

(i) $A^1$, $Q^1$ and $Q^2$ are a single bond, $A^2$ is a nitrogen atom, and $R^{1a}$ and $R^{1b}$ together form a lower alkylene group wherein one or two methylene groups constituting the lower alkylene group may be independently replaced by an oxygen atom, a sulfonyl group, a carbonyl group or a group of $-N(R^{1c})-$, and/or substituted by a hydroxyl group;

(ii) $A^1$, $Q^1$ and $Q^2$ are a single bond, $A^2$ is a methine or 1-vinyl-2-ylidene group optionally substituted by a hydroxyl group, and $R^{1a}$ and $R^{1b}$ together form a lower alkylene group wherein one methylene group constituting the lower alkylene group is replaced by a group of $-N(R^{1c})-$;

(iii) $A^1$ is an oxygen atom, $A^2$ is a methine group, $Q^1$ and $Q^2$ are a single bond, and $R^{1a}$ and $R^{1b}$ together form a lower alkylene group wherein one methylene group constituting the lower alkylene group is replaced by a group of $-N(R^{1c})-$;

(iv) $A^1$ is an oxygen atom, $A^2$ is a nitrogen atom, $Q^1$ is a single bond, $Q^2$ is an ethylene group, and $R^{1a}$ and $R^{1b}$ are independently a lower alkyl group; or (v) $A^1$ and $Q^2$ are a single bond, $A^2$ is a nitrogen atom, $Q^1$ is a methylene group, and $R^{1a}$ and $R^{1b}$ are independently a lower alkyl group.

Above all, cases (i) or (ii) are more preferably and examples of the groups are more preferably selected from the following formula (aa1'):

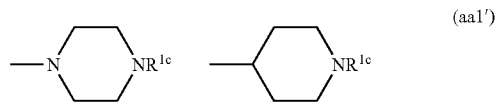

(aa1')

More concretely, the group of $-Q^1-A^1-Q^2-A^2(R^{1a})R^{1b}$ is preferably a 1-piperazinyl group, a 4-methyl-1-piperazinyl group, a 4-ethyl-1-piperazinyl group, a 4-propyl-1-piperazinyl group, a 4-isopropyl-1-piperazinyl group, a 4-tert-butyl-1-piperazinyl group, a 4-hydroxymethyl-1-piperazinyl group, a 4-(1-hydroxy-1-methylethyl)-1-piperazinyl group, a 4-cyclopropyl-1-piperazinyl group, a 4-cyclobutyl-1-piperazinyl group, a 4-cyclopropylmethyl-1-piperazinyl group, a 4-(1-acetyl-3-azetidinyl)-1-piperazinyl group, a 4-cyclopentyl-1-piperazinyl group, a 4-(2-hydroxycyclopentyl)-1-piperazinyl group, a 4-(2-hydroxyethyl)-1-piperazinyl group, a 4-(2-cyanoethyl)-1-piperazinyl group a 4-(2-methoxyethyl)-1-piperazinyl group, a 4-(2-ethoxyethyl)-1-piperazinyl group, a 4-(2-hydroxy-2-methylpropyl)-1-piperazinyl group, a 4-(3-fluoro-2-hydroxypropyl)-1-piperazinyl group, a 4-acetyl-1-piperazinyl group, a 4-propionyl-1-piperazinyl group, a 4-(2-methoxyacetyl)-1-piperazinyl group, a 4-tert-butoxycarbonyl-1-piperazinyl group, a 4-methylsulfonyl-1-piperazinyl group, a 4-(2-(methylsulfonyl)ethyl)-1-piperazinyl group, a 4-(dimethylcarbamoyl) group, a 4-(dimethylcarbamoylmethyl)-1-piperazinyl group, a 4-(2-(dimethylamino)acetyl)-1-piperazinyl group, a 4-methyl-3-oxo-1-piperazinyl group, a piperidino group, a 4-hydroxypiperidino group, a morpholino group, a thiomorpholino group, a 1,1-dioxidothiomorpholino group, a perhydro-1H-azepin-1-yl group, a perhydro-1H-1,4-diazepin-1-yl group, a 4-methyl-perhydro-1H-1,4-diazepin-1-yl group, a 5-oxo-perhydro-1H-1,4-diazepin-1-yl group, a 4-methyl-5-oxo-perhydro-1H-1,4-diazepin-1-yl group, a 3-azetidinyl group, a 4-piperidyl group, a 1-methyl-4-piperidyl group, a 1-ethyl-4-piperidyl group, a 1-(2-hydroxyethyl)-4-piperidyl group, a 1-(2-methylsulfonylethyl)-4-piperidyl group, a 4-hydroxy-4-piperidyl group, a 4-hydroxy-1-methyl-4-piperidyl group, a 1-tert-butoxycarbonyl-4-hydroxy-4-piperidyl group, a 1,2,3,6-tetrahydro-4-pyridyl group, a 3-azetidinyloxy group, a 1-methyl-3-azetidinyloxy group, a 1-ethyl-3-azetidinyloxy group, a 1-propyl-3-azetidinyloxy group, a 1-isopropyl-3-azetidinyloxy group, a 1-(2-hydroxyethyl)-3-azetidinyloxy group, a 4-piperidyloxy group, a 1-methyl-4-piperidyloxy group, a 1-ethyl-4-piperidyloxy group, a 1-cyclobutyl-4-piperidyloxy group, a 2-dimethylaminoethoxy group, a dimethylaminomethyl group, a diethylaminomethyl group, a methylpropylaminomethyl group, an isopropylmethylaminomethyl group; more preferably a 1-piperazinyl group, a 4-methyl-1-piperazinyl group, a 4-ethyl-1-piperazinyl group, a 4-isopropyl-1-piperazinyl group, a 4-tert-butyl-1-piperazinyl group, a 4-cyclopropyl-1-piperazinyl group, a 4-cyclobutyl-1-piperazinyl group, a 4-cyclopropylmethyl-1-piperazinyl group, a 4-(2-hydroxyethyl)-1-piperazinyl group, a 4-(2-methoxyethyl)-1-piperazinyl group, a 4-(2-methoxyacetyl)-1-piperazinyl group, a 4-acetyl-1-piperazinyl group, a 4-methylsulfonyl-1-piperazinyl group, a 4-methyl-3-oxo-1-piperazinyl group, a 4-hydroxypiperidino group, a morpholino group, a 1,1-dioxidothiomorpholino group, a 4-methyl-5-oxo-perhydro-1H-1,4-diazepin-1-yl group, a 4-piperidyl group, a 1-methyl-4-piperidyl group, a 1-(2-hydroxyethyl)-4-piperidyl group, a 4-hydroxy-1-methyl-4-piperidyl group, a 1,2,3,6-tetrahydro-4-pyridyl group, a 1-ethyl-3-azetidinyloxy group, a 1-isopropyl-3-azetidinyloxy group, a 1-(2-hydroxyethyl)-3-azetidinyloxy group, even more preferably a 4-methyl-1-piperazinyl group, a 4-ethyl-1-piperazinyl group, a 4-(2-hydroxyethyl)-1-piperazinyl group, a 4-acetyl-1-piperazinyl group, a 1-methyl-4-piperidyl group.

The substituent for $Ar^1$ is, for example, preferably a lower alkyl group, a hydroxy-lower alkyl group, a lower alkoxy group, a lower alkanoyl group, a heteroaromatic group optionally substituted by a lower alkyl group, or a group of $-Q^1-A^1-Q^2-A^2(R^{1a})R^{1b}$.

The "aryl group" itself of the aryl group optionally having the above-mentioned substituent for $Ar^1$ is, for example, preferably a phenyl group. The "heteroaromatic group" itself of the heteroaromatic group optionally having the above-mentioned substituent for $Ar^1$ is, for example, preferably a pyrazolyl group, a pyridyl group.

Accordingly, $Ar^1$ is, for example, preferably a phenyl, pyrazolyl or pyridyl group optionally substituted by a lower alkyl group, a hydroxy-lower alkyl group, a lower alkoxy group, a lower alkanoyl group, a heteroaromatic group optionally substituted by a lower alkyl group, or a group of $-Q^1-A^1-Q^2-A^2(R^{1a})R^{1b}$; more preferably a phenyl group substituted by one $-Q^1-A^1-Q^2-A^2(R^{1a})R^{1b}$, or a phenyl group substituted by one group of $-Q^1-A^1-Q^2-A^2(R^{1a})R^{1b}$ and additionally by a lower alkyl group or a hydroxy-lower alkyl group.

More concretely, $Ar^1$ is preferably a phenyl group, a 4-hydroxymethyl-3-methylphenyl group, a 4-isopropyloxyphenyl group, a 4-acetylphenyl group, a 3,5-dimethyl-4-(2-dimethylaminoethoxy)phenyl group, a 4-(1-methyl-1H-pyrazol-4-yl)phenyl group, a 4-(1-piperazinyl)phenyl group, a 3-methyl-4-(1-piperazinyl)phenyl group, a 3-hydroxymethyl-4-(1-piperazinyl)phenyl group, a 4-(4-methyl-1-piperazinyl)phenyl group, a 3-methyl-4-(4-methyl-1-piperazinyl)phenyl group, a 3-hydroxymethyl-4-(4-methyl-1-piperazinyl)phenyl group, a 4-(4-ethyl-1-piperazinyl)phenyl group, a 4-(4-ethyl-1-piperazinyl)-3-hydroxymethylphenyl group, a 4-(4-isopropyl-1-piperazinyl)phenyl group, a 3-methyl-4-(4-isopropyl-1-piperazinyl)phenyl group, a 4-(4-tert-butyl-1-piperazinyl)phenyl group, a 4-(4-cyclopropyl-1-piperazinyl)phenyl group, a 4-(4-cyclopropyl-1-piperazinyl)-3-methylphenyl group, a 4-(4-cyclopropyl-1-piperazinyl)-3-hydroxymethylphenyl group, a 4-(4-cyclobutyl-1-piperazinyl)phenyl group, a 4-(4-cyclobutyl-1-piperazinyl)-3-methylphenyl group, a 4-(4-cyclopropylmethyl-1-piperazinyl)phenyl group, a 4-(4-cyclopropylmethyl-1-piperazinyl)-3-methylphenyl group, a 4-(4-(2-hydroxyethyl)-1-piperazinyl)phenyl group, a 4-(4-(2-hydroxyethyl)-1-piperazinyl)-3-methylphenyl group, a 4-(4-(2-methoxyethyl)-1-piperazinyl)phenyl group, a 4-(4-acetyl-1-piperazinyl)phenyl group, a 4-(4-(2-methoxyacetyl)-1-piperazinyl)phenyl group, a 3-hydroxymethyl-4-(4-(2-methoxyacetyl)-1-piperazinyl)phenyl group, a 4-(4-methylsulfonyl-1-piperazinyl)phenyl group, a 3-methyl-4-(4-methylsulfonyl-1-piperazinyl)phenyl group, a 4-(4-methyl-3-oxo-1-piperazinyl)phenyl group, a 3-methyl-4-(4-methyl-3-oxo-1-piperazinyl)phenyl group, a 4-(4-hydroxypiperidino)phenyl group, a 4-(4-hydroxypiperidino)-3-methylphenyl group, a 4-(4-hydroxypiperidino)-3-hydroxymethylphenyl group, a 4-morpholinophenyl group, a 3-methyl-4-morpholinophenyl group, a 3-hydroxymethyl-4-morpholinophenyl group, 4-(1,1-dioxidothiomorpholino)phenyl group, a 3-methyl-4-(1,1-dioxidothiomorpholino)phenyl group, a 4-(4-methyl-5-oxoperhydro-1H-1,4-diazepin-1-yl)phenyl group, a 4-(4-piperidyl)phenyl group, a 4-(1-methyl-4-piperidyl)phenyl group, a 3-methyl-4-(4-piperidyl)phenyl group, a 4-(4-hydroxy-4-piperidyl)phenyl group, a 4-(4-hydroxy-1-methyl-4-piperidyl)phenyl group, a 4-(1-(2-hydroxyethyl)-4-piperidyl)phenyl group, a 4-(1-(2-hydroxyethyl)-4-piperidyl)-3-methylphenyl group, a 4-(1-tert-butoxycarbonyl-4-hydroxy-4-piperidyl)phenyl group, a 4-(1,2,3,6-tetrahydro-4-pyridyl)phenyl group, a 3-methyl-4-(1,2,3,6-tetrahydro-4-pyridyl)phenyl group, a 4-(3-azetidinyloxy)phenyl group, a 4-(3-azetidnyloxy)-3-methylphenyl group, a 4-(1-ethyl-3-azetidinyloxy)phenyl group, a 4-(1-ethyl-3-azetidinyloxy)-3-methylphenyl group, a 4-(1-isopropyl-3-azetidinyloxy)phenyl group, a 4-(1-isopropyl-3-azetidinyloxy)-3-methylphenyl group, a 4-(1-(2-hydroxyethyl)-3-azetidinyloxy)phenyl group, a 4-(1-(2-hydroxyethyl)-3-azetidinyloxy)-3-methylphenyl group; more preferably a 4-acetylphenyl group, a 3,5-dimethyl-4-(2-dimethylaminoethoxy)phenyl group, a 3-methyl-4-(1-piperazinyl)phenyl group, a 4-(4-methyl-1-piperazinyl)phenyl group, a 3-methyl-4-(4-methyl-1-piperazinyl)phenyl group, a 3-hydroxymethyl-4-(4-methyl-1-piperazinyl)phenyl group, a 4-(4-ethyl-1-piperazinyl)phenyl group, a 4-(4-isopropyl-1-piperazinyl)phenyl group, a 4-(4-tert-butyl-1-piperazinyl)phenyl group, a 4-(4-cyclobutyl-1-piperazinyl)-3-methylphenyl group, a 4-(4-cyclopropylmethyl-1-piperazinyl)-3-methylphenyl group, a 4-(4-(2-hydroxyethyl)-1-piperazinyl)phenyl group, a 4-(4-(2-hydroxyethyl)-1-piperazinyl)-3-methylphenyl group, a 4-(4-(2-methoxyethyl)-1-piperazinyl)phenyl group, a 4-(4-acetyl-1-piperazinyl)phenyl group, a 3-methyl-4-(4-methylsulfonyl-1-piperazinyl)phenyl group, a 4-(4-methyl-3-oxo-1-piperazinyl)phenyl group, a 3-methyl-4-(4-methyl-3-oxo-1-piperazinyl)phenyl group, a 4-(4-hydroxypiperidino)-3-methylphenyl group, a 4-(4-hydroxypiperidino)-3-hydroxymethylphenyl group, a 3-methyl-4-morpholinophenyl group, a 3-hydroxymethyl-4-morpholinophenyl group, a 3-methyl-4-(1,1-dioxidothiomorpholino)phenyl group, a 4-(4-methyl-5-oxoperhydro-1H-1,4-diazepin-1-yl)phenyl group, a 4-(4-piperidyl)phenyl group, a 4-(1-methyl-4-piperidyl)phenyl group, a 4-(4-hydroxy-1-methyl-4-piperidyl)phenyl group, a 4-(1-(2-hydroxyethyl)-4-piperidyl)-3-methylphenyl group, a 4-(1-tert-butoxycarbonyl-4-hydroxy-4-piperidyl)phenyl group, a 3-methyl-4-(1,2,3,6-tetrahydro-4-pyridyl)phenyl group, a 4-(1-ethyl-3-azetidinyloxy)-3-methylphenyl group, a 4-(1-isopropyl-3-azetidinyloxy)-3-methylphenyl group; even more preferably a 4-(4-methyl-1-piperazinyl)phenyl group, a 3-methyl-4-(4-methyl-1-piperazinyl)phenyl group, a 3-hydroxymethyl-4-(4-methyl-1-piperazinyl)phenyl group, a 4-(4-ethyl-1-piperazinyl)phenyl group, a 4-(4-(2-hydroxyethyl)-1-piperazinyl)phenyl group, a 4-(4-acetyl-1-piperazinyl)phenyl group, a 4-(1-methyl-4-piperidyl)phenyl group.

$R^1$ is a lower alkyl group, a lower alkenyl group, a lower alkynyl group or a cyclo-lower alkyl group optionally substituted by a halogen atom, or is an aryl group, an aralkyl group or a heteroaromatic group optionally having a substituent selected from a group consisting of a halogen atom, a cyano group, an amino group and a lower alkyl group.

The "alkyl group, the lower alkenyl group, the lower alkynyl group or the cyclo-lower alkyl group optionally substituted by a halogen atom" for $R^1$ means the above-mentioned unsubstituted lower alkyl, lower alkenyl, lower alkynyl or cyclo-lower alkyl group, or the above-mentioned lower alkyl, lower alkenyl, lower alkynyl or cyclo-lower alkyl group substituted by the above-mentioned halogen atom. The group may have the same or different, one or two or more, preferably from 1 to 3 halogen atoms at any substitutable position therein.

The halogen atom for the substituent is, for example, preferably a fluorine atom, a chlorine atom.

The "lower alkyl group optionally substituted by a halogen atom" for $R^1$ is, for example, preferably a methyl group, an ethyl group, a propyl group, an isopropyl group, a 2,2-difluoroethyl group, a 2,2,2-trifluoroethyl group, more preferably an ethyl group or an isopropyl group.

The "lower alkenyl group optionally substituted by a halogen atom" for $R^1$ is, for example, preferably an allyl group, a 2-methyl-2-propenyl group, a 3-methyl-2-butenyl group, especially preferably an allyl group.

The "lower alkynyl group optionally substituted by a halogen atom" for $R^1$ is, for example, preferably a 2-propynyl group.

The "cyclo-lower alkyl group optionally substituted by a halogen atom" for $R^1$ is, for example, preferably a cyclopropyl group, a cyclobutyl group.

The "aryl group, the aralkyl group or the heteroaromatic group optionally having a substituent selected from a group consisting of a halogen atom, a cyano group, an amino group and a lower alkyl group" for $R^1$ means the above-mentioned unsubstituted aryl group, aralkyl group or heteroaromatic group, or the above-mentioned aryl group, aralkyl group or heteroaromatic group having a substituent at any substitutable position therein, for which the same or different, one or two or more, preferably 1 or 2 substituents may be selected from the group consisting of a halogen atom, a cyano group, an amino group and a lower alkyl group.

The halogen atom for the substituent is, for example, preferably a fluorine atom, a chlorine atom.

The lower alkyl group for the substituent is, for example, preferably a methyl group, an ethyl group.

The substituent is preferably a halogen atom, a cyano group, an amino group, more preferably a halogen atom.

The aryl group optionally having a substituent for $R^1$ is, for example, preferably a phenyl group, a 1-naphthyl group, a 2-chlorophenyl group, a 2,6-dichlorophenyl group, a 2-cyanophenyl group, a 2-chloro-6-cyanophenyl group.

The heteroaromatic group optionally having a substituent for $R^1$ is, for example, preferably a 2-pyridyl group, a 3-chloro-2-pyridyl group.

The aralkyl group optionally having a substituent for $R^1$ is, for example, preferably a benzyl group, an α-methylbenzyl group.

Preferred embodiments of $R^1$ are, for example, a lower alkyl group optionally substituted by a halogen atom, more concretely, an ethyl group and an isopropyl group etc.

Another preferred embodiments of $R^1$ are, for example, a lower alkenyl group optionally substituted by a halogen atom, more concretely, an allyl group, a 2-methyl-2-propenyl group, a 3-methyl-2-butenyl group; more preferably an allyl group.

Another preferred embodiments of $R^1$ are, for example, a lower alkynyl group optionally substituted by a halogen atom, more concretely, a 2-propynyl group.

Another preferred embodiments of $R^1$ are, for example, a phenyl or benzyl group optionally having a substituent selected from a group consisting of a halogen atom, a cyano group, an amino group and a lower alkyl group, more concretely, a 2-chlorophenyl group, a 2,6-dichlorophenyl group, a 2-cyanophenyl group, a 2-chloro-6-cyanophenyl group, a benzyl group, an α-methylbenzyl group; more preferably a 2-chlorophenyl group.

Especially a lower alkenyl group such as an allyl group etc. is preferred for $R^1$.

$R^2$ is a hydrogen atom, a lower alkyl group, a lower alkenyl group or a lower alkynyl group, or is an aryl group, an aralkyl group or a heteroaromatic group optionally having a substituent selected from a group consisting of a halogen atom, a cyano group, a nitro group, a carboxyl group, a group of $-Q^4-A^4(R^{1g})R^{1h}$ and a group of $-Q^5-Ar^a$, wherein one or two or more methylene groups constituting the lower alkyl group, the lower alkenyl group or the lower alkynyl group may be independently replaced by an oxygen atom, a sulfur atom, a sulfinyl group, a sulfonyl group, a carbonyl group or a group of $-N(R^{1j})-$, and/or substituted by a halogen atom.

The lower alkyl group for $R^2$ is, for example, preferably a methyl group, an ethyl group.

The lower alkenyl group for $R^2$ is, for example, preferably an allyl group.

The lower alkynyl group for $R^2$ is, for example, preferably a 2-propynyl group.

One or two or more methylene groups constituting the lower alkyl group, the lower alkenyl group or the lower alkynyl group for $R^2$ may be independently replaced by an oxygen atom, a sulfur atom, a sulfinyl group, a sulfonyl group, a carbonyl group or a group of $-N(R^{1j})-$, and/or substituted by a halogen atom. The replaced or substituted group is, for example, preferably a methoxymethyl group, a methylsuflonylmethyl group, an acetyl group or a group of a formula (bb1):

$R^{1j}$ is a hydrogen atom or a lower alkyl group, for example, preferably a hydrogen atom or a methyl group.

The "aryl group, the aralkyl group or the heteroaromatic group optionally having a substituent selected from a group consisting of a halogen atom, a cyano group, a nitro group, a carboxyl group, a group of $-Q^4-A^4(R^{1g})R^{1h}$ and a group of $-Q^5-Ar^a$" for $R^2$ means the above-mentioned unsubstituted aryl, aralkyl or heteroaromatic group, or the above-mentioned aryl, aralkyl or heteroaromatic group having a substituent at any substitutable position therein, for which the same or different, one or two or more, preferably 1 or 2 substituents may be selected from a group consisting of a halogen atom, a cyano group, a nitro group, a carboxyl group, a group of $-Q^4-A^4(R^{1g})R^{1h}$ and a group of $-Q^5-Ar^a$.

The halogen atom for the substituent is, for example, preferably a fluorine atom, a chlorine atom, a bromine atom.

In the group of $-Q^4-A^4(R^{1g})R^{1h}$ for the substituent, $A^4$ is a nitrogen atom, or is a methine group optionally substituted by a halogen atom, a hydroxyl group, a lower alkyl group or a hydroxy-lower alkyl group; $Q^4$ is a single bond or a lower alkylene group, wherein one or two or more methylene groups constituting the lower alkylene group may be independently replaced by an oxygen atom or a carbonyl group, and/or substituted by a lower alkyl group; $R^{1g}$ and $R^{1h}$ are independently a hydrogen atom, a halogen atom, a cyano group, a hydroxyl group, a lower alkyl group, a lower alkoxy-lower alkyl group, a lower alkanoyl group, a lower alkoxycarbonyl group or a lower alkylsulfonyl group, or together form a lower alkylene group, wherein one or two or more methylene groups constituting the lower alkylene group may be independently replaced by an oxygen atom, a sulfur atom, a sulfinyl group, a sulfonyl group, a carbonyl group or a group of —N($R^{1i}$)—, and/or substituted by a halogen atom or a lower alkyl group.

The "methine group optionally substituted by a halogen atom, a hydroxyl group, a lower alkyl group or a hydroxy-lower alkyl group" for $A^4$ means an unsubstituted methine group, or a methine group having a substituent selected from a group consisting of a halogen atom, a hydroxyl group, a lower alkyl group and a hydroxy-lower alkyl group.

The halogen atom for the substituent is, for example, preferably a fluorine atom, a chlorine atom.

The lower alkyl group for the substituent is, for example, preferably a methyl group, an ethyl group.

The hydroxy-lower alkyl group for the substituent is, for example, preferably a hydroxymethyl group, a 2-hydroxyethyl group.

The substituent is, for example, preferably a halogen atom, a hydroxyl group, a lower alkyl group.

The lower alkylene group for $Q^4$ is, for example, preferably a methylene group, an ethylene group, a trimethylene group.

One or two or more methylene groups constituting the lower alkylene group for $Q^4$ may be independently replaced by an oxygen atom or a carbonyl group, and/or substituted by a lower alkyl group. The replaced or substituted group is, for example, preferably selected from the following formula (bb2):

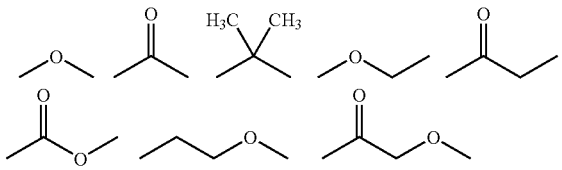

(bb2)

The halogen atom for $R^{1g}$ or $R^{1h}$ is, for example, preferably a fluorine atom, a chlorine atom.

The lower alkyl group for $R^{1g}$ or $R^{1h}$ is, for example, preferably a methyl group, an ethyl group, an isopropyl group.

The lower alkoxy-lower alkyl group for $R^{1g}$ or $R^{1h}$ is, for example, preferably a methoxymethyl group, a 2-methoxyethyl group, a 3-methoxypropyl group.

The lower alkanoyl group for $R^{1g}$ or $R^{1h}$ is, for example, preferably an acetyl group.

The lower alkoxycarbonyl group for $R^{1g}$ or $R^{1h}$ is, for example, preferably a methoxycarbonyl group, a tert-butoxycarbonyl group.

The lower alkylsulfonyl group for $R^{1g}$ or $R^{1h}$ is, for example, preferably a methylsulfonyl group, an ethylsulfonyl group.

The lower alkylene group that $R^{1g}$ and $R^{1h}$ together form is, for example, preferably an ethylene group, a trimethylene group, a tetramethylene group, a pentamethylene group. When "$A^4$" to which they bond is a nitrogen atom, then they form along with the nitrogen atom, a 1-aziridinyl group, a 1-azetidinyl group, a 1-pyrrolidinyl group, a piperidino group; when "$A^4$" is a methine group, they form along with the methine group, a cyclopropyl group, a cyclobutyl group, a cyclopentyl group, a cyclohexyl group. Above all, more preferred are a 1-pyrrolidinyl group, a piperidino group, a cyclobutyl group, a cyclohexyl group.

One or two or more methylene groups constituting the above-mentioned lower alkylene group may be independently replaced by an oxygen atom, a sulfur atom, a sulfinyl group or a sulfonyl group, a carbonyl group or a group of —N($R^{1i}$)—, and/or substituted by a halogen atom or a lower alkyl group. Examples of the replaced or substituted groups are preferably selected from the following formula (bb3):

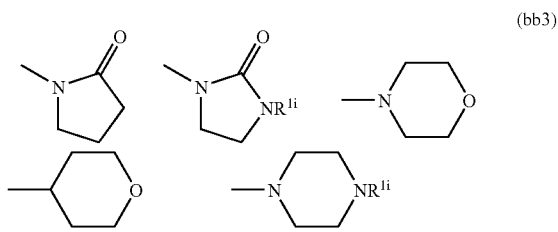

(bb3)

Above all, examples of the groups are more preferably selected from the following formula (bb3'):

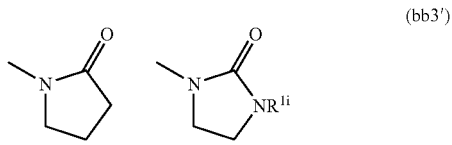

(bb3')

$R^{1i}$ in the group of —N($R^{1i}$)— is a hydrogen atom, a lower alkyl group or a halo-lower alkyl group.

The lower alkyl group for $R^{1i}$ is, for example, preferably a methyl group, an ethyl group.

The halo-lower alkyl group for $R^{1i}$ is, for example, preferably a fluoromethyl group, a difluoromethyl group.

Preferred embodiments of the group of -$Q^4$-$A^4$($R^{1g}$)$R^{1h}$ are, for example, as follows:

(i) $A^4$ is a nitrogen atom, $Q^4$ is a single bond or a methylene group optionally substituted by a lower alkyl group, and $R^{1g}$ and $R^{1h}$ are independently a hydrogen atom, a lower alkyl group, a lower alkanoyl group, a lower alkoxycarbonyl group or a lower alkylsulfonyl group;

(ii) $A^4$ is a nitrogen atom or is a methine group optionally substituted by a halogen atom, a hydroxyl group, a lower alkyl group or a hydroxy-lower alkyl group, $Q^4$ is a carbonyl group, and $R^{1g}$ and $R^{1h}$ are independently a hydrogen atom or a lower alkyl group;

(iii) $A^4$ is a methine group optionally substituted by a halogen atom, a hydroxyl group, a lower alkyl group or a hydroxy-lower alkyl group, $Q^4$ is a single bond or a methylene group optionally replaced by an oxygen atom, and $R^{1g}$ and $R^{1h}$ are independently a hydrogen atom, a halogen atom, a hydroxyl group, a lower alkyl group or a lower alkoxycarbonyl group;

(iv) $A^4$ is a methine group optionally substituted by a halogen atom, a hydroxyl group, a lower alkyl group or a hydroxy-lower alkyl group, $Q^4$ is an ethylene group, in which one or two methylene groups constituting the ethylene group may be independently replaced by an oxygen atom or a carbonyl group, and $R^{1g}$ and $R^{1h}$ are independently a hydrogen atom, a hydroxyl group or a lower alkyl group;

(v) $A^4$ is a methine group optionally substituted by a halogen atom, a hydroxyl group, a lower alkyl group or a hydroxy-lower alkyl group, Q⁴ is a single bond, and R¹ᵍ and R¹ʰ together form a lower alkylene group, in which one or two or more methylene groups constituting the lower alkylene group may be independently replaced by an oxygen atom or a group of —N(R¹ⁱ)—; or (vi) A⁴ is a nitrogen atom, Q⁴ is a single bond, and R¹ᵍ and R¹ʰ together form a lower alkylene group, in which one or two or more methylene groups constituting the lower alkylene group may be independently replaced by a carbonyl group or a group of —N(R¹ⁱ)—; more preferably above (iii).

More concretely, the group of -Q⁴-A⁴(R¹ᵍ)R¹ʰ is, for example, preferably an amino group, a methylaminomethyl group, a dimethylaminomethyl group, an isopropylmethylamino group, a 1-amino-1-methylethyl group, a methylsulfonylamino group, an N-methyl-N-acetylaminomethyl group, an N-methyl-N-methoxycarbonylaminomethyl group, an N-methyl-N-methylsulfonylaminomethyl group, a carbamoyl group, a methylcarbamoyl group, a dimethylcarbamoyl group, an acetyl group, a methyl group, a trifluoromethyl group, a 1-fluoro-1-methylethyl group, a hydroxymethyl group, a 1-hydroxyethyl group, a 1-hydroxy-1-methylethyl group, a 2-hydroxy-1,1-dimethylethyl group, a 2-hydroxy-2-methylpropyl group, a 2-hydroxy-1,1-dimethylpropyl group, a 1-methoxycarbonyl-1-methylethyl group, a methoxy group, a 2-hydroxyethoxy group, a methoxycarbonyl group, a tert-butoxycarbonyl group, a 1-hydroxycyclobutyl group, a 4-hydroxy-tetrahydropyran-4-yl group, a 2-oxo-1-pyrrolidinyl group, or a 3-methyl-2-oxoimidazolidin-1-yl group; more preferably an amino group, a dimethylaminomethyl group, a methylsulfonylamino group, an N-methyl-N-methylsulfonylaminomethyl group, a carbamoyl group, a dimethylcarbamoyl group, a methyl group, a 1-fluoro-1-methylethyl group, a hydroxymethyl group, a 1-hydroxy-1-methylethyl group, a 2-hydroxy-1,1-dimethylethyl group, a 2-hydroxy-2-methylpropyl group, a 2-hydroxy-1,1-dimethylpropyl group, a methoxy group, a 2-hydroxyethoxy group, a 1-hydroxycyclobutyl group, a 2-oxo-1-pyrrolidinyl group, or a 3-methyl-2-oxoimidazolidin-1-yl group, even more preferably a 1-hydroxy-1-methylethyl group etc.

In the group of -Q⁵-Arᵃ for the substituent for the aryl group, the aralkyl group or the heteroaromatic group for R², Arᵃ is an aryl group or a heteroaromatic group, which may have a substituent selected from a group consisting of a halogen atom, a lower alkyl group, a halo-lower alkyl group, a hydroxy-lower alkyl group and a lower alkoxy group; Q⁵ is a single bond, an oxygen atom, a sulfur atom, a carbonyl group or a lower alkylene group, wherein one or two or more methylene groups constituting the lower alkylene group may be independently replaced by an oxygen atom, a sulfur atom or a carbonyl group, and/or substituted by a halogen atom or a lower alkyl group.

The "aryl group or the heteroaromatic group, which may have a substituent selected from a group consisting of a halogen atom, a lower alkyl group, a halo-lower alkyl group, a hydroxy-lower alkyl group and a lower alkoxy group" for Arᵃ means the above-mentioned unsubstituted aryl or heteroaromatic group, or the above-mentioned aryl or heteroaromatic group having a substituent at any substitutable position therein, for which the same or different, one or two or more, preferably 1 or 2 substituents may be selected from the group consisting of a halogen atom, a lower alkyl group, a halo-lower alkyl group, a hydroxy-lower alkyl group and a lower alkoxy group.

The halogen atom for the substituent is, for example, preferably a fluorine atom, a chlorine atom.

The lower alkyl group for the substituent is, for example, preferably a methyl group, an ethyl group.

The halo-lower alkyl group for the substituent is, for example, preferably a fluoromethyl group, a difluoromethyl group, a trifluoromethyl group.

The hydroxy-lower alkyl group for the substituent is, for example, preferably a hydroxymethyl group, a 2-hydroxyethyl group.

The lower alkoxy group for the substituent is, for example, preferably a methoxy group, an ethoxy group.

The substituent is, for example, preferably a halogen atom, a lower alkyl group, a lower alkoxy group.

The "aryl group" itself of the aryl group optionally having the above-mentioned substituent for Arᵃ is, for example, preferably a phenyl group. The "heteroaromatic group" itself of the heteroaromatic group optionally having the above-mentioned substituent for Arᵃ is, for example, preferably a pyridyl group.

Accordingly, preferred examples of the aryl group or the heteroaromatic group optionally having the above-mentioned substituent for Arᵃ includes, for example, a phenyl group, a 4-methoxyphenyl group, a 2-pyridyl group, a 6-methyl-2-pyridyl group.

The lower alkylene group for Q⁵ is, for example, preferably a methylene group, an ethylene group.

One or two or more methylene groups constituting the lower alkylene group for Q⁵ may be independently replaced by an oxygen atom, a sulfur atom or a carbonyl group, and/or substituted by a halogen atom or a lower alkyl group. Examples of the replaced or substituted groups are preferably selected from the following formula (bb4):

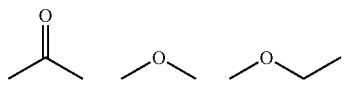

(bb4)

Accordingly, concretely, the group of -Q⁵-Arᵃ is, for example, preferably a benzyl group, a benzoyl group, a phenoxy group, a benzyloxy group, a 4-methoxybenzyloxy group, a 2-pyridyl group.

The substituent for "an aryl group, an aralkyl group or a heteroaromatic group" of R² is, for example, preferably a group of -Q⁴-A⁴(R¹ᵍ)R¹ʰ.

The "aryl group" itself of the aryl group optionally having the above-mentioned substituent for R² is, for example, preferably a phenyl group.

The "aralkyl group" itself of the aralkyl group optionally having the above-mentioned substituent for R² is, for example, preferably a benzyl group.

The "heteroaromatic group" itself of the heteroaromatic group optionally having the above-mentioned substituent for R² is, for example, preferably a thienyl group, a pyrazolyl group, a pyridyl group.

Concretely, therefore, the aryl group, the aralkyl group or the heteroaromatic group optionally having the above-mentioned substituent for R² is, for example, preferably a phenyl group, a 3-cyanophenyl group, a 3-nitrophenyl group, a 3-carboxyphenyl group, a 3-aminophenyl group, a 3-dimethylaminomethylphenyl group, a 3-methylsulfonylaminophenyl group, a 3-carbamoylphenyl group, a 3-methylcarbamoylphenyl group, a 3-dimethylcarbamoylphenyl group, a 3-hydroxymethylphenyl group, a 4-hydroxymethylphenyl group, a 3-(1-hydroxy-1-methylethyl)phenyl group, a 3-methoxycarbonylphenyl group, a 3-methoxyphenyl group, a 4-methoxyphenyl group, a 3-thienyl group, a 1-methyl-3-pyrazolyl group, a 2-pyridyl group, a 3-pyridyl group, a 4-pyridyl group, a 5-fluoro-2-pyridyl group, a 6-fluoro-2-pyridyl group, a 6-bromo-2-pyridyl group, a 5-cyano-2-pyridyl group, a 5-carboxy-2-pyridyl group, a 4-methylaminomethyl-2-pyridyl group, a 6-amino-2-pyridyl group, a 6-dimethylaminomethyl-2-pyridyl group, a 6-isopropylmethylamino-2-pyridyl group, a 6-(1-amino-1-methylethyl)-2-pyridyl group, a 6-(N-methyl-N-acetylaminomethyl)-2-pyridyl group, a 6-(N-methyl-N-methoxycarbonylaminomethyl)-2-pyridyl group, a 6-(N-methyl-N-methylsulfonylaminomethyl)-2-pyridyl group, a 6-dimethylcarbamoyl-2-pyridyl group, a 6-acetyl-2-pyridyl group, a 4-methyl-2-pyridyl group, a 6-methyl-2-pyridyl group, a 6-(1-fluoro-1-methylethyl)-2-pyridyl group, a 5-trifluoromethyl-2-pyridyl group, a 6-hydroxymethyl-2-pyridyl group, a 6-(1-hydroxyethyl)-2-pyridyl group, a 6-(1-hydroxy-1-methylethyl)-2-pyridyl group, a 6-(2-hydroxy-1,1-dimethylethyl)-2-pyridyl group, a 6-(2-hydroxy-2-methylpropyl)-2-pyridyl group, a 6-(2-hydroxy-1,1-dimethylpropyl)-2-pyridyl group, a 6-(1-methoxycarbonyl-1-methylethyl)-2-pyridyl group, a 6-methoxy-2-pyridyl group, a 6-(2-hydroxyethoxy)-2-pyridyl group, a 5-methoxycarbonyl-2-pyridyl group, a 6-(tert-butoxycarbonyl)-2-pyridyl group, a 6-(1-hydroxycyclobutyl)-2-pyridyl group, a 6-(4-hydroxy-tetrahydropyran-4-yl)-2-pyridyl group, a 6-(2-oxo-1-pyrrolidinyl)-2-pyridyl group, or a 6-(3-methyl-2-oxoimidazolidin-1-yl)-2-pyridyl group; more preferably a phenyl group, a 3-dimethylaminomethylphenyl group, a 3-dimethylcarbamoylphenyl group, a 3-(1-hydroxy-1-methylethyl)phenyl group, a 3-thienyl group, a 2-pyridyl group, a 5-fluoro-2-pyridyl group, a 6-amino-2-pyridyl group, a 6-(N-methyl-N-methylsulfonylaminomethyl)-2-pyridyl group, a 6-methyl-2-pyridyl group, a 6-(1-hydroxy-1-methylethyl)-2-pyridyl group, a 6-(2-hydroxy-1,1-dimethylethyl)-2-pyridyl group, a 6-(2-hydroxy-2-methylpropyl)-2-pyridyl group, a 6-(2-hydroxy-1,1-dimethylpropyl)-2-pyridyl group, a 6-(2-hydroxyethoxy)-2-pyridyl group, a 6-(1-hydroxycyclobutyl)-2-pyridyl group, a 6-(2-oxo-1-pyrrolidinyl)-2-pyridyl group, or a 6-(3-methyl-2-oxoimidazolidin-1-yl)-2-pyridyl group, even more preferably a 6-(1-hydroxy-1-methylethyl)-2-pyridyl group etc.

$R^2$ is preferably a lower alkyl group, or an aryl or heteroaromatic group optionally having the above-mentioned substituent.

Preferred embodiments of $R^1$ and $R^2$ in formula (I) are, for example, $R^1$ is a lower alkenyl or lower alkynyl, more preferably lower alkenyl group optionally substituted by a halogen atom, and $R^2$ is a phenyl or pyridyl, more preferably pyridyl group having a group of $-Q^4-A^4(R^{1g})R^{1h}$.

$R^3$ is a hydrogen atom or a lower alkyl group, for example, preferably a hydrogen atom, a methyl group or an ethyl group; more preferably a hydrogen atom.

$R^4$ is a hydrogen atom, a halogen atom, a hydroxyl group, a lower alkyl group or a group of $-N(R^{1k})R^{1m}$.

The halogen atom for $R^4$ is, for example, preferably a fluorine atom, a chlorine atom.

The lower alkyl group for $R^4$ is, for example, preferably a methyl group, an ethyl group, an isopropyl group.

In the group of $-N(R^{1k})R^{1m}$ for $R^4$, $R^{1k}$ and $R^{1m}$ are independently a hydrogen atom or a lower alkyl group.

The lower alkyl group for $R^{1k}$ and $R^{1m}$ is, for example, preferably a methyl group, an ethyl group, an isopropyl group.

Accordingly, the group of $-N(R^{1k})R^{1m}$ includes, for example, an amino group, a methylamino group, a dimethylamino group, an isopropylmethylamino group.

$R^4$ is preferably a hydrogen atom.

T and U are independently a nitrogen atom or a methine group, and preferably they are both nitrogen atoms.

In the compounds of the formula (I), compounds wherein $R^1$ is a methyl group and $R^2$ is an unsubstituted phenyl group are excluded from the invention.

Compounds of a general formula (I-1):

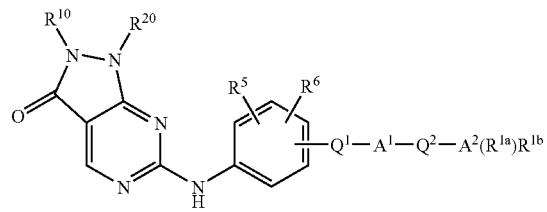

(I-1)

wherein $R^5$ and $R^6$ are independently a hydrogen atom, a halogen atom, a lower alkyl group, a halo-lower alkyl group, a hydroxy-lower alkyl group, a lower alkoxy group, a lower alkanoyl group, a hydroxy-lower alkylamino group, a carbamoyl group or a hydroxy-lower alkylcarbamoyl group; $R^{10}$ is a lower alkyl group, a lower alkenyl group or a lower alkynyl group, which may be substituted by a halogen atom; $R^{20}$ is an aryl group or a heteroaromatic group, which may have a substituent selected from a group consisting of a halogen atom, a cyano group, a nitro group, a carboxyl group, a group of $-Q^4-A^4(R^{1g})R^{1h}$ and a group of $-Q^5-Ar^a$; and $A^1$, $A^2$, $A^4$, $Ar^a$, $Q^1$, $Q^2$, $Q^4$, $Q^5$, $R^{1a}$, $R^{1b}$, $R^{1g}$ and $R^{1h}$ have the same meanings as above, provided that the compounds wherein $R^{10}$ is a methyl group and $R^{20}$ is an unsubstituted phenyl group are excluded;

compounds of a general formula (I-2):

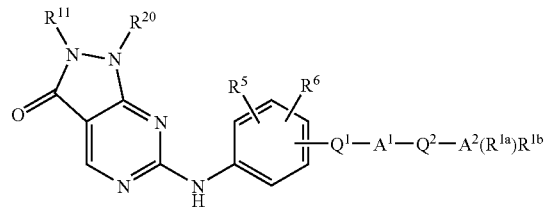

(I-2)

wherein $R^{11}$ is a group of a formula (a-1) or (a-2):

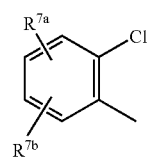

(a-1)

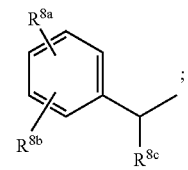

(a-2)

$R^{7a}$, $R^{7b}$, $R^{8a}$ and $R^{8b}$ are independently a hydrogen atom, a halogen atom or a cyano group; $R^{8c}$ is a hydrogen atom or a lower alkyl group; $A^1$, $A^2$, $Q^1$, $Q^2$, $R^{1a}$, $R^{1b}$, $R^5$, $R^6$ and $R^{20}$ have the same meanings as above;

and compounds of a general formula (I-3):

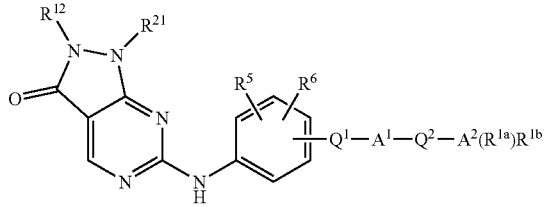

(I-3)

wherein $R^{12}$ is a group of a formula (a-1):

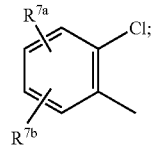

(a-1)

$R^{7a}$ and $R^{7b}$ are independently a hydrogen atom, a halogen atom or a cyano group; $R^{21}$ is a lower alkyl group; $A^1$, $A^2$, $Q^1$, $Q^2$, $R^{1a}$, $R^{1b}$, $R^5$ and $R^6$ have the same meanings as above are within the scope of the compounds of formula (I).

Preferred examples and preferred embodiments of $R^5$ and $R^6$ in the compounds of formulae (I-1), (I-2) and (I-3) are described below.

The halogen atom for $R^5$ and $R^6$ is, for example, preferably a fluorine atom, a chlorine atom.

The alkyl group for $R^5$ and $R^6$ is, for example, preferably a methyl group, an ethyl group.

The halo-lower alkyl group for $R^5$ and $R^6$ is, for example, preferably a fluoromethyl group, a difluoromethyl group, a trifluoromethyl group.

The hydroxy-lower alkyl group for $R^5$ and $R^6$ is, for example, preferably a hydroxymethyl group, a 2-hydroxyethyl group.

The lower alkoxy group for $R^5$ and $R^6$ is, for example, preferably a methoxy group, an ethoxy group.

The lower alkanoyl group for $R^5$ and $R^6$ is, for example, preferably an acetyl group.

The hydroxy-lower alkylamino group for $R^5$ and $R^6$ is, for example, preferably a hydroxymethylamino group, a 2-hydroxyethylamino group.

The hydroxy-lower-alkylcarbamoyl group for $R^5$ and $R^6$ is, for example, preferably a hydroxymethylcarbamoyl group, a 2-hydroxyethylcarbamoyl group.

Preferred embodiments of $R^5$ and $R^6$ are, for example, such that both of them are hydrogen atoms, or any one of them is a hydrogen atom and the other is a lower alkyl group, a hydroxy-lower alkyl group, a lower alkoxy group or a lower alkanoyl group.

Preferred embodiments of the group of $-Q^1-A^1-Q^2-A^2(R^{1a})R^{1b}$ in the compounds of formulae (I-1), (I-2) and (I-3) may be the same as those of the group of $-Q^1-A^1-Q^2-A^2(R^{1a})R^{1b}$ in formula (I).

Preferred examples and preferred embodiments of $R^{10}$ and $R^{20}$ in formula (I-1) are described below.

The lower alkyl group optionally substituted by a halogen atom for $R^{10}$ is, for example, preferably a methyl group, an ethyl group, a propyl group, an isopropyl group, a 2,2-difluoroethyl group, a 2,2,2-trifluoroethyl group, more preferably an ethyl group, or an isopropyl group.

The lower alkenyl group optionally substituted by a halogen atom for $R^{10}$ is, for example, preferably an allyl group, a 2-methyl-2-propenyl group, a 3-methyl-2-butenyl group; more preferably an allyl group.

The lower alkynyl group optionally substituted by a halogen atom for $R^{10}$ is, for example, preferably a 2-propynyl group.

Preferred embodiments of $R^{10}$ are, for example, a lower alkyl group optionally substituted by a halogen atom, more concretely, an ethyl group and an isopropyl group etc.

Another preferred embodiments of $R^{10}$ are, for example, a lower alkenyl group optionally substituted by a halogen atom, more concretely, an allyl group, a 2-methyl-2-propenyl group, a 3-methyl-2-butenyl group; more preferably an allyl group.

Another preferred embodiments of $R^{10}$ are, for example, a lower alkynyl group optionally substituted by a halogen atom, more concretely, a 2-propynyl group.

Especially a lower alkenyl group such as an allyl group etc. is preferred for $R^{10}$.

Preferred embodiments of "an aryl group or a heteroaromatic group, which may have a substituent selected from a group consisting of a halogen atom, a cyano group, a nitro group, a carboxyl group, a group of $-Q^4-A^4(R^{1g})R^{1h}$ and a group of $-Q^5-Ar^{a'''}$ for $R^{20}$ may be the same as those of "an aryl group or a heteroaromatic group, which may have a substituent selected from a group consisting of a halogen atom, a cyano group, a nitro group, a carboxyl group, a group of $-Q^4-A^4(R^{1g})R^{1h}$ and a group of $-Q^5-Ar^{a'''}$ for $R^2$ in formula (I).

Preferred embodiments of $R^{20}$ are, for example, a phenyl or pyridyl, more preferably pyridyl group having a group of $-Q^4-A^4(R^{1g})R^{1h}$.

Preferred embodiments of $R^{10}$ and $R^{20}$ in formula (I-1) are, for example, $R^{10}$ is a lower alkenyl or lower alkynyl, more preferably lower alkenyl group optionally substituted by a halogen atom, and $R^{20}$ is a phenyl or pyridyl, more preferably pyridyl group having a group of $-Q^4-A^4(R^{1g})R^{1h}$.

Preferred embodiments of $R^{10}$, $R^{20}$ and the group of $-Q^1-A^1-Q^2-A^2(R^{1a})R^{1b}$ in formula (I-1) are, for example, $R^{10}$ is a lower alkenyl or lower alkynyl, more preferably lower alkenyl group optionally substituted by a halogen atom, $R^{20}$ is a phenyl or pyridyl, more preferably pyridyl group having a group of $-Q^4-A^4(R^{1g})R^{1h}$, and the group of $-Q^1-A^1-Q^2-A^2(R^{1a})R^{1b}$ is selected from the formula (aa1'):

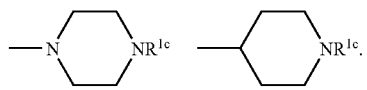

(aa1')

In the compounds of the formula (I-1), compounds wherein $R^{10}$ is a methyl group and $R^{20}$ is an unsubstituted phenyl group are excluded from the invention.

Preferred examples and preferred embodiments of $R^{11}$ and $R^{20}$ in formula (I-2) are described below.

The halogen atom for $R^{7a}$, $R^{7b}$, $R^{8a}$ and $R^{8b}$ in the group of formula (a-1) or (a-2) for $R^{11}$ is, for example, preferably a fluorine atom, a chlorine atom; and the lower alkyl group for $R^{8c}$ is, for example, preferably a methyl group, an ethyl group.

Preferred embodiments of $R^{7a}$ and $R^{7b}$ are such that they are both hydrogen atoms, or one of them is a hydrogen atom and the other is a halogen atom or a cyano group.

Preferred examples of the group of formula (a-1) are, for example, a 2-chlorophenyl group, a 2,6-dichlorophenyl group, a 2-chloro-6-cyanophenyl group.

A preferred embodiment of $R^{8a}$ and $R^{8b}$ is, for example, such that they are both hydrogen atoms.

Accordingly, preferred examples of the group of formula (a-2) are, for example, a benzyl group, an α-methylbenzyl group.

Preferred examples and preferred embodiments of $R^{12}$ and $R^{21}$ in formula (I-3) are described below.

Preferred embodiments of the group of formula (a-1) for $R^{12}$ may be the same as those of formula (a-1) in formula (I-2).

The lower alkyl group for $R^{21}$ is, for example, preferably a methyl group, an ethyl group.

The terms "any substitutable position" mean positions having substitutable hydrogen(s) on carbon, nitrogen, oxygen and/or sulfur atom(s) where the substitution of hydrogen is chemically allowed and the substitution results in a stable compound.

In the compounds of the invention, the replacement for methylene group(s) constituting the lower alkylene group by various radicals such as oxygen, sulfur, sulfinyl, sulfonyl, carbonyl, vinylene, and substituted or unsubstituted imine is allowed in case that the replacement is chemically allowed and the replacement results in a stable compound.

Depending on the type of the substituent and the salt form thereof, the compounds of the invention may be in the form of stereoisomers and tautomers such as optical isomers, diastereomers, geometrical isomers; and the compounds of the invention include all those stereoisomers and tautomers and their mixtures.

The invention includes various crystals, amorphous forms, salts, hydrates and solvates of the compounds of the invention.

Further, prodrugs of the compounds of the invention are within the scope of the invention. In general, such prodrugs are functional derivatives of the compounds of the invention that can be readily converted into compounds that are needed by living bodies. Accordingly, in the method of treatment of various diseases in the invention, the term "administration" includes not only the administration of a specific compound but also the administration of a compound which, after administered to patients, can be converted into the specific compound in the living bodies. Conventional methods for selection and production of suitable prodrug derivatives are described, for example, in "Design of Prodrugs", ed. H. Bundgaard, Elsevier, 1985, which is referred to herein and is entirely incorporated herein as a part of the present description. Metabolites of these compounds include active compounds that are produced by putting the compounds of the invention in a biological environment, and are within the scope of the invention.

Examples of the compounds of formula (I) and their salts and esters are, for example, the compounds and their salts and esters described in Examples; and more preferred are the following compounds:

3-(2-allyl-6-{[4-(4-methylpiperazin-1-yl)phenyl]amino}-3-oxo-1,2-dihydro-3H-pyrazolo[3,4-d]pyrimidin-1-yl)-N,N-dimethylbenzamide, 2-allyl-6-{[3-(hydroxymethyl)-4-(4-methylpiperazin-1-yl)phenyl]amino}-1-(3-thienyl)-1,2-dihydro-3H-pyrazolo[3,4-d]pyrimidin-3-one, 2-allyl-1-[3-(1-hydroxy-1-methylethyl)phenyl]-6-{[4-(4-methylpiperazin-1-yl)phenyl]amino}-1,2-dihydro-3H-pyrazolo[3,4-d]pyrimidin-3-one, 2-allyl-1-[3-(dimethylaminomethyl)phenyl]-6-{[4-(4-methylpiperazin-1-yl)phenyl]amino}-1,2-dihydro-3H-pyrazolo[3,4-d]pyrimidin-3-one, 3-(2-ethyl-6-{[3-methyl-4-(4-methylpiperazin-1-yl)phenyl]amino}-3-oxo-1,2-dihydro-3H-pyrazolo[3,4-d]pyrimidin-1-yl)-N,N-dimethylbenzamide, 2-allyl-6-{[3-hydroxymethyl-4-(4-methylpiperazin-1-yl)phenyl]amino}-1-pyridin-2-yl-1,2-dihydro-3H-pyrazolo[3,4-d]pyrimidin-3-one, 2-allyl-1-(6-aminopyridin-2-yl)-6-[{4-(4-methylpiperazin-1-yl)phenyl]amino}-1,2-dihydro-3H-pyrazolo[3,4-d]pyrimidin-3-one, 2-allyl-1-[6-(1-hydroxy-1-methylethyl)pyridin-2-yl]-6-{[4-(4-methylpiperazin-1-yl)phenyl]amino}-1,2-dihydro-3H-pyrazolo[3,4-d]pyrimidin-3-one, 2-allyl-6-{[4-(4-ethylpiperazin-1-yl)phenyl]amino}-1-[6-(1-hydroxy-1-methylethyl)pyridin-2-yl]-1,2-dihydro-3H-pyrazolo[3,4-d]pyrimidin-3-one, 6-{[4-(4-acetylpiperazin-1-yl)phenyl]amino}-2-allyl-1-[6-(1-hydroxy-1-methylethyl)pyridin-2-yl]-1,2-dihydro-3H-pyrazolo[3,4-d]pyrimidin-3-one, 2-allyl-6-({4-[4-(2-hydroxyethyl)piperazin-1-yl]phenyl}amino)-1-[6-(1-hydroxy-1-methylethyl)pyridin-2-yl]-1,2-dihydro-3H-pyrazolo[3,4-d]pyrimidin-3-one, 2-allyl-1-[6-(2-hydroxy-2-methylpropyl)pyridin-2-yl]-6-{[4-(1-methylpiperidin-4-yl)phenyl]amino}-1,2-dihydro-3H-pyrazolo[3,4-d]pyrimidin-3-one, 2-allyl-6-{[4-(4-methylpiperazin-1-yl)phenyl]amino}-1-[6-(2-oxopyrrolidin-1-yl)pyridin-2-yl]-1,2-dihydro-3H-pyrazolo[3,4-d]pyrimidin-3-one, N-{[6-(2-allyl-6-{[4-(4-methylpiperazin-1-yl)phenyl]amino}-3-oxo-1,2-dihydro-3H-pyrazolo[3,4-d]pyrimidin-1-yl)pyridin-2-yl]methyl}-N-methylmethanesulfonamide, 2-benzyl-6-{[3-methyl-4-(4-methylpiperazin-1-yl)phenyl]amino}-1-phenyl-1,2-dihydro-3H-pyrazolo[3,4-d]pyrimidin-3-one, 1-[6-(1-hydroxy-1-methylethyl)pyridin-2-yl]-6-{[4-(4-methylpiperazin-1-yl)phenyl]amino}-2-(2-propynyl)-1,2-dihydro-3H-pyrazolo[3,4-d]pyrimidin-3-one, 2-(2-chlorophenyl)-1-[6-(1-hydroxycyclobutyl)pyridin-2-yl]-6-{[3-methyl-4-(4-methylpiperazin-1-yl)phenyl]amino}-1,2-dihydro-3H-pyrazolo[3,4-d]pyrimidin-3-one, 1-[6-(1-hydroxy-1-methylethyl)pyridin-2-yl]-2-isopropyl-6-{[4-(4-methylpiperazin-1-yl)phenyl]amino}-1,2-dihydro-3H-pyrazolo[3,4-d]pyrimidin-3-one, 1-[6-(2-hydroxy-1,1-dimethylethyl)pyridin-2-yl]-2-isopropyl-6-{[4-(4-methylpiperazin-1-yl)phenyl]amino}-1,2-dihydro-3H-pyrazolo[3,4-d]pyrimidin-3-one, 1-[6-(1-hydroxy-1-methylethyl)pyridin-2-yl]-2-isopropyl-6-{[4-(1-methylpiperidin-4-yl)phenyl]amino}-1,2-dihydro-3H-pyrazolo[3,4-d]pyrimidin-3-one, and 2-allyl-1-[6-(3-methyl-2-oxoimidazolidin-1-yl)pyridin-2-yl]-6-{[4-(4-methylpiperazin-1-yl)phenyl]amino}-1,2-dihydro-3H-pyrazolo[3,4-d]pyrimidin-3-one, more preferably, 3-(2-allyl-6-{[4-(4-methylpiperazin-1-yl)phenyl]amino}-3-oxo-1,2-dihydro-3H-pyrazolo[3,4-d]pyrimidin-1-yl)-N,N-dimethylbenzamide, 2-allyl-6-{[3-(hydroxymethyl)-4-(4-methylpiperazin-1-yl) phenyl]amino}-1-(3-thienyl)-1,2-dihydro-3H-pyrazolo[3, 4-d]pyrimidin-3-one, 2-allyl-1-[6-(1-hydroxy-1-methylethyl)pyridin-2-yl]-6-{[4-(4-methylpiperazin-1-yl)phenyl]amino}-1,2-dihydro-3H-pyrazolo[3,4-d]pyrimidin-3-one, 1-[6-(1-hydroxy-1-methylethyl)pyridin-2-yl]-6-{[4-(4-methylpiperazin-1-yl)phenyl]amino}-2-(2-propynyl)-1,2-dihydro-3H-pyrazolo[3,4-d]pyrimidin-3-one, 1-[6-(1-hydroxy-1-methylethyl)pyridin-2-yl]-2-isopropyl-6-{[4-(1-methylpiperidin-4-yl)phenyl]amino}-1,2-dihydro-3H-pyrazolo[3,4-d]pyrimidin-3-one, and 2-allyl-1-[6-(3-methyl-2-oxoimidazolidin-1-yl)pyridin-2-yl]-6-{[4-(4-methylpiperazin-1-yl)phenyl]amino}-1,2-dihydro-3H-pyrazolo[3,4-d]pyrimidin-3-one.

Methods for producing the compounds of the invention are described below.

Compounds (I) of the invention may be produced, for example, according to the production methods mentioned below or according to the methods shown in Examples and Production Examples. However, the production methods for compounds (I) of the invention should not be limited to those reaction examples.

Production Method 1

A compound of a general formula (II):

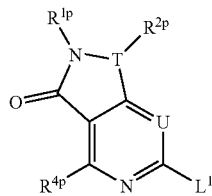

(II)

wherein;

$L^1$ is a leaving group;

$R^{1p}$ is a lower alkyl group, a lower alkenyl group, a lower alkynyl group or a cyclo-lower alkyl group, which may be substituted by a halogen atom, or is an aryl group, an aralkyl group or a heteroaromatic group, which may have a substituent selected from a group consisting of a halogen atom, a cyano group, a lower alkyl group and an optionally-protected amino group;

$R^{2p}$ is a hydrogen atom, a lower alkyl group, a lower alkenyl group or a lower alkynyl group, or is an aryl group, an aralkyl group or a heteroaromatic group, which may have a substituent selected from a group consisting of a halogen atom, a cyano group, a nitro group, a group of -$Q^{4p}$-$A^{4p}$($R^{1gp}$)$R^{1hp}$, a group of -$Q^{5p}$-$Ar^{ap}$ and an optionally-protected carboxyl group, wherein one or two or more methylene groups constituting the lower alkyl group, the lower alkenyl group or the lower alkynyl group may be independently replaced by an oxygen atom, a sulfur atom, a sulfinyl group, a sulfonyl group, an optionally-protected carbonyl group or a group of —N($R^{1jp}$)—, and/or substituted by a halogen atom;

$A^{4p}$ is a nitrogen atom, or is a methine group optionally substituted by a halogen atom, an optionally-protected hydroxyl group, a lower alkyl group or an optionally-protected hydroxy-lower alkyl group;

$Ar^{ap}$ is an aryl group or a heteroaromatic group, which may have a substituent selected from a group consisting of a halogen atom, a lower alkyl group, a halo-lower alkyl group, a lower alkoxy group an optionally-protected hydroxy-lower alkyl group;

$Q^{4p}$ is a single bond or a lower alkylene group, wherein one or two or more methylene groups constituting the lower alkylene group may be independently replaced by an oxygen atom or an optionally-protected carbonyl group, and/or substituted by a lower alkyl group;

$Q^{5p}$ is a single bond, an oxygen atom, a sulfur atom, an optionally-protected carbonyl group or a lower alkylene group, wherein one or two or more methylene groups constituting lower alkylene group may be independently replaced by an oxygen atom, a sulfur atom or an optionally-protected carbonyl group, and/or substituted by a halogen atom or a lower alkyl group;

$R^{1gp}$ and $R^{1hp}$ are independently a hydrogen atom, a halogen atom, a cyano group, an optionally-protected hydroxyl group, a lower alkyl group, a lower alkoxy-lower alkyl group, a lower alkanoyl group, a lower alkoxycarbonyl group or a lower alkylsulfonyl group, or together form a lower alkylene group wherein one or two or more methylene groups constituting the lower alkylene group may be independently replaced by an oxygen atom, a sulfur atom, a sulfinyl group, a sulfonyl group, an optionally-protected carbonyl group or a group of —N($R^{1ip}$)—, and/or substituted by a halogen atom or a lower alkyl group;

$R^{1ip}$ is an imino-protective group, a hydrogen atom, a lower alkyl group or a halo-lower alkyl group;

$R^{1jp}$ is an imino-protective group, a hydrogen atom or a lower alkyl group;

$R^{4p}$ is a hydrogen atom, a halogen atom, an optionally-protected hydroxyl group, a lower alkyl group or a group of —N($R^{1kp}$)$R^{1mp}$;

$R^{1kp}$ and $R^{1mp}$ are independently an amino or imino-protective group, a hydrogen atom or a lower alkyl group; T and U have the same meanings as above, is reacted with a compound of a general formula (III) or its salt:

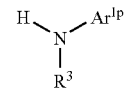

(III)

wherein;

$Ar^{1p}$ is an aryl group or a heteroaromatic group, which may have a substituent selected from a group consisting of a halogen atom, a lower alkyl group, a halo-lower alkyl group, a lower alkoxy group, a lower alkanoyl group, a carbamoyl group, a heteroaromatic group optionally substituted by a lower alkyl group, a group of $Q^{1p}$-$A^{1p}$-$Q^2$-$A^{2p}$($R^{1ap}$)$R^{1bp}$, and an optionally-protected hydroxy-lower alkyl, hydroxy-lower alkylamino and hydroxy-lower alkylcarbamoyl groups;

$A^{1p}$ is a single bond, an oxygen atom or a sulfur atom, or is an imino group optionally substituted by an imino-protective group or a lower alkyl group;

$A^{2p}$ is a nitrogen atom, or is a methine group or a 1-vinyl-2-ylidene group which may be substituted by an optionally-protected hydroxyl group, a lower alkyl group or an optionally-protected hydroxy-lower alkyl group;

$Q^{1p}$ is a single bond, an optionally-protected carbonyl group, or a methylene group optionally substituted by a lower alkyl group;

$R^{1ap}$ and $R^{1bp}$ are independently a hydrogen atom, a lower alkyl group or an optionally-protected hydroxy-lower alkyl group, or together form a lower alkylene group wherein one or two or more methylene groups constituting the lower alkylene group may be independently replaced by an oxygen atom, a sulfur atom, a sulfinyl group, a sulfonyl group, an optionally-protected carbonyl group, a vinylene group or a group of —N($R^{1cp}$)—, and/or substituted by an optionally-protected hydroxyl group or a lower alkyl group;

$R^{1cp}$ is a hydrogen atom, a lower alkenyl group, or a group of -$Q^{3p}$-$A^{3p}$($R^{1dp}$)$R^{1ep}$;

$A^{3p}$ is a nitrogen atom, or is a methine group or a 1-vinyl-2-ylidene group which may be substituted by an optionally-protected hydroxyl group, a lower alkyl group or an optionally-protected hydroxy-lower alkyl group;

$Q^{3p}$ is a single bond or a lower alkylene group, wherein one or two or more methylene groups constituting the lower alkylene group may be independently replaced by an oxygen atom, a sulfur atom, an optionally-protected carbonyl group, a sulfinyl group or a sulfonyl group, and/or substituted by a halogen atom, a cyano group, an optionally-protected hydroxyl group or a lower alkyl group;

$R^{1dp}$ and $R^{1ep}$ are independently a hydrogen atom, a halogen atom, a cyano group, an optionally-protected hydroxyl group, a lower alkyl group or an optionally-protected hydroxy-lower alkyl group, or together form a lower alkylene group wherein one or two or more methylene groups constituting the lower alkylene group may be independently replaced by an oxygen atom, a sulfur atom, a sulfinyl group, a sulfonyl group, an optionally-protected carbonyl group, a vinylene group or a group of —N($R^{1fp}$)—, and/or substituted by an optionally-protected hydroxyl group or a lower alkyl group;

$R^{1fp}$ is an imino-protective group, a hydrogen atom, a lower alkyl group, a halo-lower alkyl group, a lower alkenyl group or a lower alkanoyl group; $Q^2$ and $R^3$ have the same meanings as above, to give a compound of a general formula (IV):

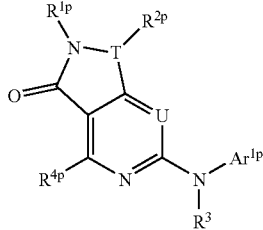

(IV)

wherein $Ar^{1p}$, $R^{1p}$, $R^{2p}$, $R^3$, $R^{4p}$, T and U have the same meanings as above, and optionally the protective group is removed from it to produce a compound of a general formula (I):

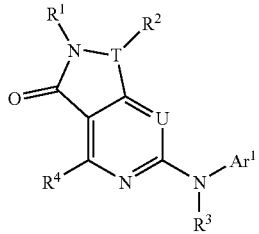

(I)

wherein $Ar^1$, $R^1$, $R^2$, $R^3$, $R^4$, T and U have the same meanings as above.

The leaving group for $L^1$ includes, for example, a halogen atom such as a chlorine atom, a bromine atom, an iodine atom; an organic sulfonyl group such as a methylsulfinyl group, a methylsulfonyl group, an ethylsulfonyl group, a phenylsulfonyl group; and an organic sulfonyloxy group such as a methylsulfonyloxy group, a trifluoromethylsulfonyloxy group, a p-tolylsulfonyloxy group; preferably a chlorine atom, a methylsulfinyl group, a methylsulfonyl group.

This production method is a general method for producing the compounds of formula (I).

In the above reaction, when the reactants have an amino group, an imino group, a hydroxyl group, a carboxyl group, a carbonyl group or the like that does not participate in the reaction, then the amino group, the imino group, the hydroxyl group, the carboxyl group and the carbonyl group may be suitably protected with an amino or imino-protective group, a hydroxyl-protective group, a carboxyl-protective group or a carbonyl-protective group, and thereafter the reactants may be reacted, and after the reaction, the protective group may be removed.

Not specifically defined, "amino or imino-protective group" may be any one having its function. For example, it includes an aralkyl group such as a benzyl group, a p-methoxybenzyl group, a 3,4-dimethoxybenzyl group, an o-nitrobenzyl group, a p-nitrobenzyl group, a benzhydryl group, a trityl group; a lower alkanoyl group such as a formyl group, an acetyl group, a propionyl group, a butyryl group, a pivaloyl group; a benzoyl group; an arylalkanoyl group such as a phenylacetyl group, a phenoxyacetyl group; a lower alkoxycarbonyl group such as a methoxycarbonyl group, an ethoxycarbonyl group, a propyloxycarbonyl group, a tert-butoxycarbonyl group; an aralkyloxycarbonyl group such as a benzyloxycarbonyl group, a p-nitrobenzyloxycarbonyl group, a phenethyloxycarbonyl group; a lower alkylsilyl group such as a trimethylsilyl group, a tert-butyldimethylsilyl group; a tetrahydropyranyl group; a trimethylsilylethoxymethyl group; a lower alkylsulfonyl group such as a methylsulfonyl group, an ethylsulfonyl group; an arylsulfonyl group such as benzenesulfonyl group, a toluenesulfonyl group; and is especially preferably an acetyl group, a benzoyl group, a tert-butoxycarbonyl group, a trimethylsilylethoxymethyl group, a methylsulfonyl group.

Not specifically defined, "hydroxyl-protective group" may be any one having its function. For example, it includes a lower alkyl group such as a methyl group, an ethyl group, a propyl group, an isopropyl group, a tert-butyl group; a lower alkylsilyl group such as a trimethylsilyl group, a tert-butyldimethylsilyl group; a lower alkoxymethyl group such as a methoxymethyl group, a 2-methoxyethoxymethyl group; a tetrahydropyranyl group; a trimethylsilylethoxymethyl group; an aralkyl group such as a benzyl group, a p-methoxybenzyl group, a 2,3-dimethoxybenzyl group, an o-nitrobenzyl group, a p-nitrobenzyl group, a trityl group; an acyl group such as a formyl group, an acetyl group; and is especially preferably a methyl group, a methoxymethyl group, a tetrahydropyranyl group, a trityl group, a trimethylsilylethoxymethyl group, a tert-butyldimethylsilyl group, an acetyl group.

Not specifically defined, "carboxyl-protective group" may be any one having its function. For example, it includes a lower alkyl group such as a methyl group, an ethyl group, a propyl group, an isopropyl group, a tert-butyl group; a halo-lower alkyl group such as a 2,2,2-trichloroethyl group; a lower alkenyl group such as an allyl group; an aralkyl group such as a benzyl group, a p-methoxybenzyl group, a p-nitrobenzyl group, a benzhydryl group, a trityl group; and is especially preferably a methyl group, an ethyl group, a tert-butyl group, an allyl group, a benzyl group, a p-methoxybenzyl group, a benzhydryl group.

Not specifically defined, "carbonyl-protective group" may be any one having its function. For example, it includes acetals and ketals such as ethylene ketal, trimethylene ketal, dimethylene ketal.

For the reaction of the compound of formula (II) and the compound of formula (III), in general, an equimolar or excessive molar amount, preferably from an equimolar amount to 1.5 mols of the compound (III) is used relative to one mol of the compound (II).

The reaction is attained generally in an inert solvent. The inert solvent is, for example, preferably toluene, benzene, methylene chloride, chloroform, tetrahydrofuran, dioxane, dimethylformamide, N-methylpyrrolidone, dimethylsulfoxide and their mixed solvents.

Preferably, the reaction is attained in the presence of a base. The base includes, for example, organic bases such as triethylamine, diisopropylethylamine, pyridine, 4-dimethylaminopyridine; and inorganic bases such as sodium hydrogencarbonate, sodium carbonate, potassium carbonate, cesium carbonate, sodium hydroxide, potassium hydroxide.

The amount of the base to be used may be generally from an equimolar amount to an excessive molar amount, preferably from 1 to 3 mols relative to one mol of the compound of formula (II).

The reaction temperature may be generally from 0° C. to 200° C., preferably from 20° C. to 150° C.

The reaction time may be generally from 5 minutes to 7 days, preferably from 30 minutes to 24 hours.

After the reaction, the system may be processed in an ordinary manner to obtain a crude product of the compound of formula (IV). Thus obtained, the compound of formula (IV) is purified in an ordinary manner, or not purified, optionally it is processed for removing the protective group of the amino group, the hydroxyl group, the carboxyl group and the carbonyl group therein, optionally as suitably combined, thereby producing the compound of formula (I).

The method of removing the protective group varies, depending on the type of the protective group and on the stability of the intended compound (I). For example, the deprotection may be attained according to methods described in references [see Protective Groups in Organic Synthesis, 3rd. Ed., by T. W. Greene, John Wiley & Sons (1999)] or according to methods similar thereto. For example, herein employable are a method of solvolysis with an acid or a base, which comprises processing the protected compound with from 0.01 mols to a large excessive amount of an acid, preferably trifluoroacetic acid, formic acid or hydrochloric acid, or with from an equimolar amount to a large excessive amount of a base, preferably potassium hydroxide or calcium hydroxide; and a method of chemical reduction with a metal hydride complex, or catalytic reduction with a palladium-carbon catalyst or a Raney nickel catalyst.

The compounds of formula (I) may be readily isolated and purified in any ordinary separation method. Examples of the method are, for example, solvent extraction, recrystallization, column chromatography, preparative thin-layer chromatography.

The compounds may be converted into their pharmaceutically-acceptable salts or esters in an ordinary manner; and on the contrary, their salts or esters may also be converted into free compounds in an ordinary manner.

"Salts" of the compound of formula (III) mean ordinary salts used in the field of organic chemistry. For example, when the compound has a carboxyl group, then its salts are base-addition salts at the carboxyl group; and when the compound has an amino group or a basic heterocyclic group, then its salt are acid-addition salts at the amino group or the basic heterocyclic group.

The base-addition salts include, for example, alkali metal salts such as sodium salts, potassium salts; alkaline earth metal salts such as calcium salts, magnesium salts; ammonium salts; organic amine salts such as trimethylamine salts, triethylamine salts, dicyclohexylamine salts, ethanolamine salts, diethanolamine salts, triethanolamine salts, procaine salts, N,N'-dibenzylethylenediamine salts.

The acid-addition salts include, for example, inorganic acid salts such as hydrochlorides, sulfates, nitrates, phosphates, perchlorates; organic acid salts such as maleates, fumarates, tartrates, citrates, ascorbates, trifluoroacetates; sulfonates such as methanesulfonates, isethionates, benzenesulfonates, p-toluenesulfonates.

The compounds of formulae (II) and (III) may be commercially available, or may be produced according to methods described in references [see WO2006/004040, WO2003/037872; Journal of Medicinal Chemistry, Vol. 48, pp. 2371-2387; Bioorg. & Med. Chem. Lett., Vol. 14, pp. 5793-5797; Journal of the Chemical Society, Perkin Transaction II, Vol. 3, p. 843] or according to methods similar thereto, or according to the methods described below, or according to the methods described in Examples and Production Examples, optionally as suitably combined.

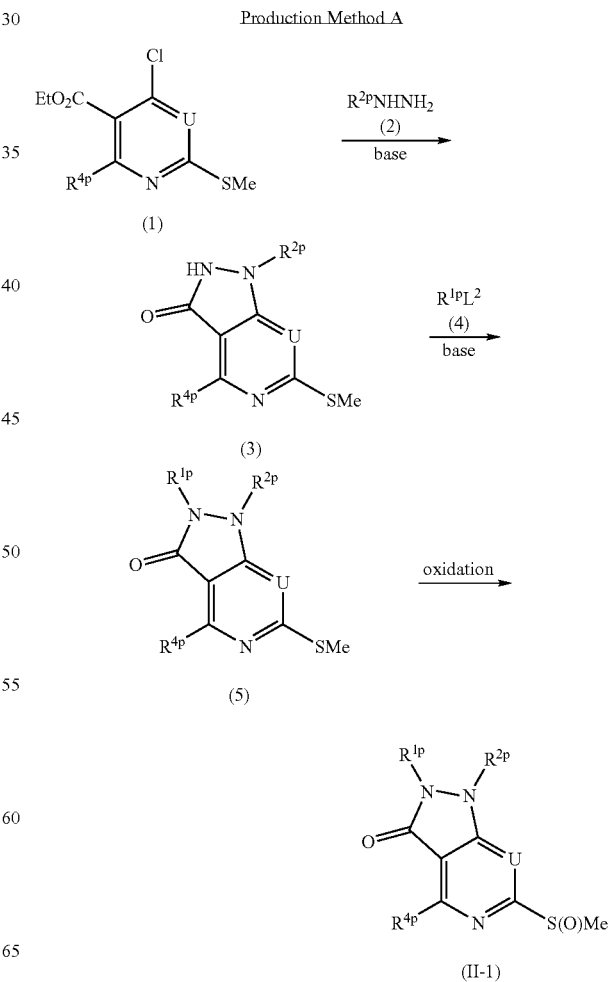

wherein Et is an ethyl group; $L^2$ is a leaving group; Me is a methyl group; $R^{1p}$, $R^{2p}$, $R^{4p}$ and U have the same meanings as above.

The production method A is a method for producing a compound of formula (II) where the leaving group for $L^1$ is a methylsulfinyl group, and T is a nitrogen atom, or that is, a compound of formula (II-1).

According to this production method, the compound of formula (II-1) can be produced by reacting a compound of formula (1) and a hydrazine derivative of formula (2) in the presence of a base to give a compound of formula (3), and thereafter introducing a group of $R^{1p}$ into the compound (3) to give a compound (5), and finally oxidizing the methylthio group in the compound (5) into a methylsulfinyl group.

In the step of reacting the compound of formula (1) and the hydrazine derivative of formula (2) in the presence of a base to give the compound of formula (3), in general, from 0.5 mols to an excessive molar amount, preferably from an equimolar amount to 3.0 mols of the hydrazine derivative (2) is used relative to one mol of the compound (1).

In general, the reaction is attained in an inert solvent. The inert solvent is, for example, preferably methylene chloride, chloroform, tetrahydrofuran, ethyl ether, benzene, toluene, dimethylformamide, or their mixed solvents.

Preferably, the reaction is attained in the presence of a base. The base includes, for example, organic bases such as triethylamine, diisopropylethylamine, pyridine, 4-dimethylaminopyridine; inorganic bases such as sodium hydroxide, potassium hydroxide, sodium carbonate, potassium carbonate, sodium hydrogencarbonate.

In general, the amount of the base to be used is preferably from an equimolar amount to an excessive molar amount relative to one mol of the compound (1). When the base is liquid, then the base may serve also as a solvent.

The reaction temperature may be generally from −78° C. to 100° C., preferably from 20° C. to 80° C.

The reaction time may be generally from 5 minutes to 7 days, preferably from 30 minutes to 24 hours.

In the step of reacting the compound (3) and the compound (4) to give the compound (5), in general, from 0.5 mols to an excessive molar amount, preferably from 2.0 mols to 5.0 mols of the compound (4) is used relative to one mol of the compound (3).

The leaving group for $L^2$ is preferably a halogen atom such as a chlorine atom, a bromine atom, an iodine atom.

In general, the reaction may be attained in an inert solvent such as tetrahydrofuran, benzene, toluene, acetonitrile, dimethylformamide in the presence of a base such as sodium hydride, sodium amide, sodium alkoxide, or in a solvent such as methanol, ethanol, acetonitrile in the presence of a base such as sodium hydroxide, potassium hydroxide, potassium carbonate.

In general, the reaction temperature is preferably from 0° C. to the boiling point of the solvent used in the reaction; and, in general, the reaction time is preferably from 1 hour to 48 hours.

To the step of oxidizing the methylthio group in the compound (5) to produce the compound (II-1), applicable is a method of oxidizing a methylthio group into a methylsulfinyl group or a methylsulfonyl group per se well known in the field of organic chemistry. In general, for example, in an inert solvent such as benzene toluene, methylene chloride, chloroform, tetrahydrofuran, acetonitrile or dimethylformamide, from 0.5 mols to an excessive molar amount, preferably from an equimolar amount to 1.5 mols of an oxidizing agent such as metachloroperbenzoic acid or oxone may be used relative to one mol of the compound (5) for the oxidization.

The reaction temperature is, in general, preferably from 0° C. to the boiling point of the solvent used in the reaction; and, in general, the reaction time is preferably from 30 minutes to 8 hours.

The compounds of formulae (1) and (2) may be commercially available, or may be produced according to known methods or according to the methods described in Examples, or according to methods similar thereto, optionally as suitably combined.

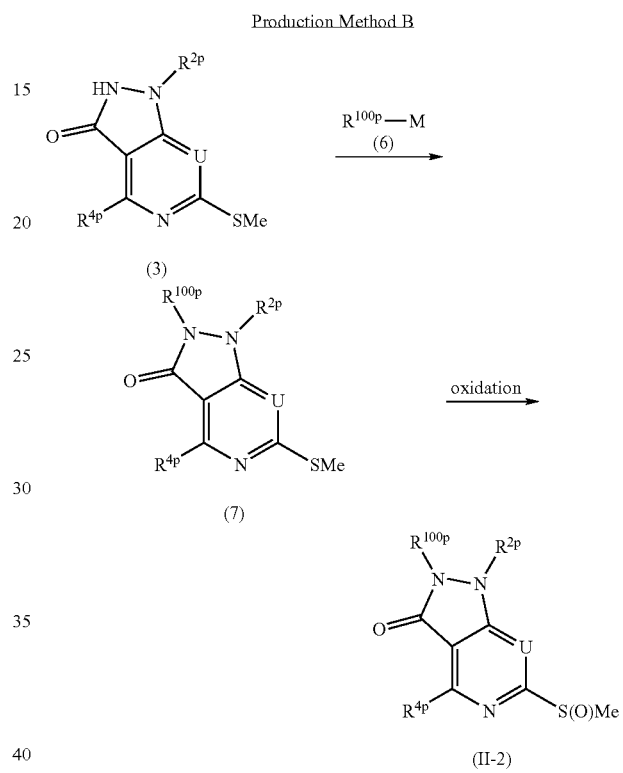

wherein M is an ordinary organic metal atom; $R^{100p}$ is an aryl group, an aralkyl group or a heteroaromatic group, which may have a substituent selected from a group consisting of a halogen atom, a cyano group, a lower alkyl group and an optionally-protected amino group; Me, $R^{2p}$, $R^{4p}$ and U have the same meanings as above.

The production method B is a method for producing a compound of formula (II) in which $R^{1p}$ is an aryl group, an aralkyl group or a heteroaromatic group which may have a substituent selected from a group consisting of a halogen atom, a cyano group, a lower alkyl group and an optionally-protected amino group, the leaving group for $L^1$ is a methylsulfinyl group, and T is a nitrogen atom, or that is, a compound of formula (II-2).

According to this production method, the compound of formula (II-2) can be produced by reacting a compound of formula (3), which is produced according to the production method A, and an organic metal compound of formula (6) in the presence of a metal salt catalyst or a metal salt reagent to give a compound of formula (7), and then oxidizing the methylthio group in the compound (7) into a methylsulfinyl group.

In the step of producing the compound (7) by reacting the compound (3) and the compound (6), in general, from 0.5 mols to 5 mols, preferably from 0.7 mols to 3 mols of the compound (6) is used relative to one mol of the compound (3) in the presence of a metal salt catalyst or a metal salt reagent.

The metal salt catalyst or the metal salt reagent to be used in the reaction is, for example, a transition metal generally used in cross-coupling reaction, such as copper, nickel, palladium; and, for example, preferred are copper(II) acetate, copper trifluoromethanesulfonate, copper iodide.

The ordinary organic metal atom for M means an organic metal atom generally used in cross-coupling reaction, including, for example, lithium, boron, silicon, magnesium, aluminium, zinc, tin, and more preferably boron, zinc, tin. Concrete modes in use are, for example, boric acid or borates with boron; zinc chloride, zinc bromide or zinc iodide with zinc; and tri-lower alkyl-tin with tin.

The reaction may be attained generally in an inert solvent. The inert solvent is, for example, preferably water, benzene, toluene, xylene, methylene chloride, chloroform, dimethoxyethane, tetrahydrofuran, dioxane, dimethylformamide, and their mixed solvents.

The reaction temperature may be generally from room temperature to the boiling point of the solvent used in the reaction, preferably from 20° C. to 200° C.

The reaction time is generally from 30 minutes to 7 days, preferably from 24 hours to 3 days.

Preferably, the reaction is attained in the presence of a base. The base includes, for example, inorganic bases such as potassium phosphate, sodium hydrogencarbonate, sodium carbonate, potassium carbonate, cesium carbonate; and organic bases such as triethylamine, diisopropylamine.

The amount of the base to be used may be generally from 0.5 mols to 5 mols, preferably from an equimolar amount to 3 mols relative to one mol of the compound (3).

The step of oxidizing the methylthio group in the compound (7) to produce the compound (II-2) may be attained in the same manner as that for the step of oxidizing the methylthio group in the compound (5) to produce the compound (II-1) in the production method A.

The compound of formula (6) may be commercially available, or may be produced according to known methods, or according to the methods described in Examples, or according to methods similar thereto, optionally as suitably combined.

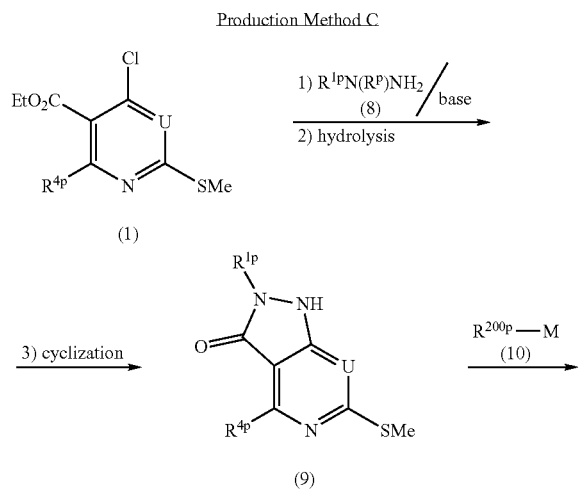

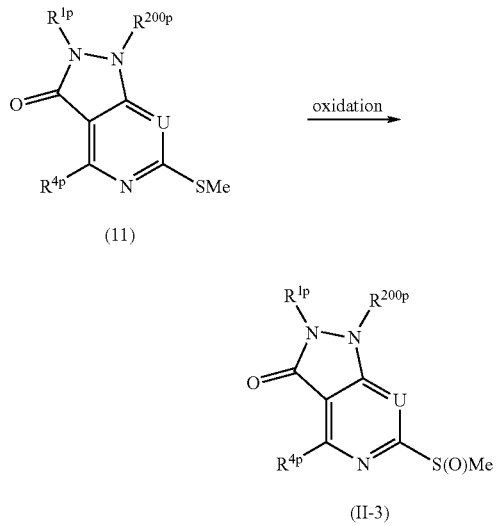

wherein $R^p$ is a hydrogen atom, or an imino-protective group; $R^{200p}$ is an aryl group, an aralkyl group or a heteroaromatic group, which may have a substituent selected from a group consisting of a halogen atom, a cyano group, a nitro group, a group of $-Q^{4p}-A^{4p}(R^{1gp})R^{1hp}$, a group of $-Q^{5p}-Ar^{ap}$ and an optionally-protected carboxyl group; $A^{4p}$, $Ar^{ap}$, Et, M, Me, $Q^{4p}$, $Q^{5p}$, $R^{1gp}$, $R^{1hp}$, $R^{1p}$, $R^{4p}$ and U have the same meanings as above.

The imino-protective group for $R^p$ is, for example, preferably a benzyl group, a paramethoxybenzyl group, a tert-butoxycarbonyl group, a benzyloxycarbonyl group.

The production method C is a method for producing a compound of formula (II) where $R^{2p}$ is an aryl group, an aralkyl group or a heteroaromatic group, which may have a substituent selected from a group consisting of a halogen atom, a cyano group, a nitro group, a group of $-Q^{4p}-A^{4p}(R^{1gp})R^{1hp}$, a group of $-Q^{5p}-Ar^{ap}$ and an optionally-protected carboxyl group, the leaving group for $L^1$ is a methylsulfinyl group, and T is a nitrogen atom, or that is, a compound of formula (II-3).

According to this production method, the compound of formula (II-3) can be produced by reacting a compound of formula (1) and a hydrazine derivative of formula (8) in the presence of a base, then hydrolyzing the resulting compound and cyclizing it to give a compound of formula (9), and thereafter reacting the compound (9) with an organic metal compound of formula (10) in the presence of a catalyst to thereby introduce a group of $R^{200p}$ thereinto to give a compound (11), and finally oxidizing the methylthio group in the compound (11) into a methylsulfonyl group.

In the step of reacting the compound of formula (1) and the hydrazine derivative of formula (8) in the presence of a base, in general, the amount of the hydrazine derivative (8) to be used may be from 0.5 mols to an excessive molar amount, preferably from an equimolar amount to 1.5 mols relative to one mol of the compound (1).

The reaction may be attained generally in the presence of an organic base such as triethylamine, diisopropylethylamine, pyridine, 4-dimethylaminopyridine, or an inorganic base such as sodium hydroxide, potassium hydroxide, sodium carbonate, potassium carbonate, sodium hydrogencarbonate, in an inert solvent such as methylene chloride, chloroform, tetrahydrofuran, ethyl ether, benzene, toluene, dimethylformamide, or their mixed solvents.

In general, the amount of the base to be used is preferably from an equimolar amount to an excessive molar amount relative to one mol of the compound (1). When the base is liquid, the base may serve also as a solvent.

The reaction temperature may be generally from −78° C. to 200° C., preferably from 20° C. to 100° C.

The reaction time may be generally from 5 minutes to 7 days, preferably from 8 hours to 24 hours.

To the step of hydrolyzing the compound obtained in the above reaction, applicable is a method of hydrolysis of carboxylates per see well known in the field of organic chemistry. In general, in a solvent such as methanol, ethanol, tetrahydrofuran, dioxane, water or in their mixed solvent, the compound may be processed with an acid such as hydrochloric acid or sulfuric acid, or a base such as sodium hydroxide, potassium hydroxide or calcium hydroxide.

In general, the reaction temperature is preferably from 50° C. to the boiling point of the solvent used in the reaction; and in general, the reaction time is preferably from 1 hour to 48 hours.

After the hydrolysis, the resulting compound is cyclized to produce the compound (9). For this, the reaction liquid may be made acidic after the hydrolysis, whereupon the cyclization may go on as such. In case where the cyclization does not go on, then the hydrolyzed compound may be refluxed under heat in the presence of acetic anhydride, or the hydrolyzed compound may be processed with thionyl chloride to attain the intended cyclization of the compound.

In the cyclization with acetic anhydride, the amount of acetic anhydride to be used is preferably an excessive molar amount, and the reaction time is, in general, preferably from 1 hour to 48 hours.

In case where the hydrolyzed compound is processed with thionyl chloride, the amount of thionyl chloride to be used is preferably an excessive molar amount, and the reaction time is, in general, preferably from 1 hour to 48 hours.

The step of reacting the compound (9) with the organic metal compound of formula (10) in the presence of a catalyst to thereby introduce a group of $R^{200p}$ thereinto to produce the compound (11) may be attained in the same manner as that for the step of producing the compound (6) from the compound (3) in the production method B.

The above step may also be attained, using a halide compound having a group of $R^{200p}$ in place of the organic metal compound of formula (10). When such a halide compound is used, then the catalyst is preferably a copper(I) iodide-diamine complex.

The step of oxidizing the methylthio group in the compound (11) to produce the compound (II-3) may be attained in the same manner as that for the step of oxidizing the methylthio group in the compound (5) to produce the compound (II-1) in the production method A.

The compound of formula (8) may be commercially available, or may be produced according to known methods or according to the methods described in Examples, or according to methods similar thereto, optionally as suitably combined.

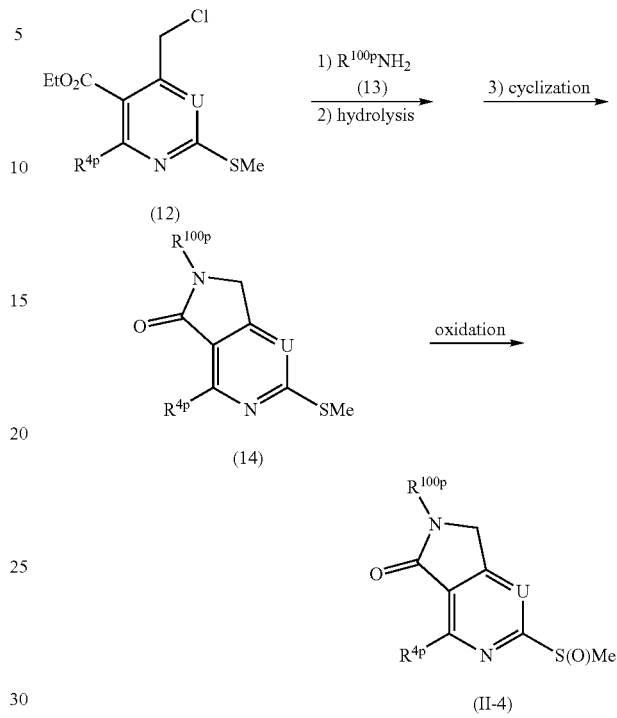

wherein Et, Me, $R^{4p}$, $R^{100p}$ and U have the same meanings as above.

The production method D is a method for producing a compound of formula (II) in which $R^{1p}$ is an aryl group, an aralkyl group or a heteroaromatic group, which may have a substituent selected from a group consisting of a halogen atom, a cyano group, a lower alkyl group and an optionally-protected amino group, the leaving group for $L^1$ is a methylsulfinyl group, and T is a methine group, or that is, a compound of formula (II-4).

According to this production method, the compound of formula (II-4) can be produced by reacting a compound of formula (12) and an amino compound of formula (13), then hydrolyzing the resulting compound and cyclizing it to give a compound of formula (14), and thereafter oxidizing the methylthio group in the compound (14) into a methylsulfinyl group.

In the reaction of the compound of formula (12) and amino compound of formula (13), in general, the amount of the amino compound (13) may be from 0.5 mols to an excessive molar amount, preferably from an equimolar amount to 1.5 mols relative to one mol of the compound (12).

In general, the reaction may be effected in an inert solvent. The insert solvent is, for example, preferably methanol, ethanol, methylene chloride, chloroform, tetrahydrofuran, ethyl ether, benzene, toluene, dimethylformamide, or their mixed solvents.

Preferably, the reaction is attained in the presence of a base. The base includes, for example, organic bases such as triethylamine, diisopropylethylamine, pyridine, 4-dimethylaminopyridine, 2,6-lutidine; and inorganic bases such as sodium hydroxide, potassium hydroxide, sodium carbonate, potassium carbonate, sodium hydrogencarbonate.

In general, the amount of the base to be used is preferably from an equimolar amount to an excessive molar amount relative to one mol of the compound (12). When the base is liquid, the base may serve also as a solvent.

In general, the reaction temperature may be from −78° C. to 200° C., preferably from 20° C. to 120° C.

The reaction time may be generally from 5 minutes to 7 days, preferably from 30 minutes to 24 hours.

To the step of hydrolyzing the compound obtained in the above reaction, applicable is a method of hydrolysis of carboxylates per se well known in the field of organic chemistry. The step of hydrolysis may be attained in the same manner as that for the step of hydrolysis after the reaction of the compound (1) and the hydrazine compound (8) in the production method C.

After the hydrolysis, the resulting compound is cyclized to produce the compound (14). In this step, for example, the compound obtained after the hydrolysis may be processed with a condensing agent such as N,N'-dicyclohexylcarbodiimide, N,N'-diisopropylcarbodiimide, 1-(3-dimethylaminopropyl)-3-ethylcarbodiimide, 1-(3-dimethylaminopropyl)-3-ethylcarbodiimide hydrochloride, benzotriazol-1-yloxy-tris-(dimethylamino)phosphonium hexafluorophosphate, benzotriazol-1-yloxy-tris-pyrrolidinophosphonium hexafluorophosphate, bromo-tris(dimethylamino)phosphonium hexafluorophosphate, diphenylphosphoryl azide, 1,1'-carbonyldiimidazole, in an inert solvent such as methylene chloride, butanol, chloroform, tetrahydrofuran, dimethylformamide, pyridine or their mixture.

In general, the amount of the condensing agent to be used may be from 1 mol to an excessive molar amount, preferably from 1 mol to 1.5 mols relative to one mol of the starting compound.

The reaction temperature may be generally from −5° C. to 100° C., preferably from −20° C. to 50° C.

The reaction time may be generally from 30 minutes to 7 days, preferably from 1 hour to 24 hours.

The step of oxidizing the methylthio group in the compound (14) to produce the compound (II-4) may be attained in the same manner as that for the step of oxidizing the methylthio group in the compound (5) to produce the compound (II-1) in the production method A.

The compounds of formulae (12) and (13) may be commercially available, or may be produced according to known methods or according to the methods described in Examples or according to methods similar thereto, optionally as suitably combined.

The pharmaceutical test examples for the compounds of the invention are shown below.

Pharmaceutical Test 1 (Wee1 Kinase-Inhibitory Effect)

(1) Purification of Wee1 Kinase:

A cDNA of Wee1 kinase with glutathione-5-transferase (GST) fused at the amino terminal thereof was inserted into a baculovirus expression vector to construct a recombinant baculovirus, with which cells of an insect cell line Sf9 were infected for high expression therein. The infected cells were recovered and solubilized, and then the GST-tagged Wee1 kinase protein was adsorbed by a glutathione column, and eluted from the column with glutathione, and the active fraction was desalted in a desalting column to give a purified enzyme.

(2) Determination of Wee1 Kinase Activity:

In determination of the Wee1 kinase activity, a synthetic peptide, Poly(Lys,Tyr) Hydrobromide (Lys:Tyr (4:1)) bought from Sigma was used as the substrate.

The amount of the reaction mixture was 21.1 µL; and the composition of the reaction buffer was 50 mM Tris-HCl buffer (pH 7.4)/10 mM magnesium chloride/1 mM dithiothreitol. The purified Wee1 kinase, 2.5 µg of the substrate peptide, 10 µM of non-labeled adenosine triphosphate (ATP) and 1 µCi of [γ-$^{33}$P]-labeled ATP (2500 Ci/mmol or more) were added to it, and incubated at 30° C. for 30 minutes. Next, 10 µL of 350 mM phosphate buffer was added to the reaction mixture to stop the reaction. The substrate peptide was adsorbed by a P81 paper filter 96-well plate, then washed a few times with 130 mM phosphate buffer, and its radioactivity was counted with a liquid scintillation counter. The [γ-$^{33}$P]-labeled ATP was bought from Amersham Bioscience.

To add the test compound to the reaction system, the compound was diluted with dimethylsulfoxide (DMSO) to prepare a series of dilutions. 1.1 µL of each dilution was added to the reaction system. As a control, 1.1 µL of DMSO was added to the reaction system.

As in Table 1, the compounds of the invention exhibit an excellent Wee1-inhibitory activity.

TABLE 1

| Compound | Wee1-Inhibitory Effect (IC50, nM) |
|---|---|
| Example 1 | 7 |
| Example 3 | 7.6 |
| Example 19 | 13 |
| Example 26 | 18 |
| Example 29 | 20 |
| Example 52 | 12 |
| Example 53 | 11 |
| Example 98 | 14 |
| Example 99 | 8.8 |
| Example 111 | 24 |
| Example 113 | 6.3 |
| Example 137 | 26 |
| Example 147 | 24 |
| Example 148 | 17 |

The Cdc2 tyrosine 15-phosphorylation-inhibitory effect of the compounds of formula (I) of the invention is described below.

Pharmaceutical Text 2 (Method of Determining Drug Potency in Cells (Cdc2 (Cdk1) Tyrosine 15-Phosphorylation-Inhibitory Effect))

a) Reagents:

Fetal bovine serum (FBS) was obtained from Morgate; media RPMI1640 and DMEM were from Invitrogen; camptothecin was from Sigma; gemcitabine was from Nippon Eli Lilly; nocodazole and protease inhibitor cocktail were from Sigma; rabbit anti-Cdc2 antibody and mouse anti-Cdc2 antibody were from Santa Cruz Biotechnology; rabbit anti-tyrosine 15-phosphorylated Cdc2 antibody and horseradish peroxidase-labeled anti-mouse IgG antibody were from Cell Signaling Technology; sure blue reserve TMB peroxidase substrate was from Kirkegaard and Perry Laboratories.

b) Cells:

Human non-small cell lung cancer cells (NCI-H1299) and human colon cancer cells (WiDr) were obtained from American Type Culture Collection (ATCC).

c) Method of Effect Determination:

In the method of using NCI-H1299 cells, the cells were suspended in RPMI1640 containing 10% FBS, and the cell suspension was applied to a 96-well Nunclondelta-processed plastic plate (bought from Nunc), in an amount of 2000 cells/100 µL/well, in which the cells were incubated overnight in 5% $CO_2$-95% air at 37° C. Camptothecin was dissolved in dimethylsulfoxide (DMSO), and diluted with RPMI1640 containing 10% FBS, and then this was applied to the plate on which the cells had been previously sowed, in an amount of 50 μL/well in such a manner that the final concentration of camptothecin could be 200 nM. Then, the cells were incubated for 16 hours at 37° C. in 5% $CO_2$-95% air. The test compound was stepwise diluted with DMSO, then diluted with 4000 nM nocodazole-containing RPMI1640 containing 10% FBS, and applied to the plate on which the camptothecin-treated cells had been sowed, in an amount of 50 μL/well. The cells were incubated for 8 hours at 37° C. in 5% $CO_2$-95% air, then the medium was removed, and a cytolytic buffer was added to the plate in an amount of 100 μL/well, shaken at 4° C. for 2 hours, then frozen at −80° C., and melted to give a cell solution. Cdc2 and tyrosine 15-phosphorylated Cdc2 in the cell solution were determined through enzyme-linked immunosorbent assay (ELISA), and the ratio of tyrosine 15-phosphorylated Cdc2 to Cdc2 was calculated to obtain the 50% phosphorylation-inhibitory concentration of the test compound to the cells ($EC_{50}$, nM). The cytolytic buffer used herein is an aqueous solution containing 20 mM Hepes (pH 7.5), 150 mM sodium chloride, 1 mM disodium ethylenediaminetetraacetate, 0.1% polyoxyethylene (10) octylphenyl ether, 1% protease inhibitor cocktail, 1 mM dithiothreitol, 2 mM sodium orthovanadate, 10 mM sodium fluoride and 10 mM glycerol diphosphate. Cdc2 was determined through ELISA as follows: A rabbit anti-Cdc2 antibody solution, which had been diluted 200-fold with 50 mM carbonate-bicarbonate buffer (pH 9.6), was applied to a 96-well maxisorpimmuno plate (bought from Nunc), in an amount of 50 μL/well, and statically kept overnight at 4° C. so as to fix the antibody on the plate. Next, this was washed three times with phosphate-buffered saline (PBS), and 5% bovine serum albumin-containing PBS (5% BSA/PBS) was added thereto in an amount of 300 μL/well, and statically kept at room temperature for 2 hours, and then again washed three times with PBS. A mouse anti-Cdc2 antibody solution that had been diluted 100-fold with 0.05% polyoxyethylene sorbitan monolaurate and 1% BSA-containing Tris-HCl-buffered saline (1% BSA/TBS-T) was added to it in an amount of 50 μL/well, and the cell solution was added thereto in an amount of 5 μL/well and statically kept overnight at 4° C. Next, this was washed three times with 0.05% polyoxyethylene sorbitan monolaurate and 0.1% BSA-containing Tris-HCl-buffered saline (0.1% BSA/TBS-T), and then a horseradish peroxidase-labeled anti-mouse IgG antibody solution that had been diluted 2000-fold with 1% BSA/TBS-T was added thereto in an amount of 70 μL/well, and statically kept at room temperature for 3 hours. Finally, this was washed five times with 0.1% BSA/TBS-T, then a substrate of sure blue reserve TMB peroxidase was added to it in an amount of 100 μL/well, and left for coloration in a dark place at room temperature for 15 minutes. Then, 1 M hydrochloric acid was added to it in an amount of 100 μL/well to stop the reaction, and this was analyzed through colorimetry. Tyrosine 15-phosphorylated Cdc2 was determined through ELISA as follows: A rabbit anti-tyrosine 15-phosphorylated Cdc2 antibody solution, which had been diluted 100-fold with 50 mM carbonate-bicarbonate buffer (pH 9.6), was applied to a 96-well maxisorpimmuno plate in an amount of 50 μL/well, and statically kept overnight at 4° C. so as to fix the antibody on the plate. Next, this was washed three times with PBS, and 5% BSA/PBS was added thereto in an amount of 300 μL/well, and statically kept at room temperature for 2 hours, and then again washed three times with PBS. A mouse anti-Cdc2 antibody solution that had been diluted 100-fold with 1% BSA/TBS-T was added to it in an amount of 50 μL/well, and the cell solution was added thereto in an amount of 5 μL/well and statically kept overnight at 4° C. Next, this was washed three times with 0.1% BSA/TBS-T, and then a horseradish peroxidase-labeled anti-mouse IgG antibody solution that had been diluted 2000-fold with 1% BSA/TBS-T was added thereto in an amount of 70 μL/well, and statically kept at room temperature for 3 hours. Finally, this was washed five times with 0.1% BSA/TBS-T, then a substrate of sure blue reserve TMB peroxidase was added to it in an amount of 100 μL/well, and left for coloration in a dark place at room temperature for 5 minutes. Then, 1 M hydrochloric acid was added to it in an amount of 100 μL/well to stop the reaction, and this was analyzed through colorimetry.

In the method of using WiDr cells, the cells were suspended in DMEM containing 10% FBS, and the cell suspension was applied to a 96-well Nunclondelta-processed plastic plate in an amount of 2000 cells/100 μL/well, in which the cells were incubated overnight in 5% $CO_2$-95% air at 37° C. Gemcitabine was dissolved in PBS, and diluted with DMEM containing 10% FBS, and then this was applied to the plate on which the cells had been previously sowed, in an amount of 50 μL/well in such a manner that the final concentration of gemcitabine could be 100 nM. Then, the cells were incubated for 24 hours at 37° C. in 5% $CO_2$-95% air. The test compound was stepwise diluted with DMSO, then diluted with 1200 nM nocodazole-containing DMEM containing 10% FBS, and applied to the plate on which the gemcitabine-treated cells had been sowed, in an amount of 50 μL/well. The cells were incubated for 8 hours at 37° C. in 5% $CO_2$-95% air, then the culture was removed, and a cytolytic buffer was added to the plate in an amount of 100 μL/well, shaken at 4° C. for 2 hours, then frozen at −80° C., and melted to give a cell solution. Cdc2 and tyrosine 15-phosphorylated Cdc2 in the cell solution were determined through ELISA, and the ratio of tyrosine 15-phosphorylated Cdc2 to Cdc2 was calculated to obtain the 50% phosphorylation-inhibitory concentration of the test compound to the cells ($EC_{50}$, nM). Cdc2 was determined through ELISA as follows: A rabbit anti-Cdc2 antibody solution, which had been diluted 200-fold with 50 mM carbonate-bicarbonate buffer (pH 9.6), was applied to a 96-well maxisorp plastic plate in an amount of 50 μL/well, and statically kept overnight at 4° C. so as to fix the antibody on the plate. Next, this was washed three times with PBS, and 5% BSA/PBS was added thereto in an amount of 300 μL/well, and statically kept at room temperature for 2 hours, and then again washed three times with PBS. A mouse anti-Cdc2 antibody solution that had been diluted 100-fold with 1% BSA/TBS-T was added to it in an amount of 50 μL/well, and the cell solution was added thereto in an amount of 10 μL/well and statically kept overnight at 4° C. Next, this was washed three times with 0.1% BSA/TBS-T, and then a horseradish peroxidase-labeled anti-mouse IgG antibody solution that had been diluted 2000-fold with 1% BSA/TBS-T was added thereto in an amount of 70 μL/well, and statically kept at room temperature for 3 hours. Finally, this was washed five times with 0.1% BSA/TBS-T, then a substrate of sure blue reserve TMB peroxidase was added to it in an amount of 100 μL/well, and left for coloration in a dark place at room temperature for 15 minutes. Then, 1 M hydrochloric acid was added to it in an amount of 100 μL/well to stop the reaction, and this was analyzed through colorimetry. Tyrosine 15-phosphorylated Cdc2 was determined through ELISA as follows: A rabbit anti-tyrosine 15-phosphorylated Cdc2 antibody solution, which had been diluted 100-fold with 50 mM carbonate-bicarbonate buffer (pH 9.6), was applied to a 96-well maxisorp plastic plate in an amount of 50 μL/well, and statically kept overnight at 4° C. so as to fix the antibody on the plate. Next, this was washed three times with PBS, and 5% BSA/PBS was added thereto in an amount of 300 μL/well, and statically kept at room temperature for 2 hours, and then again washed three times with PBS. A mouse anti-Cdc2 antibody solution that had been diluted 100-fold with 1% BSA/TBS-T was added to it in an amount of 50 μL/well, and the cell solution was added thereto in an amount of 10 μL/well and statically kept overnight at 4° C. Next, this was washed three times with 0.1% BSA/TBS-T, and then a horseradish peroxidase-labeled anti-mouse IgG antibody solution that had been diluted 2000-fold with 1% BSA/TBS-T was added thereto in an amount of 70 μL/well, and statically kept at room temperature for 3 hours. Finally, this was washed five times with 0.1% BSA/TBS-T, then a substrate of sure blue reserve TMB peroxidase was added to it in an amount of 100 μL/well, and left for coloration in a dark place at room temperature for 10 minutes. Then, 1 M hydrochloric acid was added to it in an amount of 100 μL/well to stop the reaction, and this was analyzed through colorimetry.

As in Table 2 and Table 3, the compounds of the invention exhibit an excellent Cdc2-tyrosine 15 phosphorylation-inhibitory effect human cancer cells (NCI-H11299 and WiDr).

TABLE 2

| Compound | Cdc2-Y15 Phosphorylation-Inhibitory Effect (H1299, + camptothecin) (EC50, nM) |
| --- | --- |
| Example 1 | 104 |
| Example 3 | 61 |
| Example 19 | 247 |
| Example 26 | 114 |
| Example 29 | 188 |
| Example 52 | 46 |
| Example 53 | 68 |
| Example 98 | 83 |
| Example 99 | 86 |
| Example 111 | 93 |
| Example 137 | 107 |
| Example 147 | 100 |
| Example 148 | 79 |

TABLE 3

| Compound | Cdc2-Y15 Phosphorylation-Inhibitory Effect (WiDr, + gemcitabine) (EC50, nM) |
| --- | --- |
| Example 1 | 143 |
| Example 3 | 130 |
| Example 19 | 350 |
| Example 53 | 119 |
| Example 98 | 39 |
| Example 99 | 122 |
| Example 113 | 8 |
| Example 137 | 144 |
| Example 148 | 86 |

The checkpoint escape effect of the compounds of formula (I) of the invention in cells is described below.

Pharmaceutical Text 3 (Method of Determining Drug Potency in Cells (Checkpoint-Removing Effect))

a) Reagents:

Fetal bovine serum (FBS) was obtained from Morgate; DMEM was from Invitrogen; gemcitabine was from Nippon Eli Lilly; nocodazole and 4',6-diamidino-2-phenylindole were from Sigma; rabbit anti-phosphorylated histone H3 antibody was from Upstate; and fluorescence-labeled (Alexa Fluor 488) anti-rabbit IgG antibody was from Molecular Probe.

b) Cells:

Human colon cancer cells (WiDr) were obtained from American Type Culture Collection (ATCC).

c) Method of Effect Determination:

The cells were suspended in DMEM containing 10% FBS, and the cell suspension was applied to a poly-D-lysine-coated 96-well plastic plate (bought from Becton Dickinson) in an amount of 2000 cells/100 μL/well, in which the cells were incubated overnight in 5% $CO_2$-95% air at 37° C. Gemcitabine was dissolved in phosphate-buffered saline (PBS), and diluted with DMEM containing 10% FBS, and then this was applied to the plate on which the cells had been previously sowed, in an amount of 50 μL/well in such a manner that the final concentration of gemcitabine could be 100 nM. Then, the cells were incubated for 24 hours at 37° C. in 5% $CO_2$-95% air. The test compound was stepwise diluted with dimethylsulfoxide, then diluted with 1200 nM nocodazole-containing DMEM containing 10% FBS, and applied to the plate on which the gemcitabine-treated cells had been sowed, in an amount of 50 μL/well. The cells were incubated for 8 hours at 37° C. in 5% $CO_2$-95% air, then the culture was removed, and methanol that had been cooled to −20° C. was added to it in an amount of 100 μL/well. Then, the plate was kept overnight at −20° C. so as to fix the cells thereon. Next, the methanol-fixed cells were washed with PBS, and 1% bovine serum albumin-containing PBS (1% BSA/PBS) was added to it in an amount of 50 μL/well, and statically kept at room temperature for 30 minutes, and then rabbit anti-phosphorylated histone H3 antibody that had been diluted 250-fold with 1% BSA/PBS was added thereto in an amount of 50 μL/well, and statically kept at room temperature for 90 minutes. Next, this was washed with PBS, and a solution containing 4',6-diamidino-2-phenylindole that had been diluted with 1% BSA/PBS to have a concentration 10 μg/mL and a fluorescence-labeled (Alexa Fluor 488) anti-rabbit IgG antibody that had been diluted 250-fold was added to it in an amount 50 μL/well, and reacted in a dark place at room temperature for 60 minutes. Finally, this was washed with PBS, and its fluorescence intensity was determined to calculate the ratio of the phosphorylated histone H3-positive cells (cells that had been in a cell division cycle through removal of checkpoint). From this, obtained was the 50% checkpoint escape concentration to the cells of the test compound ($EC_{50}$, nM).

As in Table 4, the compound of the invention exhibits an excellent checkpoint escape effect in human cancer cells (WiDr).

TABLE 4

| Compound | Checkpoint Escape Effect (WiDr + gemcitabine) (EC50, nM) |
| --- | --- |
| Example 3 | 268 |
| Example 53 | 210 |
| Example 147 | 110 |
| Example 148 | 100 |

Pharmaceutical Test 4 (Tumor Growth-Inhibitory Effect)

Human colon cancer cells WiDr (gotten from ATCC) were implanted into the subcutaneous area of the back of F344/N Jcl-mu nude rats. Eight days after the implantation, gemcitabine (50 mg/kg, Gemzar injection, Eli-Lilly) was intravenously administered to them; and after 24 hours, a test compound was dissolved in a solvent (5% glucose) and given to them through continuous intravenous injection for 8 hours. The tumor volume (0.5×(major diameter)×(minor diameter)$^2$) was determined on day 0, 3, 6, 10 and 13. Day 0 means the day on which gemcitabine was administered. The relative tumor volume is a relative value, as calculated on the basis of the tumor volume of 1 on day 0. The tumor growth percentage (% T/C) was obtained according to the following formula:

When the tumor volume change from day 0 in the group subjected to test compound administration is more than 0 (>0):

% T/C=[(tumor volume change in the test compounds on day 3, 6, 10, 13)/(tumor volume change in the control on day 3, 6, 10, 13)]×100.

When the tumor volume change from day 0 in the group subjected to test compound administration is less than 0 (<0):

% T/C=[(tumor volume change in the test compounds on day 3, 6, 10, 13)/(tumor volume change in the test compounds on day 0)]×100.

The data of the tumor growth-inhibiting effect are shown in Table 5.

TABLE 5

| Compound | n | % T/C | | | |
| --- | --- | --- | --- | --- | --- |
| | | day 3 | day 6 | day 10 | day 13 |
| Control | 4 | 100 | 100 | 100 | 100 |
| Gemcitabine 50 mg/kg | 4 | 22 | 31 | 54 | 65 |
| Compound of Example 53, 0.75 mg/kg/hr | 3 | 86 | 74 | 81 | 89 |
| Gemcitabine + Compound of Example 53, 0.5 mg/kg/hr | 3 | −1 | 3 | 24 | 43 |
| Gemcitabine + Compound of Example 53, 0.75 mg/kg/hr | 4 | −20 | −37 | 2 | 14 |

Gemcitabine administration reduced the tumor growth percentage, but when gemcitabine is combined with the compound of the invention, then the tumor growth percentage was further reduced. In particular, in the group where the chemical dose was high, the animals showed tumor involution.

As mentioned above, the compound of the invention in combination with other anticancer agent augmented the effect of the other anticancer agent.

Pharmaceutical Test 5 (Method of Determining Drug Potency with Cells (Radiation (X-Ray) Sensitizing Effect))

a) Reagents:

Fetal bovine serum (FBS) was gotten from Morgate; RPMI 1640 medium and 0.25% trypsin EDTA were from Invitrogen; cycle test plus DNA reagent kit was from Becton Dickinson; and nylon net filter was from Millipore.

b) Cells:

Human non-small-cell lung cancer cells (NCI-H1299) were gotten from ATCC.

c) Method of Effect Determination:

NCI-H1299 cells were suspended in 10% FBS-added RPMI 1640 medium, and the cell suspension was applied to a 6-well Nunclondelta-processed plastic plate bought from Nunc, in an amount of 100,000 cell/2 ml/well, and incubated overnight in 5% $CO_2$-95% air at 37° C. Using Softex's M-150WE, the cells were irradiated with 5000 R X-rays, and then further incubated in 5% $CO_2$-95% air at 37° C. for 16 hours. A test compound was stepwise diluted with DMSO, and applied to a plate with the X-ray-processed cells sowed thereon, in an amount of 2 μL. This was incubated in 5% $CO_2$-95% air at 37° C. for 8 hours, and then the culture was partly taken out. 0.25% trypsin was added to the cells remaining on the plate, in an amount of 600 μL, and statically kept at room temperature to prepare a single cell suspension. The single cell suspension and the previously-taken culture were mixed for every sample, then centrifuged, and the supernatant was removed. Sampling was thus completed. The sample was suspended in a buffer (1 mL) of cycle test plus DNA reagent kid, and frozen and stored at −80° C. The stored sample was thawed on the test date, centrifuged and the supernatant was removed, and this was suspended in cycle test plus A solution (250 μL), left statically at room temperature for 10 minutes, and then B solution (150 μL) was added thereto and further kept statically at room temperature for 10 minutes. Next, C solution (150 μL) was added to it, kept statically at 4° C. for 10 minutes, and then filtered through nylon net filter to thereby complete DNA staining. Using Becton Dickinson's FACS Calibur, the DNA amount in each cell was quantitatively determined according to a FACS process, and the ratio of the cells having caused DNA fragmentation was determined.

TABLE 6

| DNA Fragmentation-Inducing Effect (H1299) (subG1, %) | | |
| --- | --- | --- |
| X-ray | Compound of Example 53 | X-ray + Compound of Example 53 |
| 27.1 | 3.9 | 54.8 |

As in Table 6, the compound of the invention has an excellent DNA fragmentation-inducing effect to human-derived cancer cells (NCI-H1299).

As mentioned above, the compound of the invention in combination with X-ray augmented the effect of the X-ray.

The compounds of formula (I) can be administered orally or parenterally, and after formulated into preparations suitable to such administration modes, the compounds can be used as pharmaceutical compositions and anticancer agents.

The term "cancer" as referred to in this description includes various sarcoma and carcinoma and includes solid cancer and hematopoietic cancer. The solid cancer as referred to herein includes, for example, brain tumor, cervicocerebral cancer, esophageal cancer, thyroid cancer, small cell cancer, non-small cell cancer, breast cancer, lung cancer, stomach cancer, gallbladder/bile duct cancer, liver cancer, pancreatic cancer, colon cancer, rectal cancer, ovarian cancer, choriocarcinoma, uterus body cancer, uterocervical cancer, renal pelvis/ureter cancer, bladder cancer, prostate cancer, penis cancer, testicles cancer, fetal cancer, Wilms' tumor, skin cancer, malignant melanoma, neuroblastoma, osteosarcoma, Ewing's tumor, soft part sarcoma. On the other hand, the hematopoietic cancer includes, for example, acute leukemia, chronic lymphatic leukemia, chronic myelocytic leukemia, polycythemia vera, malignant lymphoma, multiple myeloma, Hodgkin's lymphoma, non-Hodgkin's lymphoma.

The term "treatment of cancer" as referred to in this description means that an anticancer agent is administered to a cancer case so as to inhibit the growth of the cancer cells in the case. Preferably, the treatment results in cancer growth regression, or that is, it reduces the size of a detectable cancer. More preferably, the treatment results in complete disappearance of cancer.

The compounds of the invention are expected to be effective especially to human solid cancer. The human solid cancer includes, for example, brain cancer, cervicocerebral cancer, esophageal cancer, thyroid cancer, small cell cancer, non-small cell cancer, breast cancer, lung cancer, stomach cancer, gallbladder/bile duct cancer, liver cancer, pancreatic cancer, colon cancer, rectal cancer, ovarian cancer, choriocarcinoma, uterus body cancer, uterocervical cancer, renal pelvis/ureter cancer, bladder cancer, prostate cancer, penis cancer, testicles cancer, fetal cancer, Wilms' cancer, skin cancer, malignant melanoma, neuroblastoma, osteosarcoma, Ewing's tumor, soft part sarcoma, acute leukemia, chronic lymphatic leukemia, chronic myelocytic leukemia, Hodgkin's lymphoma.

The pharmaceutical composition and anticancer agent of the invention may contain a pharmaceutically acceptable carrier or diluent. Here, the "pharmaceutically acceptable carrier or diluent" refers to excipients [e.g., fats, beeswax, semi-solid and liquid polyols, natural or hydrogenated oils, etc.]; water (e.g., distilled water, particularly distilled water for injection, etc.), physiological saline, alcohol (e.g., ethanol), glycerol, polyols, aqueous glucose solution, mannitol, plant oils, etc.); additives [e.g., extending agent, disintegrating agent, binder, lubricant, wetting agent, stabilizer, emulsifier, dispersant, preservative, sweetener, colorant, seasoning agent or aromatizer, concentrating agent, diluent, buffer substance, solvent or solubilizing agent, chemical for achieving storage effect, salt for modifying osmotic pressure, coating agent or antioxidant], and the like.

With regard to each preparation of the pharmaceutical composition and anticancer agent of the invention, various preparation forms can be selected, and examples thereof include oral preparations such as tablets, capsules, powders, granules or liquids, or sterilized liquid parenteral preparations such as solutions or suspensions, suppositories, ointments and the like.

Solid preparations can be prepared in the forms of tablet, capsule, granule and powder without any additives, or prepared using appropriate carriers (additives). Examples of such carriers (additives) may include saccharides such as lactose or glucose; starch of corn, wheat or rice; fatty acids such as stearic acid; inorganic salts such as magnesium metasilicate aluminate or anhydrous calcium phosphate; synthetic polymers such as polyvinylpyrrolidone or polyalkylene glycol; alcohols such as stearyl alcohol or benzyl alcohol; synthetic cellulose derivatives such as methylcellulose, carboxymethylcellulose, ethylcellulose or hydroxypropylmethylcellulose; and other conventionally used additives such as gelatin, talc, plant oil and gum arabic.

These solid preparations such as tablets, capsules, granules and powders may generally contain, for example, 0.1 to 100% by weight, and preferably 5 to 98% by weight, of the compound of the above Formula (I) as an active ingredient, based on the total weight of the preparation.

Liquid preparations are produced in the forms of suspension, syrup, injection and drip infusion (intravenous fluid) using appropriate additives that are conventionally used in liquid preparations, such as water, alcohol or a plant-derived oil such as soybean oil, peanut oil and sesame oil.

In particular, when the preparation is administered parenterally in a form of intramuscular injection, intravenous injection or subcutaneous injection, appropriate solvent or diluent may be exemplified by distilled water for injection, an aqueous solution of lidocaine hydrochloride (for intramuscular injection), physiological saline, aqueous glucose solution, ethanol, polyethylene glycol, propylene glycol, liquid for intravenous injection (e.g., an aqueous solution of citric acid, sodium citrate and the like) or an electrolytic solution (for intravenous drip infusion and intravenous injection), or a mixed solution thereof.

Such injection may be in a form of a preliminarily dissolved solution, or in a form of powder per se or powder associated with a suitable carrier (additive) which is dissolved at the time of use. The injection liquid may contain, for example, 0.1 to 10% by weight of an active ingredient based on the total weight of the preparation.

Liquid preparations such as suspension or syrup for oral administration may contain, for example, 0.1 to 10% by weight of an active ingredient based on the total weight of the preparation.

The preparation can be prepared by a person having ordinary skill in the art according to conventional methods or common techniques. For example, a preparation can be carried out, if the preparation is an oral preparation, for example, by mixing an appropriate amount of the compound of the invention with an appropriate amount of lactose and filling this mixture into hard gelatin capsules which are suitable for oral administration. On the other hand, preparation can be carried out, if the preparation containing the compound of the invention is an injection, for example, by mixing an appropriate amount of the compound of the invention with an appropriate amount of 0.9% physiological saline and filling this mixture in vials for injection.

The compounds of the invention may be sued, optionally as combined with any other agent useful for treatment of various cancers or with radiotherapy. The individual ingredients for such combination may be administered at different times or at the same time as divided preparations or one preparation during the term of treatment. Accordingly, the invention should be so interpreted that it includes all modes of administration at the same time or at different times, and the administration in this invention should be interpreted so. The scope of the combination of the compound of the invention and any other agent useful for the above-mentioned diseases should include, in principle, any and every combination thereof with any and every pharmaceutical agent useful for the treatment of the above-mentioned diseases.

Radiation therapy itself means an ordinary method in the field of treatment of cancer. For radiation therapy, employable are various radiations such as X-ray, γ-ray, neutron ray, electron beam, proton beam; and radiation sources. In a most popular radiation therapy, a linear accelerator is used for irradiation with external radiations, γ-ray.

The compounds of the invention may be combined with radiation therapy to enhance the therapeutical effect in radiation therapy; and the compounds may be therefore useful as a radiation sensitizer in the field of treatment of cancer.

Another aspect of the compounds of the invention is that the compounds are also useful as a sensitizer for any other anticancer agents in the field of treatment of cancer.

The compounds of the invention may be combined with radiation therapy and/or combined with any other anticancer agents described below in their use for treatment of cancer.

"Sensitizer" for radiation therapy or anticancer agent as referred to herein is meant to indicate a medical agent which, when used as combined with radiation therapy and/or chemotherapy with an anticancer agent, may additively or synergistically augment the therapeutical effect of that radiation therapy and/or chemotherapy.

The agents to be in the combined preparations in the invention may have any forms selected in any manner, and they may be produced in the same manner as that for the above-mentioned preparations. The combined agent comprising the compound of the invention and some other anticancer agent may be readily produced by anyone skilled in the art according to ordinary methods or conventional techniques.

The above-mentioned combination includes not only the compositions of the invention that contain one other active substance but also those containing two or more other active substances. There are a lot of examples of the combination of the composition of the invention and one or two or more active substances selected from the remedies for the above-mentioned diseases.

The agents to be combined with the compositions include, for example, an anticancer agent selected from the group consisting of anticancer alkylating agents, anticancer antimetabolites, anticancer antibiotics, plant-derived anticancer agents, anticancer platinum coordination compounds, anticancer camptothecin derivatives, anticancer tyrosine kinase inhibitors, monoclonal antibodies, interferons, biological response modifiers and other anticancer agents as well as pharmaceutically acceptable salt(s) or ester(s) thereof.

The term "anticancer alkylating agent" as used in the present specification refers to an alkylating agent having anticancer activity, and the term "alkylating agent" herein generally refers to an agent giving an alkyl group in the alkylation reaction in which a hydrogen atom of an organic compound is substituted with an alkyl group. The term "anticancer alkylating agent" may be exemplified by nitrogen mustard N-oxide, cyclophosphamide, ifosfamide, melphalan, busulfan, mitobronitol, carboquone, thiotepa, ranimustine, nimustine, temozolomide or carmustine.

The term "anticancer antimetabolite" as used in the specification refers to an antimetabolite having anticancer activity, and the term "antimetabolite" herein includes, in a broad sense, substances which disturb normal metabolism and substances which inhibit the electron transfer system to prevent the production of energy-rich intermediates, due to their structural or functional similarities to metabolites that are important for living organisms (such as vitamins, coenzymes, amino acids and saccharides). The term "anticancer antimetabolites" may be exemplified methotrexate, 6-mercaptopurine riboside, mercaptopurine, 5-fluorouracil, tegafur, doxifluridine, carmofur, cytarabine, cytarabine ocfosfate, enocitabine, S-1, gemcitabine, fludarabine or pemetrexed disodium, and preferred are cytarabine, gemcitabine and the like.

The term "anticancer antibiotic" as used in the specification refers to an antibiotic having anticancer activity, and the "antibiotic" herein includes substances that are produced by microorganisms and inhibit cell growth and other functions of microorganisms and of other living organisms. The term "anticancer antibiotic" may be exemplified by actinomycin D, doxorubicin, daunorubicin, neocarzinostatin, bleomycin, peplomycin, mitomycin C, aclarubicin, pirarubicin, epirubicin, zinostatin stimalamer, idarubicin, sirolimus or valrubicin, and preferred are doxorubicin, mitomycin C and the like.

The term "plant-derived anticancer agent" as used in the specification includes compounds having anticancer activities which originate from plants, or compounds prepared by applying chemical modification to the foregoing compounds. The term "plant-derived anticancer agent" may be exemplified by vincristine, vinblastine, vindesine, etoposide, sobuzoxane, docetaxel, paclitaxel and vinorelbine, and preferred are etoposide and the like.

The term "anticancer camptothecin derivative" as used in the specification refers to compounds that are structurally related to camptothecin and inhibit cancer cell growth, including camptothecin per se. The term "anticancer camptothecin derivative" is not particularly limited to, but may be exemplified by, camptothecin, 10-hydroxycamptothecin, topotecan, irinotecan or 9-aminocamptothecin, with camptothecin being preferred. Further, irinotecan is metabolized in vivo and exhibits anticancer effect as SN-38. The action mechanism and the activity of the camptothecin derivatives are believed to be virtually the same as those of camptothecin (e.g., Nitta, et al., *Gan to Kagaku Ryoho,* 14, 850-857 (1987)).

The term "anticancer platinum coordination compound" as used in the specification refers to a platinum coordination compound having anticancer activity, and the term "platinum coordination compound" herein refers to a platinum coordination compound which provides platinum in ion form. Preferred platinum compounds include cisplatin; cis-diamminediaquoplatinum (II)-ion; chloro(diethylenetriamine)-platinum (II) chloride; dichloro(ethylenediamine)-platinum (II); diammine(1,1-cyclobutanedicarboxylato)platinum (II) (carboplatin); spiroplatin; iproplatin; diammine(2-ethylmalonato)platinum (II); ethylenediaminemalonatoplatinum (II); aqua(1,2-diaminodicyclohexane)sulfatoplatinum (II); aqua (1,2-diaminodicyclohexane)malonatoplatinum (II); (1,2-diaminocyclohexane)malonatoplatinum (II); (4-carboxyphthalato)(1,2-diaminocyclohexane) platinum (II); (1,2-diaminocyclohexane)-(isocitrato)platinum (II); (1,2-diaminocyclohexane)oxalatoplatinum (II); ormaplatin; tetraplatin; carboplatin, nedaplatin and oxaliplatin, and preferred is cisplatin. Further, other anticancer platinum coordination compounds mentioned in the specification are known and are commercially available and/or producible by a person having ordinary skill in the art by conventional techniques.

The term "anticancer tyrosine kinase inhibitor" as used in the specification refers to a tyrosine kinase inhibitor having anticancer activity, and the term "tyrosine kinase inhibitor" herein refers to a chemical substance inhibiting "tyrosine kinase" which transfers a γ-phosphate group of ATP to a hydroxyl group of a specific tyrosine in protein. The term "anticancer tyrosine kinase inhibitor" may be exemplified by gefitinib, imatinib or erlotinib.

The term "monoclonal antibody" as used in the specification, which is also known as single clonal antibody, refers to an antibody produced by a monoclonal antibody-producing cell, and examples thereof include cetuximab, bevacizumab, rituximab, alemtuzumab and trastuzumab.

The term "interferon" as used in the specification refers to an interferon having anticancer activity, and it is a glycoprotein having a molecular weight of about 20,000 which is produced and secreted by most animal cells upon viral infection. It has not only the effect of inhibiting viral growth but also various immune effector mechanisms including inhibition of growth of cells (in particular, tumor cells) and enhancement of the natural killer cell activity, thus being designated as one type of cytokine. Examples of "interferon" include interferon α, interferon α-2a, interferon α-2b, interferon β, interferon γ-1a and interferon γ-n1.

The term "biological response modifier" as used in the specification is the so-called biological response modifier or BRM and is generally the generic term for substances or drugs for modifying the defense mechanisms of living organisms or biological responses such as survival, growth or differentiation of tissue cells in order to direct them to be useful for an individual against tumor, infection or other diseases. Examples of the "biological response modifier" include krestin, lentinan, sizofuran, picibanil and ubenimex.

The term "other anticancer agent" as used in the specification refers to an anticancer agent which does not belong to any of the above-described agents having anticancer activities. Examples of the "other anticancer agent" include mitoxantrone, L-asparaginase, procarbazine, dacarbazine, hydroxycarbamide, pentostatin, tretinoin, alefacept, darbepoetin alfa, anastrozole, exemestane, bicalutamide, leuprorelin, flutamide, fulvestrant, pegaptanib octasodium, denileukin diftitox, aldesleukin, thyrotropin alfa, arsenic trioxide, bortezomib, capecitabine, and goserelin.

The above-described terms "anticancer alkylating agent", "anticancer antimetabolite", "anticancer antibiotic", "plant-derived anticancer agent", "anticancer platinum coordination compound", "anticancer camptothecin derivative", "anticancer tyrosine kinase inhibitor", "monoclonal antibody", "interferon", "biological response modifier" and "other anticancer agent" are all known and are either commercially available or producible by a person skilled in the art by methods known per se or by well-known or conventional methods. The process for preparation of gefitinib is described, for example, in U.S. Pat. No. 5,770,599; the process for preparation of cetuximab is described, for example, in WO 96/40210; the process for preparation of bevacizumab is described, for example, in WO 94/10202; the process for preparation of oxaliplatin is described, for example, in U.S. Pat. Nos. 5,420,319 and 5,959,133; the process for preparation of gemcitabine is described, for example, in U.S. Pat. Nos. 5,434,254 and 5,223,608; and the process for preparation of camptothecin is described in U.S. Pat. Nos. 5,162,532, 5,247,089, 5,191,082, 5,200,524, 5,243,050 and 5,321,140; the process for preparation of irinotecan is described, for example, in U.S. Pat. No. 4,604,463; the process for preparation of topotecan is described, for example, in U.S. Pat. No. 5,734,056; the process for preparation of temozolomide is described, for example, in JP-B No. 4-5029; and the process for preparation of rituximab is described, for example, in JP-W No. 2-503143.

The above-mentioned anticancer alkylating agents are commercially available, as exemplified by the following: nitrogen mustard N-oxide from Mitsubishi Pharma Corp. as Nitromin (tradename); cyclophosphamide from Shionogi & Co., Ltd. as Endoxan (tradename); ifosfamide from Shionogi & Co., Ltd. as Ifomide (tradename); melphalan from GlaxoSmithKline Corp. as Alkeran (tradename); busulfan from Takeda Pharmaceutical Co., Ltd. as Mablin (tradename); mitobronitol from Kyorin Pharmaceutical Co., Ltd. as Myebrol (tradename); carboquone from Sankyo Co., Ltd. as Esquinon (tradename); thiotepa from Sumitomo Pharmaceutical Co., Ltd. as Tespamin (tradename); ranimustine from Mitsubishi Pharma Corp. as Cymerin (tradename); nimustine from Sankyo Co., Ltd. as Nidran (tradename); temozolomide from Schering Corp. as Temodar (tradename); and carmustine from Guilford Pharmaceuticals Inc. as Gliadel Wafer (tradename).

The above-mentioned anticancer antimetabolites are commercially available, as exemplified by the following: methotrexate from Takeda Pharmaceutical Co., Ltd. as Methotrexate (tradename); 6-mercaptopurine riboside from Aventis Corp. as Thioinosine (tradename); mercaptopurine from Takeda Pharmaceutical Co., Ltd. as Leukerin (tradename); 5-fluorouracil from Kyowa Hakko Kogyo Co., Ltd. as 5-FU (tradename); tegafur from Taiho Pharmaceutical Co., Ltd. as Futraful (tradename); doxyfluridine from Nippon Roche Co., Ltd. as Furutulon (tradename); carmofur from Yamanouchi Pharmaceutical Co., Ltd. as Yamafur (tradename); cytarabine from Nippon Shinyaku Co., Ltd. as Cylocide (tradename); cytarabine ocfosfate from Nippon Kayaku Co., Ltd. as Strasid (tradename); enocitabine from Asahi Kasei Corp. as Sanrabin (tradename); S-1 from Taiho Pharmaceutical Co., Ltd. as TS-1 (tradename); gemcitabine from Eli Lilly & Co. as Gemzar (tradename); fludarabine from Nippon Schering Co., Ltd. as Fludara (tradename); and pemetrexed disodium from Eli Lilly & Co. as Alimta (tradename).

The above-mentioned anticancer antibiotics are commercially available, as exemplified by the following: actinomycin D from Banyu Pharmaceutical Co., Ltd. as Cosmegen (tradename); doxorubicin from Kyowa Hakko Kogyo Co., Ltd. as adriacin (tradename); daunorubicin from Meiji Seika Kaisha Ltd. as Daunomycin; neocarzinostatin from Yamanouchi Pharmaceutical Co., Ltd. as Neocarzinostatin (tradename); bleomycin from Nippon Kayaku Co., Ltd. as Bleo (tradename); pepromycin from Nippon Kayaku Co, Ltd. as Pepro (tradename); mitomycin C from Kyowa Hakko Kogyo Co., Ltd. as Mitomycin (tradename); aclarubicin from Yamanouchi Pharmaceutical Co., Ltd. as Aclacinon (tradename); pirarubicin from Nippon Kayaku Co., Ltd. as Pinorubicin (tradename); epirubicin from Pharmacia Corp. as Pharmorubicin (tradename); zinostatin stimalamer from Yamanouchi Pharmaceutical Co., Ltd. as Smancs (tradename); idarubicin from Pharmacia Corp. as Idamycin (tradename); sirolimus from Wyeth Corp. as Rapamune (tradename); and valrubicin from Anthra Pharmaceuticals Inc. as Valstar (tradename).

The above-mentioned plant-derived anticancer agents are commercially available, as exemplified by the following: vincristine from Shionogi & Co., Ltd. as Oncovin (tradename); vinblastine from Kyorin Pharmaceutical Co., Ltd. as Vinblastine (tradename); vindesine from Shionogi & Co., Ltd. as Fildesin (tradename); etoposide from Nippon Kayaku Co., Ltd. as Lastet (tradename); sobuzoxane from Zenyaku Kogyo Co., Ltd. as Perazolin (tradename); docetaxel from Aventis Corp. as Taxsotere (tradename); paclitaxel from Bristol-Myers Squibb Co. as Taxol (tradename); and vinorelbine from Kyowa Hakko Kogyo Co., Ltd. as Navelbine (tradename).

The above-mentioned anticancer platinum coordination compounds are commercially available, as exemplified by the following: cisplatin from Nippon Kayaku Co., Ltd. as Randa (tradename); carboplatin from Bristol-Myers Squibb Co. as Paraplatin (tradename); nedaplatin from Shionogi & Co., Ltd. as Aqupla (tradename); and oxaliplatin from Sanofi-Synthelabo Co. as Eloxatin (tradename).

The above-mentioned anticancer camptothecin derivatives are commercially available, as exemplified by the following: irinotecan from Yakult Honsha Co., Ltd. as Campto (tradename); topotecan from GlaxoSmithKline Corp. as Hycamtin (tradename); and camptothecin from Aldrich Chemical Co., Inc., U.S.A.

The above-mentioned anticancer tyrosine kinase inhibitors are commercially available, as exemplified by the following: gefitinib from AstraZeneca Corp. as Iressa (tradename); imatinib from Novartis AG as Gleevec (tradename); and erlotinib from OSI Pharmaceuticals Inc. as Tarceva (tradename).

The above-mentioned monoclonal antibodies are commercially available, as exemplified by the following: cetuximab from Bristol-Myers Squibb Co. as Erbitux (tradename); bevacizumab from Genentech, Inc. as Avastin (tradename); rituximab from Biogen Idec Inc. as Rituxan (tradename); alemtuzumab from Berlex Inc. as Campath (tradename); and trastuzumab from Chugai Pharmaceutical Co., Ltd. as Herceptin (tradename).

The above-mentioned interferons are commercially available, as exemplified by the following: interferon α from Sumitomo Pharmaceutical Co., Ltd. as Sumiferon (tradename); interferon α-2a from Takeda Pharmaceutical Co., Ltd. as Canferon-A (tradename); interferon α-2b from Schering-Plough Corp. as Intron A (tradename); interferon β from Mochida Pharmaceutical Co., Ltd. as IFNβ (tradename); interferon γ-1a from Shionogi & Co., Ltd. as Imunomax-γ (tradename); and interferon γ-n1 from Otsuka Pharmaceutical Co., Ltd. as Ogamma (tradename).

The above-mentioned biological response modifiers are commercially available, as exemplified by the following: krestin from Sankyo Co., Ltd. as krestin (tradename); lentinan from Aventis Corp. as Lentinan (tradename); sizofuran from Kaken Seiyaku Co., Ltd. as Sonifuran (tradename); picibanil from Chugai Pharmaceutical Co., Ltd. as Picibanil (tradename); and ubenimex from Nippon Kayaku Co., Ltd. as Bestatin (tradename).

The above-mentioned other anticancer agents are commercially available, as exemplified by the following: mitoxantrone from Wyeth Lederle Japan, Ltd. as Novantrone (tradename); L-asparaginase from Kyowa Hakko Kogyo Co., Ltd. as Leunase (tradename); procarbazine from Nippon Roche Co., Ltd. as Natulan (tradename); dacarbazine from Kyowa Hakko Kogyo Co., Ltd. as Dacarbazine (tradename); hydroxycarbamide from Bristol-Myers Squibb Co. as Hydrea (tradename); pentostatin from Kagaku Oyobi Kessei Ryoho Kenkyusho as Coforin (tradename); tretinoin from Nippon Roche Co., Ltd. As Vesanoid (tradename); alefacept from Biogen Idec Inc. as Amevive (tradename); darbepoetin alfa from Amgen Inc. as Aranesp (tradename); anastrozole from AstraZeneca Corp. as Arimidex (tradename); exemestane from Pfizer Inc. as Aromasin (tradename); bicalutamide from AstraZeneca Corp. as Casodex (tradename); leuprorelin from Takeda Pharmaceutical Co., Ltd. as Leuplin (tradename); flutamide from Schering-Plough Corp. as Eulexin (tradename); fulvestrant from AstraZeneca Corp. as Faslodex (tradename); pegaptanib octasodium from Gilead Sciences, Inc. as Macugen (tradename); denileukin diftitox from Ligand Pharmaceuticals Inc. as Ontak (tradename); aldesleukin from Chiron Corp. as Proleukin (tradename); thyrotropin alfa from Genzyme Corp. as Thyrogen (tradename); arsenic trioxide from Cell Therapeutics, Inc. as Trisenox (tradename); bortezomib from Millennium Pharmaceuticals, Inc. as Velcade (tradename); capecitabine from Hoffmann-La Roche, Ltd. as Xeloda (tradename); and goserelin from AstraZeneca Corp. as Zoladex (tradename).

The invention also relates to a method for the treatment of cancer, which comprises administering to a subject in need thereof a therapeutically-effective amount of the compound of the invention or its salt or ester thereof.

In the process according to the invention, preferred therapeutic unit may vary in accordance with, for example, the administration route of the compound of the invention, the type of the compound of the invention used, and the dosage form of the compound of the invention used; the type, administration route and dosage form of the other anticancer agent used in combination; and the type of cells to be treated, the condition of patient, and the like. The optimal treatment under the given conditions can be determined by a person skilled in the art, based on the set conventional therapeutic unit and/or based on the content of the present specification.

In the process according to the invention, the therapeutic unit for the compound of the invention may vary in accordance with, specifically, the type of compound used, the type of compounded composition, application frequency and the specific site to be treated, seriousness of the disease, age of the patient, doctor's diagnosis, the type of cancer, or the like. However, as an exemplary reference, the daily dose for an adult may be within a range of, for example, 1 to 1,000 mg in the case of oral administration. In the case of parenteral administration, preferably intravenous administration, and more preferably intravenous drip infusion, the daily dose may be within a range of, for example, 1 to 100 mg/m$^2$ (body surface area). Here, in the case of intravenous drip infusion, administration may be continuously carried out for, for example, 1 to 48 hours. Moreover, the administration frequency may vary depending on the administering method and symptoms, but it is, for example, once to five times a day. Alternatively, periodically intermittent administration such as administration every other day, administration every two days or the like may be employed as well in the administering method. The period of withdraw from medication in the case of parenteral administration is, for example, 1 to 6 weeks.

Although the therapeutic unit for the other anticancer agent used in combination with the compound of the invention is not particularly limited, it can be determined, if needed, by those skilled in the art according to known literatures. Examples may be as follows.

The therapeutic unit of 5-fluorouracil (5-FU) is such that, in the case of oral administration, for example, 200 to 300 mg per day is administered in once to three times consecutively, and in the case of injection, for example, 5 to 15 mg/kg per day is administered once a day for the first 5 consecutive days by intravenous injection or intravenous drip infusion, and then 5 to 7.5 mg/kg is administered once a day every other day by intravenous injection or intravenous drip infusion (the dose may be appropriately increased or decreased).

The therapeutic unit of S-1 (Tegafur, Gimestat and Ostat potassium) is such that, for example, the initial dose (singe dose) is set to the following standard amount in accordance with the body surface area, and it is orally administered twice a day, after breakfast and after dinner, for 28 consecutive days, followed by withdrawal from medication for 14 days. This is set as one course of administration, which is repeated. The initial standard amount per unit body surface area (Tegafur equivalent) is 40 mg in one administration for an area less than 1.25 m$^2$; 50 mg in one administration for an area of 1.25 m$^2$ to less than 1.5 m$^2$; 60 mg in one administration for an area of 1.5 m$^2$ or more. This dose is appropriately increased or decreased depending on the condition of the patient.

The therapeutic unit for gemcitabine is, for example, 1 g as gemcitabine/m$^2$ in one administration, which is administered by intravenous drip infusion over a period of 30 minutes, and one administration per week is continued for 3 weeks, followed by withdrawal from medication on the fourth week. This is set as one course of administration, which is repeated. The dose is appropriately decreased in accordance with age, symptom or development of side-effects.

The therapeutic unit for doxorubicin (e.g., doxorubicin hydrochloride) is such that, for example, in the case of intravenous injection, 10 mg (0.2 mg/kg) (titer) is administered once a day by intravenous one-shot administration for 4 to 6 consecutive days, followed by withdrawal from medication for 7 to 10 days. This is set as one course of administration, which is repeated two or three times. Here, the total dose is preferably 500 mg (titer)/m$^2$ (body surface area) or less, and it may be appropriately increased or decreased within the range.

The therapeutic unit for etoposide is such that, for example, in the case of intravenous injection, 60 to 100 mg/m$^2$ (body surface area) per day is administered for 5 consecutive days, followed by withdrawal from medication for three weeks (the dose may be appropriately increased or decreased). This is set as one course of administration, which is repeated. Meanwhile, in the case of oral administration, for example, 175 to 200 mg per day is administered for 5 consecutive days, followed by withdrawal from medication for three weeks (the dose may be appropriately increased or decreased). This is set as one course of administration, which is repeated.

The therapeutic unit for docetaxel (docetaxel hydrate) is such that, for example, 60 mg as docetaxel/m$^2$ (body surface area) is administered once a day by intravenous drip infusion over a period of 1 hour or longer at an interval of 3 to 4 weeks (the dose may be appropriately increased or decreased).

The therapeutic unit of paclitaxel is such that, for example, 210 mg/m$^2$ (body surface area) is administered once a day by intravenous drip infusion over a period of 3 hours, followed by withdrawal from medication for at least 3 weeks. This is set as one course of administration, which is repeated. The dose may be appropriately increased or decreased.

The therapeutic unit for cisplatin is such that, for example, in the case of intravenous injection, 50 to 70 mg/m$^2$ (body surface area) is administered once a day, followed by withdrawal from medication for 3 weeks or longer (the dose may be appropriately increased or decreased). This is set as one course of administration, which is repeated.

The therapeutic unit for carboplatin is such that, for example, 300 to 400 mg/m² is administered once a day by intravenous drip infusion over a period of 30 minutes or longer, followed by withdrawal from medication for at least 4 weeks (the dose may be appropriately increased or decreased). This is set as one course of administration, which is repeated.

The therapeutic unit for oxaliplatin is such that 85 mg/m² is administered once a day by intravenous injection, followed by withdrawal from medication for two weeks. This is set as one course of administration, which is repeated.

The therapeutic unit for irinotecan (e.g., irinotecan hydrochloride) is such that, for example, 100 mg/m² is administered once a day by intravenous drip infusion for 3 or 4 times at an interval of one week, followed by withdrawal from medication for at least two weeks.

The therapeutic unit for topotecan is such that, for example, 1.5 mg/m² is administered once a day by intravenous drip infusion for 5 days, followed by withdrawal from medication for at least 3 weeks.

The therapeutic unit for cyclophosphamide is such that, for example, in the case of intravenous injection, 100 mg is administered once a day by intravenous injection for consecutive days. If the patient can tolerate, the daily dose may be increased to 200 mg. The total dose is 3,000 to 8,000 mg, which may be appropriately increased or decreased. If necessary, it may be injected or infused intramuscularly, intrathoracically or intratumorally. On the other hand, in the case of oral administration, for example, 100 to 200 mg is administered a day.

The therapeutic unit for gefitinib is such that 250 mg is orally administered once a day.

The therapeutic unit for cetuximab is such that, for example, 400 mg/m² is administered on the first day by intravenous drip infusion, and then 250 mg/m² is administered every week by intravenous drip infusion.

The therapeutic unit for bevacizumab is such that, for example, 3 mg/kg is administered every week by intravenous drip infusion.

The therapeutic unit for trastuzumab is such that, for example, typically for an adult, once a day, 4 mg as trastuzumab/kg (body weight) is administered initially, followed by intravenous drip infusion of 2 mg/kg over a period of 90 minutes or longer every week from the second administration.

The therapeutic unit for exemestane is such that, for example, typically for an adult, 25 mg is orally administered once a day after meal.

The therapeutic unit for leuprorelin (e.g., leuprorelin acetate) is such that, for example, typically for an adult, 11.25 mg is subcutaneously administered once in 12 weeks.

The therapeutic unit for imatinib is such that, for example, typically for an adult in the chronic phase of chronic myelogenous leukemia, 400 mg is orally administered once a day after meal.

The therapeutic unit for a combination of 5-FU and leucovorin is such that, for example, 425 mg/m² of 5-FU and 200 mg/m² of leucovorin are administered from the first day to the fifth day by intravenous drip infusion, and this course is repeated at an interval of 4 weeks.

BEST MODE FOR CARRYING OUT THE INVENTION

The invention is described more concretely with reference to the following Examples and Production Examples, which, however, are not intended to restrict the scope of the invention.

In thin-layer chromatography in Examples and Production Examples, Silica gel$_{60}$F$_{254}$ (Merck) was used for the plate, and a UV detector was used for detection. Wakogel™ C-300 or C-200 (Wako Pure Chemical Industries) or NH (Fuji Silysia Chemical) was used for column silica gel. In MS spectrometry, used was JMS-SX102A (JEOL) or QUATTROII (Micromass). In NMR spectrometry, dimethylsulfoxide was used as the internal standard in a heavy dimethylsulfoxide solution; a spectrometer of Gemini-300 (300 MHz; Varian), VXR-300 (300 MHz; Varian), Mercury 400 (400 MHz; Varian) or Inova 400 (400 MHz; Varian) was used; and all $\delta$ values are by ppm.

The meanings of the abbreviations in NMR are mentioned below.

s: singlet
d: doublet
dd: double doublet
t: triplet
dt: double triplet
q: quartet
m: multiplet
br: broad
J: coupling constant
Hz: hertz
DMSO-d$_6$: heavy dimethylsulfoxide Production Example 1

Production of 2-allyl-6-(methylthio)-1,2-dihydro-3H-pyrazolo[3,4-d]pyrimidin-3-one 1) Tert-butyl 1-allylhydrazinecarboxylate 250 g of tert-butyl hydrazinecarboxylate was added to toluene (3 L) solution of 280 g of phthalic anhydride. Using a Dean-Stark water separator, the reaction mixture was heated under reflux for 3 hours. This was cooled to room temperature, the formed solid was taken out through filtration to obtain 516 g of crude tert-butyl (1,3-dioxo-1,3-dihydro-2H-isoindol-2-yl)carbamate.

520 g of potassium carbonate, 43.3 g of benzyltriethylammonium chloride and 250 µL of allyl bromide were added in that order to acetonitrile (3.5 L) solution of the above compound, and stirred at room temperature for 18 hours. 1.5 L of water was added to the reaction solution, and the acetonitrile layer was separated and concentrated. One L of water was added to the residue and the aqueous layer, extracted with ethyl acetate, and the ethyl acetate layer was washed with saturated saline water, and then dried with anhydrous sodium sulfate. The solvent was evaporated away under reduced pressure, and the precipitated colorless solid was washed with hexane and dried to obtain 460 g of crude tert-butyl allyl(1,3-dioxo-1,3-dihydro-2H-isoindol-2-yl)carbamate.

With cooling in an ice bath, 100 mL of methylhydrazine was added to tetrahydrofuran (3.0 L) solution of the above compound, then restored to room temperature, and stirred for 18 hours. The precipitated insoluble matter was taken out through filtration, and the filtrate was concentrated. A mixed solvent of hexane/ethyl acetate (3/1) was added to the residue, and the precipitated insoluble matter was taken out through filtration. This operation was repeated five times, then the filtrate was concentrated under reduced pressure, the resulting residue was distilled under reduced pressure to obtain 211 g of the entitled compound as a pale yellow oily substance.

ESI-MS Found: m/z[M+H]+ 173.4.

2) Production of 2-allyl-6-(methylthio)-1,2-dihydro-3H-pyrazolo[3,4-d]pyrimidin-3-one 260 mL of N,N-diisopropylethylamine and 106 g of the hydrazine obtained in the above 1 were added to tetrahydrofuran (1.5 L) solution of 142 g of ethyl 4-chloro-2-(methylthio)pyridine-5-carboxylate, and stirred with heating under reflux for 18 hours. After cooled to room temperature, the reaction solution was evaporated under reduced pressure, and 500 mL of diethyl ether was added to the residue, and the precipitated solid was separated through filtration. The filtrate was evaporated under reduced pressure, the residue was cooled in an ice bath, 400 mL of trifluoroacetic acid was gradually added thereto, and stirred at room temperature for 1 hour and then at 70° C. for 1 hour. The reaction solution was evaporated under reduced pressure, 500 mL of ethanol was added thereto and cooled in an ice bath, and 1.0 L of 6 N sodium hydroxide solution was added thereto and stirred at room temperature for 15 minutes. Cooled in an ice bath, the reaction solution was made acidic with 400 mL of concentrated hydrochloric acid, and then evaporated under reduced pressure. The residue was partitioned in chloroform and water, and the chloroform layer was extracted, washed with saturated saline water, and dried with anhydrous sodium sulfate. The solvent was evaporated away under reduced pressure, and the formed yellow solid was taken out through filtration, washed with ethanol and diethyl ether, and dried to obtain 99.1 g of the entitled compound as a yellow solid.

$^1$H-NMR (400 MHz, DMSO-d$_6$) δ: 8.66 (1.0H, brs), 5.83 (1.0H, ddt, J=17.1, 9.8, 5.4 Hz), 5.13 (1.0H, d, J=9.8 Hz), 5.06 (1.0H, d, J=17.1 Hz), 4.34 (2.0H, d, J=5.4 Hz), 2.51 (3.0H, s).

ESI-MS Found: m/z[M+H]+ 223.3.

Production Example 2

Production of 2-(2-chlorophenyl)-6-(methylthio)-1,2-dihydro-3H-pyrazolo[3,4-d]pyrimidin-3-one 1) Production of ethyl 4-[2-(2-chlorophenyl)hydrazino]-2-(methylthio)pyrimidine-5-carboxylate At room temperature, 16.2 mL of N,N-diisopropylethylamine was added to tetrahydrofuran (300 mL) solution of 9.4 g of ethyl 4-chloro-2-(methylthio)pyrimidine-5-carboxylate and 8.3 g of 2-chlorophenylhydrazine hydrochloride, and heated under reflux for 18 hours. The solvent was concentrated under reduced pressure, water was added to this, and extracted with ethyl acetate, and the ethyl acetate layer was washed with saturated saline water, and dried with anhydrous sodium sulfate. The solvent was evaporated away under reduced pressure to obtain crude ethyl 4-[2-(2-chlorophenyl) hydrazino]-2-(methylthio)pyrimidine-5-carboxylate as a yellow oily substance.

2) Production of 2-(2-chlorophenyl)-6-(methylthio)-1,2-dihydro-3H-pyrazolo[3,4-d]pyrimidin-3-one 50 mL of aqueous 5 N sodium hydroxide solution was added to methanol (100 mL)-tetrahydrofuran (100 mL) solution of 13.8 g of the compound obtained in the above 1, and stirred at room temperature for 3 hours. The reaction system was concentrated under reduced pressure, the residue was made acidic with aqueous 5 N hydrochloric acid added thereto, and then extracted with a mixed solvent of 2-propanol/chloroform (20/80). The solvent was evaporated away under reduced pressure to obtain crude 4-[2-(2-chlorophenyl) hydrazino]-2-(methylthio)pyrimidine-5-carboxylic acid as a white solid.

500 mL of toluene and 60 mL of thionyl chloride were added to the above compound, and heated under reflux for 1 hour. The solvent was evaporated away under reduced pressure, Water was added to the residue, extracted with a mixed solvent of 2-propanol/chloroform (20/80), and dried with anhydrous sodium sulfate. The solvent was evaporated away under reduced pressure to obtain 5.8 g of the entitled compound as a yellow solid.

$^1$HNMR (400 MHz, DMSO-d$_6$) δ: 8.78 (1H, s), 7.44-7.77 (4H, m), 2.56 (3H, s).

APCI-MS Found: m/z[M+H]+ 293.0.

Production Example 3

Production of 2-isopropyl-6-(methylthio)-1,2-dihydro-3H-pyrazolo[3,4-d]pyrimidin-3-one 1) Production of ethyl 4-hydrazino-2-(methylthio)pyrimidine-5-carboxylate 9.71 g of hydrazine monohydrate was dissolved in 200 mL of ethanol, and cooled to 0° C. To this was added a solution prepared by dissolving 15.0 g of ethyl 4-chloro-2-(methylthio)pyrimidine-5-carboxylate in 200 mL of ethanol, and stirred for 1 hour. The precipitated solid was taken out through filtration, washed with distilled water, and dried to obtain 9.66 g of the entitled compound as a white solid.

$^1$H-NMR (400 MHz, CD$_3$OD) δ: 8.56 (1H, s), 4.36 (2H, q, J=7.2 Hz), 2.62 (3H, s), 1.39 (3H, t, J=7.2 Hz).

ESI-MS Found: m/z[M+H]+ 229.

2) Production of ethyl 4-[2-(1-methylethylidene) hydrazino]-2-(methylthio)pyrimidine-5-carboxylate 9.66 g of the above compound was dissolved in 300 mL of acetone, and stirred at 70° C. for 12 hours. The reaction solution was cooled to room temperature, and the solvent was evaporated away under reduced pressure to obtain 9.66 g of the entitled compound as a white solid.

$^1$H-NMR (400 MHz, CDCl$_3$) δ: 8.75 (1H, s), 4.36 (2H, q, J=6.8 Hz), 2.60 (3H, s), 2.17 (3H, s), 2.04 (3H, s), 1.40 (3H, t, J=6.8 Hz).

ESI-MS Found: m/z[M+H]+ 269.

3) Production of ethyl 4-(2-isopropylhydrazino)-2-(methylthio)pyrimidine-5-carboxylate 9.66 g of the above compound was dissolved in 180 mL of methanol, and cooled to 0° C. Methanol (36 mL) solution of 2.26 g of sodium cyanoborohydride and 0.15 mL of concentrated hydrochloric acid were added to the reaction solution, and stirred for 30 minutes. Aqueous saturated sodium hydrogencarbonate solution was added to the reaction solution, and extracted with ethyl acetate. This was dried with anhydrous sodium sulfate, and the solvent was evaporated away under reduced pressure to obtain 10.2 g of the entitled compound as a yellow amorphous substance.

$^1$H-NMR (400 MHz, CDCl$_3$) δ: 9.39 (1H, s), 8.62 (1H, s), 4.34 (2H, q, J=7.2 Hz), 3.24 (1H, septet, J=6.3 Hz), 2.56 (4H, t, J=17.1 Hz), 1.37 (4H, t, J=7.1 Hz), 1.14 (7H, d, J=6.3 Hz).

ESI-MS Found: m/z[M+H]+ 271.

4) Production of 2-isopropyl-6-(methylthio)-1,2-dihydro-3H-pyrazolo[3,4-d]pyrimidin-3-one 300 mL of aqueous 5 N sodium hydroxide solution was added to methanol (100 mL) solution of 10.2 g of the above compound, and stirred for 3 hours. Methanol was evaporated away under reduced pressure, aqueous 5 N hydrochloric acid solution was added to the residue to make it have a pH of about 2, and then stirred for 3.5 hours. The reaction solution was extracted with chloroform, washed with saturated saline water, and dried with anhydrous sodium sulfate. The solvent was evaporated away under reduced pressure to obtain 7.52 g of the entitled compound as an orange amorphous substance.

$^1$H-NMR (400 MHz, CDCl$_3$) δ: 8.71 (1H, s), 4.85 (1H, septet, J=6.8, 6.8 Hz), 2.60 (3H, s), 1.44 (6H, d, J=6.8 Hz).

ESI-MS Found: m/z[M+H]+ 225.

Production Example 4

Production of 6-(methylthio)-1-phenyl-1,2-dihydro-3H-pyrazolo[3,4-d]pyrimidin-3-one 60 mL of triethylamine was added to tetrahydrofuran (200 mL) solution of 25 g of ethyl 4-chloro-2-(methylthio)pyrimidine-5-carboxylate and 12.7 mL of phenylhydrazine, and stirred at room temperature for 18 hours. The solvent was concentrated under reduced pressure, water was added to the residue, then washed with ether, and made acidic with aqueous 5 N hydrochloric acid solution added thereto. The precipitated solid was taken out through filtration, and washed with water and 2-propanol to obtain 10.8 g of the entitled compound as a white solid.

$^1$H-NMR (400 MHz, CDCl$_3$) δ: 12.18 (1H, s), 9.02 (1H, s), 8.13 (2H, dd, J=8.8, 1.0 Hz), 7.52 (2H, td, J=7.1, 1.6 Hz), 7.26 (1H, tt, J=7.1, 1.0 Hz), 2.61 (3H, s).

ESI-MS Found: m/z[M+H]+ 259.1.

Production Example 5

Production of [5-amino-2-(4-ethylpiperazin-1-yl)phenyl]methanol

1) Production of [5-nitro-2-(4-ethylpiperazin-1-yl)phenyl]methanol 4.24 g of potassium carbonate was added to N-methylpyrrolidone (4.24 mL) solution of 4.24 g of 2-fluoro-5-nitrobenzyl alcohol and 4.24 g of N-ethylpiperazine, and stirred at 140° C. for 14 hours. Water was added to the reaction liquid, and extracted with ethyl acetate. The organic layer was washed with water and saturated saline water in that order, then dried with anhydrous magnesium sulfate, and the solvent was evaporated away under reduced pressure. The crude product was purified through silica gel column chromatography (hexane/ethyl acetate) to obtain the entitled compound as a yellow solid.

2) Production of [5-amino-2-(4-ethylpiperazin-1-yl)phenyl]methanol 7.0 g of iron and 15 g of ammonium chloride were added to ethanol/water (1/1, 80 mL) solution of the compound obtained in the above reaction, and heated under reflux for 1 hour. The reaction liquid was concentrated under reduced pressure, and made basic with aqueous 5 N sodium hydroxide solution added thereto. This was extracted with chloroform/isopropanol (80/20), the organic layer was dried with anhydrous magnesium sulfate, and the solvent was evaporated away to obtain 2.49 g of the entitled compound.

$^1$H-NMR (400 MHz, CDCl$_3$) δ: 8.27 (1H, d, J=2.4 Hz), 8.14 (1H, dd, J=8.8, 2.9 Hz), 7.16 (1H, d, J=9.3 Hz), 4.80 (2H, s), 3.10 (4H, t, J=4.9 Hz), 2.66 (4H, brs), 2.51 (2H, q, J=7.3 Hz), 1.14 (3H, t, J=7.1 Hz).

ESI-MS Found: m/z[M+H]+ 235.

Production Example 6

Production of 4-[4-(2-ethoxyethyl)piperazin-1-yl]-3-methylaniline

1) Production of 1-(2-ethoxyethyl)-4-(2-methyl-4-nitrophenyl)piperazine

In the same manner as in Production Example 5-1, but using 4-(2-ethoxyethyl)piperazine in place of N-ethylpiperazine used in Production Example 5-1, using 4-nitrofluorobenzene in place of 2-fluoro-5-nitrobenzyl alcohol, and using dimethylsulfoxide in place of N-methylpyrrolidone, 1.50 g of the entitled compound was obtained as a yellow solid.

2) Production of 4-[4-(2-ethoxyethyl)piperazin-1-yl]-3-methylaniline

In the same manner as in Production Example 5-2, but using 1-(2-ethoxyethyl)-4-(2-methyl-4-nitrophenyl)piperazine in place of [5-nitro-2-(4-ethylpiperazin-1-yl)phenyl]methanol used in Production Example 5-2, 1.01 g of the entitled compound was obtained as a white solid.

$^1$H-NMR (400 MHz, DMSO-d$_6$) δ: 6.66 (2H, dd, J=6.6, 2.2 Hz), 6.47 (2H, dd, J=6.6, 2.2 Hz), 4.57 (2H, s), 3.48 (2H, t, J=5.9 Hz), 3.42 (2H, q, J=7.0 Hz), 2.88 (4H, t, J=4.9 Hz), 2.55-2.47 (6H, m), 1.10 (3H, t, J=7.0 Hz).

ESI-MS Found: m/z[M+H]+ 250.

Production Example 7

Production of 4-[4-(2-hydroxyethyl)piperazin-1-yl]-3-methylaniline

1) Production of 1-(2-hydroxyethyl)-4-(2-methyl-4-nitrophenyl)piperazine

In the same manner as in Production Example 5-1, but using 4-(2-ethoxyethyl)piperazine in place of N-ethylpiperazine used in Production Example 5-1, using 5-nitro-2-fluorotoluene in place of 2-fluoro-5-nitrobenzyl alcohol, using N,N-diisopropylethylamine in place of potassium carbonate, and using dimethylsulfoxide in place of N-methylpyrrolidone, the entitled compound was obtained as a yellow solid.

2) Production of 4-[4-(2-hydroxyethyl)piperazin-1-yl]-3-methylaniline

In the same manner as in Production Example 5-2, but using 1-(2-hydroxyethyl)-4-(2-methyl-4-nitrophenyl)piperazine in place of [5-nitro-2-(4-ethylpiperazin-1-yl)phenyl]methanol used in Production Example 5-2, the entitled compound was obtained as a white solid.

$^1$H-NMR (400 MHz, DMSO-d$_6$) δ 6.73 (1H, d, J=8.3 Hz), 6.37 (1H, d, J=2.4 Hz), 6.33 (1H, dd, J=8.3, 2.4 Hz), 4.63 (2H, s), 4.38 (1H, t, J=5.4 Hz), 3.50 (2H, q, J=6.3 Hz), 2.67 (4H, t, J=4.6 Hz), 2.53-2.48 (4H, m), 2.41 (2H, t, J=6.3 Hz), 2.09 (3H, s).

ESI-MS Found: m/z[M+H]+ 236.

Production Example 8

Production of 4-[4-(cyclopropylmethyl)piperazin-1-yl]-3-methylaniline

1) Production of 1-(cyclopropylmethyl)-4-(2-ethyl-4-nitrophenyl)piperazine

In the same manner as in Production Example 5-1, but using 4-(cyclopropylmethyl)piperazine in place of N-ethylpiperazine used in Production Example 5-1, using 2-fluoro-5-nitrotoluene in place of 2-fluoro-5-nitrobenzyl alcohol, using N,N-diisopropylethylamine in place of potassium carbonate, and using dimethylsulfoxide in place of N-methylpyrrolidone, 280 mg of the entitled compound was obtained as a yellow solid.
$^1$H-NMR (400 MHz, CDCl$_3$) δ: 8.02 (1H, s), 8.03 (1H, d, J=8.7 Hz), 6.99 (1H, d, J=8.7 Hz), 3.04-3.10 (4H, m), 2.67-2.751 (4H, m), 2.36 (3H, s), 2.33 (2H, s), 0.82-0.97 (1H, m), 0.51-0.58 (2H, m), 0.11-0.17 (2H, m).

2) Production of 4-[4-(cyclopropylmethyl)piperazin-1-yl]-3-methylaniline

In the same manner as in Production Example 5-2, but using 1-(cyclopropylmethyl)-4-(2-methyl-4-nitrophenyl)piperazine in place of [5-nitro-2-(4-ethylpiperazin-1-yl)phenyl]methanol used in Production Example 5-2, 230 mg of the entitled compound was obtained as a white solid.
$^1$H-NMR (400 MHz, DMSO-d$_6$) δ: 6.67 (1H, d, J=8.3 Hz), 6.30 (1H, d, J=2.4 Hz), 6.26 (1H, dd, J=8.3, 2.4 Hz), 4.55 (2H, s), 2.61 (4H, t, J=4.4 Hz), 2.51-2.38 (4H, m), 2.12 (2H, d, J=6.8 Hz), 2.02 (3H, s), 0.79-0.71 (1H, m), 0.41-0.35 (2H, m), 0.02-0.03 (2H, m).
ESI-MS Found: m/z[M+H]+ 246.

Production Example 9

Production of 4-(4-cyclopropylpiperazin-1-yl)-3-methylaniline

1) Production of 1-(2-methyl-4-nitrophenyl)piperazine hydrochloride

In the same manner as in Production Example 5-1, but using tert-butyl piperazine-1-carboxylate in place of N-ethylpiperazine used in Production Example 5-1, using 2-fluoro-5-nitrotoluene in place of 2-fluoro-5-nitrobenzyl alcohol, using N,N-diisopropylethylamine in place of potassium carbonate, and using dimethylsulfoxide in place of N-methylpyrrolidone, 4.91 g of crude tert-butyl 4-[2-methyl-4-nitrophenyl]piperazine-1-carboxylate was obtained as a yellow solid.
4 N hydrochloric acid/ethyl acetate solution was added to methanol (50 mL) solution of the compound obtained in the above reaction, and stirred at room temperature for 30 minutes. The reaction liquid was concentrated under reduced pressure to obtain 3.86 g of crude 4-(2-methyl-4-nitrophenyl)piperazine hydrochloride.

2) Production of 1-cyclopropyl-4-(2-methyl-4-nitrophenyl)piperazine 0.777 mL of [(1-ethoxycyclopropyl)-oxy]trimethylsilane, 244 mg of sodium cyanoborohydride and 0.1 mL of acetic acid were added to methanol (20 mL) solution of 500 mg of the compound obtained in Production Example 9-1, and stirred at room temperature for 15 hours. The reaction liquid was concentrated under reduced pressure, and the residue was made basic with aqueous 2 N sodium hydroxide solution added thereto. This was extracted with chloroform, the organic layer was dried with anhydrous magnesium sulfate, and the solvent was evaporated away. The crude product was purified through silica gel column chromatography (hexane/ethyl acetate) to obtain 441 mg of the entitled compound as a yellow solid.
$^1$H-NMR (400 MHz, CDCl$_3$) δ: 8.03 (1H, s), 8.02 (1H, d, J=8.8 Hz), 6.97 (1H, d, J=8.8 Hz), 2.96-3.03 (4H, m), 2.76-2.81 (4H, m), 2.36 (3H, s), 1.66-1.73 (1H, m), 0.42-0.50 (4H, m).
ESI-MS Found: m/z[M+H]+ 262.

3) Production of 4-(4-cyclopropylpiperazin-1-yl)-3-methylaniline

In the same manner as in Production Example 5-2, but using 1-cyclopropyl-4-(2-methyl-4-nitrophenyl)piperazine in place of [5-nitro-2-(4-ethylpiperazin-1-yl)phenyl]methanol used in Production Example 5-2, 326 mg of the entitled compound was obtained as a white solid.
$^1$H-NMR (400 MHz, DMSO-d$_6$) δ: 6.41 (1H, d, J=8.3 Hz), 6.07 (1H, d, J=2.4 Hz), 6.02 (1H, dd, J=8.3, 2.4 Hz), 4.33 (2H, s), 2.37-2.28 (4H, m), 2.21-2.17 (4H, m), 1.80 (3H, s), 1.36-1.31 (1H, m), 0.11 (2H, td, J=6.3, 4.1 Hz), 0.01-0.03 (2H, m).
ESI-MS Found: m/z[M+H]+ 232.

Production Example 10

Production of [5-amino-2-(4-cyclopropylpiperazin-1-yl)phenyl]methanol

1) Production of (5-nitro-2-piperazin-1-ylphenyl)methanol hydrochloride

In the same manner as in Production Example 5-1, but using tert-butyl piperazine-1-carboxylate in place of N-ethylpiperazine used in Production Example 5-1, using N,N-diisopropylethylamine in place of potassium carbonate, and using dimethylsulfoxide in place of N-methylpyrrolidone, 5.6 g of crude tert-butyl 4-[2-(hydroxymethyl)-4-nitrophenyl]piperazine-1-carboxylate was obtained as a yellow solid.
4 N hydrochloric acid/ethyl acetate solution was added to methanol (50 mL) solution of 5.6 g of the compound obtained in the above reaction, and stirred at room temperature for 30 minutes. The reaction liquid was concentrated under reduced pressure to obtain 4.5 g of crude (5-nitro-2-piperazin-1-ylphenyl)methanol hydrochloride as a white solid.

2) Production of [2-(4-cyclopropylpiperazin-1-yl)-5-nitrophenyl]methanol

In the same manner as in Production Example 9-2, but using (5-nitro-2-piperazin-1-ylphenyl)methanol in place of 4-(2-methyl-4-nitrophenyl)piperazine hydrochloride used in Production Example 9-2, 0.4 g of the entitled compound was obtained as a yellow solid.
$^1$H-NMR (400 MHz, CDCl$_3$) δ: 8.26 (1H, d, J=2.9 Hz), 8.13 (1H, dd, J=8.8, 2.9 Hz), 7.14 (1H, d, J=8.8 Hz), 4.81 (2H, s), 3.45 (1H, s), 3.07-3.00 (4H, m), 2.87-2.78 (4H, m), 1.76-1.69 (1H, m), 0.56-0.40 (4H, m).

3) Production of 5-amino-2-(4-cyclopropylpiperazin-1-yl)phenyl]methanol

In the same manner as in Production Example 5-2, but using [2-(4-cyclopropylpiperazin-1-yl)-5-nitrophenyl]methanol in place of [5-nitro-2-(4-ethylpiperazin-1-yl)phenyl]methanol used in Production Example 5-2, 340 mg of the entitled compound was obtained as a white solid.

$^1$H-NMR (400 MHz, DMSO-d$_6$) δ: 6.47 (1H, d, J=8.3 Hz), 6.35 (1H, d, J=2.4 Hz), 6.07 (1H, dd, J=8.3, 2.4 Hz), 4.65 (1H, t, J=5.6 Hz), 4.44 (2H, s), 4.16 (2H, d, J=5.6 Hz), 2.37-2.27 (4H, m), 2.20-2.19 (4H, m), 1.36-1.32 (1H, m), 0.11 (2H, td, J=6.2, 4.2 Hz), 0.01-0.02 (2H, m).

ESI-MS Found: m/z[M+H]+ 248.

Production Example 11

Production of 4-(4-isopropylpiperazin-1-yl)-3-methylaniline

1) Production of 1-isopropyl-4-(2-methyl-4-nitrophenyl)piperazine 1.13 g of acetone and 183 mg of sodium cyanoborohydride were added to ethanol (20 mL) solution of 500 mg of the compound obtained in Production Example 9-1, and stirred at room temperature for 15 hours. The reaction liquid was concentrated under reduced pressure, and made basic with aqueous 2 N sodium hydroxide solution added thereto. This was extracted with chloroform, the organic layer was dried with anhydrous magnesium sulfate, and the solvent was evaporated away. The crude product was purified through silica gel column chromatography (hexane/ethyl acetate) to obtain 120 mg of the entitled compound as a yellow solid.

2) Production of 4-(4-isopropylpiperazin-1-yl)-3-methylaniline

In the same manner as in Production Example 5-2, but using 1-isopropyl-4-(2-methyl-4-nitrophenyl)piperazine in place of [5-nitro-2-(4-ethylpiperazin-1-yl)phenyl]methanol used in Production Example 5-2, 91 mg of the entitled compound was obtained as a white solid.

$^1$H-NMR (400 MHz, DMSO-d$_6$) δ: 6.73 (1.0H, d, J=8.3 Hz), 6.37 (1.0H, d, J=2.4 Hz), 6.32 (1.0H, dd, J=8.3, 2.4 Hz), 4.62 (2.0H, s), 2.66 (4.0H, t, J=4.9 Hz), 2.66-2.60 (1.0H, m), 2.54-2.47 (4.0H, m), 2.09 (3.0H, s), 0.98 (6.0H, d, J=6.3 Hz).

ESI-MS Found: m/z[M+H]+ 234.

Production Example 12

Production of {5-amino-2-[4-(methoxyacetyl)piperazin-1-yl]phenyl}methanol

1) Production of {2-[4-(methoxyacetyl)piperazin-1-yl]-5-nitrophenyl}methanol 0.167 mL of methoxyacetyl chloride and 506 mg of potassium carbonate were added to tetrahydrofuran (20 mL)-N,N-dimethylformamide (5 mL) solution of 500 mg of the compound obtained in Production Example 9-1, and stirred at room temperature for 2 hours. Water was added to the reaction liquid, extracted with chloroform, and the organic layer was dried with anhydrous magnesium sulfate. The solvent was evaporated away to obtain 135 mg of crude {2-[4-(methoxyacetyl)piperazin-1-yl]-5-nitrophenyl}methanol as a yellow solid.

2) Production of {5-amino-2-[4-(methoxyacetyl)piperazin-1-yl]phenyl}methanol In the same manner as in Production Example 5-2, but using {2-[4-(methoxyacetyl)piperazin-1-yl]-5-nitrophenyl}methanol in place of [5-nitro-2-(4-ethylpiperazin-1-yl)phenyl]methanol used in Production Example 5-2, the entitled compound was obtained as a white solid.

$^1$H-NMR (400 MHz, DMSO-d$_6$) δ: 6.76 (1.0H, d, J=8.3 Hz), 6.67 (1.0H, d, J=2.4 Hz), 6.38 (1.0H, dd, J=8.3, 2.4 Hz), 4.89 (1.0H, t, J=5.6 Hz), 4.79 (2.0H, s), 4.48 (2.0H, d, J=5.6 Hz), 4.09 (2.0H, s), 3.54-3.41 (4.0H, m), 3.28 (3.0H, s), 2.70-2.62 (4.0H, m).

ESI-MS Found: m/z[M+H]+ 280.

Production Example 13

Production of 4-{4-[2-(methylsulfonyl)ethyl]piperazin-1-yl}aniline]

1) Production of 1-(4-nitrophenyl)piperazine hydrochloride

In the same manner as in Production Example 9-1, but using 4-fluoronitrobenzene in place of 2-fluoro-5-nitrotoluene used in Production Example 9-1, 4.33 g of crude 4-(4-nitrophenyl)piperazine hydrochloride was obtained.

2) Production of 1-[2-(methylsulfonyl)ethyl]-4-(4-nitrophenyl)piperazine 0.49 mL of methylvinyl sulfone and 0.5 mL of N,N-diisopropylethylamine were added to ethanol (10 mL) solution of 458 mg of the compound obtained in Production Example 13-1, and stirred at room temperature for 15 hours. Aqueous saturated sodium hydrogencarbonate solution was added to the reaction liquid, and extracted three times with ethyl acetate. The organic layer was washed with saturated saline water, and dried with anhydrous magnesium sulfate. The solvent was evaporated away to obtain crude 1-[2-(methylsulfonyl)ethyl]-4-(4-nitrophenyl)piperazine.

3) Production of 4-{4-[2-(methylsulfonyl)ethyl]piperazin-1-yl}aniline 200 mg of 10% palladium-carbon was added to methanol (20 mL) solution of the compound obtained in Production Example 13-2, and stirred in one-atmospheric hydrogen atmosphere at room temperature for 4 hours. Palladium-carbon was removed through filtration, and the filtrate was concentrated under reduced pressure to obtain 611 mg of the entitled compound.

$^1$H-NMR (400 MHz, DMSO-d$_6$) δ: 6.67 (2H, d, J=8.8 Hz), 6.47 (2H, d, J=8.8 Hz), 4.64 (2H, s), 3.35-3.28 (4H, m), 3.02 (2H, s), 2.92 (3H, s), 2.91-2.86 (4H, m), 2.72 (2H, t, J=6.6 Hz), 2.53 (4H, t, J=4.6 Hz).

ESI-MS Found: m/z[M+H]+ 284.

Production Example 14

Production of 4-(1,1-dioxidothiomorpholin-4-yl)-3-methylaniline

1) Production of 4-(2-methyl-4-nitrophenyl)thiomorpholine 1,1-dioxide

In the same manner as in Production Example 5-1, but using thiomorpholine in place of N-ethylpiperazine used in Production Example 5-1, using 5-nitro-2-fluorotoluene in place of 2-fluoro-5-nitrobenzyl alcohol, using N,N-diisopropylethylamine in place of potassium carbonate, and using dimethylsulfoxide in place of N-methylpyrrolidone, crude 4-(2-methyl-4-nitrophenyl)thiomorpholine was obtained.

19 g of m-chloroperbenzoic acid was added to chloroform (100 mL) solution of the compound obtained in the above reaction, and stirred with cooling with ice for 24 hours. The reaction liquid was washed with aqueous sodium sulfite solution and aqueous saturated sodium hydrogencarbonate solution in that order, and dried with anhydrous sodium sulfate. The solvent was evaporated away under reduced pressure to obtain 4.85 g of the entitled compound.

2) Production of
4-(1,1-dioxidothiomorpholin-4-yl)-3-methylaniline

In the same manner as in Production Example 13-3, but using 4-(2-methyl-4-nitrophenyl)thiomorpholine 1,1-dioxide in place of 1-[2-(methylsulfonyl)ethyl]-4-(4-nitrophenyl)piperazine used in Production Example 13-3, 1.01 g of the entitled compound was obtained as a white solid.
$^1$H-NMR (400 MHz, DMSO-$d_6$) δ: 10.08-9.87 (2H, m), 7.19 (1H, d, J=8.3 Hz), 7.14-7.10 (1H, m), 7.13 (1H, s), 3.26 (8H, s), 2.28 (3H, s).
ESI-MS Found: m/z[M+H]+ 241.

Production Example 15

Production of
4-[2-(dimethylamino)ethoxy]-3-methylaniline

1) Production of
N,N-dimethyl-2-(2-methyl-4-nitrophenoxy)ethylamine

Acetonitrile (30 mL) solution of 2 g of 2-methyl-4-nitrophenol, 1.87 g of 2-dimethylaminoethyl chloride and 5.4 g of potassium carbonate was stirred at 120° C. for 23 hours. The reaction liquid was concentrated under reduced pressure, and the residue was dissolved in ethyl acetate. The organic layer was washed with water, and dried with anhydrous sodium sulfate. The solvent was evaporated away under reduced pressure, and the crude product was purified through silica gel column chromatography (chloroform/methanol) to obtain 600 mg of the entitled compound as a white solid.

2) Production of
4-[2-(dimethylamino)ethoxy]-3-methylaniline

In the same manner as in Production Example 13-3, but using N,N-dimethyl-2-(2-methyl-4-nitrophenoxy)ethylamine in place of 1-[2-(methylsulfonyl)ethyl]-4-(4-nitrophenyl)piperazine used in Production Example 13-3, 542 mg of the entitled compound was obtained as a white solid.
$^1$H-NMR (400 MHz, DMSO-$d_6$) δ: 6.60 (1H, d, J=8.5 Hz), 6.34 (1H, d, J=2.4 Hz), 6.29 (1H, dd, J=8.5, 2.4 Hz), 3.98 (2H, t, J=5.6 Hz), 2.98 (2H, t, J=5.6 Hz), 2.49 (6H, s), 2.00 (3H, s).
ESI-MS Found: m/z[M+H]+ 195.

Production Example 16

Production of
4-[2-(dimethylamino)ethoxy]-3,5-dimethylaniline

1) Production of 2-(2,6-dimethyl-4-nitrophenoxy)-N,N-dimethylethylamine 3.4 mL of diisopropyl azodicarboxylate was added to 1.9 g of 2,6-dimethyl-4-nitrophenol and 1.71 mL of 2-dimethylaminoethanol, and stirred at room temperature for 16 hours. The reaction liquid was diluted with ethyl acetate, and the organic layer was extracted with 2 N hydrochloric acid. The aqueous layer was made basic with aqueous 2 N sodium hydroxide solution, and then extracted with ethyl acetate. The organic layer was dried with anhydrous sodium sulfate, and the solvent was evaporated away under reduced pressure to obtain 667 mg of the entitled compound.

2) Production of
4-[2-(dimethylamino)ethoxy]-3,5-dimethylaniline

In the same manner as in Production Example 13-3, but using 2-(2,6-dimethyl-4-nitrophenoxy)-N,N-dimethylethylamine in place of 1-[2-(methylsulfonyl)ethyl]-4-(4-nitrophenyl)piperazine used in Production Example 13-3, 305 mg of the entitled compound was obtained as a white solid.
$^1$H-NMR (400 MHz, DMSO-$d_6$) δ: 6.19 (2H, s), 3.88 (2H, t, J=4.9 Hz), 3.40-3.23 (2H, m), 3.25 (2H, t, J=4.9 Hz), 2.72 (6H, s), 2.09 (6H, s).
ESI-MS Found: m/z[M+H]+ 209.

Production Example 17

Production of
3-methyl-4-(1-methyl-1H-pyrazol-4-yl)aniline

1) Production of 1-methyl-4-(2-methyl-4-nitrophenyl)-1H-pyrazole 5 mL of aqueous 2 M sodium carbonate solution was added to 1,2-dimethoxyethane (10 mL) solution of 216 mg of 2-bromo-5-nitrotoluene, 208 mg of 1-methyl-4-(4,4,5,5-tetramethyl-1,3,2-dioxaboroloran-1-yl)-1H-pyrazole and 10 mg of tetrakis(triphenylphosphine)palladium(0), and heated under reflux for 16 hours. The reaction liquid was washed with water, and the organic layer was dried with anhydrous sodium sulfate. The solvent was evaporated away under reduced pressure, and the crude product was purified through silica gel column chromatography (hexane/ethyl acetate) to obtain 357 mg of the entitled compound as a white solid.
$^1$H-NMR (400 MHz, CDCl$_3$) δ: 8.12 (1H, d, J=2.3 Hz), 8.04 (1H, dd, J=7.3, 2.3 Hz), 7.70 (1H, s), 7.58 (1H, s), 8.12 (1H, d, J=7.3 Hz), 4.00 (3H, s), 2.51 (3H, s).
ESI-MS Found: m/z[M+H]+ 218.

2) Production of 3-methyl-4-(1-methyl-1H-pyrazol-4-yl)aniline

In the same manner as in Production Example 5-2, but using 1-methyl-4-(2-methyl-4-nitrophenyl)-1H-pyrazole in place of [5-nitro-2-(4-ethylpiperazin-1-yl)phenyl]methanol used in Production Example 5-2, 311 mg of the entitled compound was obtained as a white solid.
ESI-MS Found: m/z[M+H]+ 188.

Production Example 18

Production of 3-methyl-4-{1-[2-(methylsulfonyl)ethyl]piperidin-4-yl}aniline

1) Production of 1-[2-(methylsulfonyl)ethyl]-4-(4-nitrophenyl)piperidine

In the same manner as in Production Example 13-2 but using 4-(4-nitrophenyl)piperidine in place of 1-(4-nitrophenyl)piperazine hydrochloride used in Production Example 13-2, the entitled compound was obtained.

2) Production of 3-methyl-4-{1-[2-(methylsulfonyl)ethyl]piperidin-4-yl}aniline In the same manner as in Production Example 13-3 but using 1-[2-(methylsulfonyl)ethyl]-4-(4-nitrophenyl)piperidine in place of 1-[2-(methylsulfonyl)ethyl]-4-(4-nitrophenyl)piperazine used in Production Example 13-3, 390 mg of the entitled compound was obtained as a white solid.

$^1$H-NMR (400 MHz, CDCl$_3$) δ: 7.00 (2H, d, J=8.3 Hz), 6.64 (2H, d, J=8.3 Hz), 3.58 (2H, s), 3.17 (2H, t, J=6.6 Hz), 3.07 (3H, s), 3.02 (2H, d, J=11.7 Hz), 2.89 (2H, t, J=6.6 Hz), 2.41 (1H, tt, J=12.0, 3.7 Hz), 2.15 (2H, td, J=11.7, 2.4 Hz), 1.84 (2H, d, J=12.0 Hz), 1.66 (2H, ddd, J=25.4, 12.0, 3.7 Hz).

ESI-MS Found: m/z[M+H]+ 283.

Production Example 19

Production of 2-methyl-N$^1$-(1-methylpiperidin-4-yl)benzene-1,4-diamine

1) Production of 1-methyl-N-(2-methyl-4-nitrophenyl)piperidine-4-amine

In the same manner as in Production Example 5-1 but using 1-methylpiperidine-4-amine in place of N-ethylpiperazine used in Production Example 5-1, using 2-fluoro-5-nitrotoluene in place of 2-fluoro-5-nitrobenzyl alcohol and using dimethylsulfoxide in place of N-methylpyrrolidone, 1.2 g of the entitled compound was obtained as a yellow solid.

$^1$H-NMR (400 MHz, CD$_3$OD) δ: 7.99 (1H, dd, J=9.2, 2.7 Hz), 7.92 (1H, d, J=2.7 Hz), 6.68 (1H, d, J=9.2 Hz), 3.57-3.48 (1H, m), 2.97-2.89 (2H, m), 2.33 (3H, s), 2.30-2.21 (2H, m), 2.19 (3H, s), 2.09-2.01 (2H, m), 1.73-1.61 (2H, m).

2) Production of 2-methyl-N$^1$-(1-methylpiperidin-4-yl)benzene-1,4-diamine In the same manner as in Production Example 13-3 but using 1-methyl-N-(2-methyl-4-nitrophenyl)piperidine-4-amine in place of 1-[2-(methylsulfonyl)ethyl]-4-(4-nitrophenyl)piperazine used in Production Example 13-3, 1.05 g of the entitled compound was obtained as a blue-violet solid.

$^1$H-NMR (400 MHz, CDCl$_3$) δ: 6.38-6.29 (3H, m), 3.17 (1H, d, J=4.9 Hz), 3.09-2.98 (1H, m), 2.83-2.73 (2H, m), 2.23 (3H, s), 2.16-2.04 (2H, m), 1.99 (3H, s), 1.90-1.82 (2H, m), 1.47-1.35 (2H, m).

ESI-MS Found: m/z[M+H]+ 220.

Production Example 20

Production of 3-methyl-4-[4-(methylsulfonyl)piperazin-1-yl]aniline

1) Production of 1-(2-methyl-4-nitrophenyl)-4-(methylsulfonyl)piperazine

In the same manner as in Production Example 12-1 but using methanesulfonyl chloride in place of methoxyacetyl chloride used in Production Example 12-1, 297 mg of the entitled compound was obtained as an orange solid.

$^1$H-NMR (400 MHz, CDCl$_3$) δ: 8.10-8.04 (2H, m), 7.04 (1H, d, J=8.3 Hz), 3.46-3.40 (4H, m), 3.15-3.10 (4H, m), 2.87 (3H, s), 2.38 (3H, s).

ESI-MS Found: m/z[M+H]+ 300.

2) Production of 3-methyl-4-[4-(methylsulfonyl)piperazin-1-yl]aniline

In the same manner as in Production Example 13-3 but using 1-(2-methyl-4-nitrophenyl)-4-(methylsulfonyl)piperazine in place of 1-[2-(methylsulfonyl)ethyl]-4-(4-nitrophenyl)piperazine used in Production Example 13-3, 219 mg of the entitled compound was obtained as a pale brown solid.

$^1$H-NMR (400 MHz, CDCl$_3$) δ: 6.87 (1H, d, J=8.4 Hz), 6.57 (1H, d, J=2.8 Hz), 6.53 (1H, dd, J=8.4, 2.8 Hz), 3.63 (2H, brs), 3.40-3.31 (4H, m), 2.95-2.90 (4H, m), 2.84 (3H, s), 2.23 (3H, s).

ESI-MS Found: m/z[M+H]+ 270.

Production Example 21

Production of 4-[(1-isopropylazetidin-3-yl)oxy]-3-methylaniline

1) Production of 3-(2-methyl-4-nitrophenoxy)azetidine hydrochloride

Tert-butyl 3-(2-methyl-4-nitrophenoxy)azetidine-1-carboxylate was obtained in the same manner as in Production Example 16-1, for which, however, 2-methyl-4-nitrophenol was used in place of 2,6-dimethyl-4-nitrophenol used in Production Example 16-1, and tert-butyl 3-hydroxyazetidine-1-carboxylate was used in place of 2-dimethylaminoethanol.

4 N hydrochloric acid/ethyl acetate solution was added to methanol (50 mL) solution of the compound obtained in the above reaction, and stirred at room temperature for 30 minutes. The reaction liquid was concentrated under reduced pressure to obtain 1.46 g of 3-(2-methyl-4-nitrophenoxy)azetidine hydrochloride as a colorless solid.

$^1$H-NMR (400 MHz, DMSO-d$_6$) δ: 9.37 (2H, brs), 8.14 (1H, d, J=2.9 Hz), 8.06 (1H, dd, J=9.0, 2.9 Hz), 6.93 (1H, d, J=9.0 Hz), 5.23 (1H, tt, J=6.6, 4.8 Hz), 4.47 (2H, dd, J=12.5, 6.6 Hz), 4.02 (2H, dd, J=12.5, 4.8 Hz), 2.30 (3H, s).

ESI-MS Found: m/z[M+H]+ 209.

2) Production of 1-isopropyl-3-(2-methyl-4-nitrophenoxy)azetidine

In the same manner as in Production Example 11-1 but using 3-(2-methyl-4-nitrophenoxy)azetidine hydrochloride in place of 1-(2-methyl-4-nitrophenyl)piperazine hydrochloride used in Production Example 11-1, 142 mg of the entitled compound was obtained as a pale yellow solid.

$^1$H-NMR (400 MHz, CDCl$_3$) δ: 8.09-8.02 (2H, m), 6.63-6.58 (1H, m), 4.84 (1H, quint, J=5.8 Hz), 3.91-3.84 (2H, m), 3.17-3.10 (2H, m), 2.43 (1H, sept, J=6.2 Hz), 2.29 (3H, s), 0.99 (6H, d, J=6.2 Hz).

ESI-MS Found: m/z[M+H]+ 251.

3) Production of 4-[(1-isopropylazetidin-3-yl)oxy]-3-methylaniline

In the same manner as in Production Example 13-3 but using 1-(2-methyl-4-nitrophenyl)-4-(methylsulfonyl)piperazine in place of 1-[2-(methylsulfonyl)ethyl]-4-(4-nitrophenyl)piperazine used in Production Example 13-3, 107 mg of the entitled compound was obtained as a pale brown solid.

$^1$H-NMR (400 MHz, CDCl$_3$) δ: 6.55-6.52 (1H, m), 6.47-6.40 (2H, m), 4.64 (1H, quint, J=6.0 Hz), 3.85-3.78 (2H, m), 3.37 (2H, brs), 3.07-3.00 (2H, m), 2.40 (1H, sept, J=6.2 Hz), 2.15 (3H, s), 0.97 (6H, d, J=6.2 Hz).
ESI-MS Found: m/z[M+H]+ 221.

Production Example 22

Production of 3-[4-(4-aminophenylpiperazin-1-yl)]propanenitrile

1) Production of 3-[4-(4-nitrophenyl)piperazin-1-yl]propanenitrile

In the same manner as in Production Example 13-2 but using acrylonitrile in place of methylvinyl sulfone used in Production Example 13-2, 1.08 g of the entitled compound was obtained as a yellow solid.

2) Production of 3-[4-(4-aminophenylpiperazin-1-yl)]propanenitrile

In the same manner as in Production Example 5-2 but using 3-[4-(4-nitrophenyl)piperazin-1-yl]propanenitrile in place of [5-nitro-2-(4-ethylpiperazin-1-yl)phenyl]methanol used in Production Example 5-2, 159 mg of the entitled compound was obtained as a light brown solid.
$^1$H-NMR (400 MHz, CDCl$_3$) δ: 6.83 (2H, d, J=8.4 Hz), 6.65 (2H, d, J=8.4 Hz), 3.08 (4H, brs), 2.76 (2H, t, J=6.8 Hz), 2.69 (4H, brs), 2.56 (2H, t, J=6.8 Hz).
ESI-MS Found: m/z[M+H]+ 231.

Production Example 23

Production of 1-[4-(4-aminophenyl)piperazin-1-yl]-3-fluoropropan-2-ol

1) Production of 1-fluoro-3-[4-(4-nitrophenyl)piperazin-1-yl]propan-2-ol

Ethanol (15 mL) solution of 272 mg of epifluorohydrin and 500 mg of 1-(4-nitrophenyl)piperazine was heated under reflux for 15 hours, and then the reaction liquid was concentrated under reduced pressure. The residue was solidified from ethyl acetate to obtain 300 mg of the entitled compound as a yellow solid.

2) Production of 1-[4-(4-aminophenyl)piperazin-1-yl]-3-fluoropropan-2-ol

In the same manner as in Production Example 5-2 but using 1-fluoro-3-[4-(4-nitrophenyl)piperazin-1-yl]propan-2-ol in place of [5-nitro-2-(4-ethylpiperazin-1-yl)phenyl]methanol used in Production Example 5-2, 169 mg of the entitled compound was obtained as a brown liquid.
ESI-MS Found: m/z[M+H]+ 254.

Production Example 24

Production of 1-[4-(4-aminophenyl)piperazin-1-yl]-2-methylpropan-2-ol

1) Production of 2-methyl-1-[4-(4-nitrophenyl)piperazin-1-yl]propan-2-ol

In the same manner as in Production Example 23-1 but using 1,2-epoxy-2-methylpropane in place of epifluorohydrin used in Production Example 23-1, 250 mg of the entitled compound was obtained as a yellow solid.

2) Production of 1-[4-(4-aminophenyl)piperazin-1-yl]-2-methylpropan-2-ol

In the same manner as in Production Example 5-2 but using 2-methyl-1-[4-(4-nitrophenyl)piperazin-1-yl]propan-2-ol in place of [5-nitro-2-(4-ethylpiperazin-1-yl)phenyl]methanol used in Production Example 5-2, 180 mg of the entitled compound was obtained as a brown solid.
$^1$H-NMR (400 MHz, CDCl$_3$) δ: 6.81 (2H, d, J=8.4 Hz), 6.65 (2H, d, J=8.4 Hz), 3.08 (4H, brs), 2.83 (4H, brs), 2.43 (2H, s), 1.21 (6H, s).
ESI-MS Found: m/z[M+H]+ 250.

Production Example 25

Production of 2-[4-(4-aminophenyl)piperazin-1-yl]cyclopentanol

1) Production of 2-[4-(4-nitrophenyl)piperazin-1-yl]cyclopentanol

In the same manner as in Production Example 23-1 but using cyclopentene oxide in place of epifluorohydrin used in Production Example 23-1, 670 mg of the entitled compound was obtained as a yellow solid.

2) Production of 2-[4-(4-aminophenyl)piperazin-1-yl]cyclopentanol

In the same manner as in Production Example 5-2 but using 2-[4-(4-nitrophenyl)piperazin-1-yl]cyclopentanol in place of [5-nitro-2-(4-ethylpiperazin-1-yl)phenyl]methanol used in Production Example 5-2, 159 mg of the entitled compound was obtained as a brown liquid.
$^1$H-NMR (400 MHz, CDCl$_3$) δ: 6.81 (2H, d, J=8.4 Hz), 6.65 (2H, d, J=8.4 Hz), 4.20-4.24 (1H, m), 3.11 (4H, brs), 2.81 (4H, brs), 2.58-2.64 (1H, m), 1.94-2.03 (2H, m), 1.59-1.74 (4H, m).
ESI-MS Found: m/z[M+H]+ 262.

Production Example 26

Production of 4-(4-aminophenyl)-N,N-dimethylpiperazine-1-carboxamide

1) Production of N,N-dimethyl-4-(4-nitrophenyl)piperazine-1-carboxamide

In the same manner as in Production Example 12-1 but using dimethylcarbamoyl chloride in place of methoxyacetyl chloride used in Production Example 12-1, 560 mg of the entitled compound was obtained as a yellow solid.

2) Production of 4-(4-aminophenyl)-N,N-dimethylpiperazine-1-carboxamide

In the same manner as in Production Example 13-3 but using N,N-dimethyl-4-(4-nitrophenyl)piperazine-1-carboxamide in place of 1-[2-(methylsulfonyl)ethyl]-4-(4-nitrophenyl)piperazine used in Production Example 13-3, 176 mg of the entitled compound was obtained as a brown solid.
$^1$H-NMR (400 MHz, CDCl$_3$) δ: 6.86 (2H, d, J=8.4 Hz), 6.65 (2H, d, J=8.4 Hz), 3.42 (4H, brs), 3.05 (4H, brs), 2.86 (6H, s).
ESI-MS Found: m/z[M+H]+ 249.

Production Example 27

Production of 4-[4-(1-acetylazetidin-3-yl)piperazin-1-yl]aniline

1) Production of 1-(1-acetylazetidin-3-yl)-4-(4-nitrophenyl)piperazine 0.581 mL of triethylamine and 0.185 mL of methanesulfonyl chloride were added to chloroform (15 mL) solution of 500 mg of N-(diphenylmethyl)-3-hydroxyazetidine, and stirred at room temperature for 3 hours. Aqueous sodium carbonate solution was added to the reaction liquid, extracted with chloroform, dried with sodium sulfate, and evaporated under reduced pressure to obtain crude N-(diphenylmethyl)-3-(methanesulfonyloxy)azetidine. 433 mg of 1-(4-nitrophenyl)piperazine and 433 mg of potassium carbonate were added to DMSO (10 mL) solution of the compound obtained in the above reaction, and heated at 100° C. for 3 hours. Water was added to the reaction liquid, extracted with ethyl acetate, and the organic layer was washed with saturated saline water. The organic layer was dried with sodium sulfate, concentrated under reduced pressure, and the crude product was purified through column chromatography (ethyl acetate/hexane=2/1). A catalytic amount of trifluoroborane ether solution was added to acetic anhydride (6 mL) solution of the obtained diphenylmethyl compound, and heated at 90° C. for 4 hours. The reaction liquid was concentrated under reduced pressure, sodium hydrogencarbonate was added to the residue, and extracted with chloroform. The organic layer was dried with sodium sulfate, and then concentrated under reduced pressure. The crude product was purified through column chromatography (methanol/chloroform=1/10), and then solidified from ethyl acetate/hexane to obtain 160 mg of the entitled compound as a yellow solid.

2) Production of 4-[4-(1-acetylazetidin-3-yl)piperazin-1-yl]aniline

In the same manner as in Production Example 5-2 but using 1-(1-acetylazetidin-3-yl)-4-(4-nitrophenyl)piperazine in place of [5-nitro-2-(4-ethylpiperazin-1-yl)phenyl]methanol used in Production Example 5-2, 110 mg of the entitled compound was obtained as a brown solid.

$^1$H-NMR (400 MHz, CDCl$_3$) δ: 6.82 (2H, d, J=8.4 Hz), 6.66 (2H, d, J=8.4 Hz), 3.85-4.15 (4H, m), 3.18-3.25 (1H, m), 3.08 (4H, brs), 2.54 (4H, brs), 1.87 (3H, s).
ESI-MS Found: m/z[M+H]+ 275.

Production Example 28

Production of 2-[4-(4-aminophenyl)piperazin-1-yl]-N,N-dimethylacetamide

1) Production of N,N-dimethyl-2-[4-(4-nitrophenyl)piperazin-1-yl]acetamide

In the same manner as in Production Example 27-1 but using 2-chloro-N,N-dimethylacetamide in place of N-(diphenylmethyl)-3-(methanesulfonyloxy)azetidine used in Production Example 27-1, 1.53 g of the entitled compound was used as a yellow solid.

2) Production of 2-[4-(4-aminophenyl)piperazin-1-yl]-N,N-dimethylacetamide

In the same manner as in Production Example 5-2 but using N,N-dimethyl-2-[4-(4-nitrophenyl)piperazin-1-yl]acetamide in place of 1-[2-(methylsulfonyl)ethyl]-4-(4-nitrophenyl)piperazine used in Production Example 5-2, 1.2 g of the entitled compound was obtained as a brown solid.

$^1$H-NMR (CDCl$_3$) δ: 6.82 (2H, d, J=8.4 Hz), 6.65 (2H, d, J=8.4 Hz), 3.23 (2H, s), 3.09 (4H, brs), 3.08 (3H, s), 2.96 (3H, s), 2.70 (4H, brs).
ESI-MS Found: m/z[M+H]+ 263.

Example 1

Production of 3-(2-allyl-6-{[4-(4-methylpiperazin-1-yl)phenyl]amino}-3-oxo-1,2-dihydro-3H-pyrazolo[3,4-d]pyrimidin-1-yl)-N,N-dimethylbenzamide

1) Production of methyl 3-[2-allyl-6-(methylthio)-3-oxo-1,2-dihydro-3H-pyrazolo[3,4-d]pyrimidin-1-yl]benzoate 20 mL of pyridine was added to a chloroform solution of 7.5 g of 2-allyl-6-(methylthio)-1,2-dihydro-3H-pyrazolo[3,4-d]pyrimidin-3-one, 6.1 g of copper(II) acetate and 10 g of [3-(methoxycarbonyl)]phenylboronic acid, and stirred at room temperature for 3 days. Aqueous 30% ammonia solution and saturated saline water were added to the reaction liquid in that order, and extracted with chloroform. The organic layer was washed with saturated saline water, then dried with anhydrous magnesium sulfate, and the solvent was evaporated away. The crude product was purified through silica gel column chromatography (hexane/ethyl acetate) to obtain 6.7 g of methyl 3-[2-allyl-6-(methylthio)-3-oxo-1,2-dihydro-3H-pyrazolo[3,4-d]pyrimidin-1-yl]benzoate as a yellow oily substance.

$^1$H-NMR (400 MHz, CDCl$_3$) δ: 8.92 (1H, s), 8.11-8.06 (2H, m), 7.65-7.59 (2H, m), 5.68 (1H, ddd, J=17.1, 10.2, 5.9 Hz), 5.13 (1H, dd, J=10.2, 1.0 Hz), 4.97 (1H, dd, J=17.1, 1.0 Hz), 4.45 (2H, d, J=5.9 Hz), 3.96 (3H, s), 2.51 (3H, s).

2) Production of methyl 3-[2-allyl-6-(methylsulfinyl)-3-oxo-1,2-dihydro-3H-pyrazolo[3,4-d]pyrimidin-1-yl]benzoate At 0° C., 6.5 g of m-chloroperbenzoic acid was added to a chloroform solution of 6.7 g of the compound obtained in the above reaction, and stirred for 30 minutes. Aqueous saturated sodium hydrogencarbonate solution was added to the reaction liquid, and extracted with chloroform/isopropanol (80/20). The organic layer was dried with anhydrous magnesium sulfate, and the solvent was evaporated away to obtain 5.6 g of crude methyl 3-[2-allyl-6-(methylsulfinyl)-3-oxo-1,2-dihydro-3H-pyrazolo[3,4-d]pyrimidin-1-yl]benzoate.

3) Production of methyl 3-(2-allyl-6-{[4-(4-methylpiperazin-1-yl)phenyl]amino}-3-oxo-1,2-dihydro-3H-pyrazolo[3,4-d]pyrimidin-1-yl)benzoate 0.87 g of 4-(4-methyl-1-piperazinyl)aniline and 2 mL of N,N-diisopropylethylamine were added to a toluene solution of 1.7 g of the crude product obtained in the above reaction, and stirred at 70° C. for 12 hours. The solvent was evaporated away, and the product was purified through silica gel column chromatography (chloroform/methanol) to obtain 2.2 g of methyl 3-(2-allyl-6-{[4-(4-methylpiperazin-1-yl)phenyl]amino}-3-oxo-1,2-dihydro-3H-pyrazolo[3,4-d]pyrimidin-1-yl)benzoate as a pale yellow solid.

$^1$H-NMR (400 MHz, CDCl$_3$) δ: 8.81 (1H, s), 8.18-8.13 (1H, m), 8.04 (1H, d, J=7.8 Hz), 7.66-7.56 (2H, m), 7.45 (2H, d, J=8.5 Hz), 6.88 (2H, d, J=8.5 Hz), 5.68 (1H, ddd, J=17.1, 10.2, 6.3 Hz), 5.10 (1H, dd, J=10.2, 1.0 Hz), 4.98 (1H, dd, J=17.1, 1.0 Hz), 4.40 (2H, d, J=6.3 Hz), 3.97 (3H, s), 3.26-3.21 (4H, m), 2.72-2.64 (4H, m), 2.43 (3H, brs).

4) Production of 3-(2-allyl-6-{[4-(4-methylpiperazin-1-yl)phenyl]amino}-3-oxo-1,2-dihydro-3H-pyrazolo[3,4-d]pyrimidin-1-yl)-N,N-dimethylbenzamide Aqueous 1 N sodium hydroxide solution was added to a 1,4-dioxane/methanol (50/50) solution of 2.2 g of methyl 3-(2-allyl-6-{[4-(4-methylpiperazin-1-yl)phenyl]amino}-3-oxo-1,2-dihydro-3H-pyrazolo[3,4-d]pyrimidin-1-yl]benzoate, and stirred at room temperature for 2.5 hours. This was neutralized with 1 N hydrochloric acid, and the solvent was evaporated away to obtain a free carboxylic acid of the starting ester. To an N,N-dimethylformamide solution of the resulting carboxylic acid, added were 1.67 g of 1-(3-dimethylaminopropyl)-3-ethylcarbodiimide hydrochloride, 1.18 g of 1-hydroxybenzotriazole, and 11 mL of 1.0 M dimethylamine/tetrahydrofuran solution, and stirred at room temperature for 6 hours. Aqueous saturated sodium hydrogencarbonate solution and water were added to the reaction liquid, extracted with chloroform/isopropanol (80/20), and purified through silica gel column chromatography (chloroform/methanol) to obtain 560 mg of 3-(2-allyl-6-{[4-(4-methylpiperazin-1-yl)phenyl]amino}-3-oxo-1,2-dihydro-3H-pyrazolo[3,4-d]pyrimidin-1-yl)-N,N-dimethylbenzamide as a pale yellow solid.

$^1$H-NMR (400 MHz, CDCl$_3$) δ: 8.81 (1H, s), 7.57-7.51 (2H, m), 7.49-7.38 (4H, m), 6.90 (2H, d, J=8.8 Hz), 5.69 (1H, ddt, J=17.1, 10.2, 6.3 Hz), 5.10 (1H, dd, J=10.2, 1.0 Hz), 5.00 (1H, dd, J=17.1, 1.0 Hz), 4.40 (2H, d, J=6.3 Hz), 3.32 (3H, s), 3.14 (3H, s), 2.99-2.92 (4H, m), 2.84-2.71 (4H, m), 2.50 (3H, s).

ESI-MS Found: m/z[M+H]+ 513.

Example 2

Production of 2-allyl-6-{[3-(hydroxymethyl)-4-(4-methylpiperazin-1-yl)phenyl]amino}-1-phenyl-1,2-dihydro-3H-pyrazolo[3,4-d]pyrimidin-3-one 57 mg of the entitled compound was obtained as a yellow solid in the same manner as in Example 1-1 to 1-3, for which, however, 2-phenyl-1,3,2-dioxaborynan was used in place of [3-(methoxycarbonyl)]phenylboric acid used in Example 1-1, and [5-amino-2-(4-methylpiperazin-1-yl)phenyl]methanol was used in place of 4-(4-methylpiperazin-1-yl)aniline used in Example 1-3.

$^1$H-NMR (400 MHz, CDCl$_3$) δ: 8.83 (1H, s), 7.15-7.62 (8H, m), 5.65-5.76 (1H, m), 5.10 (1H, d, J=10.3 Hz), 4.98 (1H, d, J=17.1 Hz), 4.74 (2H, s), 4.40 (2H, d, J=5.8 Hz), 2.97-3.06 (4H, m), 2.51-2.77 (4H, m), 2.38 (3H, s).

ESI-MS Found: m/z[M+H]+ 472.

Example 3

Production of 2-allyl-6-{[3-(hydroxymethyl)-4-(4-methylpiperazin-1-yl)phenyl]amino}-1-(3-thienyl)-1,2-dihydro-3H-pyrazolo[3,4-d]pyrimidin-3-one 17.5 mg of the entitled compound was obtained as a yellow solid in the same manner as in Example 1-1 to 1-3, for which, however, 3-thienylboronic acid was used in place of [3-(methoxycarbonyl)]phenylboric acid used in Example 1-1, and [5-amino-2-(4-methylpiperazin-1-yl)phenyl]methanol was used in place of 4-(4-methylpiperazin-1-yl)aniline used in Example 1-3.

$^1$H-NMR (400 MHz, CDCl$_3$) δ: 8.82 (1H, s), 7.17-7.63 (6H, m), 5.65-5.77 (1H, m), 5.13 (1H, d, J=10.2 Hz), 5.04 (1H, d, J=17.1 Hz), 4.76 (2H, s), 4.42 (2H, d, J=6.3 Hz), 2.98-3.06 (4H, m), 2.50-2.76 (4H, m), 2.39 (3H, s).

ESI-MS Found: m/z[M+H]+ 478.

Example 4

Production of 2-allyl-6-{[3-(hydroxymethyl)-4-morpholin-4-ylphenyl]amino}-1-(3-thienyl)-1,2-dihydro-3H-pyrazolo[3,4-d]pyrimidin-3-one 35.8 mg of the entitled compound was obtained as a yellow solid in the same manner as in Example 1-1 to 1-3, for which, however, 3-thienylboronic acid was used in place of [3-(methoxycarbonyl)]phenylboric acid used in Example 1-1, and (5-amino-2-morpholin-4-ylphenyl)methanol was used in place of 4-(4-methylpiperazin-1-yl)aniline used in Example 1-3.

$^1$H-NMR (400 MHz, CDCl$_3$) δ: 8.83 (1H, s), 7.67-7.69 (1H, bs), 7.47-7.49 (2H, m), 7.37 (1H, m), 7.15-7.23 (2H, m), 5.66-5.77 (1H, m), 5.14 (1H, d, J=10.3 Hz), 5.04 (1H, d, J=18.5 Hz), 4.77 (2H, s), 4.42 (2H, d, 5.8 Hz), 3.83-3.89 (4H, m), 2.95-2.99 (4H, m).

ESI-MS Found: m/z[M+H]+ 465.

Example 5

Production of 2-allyl-1-[3-(hydroxymethyl)phenyl]-6-{[3-methyl-4-(4-methylpiperazin-1-yl)phenyl]amino}-1,2-dihydro-3H-pyrazolo[3,4-d]pyrimidin-3-one 5.0 mg of the entitled compound was obtained as a yellow solid in the same manner as in Example 1-1 to 1-3, for which, however, [3-(hydroxyethyl)phenyl]boronic acid was used in place of [3-(methoxycarbonyl)]phenylboric acid used in Example 1-1, and 3-methyl-4-(4-methylpiperazin-1-yl)aniline was used in place of 4-(4-methylpiperazin-1-yl)aniline used in Example 1-3.

$^1$H-NMR (400 MHz, CDCl$_3$) δ: 8.80 (1H, s), 7.53-7.45 (2H, m), 7.41-7.32 (4H, m), 6.99 (1H, d, J=8.3 Hz), 5.69 (1H, ddt, J=17.1, 10.2, 6.3 Hz), 5.10 (1H, dd, J=10.2, 1.0 Hz), 4.99 (1H, dd, J=17.1, 1.5 Hz), 4.79 (2H, s), 4.39 (2H, d, J=6.3 Hz), 2.96-2.91 (4H, m), 2.68-2.58 (4H, m), 2.40 (3H, s), 2.26 (3H, s).

ESI-MS Found: m/z[M+H]+ 486.

Example 6

Production of 2-allyl-1-[4-(hydroxymethyl)phenyl]-6-{[3-methyl-4-(4-methylpiperazin-1-yl)phenyl]amino}-1,2-dihydro-3H-pyrazolo[3,4-d]pyrimidin-3-one 5.6 mg of the entitled compound was obtained as a yellow solid in the same manner as in Example 1-1 to 1-3, for which, however, [4-(hydroxymethyl)phenyl]boronic acid was used in place of [3-(methoxycarbonyl)]phenylboric acid used in Example 1-1, and 3-methyl-4-(4-methylpiperazin-1-yl)aniline was used in place of 4-(4-methylpiperazin-1-yl)aniline used in Example 1-3.

$^1$H-NMR (400 MHz, CDCl$_3$) δ: 8.81 (1H, s), 7.52 (2H, d, J=8.8 Hz), 7.50-7.39 (1H, m), 7.44 (2H, d, J=8.8 Hz), 7.26-7.22 (1H, m), 6.97 (1H, d, J=8.3 Hz), 5.69 (1H, ddt, J=17.1, 10.2, 6.3 Hz), 5.10 (1H, dd, J=10.2, 1.0 Hz), 4.98 (1H, dd, J=17.1, 1.0 Hz), 4.78 (2H, s), 4.38 (2H, d, J=6.3 Hz), 2.97-2.89 (4H, m), 2.70-2.55 (4H, m), 2.40 (3H, s), 2.28 (3H, s).

ESI-MS Found: m/z[M+H]+ 486.

Example 7

Production of 3-(2-allyl-6-{[3-methyl-4-(4-methylpiperazin-1-yl)phenyl]amino}-3-oxo-1,2-dihydro-3H-pyrazolo[3,4-d]pyrimidin-1-yl)benzonitrile 62 mg of the entitled compound was obtained as a yellow solid in the same manner as in Example 1-1 to 1-3, for which, however, 3-cyanophenylboronic acid was used in place of [3-(methoxycarbonyl)]phenylboric acid used in Example 1-1, and 3-methyl-4-(4-methylpiperazin-1-yl)aniline was used in place of 4-(4-methylpiperazin-1-yl)aniline used in Example 1-3.

$^1$H-NMR (400 MHz, CDCl$_3$) δ: 8.82 (1H, s), 7.86 (1H, s), 7.69-7.59 (3H, m), 7.36-7.32 (2H, m), 7.06 (1H, d, J=8.8 Hz), 5.68 (1H, ddt, J=17.1, 10.2, 5.9 Hz), 5.13 (1H, dd, J=10.2, 1.0 Hz), 5.00 (1H, dd, J=17.1, 1.0 Hz), 4.38 (2H, d, J=5.9 Hz), 2.98-2.91 (4H, m), 2.66-2.52 (4H, m), 2.38 (3H, s), 2.31 (3H, s).

ESI-MS Found: m/z[M+H]+ 481.

Example 8

Production of 2-allyl-1-(3-methoxyphenyl)-6-{[3-methyl-4-(4-methylpiperazin-1-yl)phenyl]amino}-1,2-dihydro-3H-pyrazolo[3,4-d]pyrimidin-3-one 52 mg of the entitled compound was obtained as a yellow solid in the same manner as in Example 1-1 to 1-3, for which, however, 3-methoxyphenylboronic acid was used in place of [3-(methoxycarbonyl)]phenylboric acid used in Example 1-1, and 3-methyl-4-(4-methylpiperazin-1-yl)aniline was used in place of 4-(4-methylpiperazin-1-yl)aniline used in Example 1-3.

$^1$H-NMR (400 MHz, CDCl$_3$) δ: 8.81 (1H, s), 7.50-7.40 (1H, m), 7.41 (1H, t, J=8.0 Hz), 7.30 (1H, dd, J=8.0, 2.7 Hz), 7.05-6.90 (4H, m), 5.71 (1H, ddt, J=17.1, 10.2, 5.9 Hz), 5.11 (1H, dd, J=10.2, 1.0 Hz), 5.01 (1H, dd, J=17.1, 1.0 Hz), 4.40 (2H, d, J=5.9 Hz), 3.83 (3H, s), 2.94-2.89 (4H, m), 2.64-2.54 (4H, m), 2.37 (3H, s), 2.27 (3H, s).

ESI-MS Found: m/z[M+H]+ 486.

Example 9

Production of 3-(2-allyl-6-{[3-methyl-4-(4-methylpiperazin-1-yl)phenyl]amino}-3-oxo-1,2-dihydro-3H-pyrazolo[3,4-d]pyrimidin-1-yl)-N,N-dimethylbenzamide 30 mg of the entitled compound was obtained as a yellow solid in the same manner as in Example 1-1 to 1-4, for which, however, 3-methyl-4-(4-methylpiperazin-1-yl)aniline was used in place of 4-(4-methylpiperazin-1-yl)aniline used in Example 1-3.

$^1$H-NMR (400 MHz, CDCl$_3$) δ: 8.81 (1H, s), 7.58-7.52 (3H, m), 7.49-7.47 (1H, m), 7.44-7.40 (1H, m), 7.38-7.32 (2H, m), 6.98 (1H, d, J=8.8 Hz), 5.69 (1H, ddt, J=17.1, 10.2, 5.9 Hz), 5.10 (1H, dd, J=10.2, 1.0 Hz), 5.00 (1H, dd, J=17.1, 1.0 Hz), 4.39 (2H, d, J=5.9 Hz), 3.13 (3H, s), 2.97 (3H, s), 2.95-2.91 (4H, m), 2.67-2.55 (4H, m), 2.38 (3H, s), 2.28 (3H, s).

ESI-MS Found: m/z[M+H]+ 527.

Example 10

Production of 3-[2-allyl-6-({4-[4-(2-hydroxyethyl)piperazin-1-yl]-3-methylphenyl}amino)-3-oxo-1,2-dihydro-3H-pyrazolo[3,4-d]pyrimidin-1-yl]-N,N-dimethylbenzamide 13.6 mg of the entitled compound was obtained as a yellow solid in the same manner as in Example 1-1 to 1-4, for which, however, 3-methyl-4-[(4-hydroxyethyl)piperazin-1-yl]aniline was used in place of 4-(4-methylpiperazin-1-yl)aniline used in Example 1-3.

$^1$H-NMR (400 MHz, CDCl$_3$) δ: 8.82 (1H, s), 7.59-7.53 (2H, m), 7.48 (1H, d, J=1.0 Hz), 7.44-7.41 (1H, m), 7.38-7.33 (2H, m), 6.98 (1H, d, J=8.3 Hz), 5.69 (1H, ddt, J=17.1, 10.2, 6.3 Hz), 5.11 (1H, dd, J=10.2, 1.5 Hz), 5.00 (1H, dd, J=17.1, 1.5 Hz), 4.40 (2H, d, J=6.3 Hz), 3.68 (2H, t, J=5.4 Hz), 3.14 (3H, s), 2.98 (3H, s), 2.96-2.91 (4H, m), 2.76-2.67 (4H, m), 2.65 (2H, t, J=5.4 Hz), 2.28 (3H, s).

ESI-MS Found: m/z[M+H]+ 557.

Example 11

Production of 3-(2-allyl-6-{[4-(4-cyclopropylpiperazin-1-yl)phenyl]amino}-3-oxo-1,2-dihydro-3H-pyrazolo[3,4-d]pyrimidin-1-yl]-N,N-dimethylbenzamide 32.3 mg of the entitled compound was obtained as a yellow solid in the same manner as in Example 1-1 to 1-4, for which, however, 4-(4-cyclopropylpiperazin-1-yl)aniline was used in place of 4-(4-methylpiperazin-1-yl)aniline used in Example 1-3.

$^1$H-NMR (400 MHz, CDCl$_3$) δ: 8.80 (1H, s), 7.41-7.54 (5H, m), 6.88 (1H, d, J=8.3 Hz), 5.63-5.74 (1H, m), 5.09 (1H, d, J=10.0 Hz), 4.99 (1H, d, J=17.2 Hz), 4.39 (2H, d, J=5.8 Hz), 3.10-3.21 (6H, m), 2.75-2.99 (8H, m), 1.67-1.82 (1H, m), 0.45-0.55 (4H, m).

ESI-MS Found: m/z[M+H]+ 539.

Example 12

Production of 3-(2-allyl-6-{[4-(4-cyclopropylpiperazin-1-yl)-3-methylphenyl]amino}-3-oxo-1,2-dihydro-3H-pyrazolo[3,4-d]pyrimidin-1-yl)-N,N-dimethylbenzamide 49.6 mg of the entitled compound was obtained as a yellow solid in the same manner as in Example 1-1 to 1-4, for which, however, 3-methyl-4-(4-cyclopropylpiperazin-1-yl)aniline was used in place of 4-(4-methylpiperazin-1-yl)aniline used in Example 1-3.

$^1$H-NMR (400 MHz, CDCl$_3$) δ: 8.81 (1H, s), 7.26-7.56 (6H, m), 6.95 (1H, d, J=8.5 Hz), 5.63-5.73 (1H, m), 5.10 (1H, d, J=10.1 Hz), 4.98 (1H, d, J=16.9 Hz), 4.39 (2H, d, J=5.9 Hz), 3.13 (3H, s), 2.97 (3H, s), 2.89 (4H, s), 2.79 (4H, s), 2.29 (3H, s), 1.67-1.85 (1H, m), 0.47-0.54 (4H, m).

ESI-MS Found: m/z[M+H]+ 553.

Example 13

Production of 3-(2-allyl-6-{[4-(4-cyclopropylpiperazin-1-yl)-3-(hydroxymethyl)phenyl]amino}-3-oxo-1,2-dihydro-3H-pyrazolo[3,4-d]pyrimidin-1-yl)-N,N-dimethylbenzamide 24.3 mg of the entitled compound was obtained as a yellow solid in the same manner as in Example 1-1 to 1-4, for which, however, [5-amino-2-(4-cyclopropylpiperazin-1-yl)phenyl]methanol was used in place of 4-(4-methylpiperazin-1-yl)aniline used in Example 1-3.

$^1$H-NMR (400 MHz, CDCl$_3$) δ: 8.82 (1H, s), 7.27-7.65 (6H, m), 7.12 (1H, d, J=8.0 Hz), 6.63-6.72 (1H, m), 5.10 (1H, d, J=10.0 Hz), 4.97 (1H, d, J=17.1 Hz), 4.74 (2H, s), 4.39 (2H, d, J=5.8 Hz), 3.14 (3H, s), 2.99 (3H, s), 2.95 (4H, s), 2.75-2.92 (4H, m), 2.69-2.75 (1H, m), 0.45-0.56 (4H, m).
ESI-MS Found: m/z[M+H]+ 569.

Example 14

Production of 3-(2-allyl-6-{[4-(1,1-dioxido-thiomorpholin-4-yl)-3-methylphenyl]amino}-3-oxo-1,2-dihydro-3H-pyrazolo[3,4-d]pyrimidin-1-yl)-N,N-dimethylbenzamide 10.8 mg of the entitled compound was obtained as a yellow solid in the same manner as in Example 1-1 to 1-4, for which, however, 3-methyl-4-(1,1-dioxido-thiomorpholin-4-yl)aniline was used in place of 4-(4-methylpiperazin-1-yl)aniline used in Example 1-3.

$^1$H-NMR (400 MHz, CDCl$_3$) δ: 8.82 (1H, s), 7.39-7.61 (6H, m), 7.04 (1H, d, J=8.0 Hz), 5.65-5.77 (1H, m), 5.11 (1H, d, J=10.1 Hz), 5.99 (1H, d, J=17.3 Hz), 4.40 (2H, d, J=5.9 Hz), 3.37-3.42 (4H, m), 3.18-3.21 (4H, m), 3.15 (3H, s), 3.01 (3H, s), 2.28 (3H, s).
ESI-MS Found: m/z[M+H]+ 562.

Example 15

Production of 3-(2-allyl-6-{[4-(4-methylpiperazin-1-yl)phenyl]amino}-3-oxo-1,2-dihydro-3H-pyrazolo[3,4-d]pyrimidin-1-yl)-N,N-diethylbenzamide 58.5 mg of the entitled compound was obtained as a yellow solid in the same manner as in Example 1-1 to 1-4, for which, however, N,N-diethylamine was used in place of N,N-dimethylamine used in Example 1-4.

$^1$HNMR (400 MHz, CDCl$_3$) δ: 8.80 (1H, s), 7.56-7.43 (5H, m), 7.37 (1H, d, J=7.3 Hz), 6.91 (2H, d, J=8.8 Hz), 5.69 (1H, ddt, J=17.1, 10.2, 5.9 Hz), 5.10 (1H, dd, J=10.2, 1.0 Hz), 4.99 (1H, dd, J=17.1, 1.0 Hz), 4.39 (2H, d, J=5.9 Hz), 3.57 (2H, brs), 3.25 (4H, brs), 2.67 (4H, s), 2.42 (3H, s), 1.26 (3H, brs), 1.10 (3H, brs).
ESI-MS Found: m/z[M+H]+ 541.

Example 16

Production of 3-(2-allyl-6-{[4-(4-methylpiperazin-1-yl)phenyl]amino}-3-oxo-1,2-dihydro-3H-pyrazolo[3,4-d]pyrimidin-1-yl)-N-ethyl-N-methylbenzamide 65.2 mg of the entitled compound was obtained as a yellow amorphous substance in the same manner as in Example 1-1 to 1-4, for which, however, N-ethyl-N-methylamine was used in place of N,N-dimethylamine used in Example 1-4.

$^1$H-NMR (400 MHz, CDCl$_3$) δ: 8.80 (1H, s), 7.57-7.35 (6H, m), 6.90 (2H, d, J=8.3 Hz), 5.69 (1H, ddt, J=17.1, 10.0, 6.3 Hz), 5.10 (1H, dd, J=10.0, 1.2 Hz), 5.00 (1H, dd, J=17.1, 1.5 Hz), 4.40 (2H, d, J=6.3 Hz), 3.60 (1H, brs), 3.22 (5H, s), 3.09 (2H, s), 2.91 (1H, s), 2.64 (4H, s), 2.39 (3H, s), 1.25 (3H, brs), 1.10 (3H, brs).
ESI-MS Found: m/z[M+H]+ 527.

Example 17

Production of 3-(2-allyl-6-{[4-(4-methylpiperazin-1-yl)phenyl]amino}-3-oxo-1,2-dihydro-3H-pyrazolo[3,4-d]pyrimidin-1-yl)-N-(2-hydroxyethyl)-N-methylbenzamide 76.1 mg of the entitled compound was obtained as a yellow amorphous substance in the same manner as in Example 1-1 to 1-4, for which, however, N-(2-hydroxyethyl)-N-methylamine was used in place of N,N-dimethylamine used in Example 1-4.

$^1$H-NMR (400 MHz, CDCl$_3$) δ: 8.80 (1H, s), 7.67-7.37 (6H, m), 6.91 (2H, d, J=7.3 Hz), 5.68 (1H, ddt, J=17.1, 10.2, 6.3 Hz), 5.10 (1H, dd, J=10.2, 1.0 Hz), 4.99 (1H, d, J=17.1 Hz), 4.39 (2H, d, J=6.3 Hz), 3.91 (1H, s), 3.73 (1H, s), 3.41 (1H, s), 3.23-3.11 (6H, brm), 3.00 (2H, brs), 2.61 (4H, s), 2.37 (3H, s).
ESI-MS Found: m/z[M+H]+ 543.

Example 18

Production of 2-allyl-6-{[3-methyl-4-(4-methylpiperazin-1-yl)phenyl]amino}-1-(3-nitrophenyl)-1,2-dihydro-3H-pyrazolo[3,4-d]pyrimidin-3-one 32 mg of the entitled compound was obtained as a yellow solid in the same manner as in Example 1-1 to 1-3, for which, however, 3-nitrophenylboronic acid was used in place of [3-(methoxycarbonyl)]phenylboronic acid used in Example 1-1 and 3-methyl-4-(4-methylpiperazin-1-yl)aniline was used in place of 4-(4-methylpiperazin-1-yl)aniline used in Example 1-3.

$^1$H-NMR (400 MHz, CDCl$_3$) δ: 8.83 (1H, s), 8.41 (1H, s), 8.22-8.18 (1H, m), 7.81-7.77 (1H, m), 7.68 (1H, t, J=8.0 Hz), 7.41-7.36 (1H, m), 7.30 (1H, d, J=2.4 Hz), 7.02 (1H, d, J=8.0 Hz), 5.70 (1H, ddt, J=17.2, 10.2, 6.3 Hz), 5.13 (1H, dd, J=10.2, 1.0 Hz), 5.01 (1H, dd, J=17.2, 1.0 Hz), 4.41 (3H, d, J=6.3 Hz), 2.97-2.92 (4H, m), 2.67-2.54 (4H, m), 2.39 (3H, s), 2.27 (3H, s).
ESI-MS Found: m/z[M+H]+ 501.

Example 19

Production of 2-allyl-1-[3-(1-hydroxy-1-methylethyl)phenyl]-6-{[4-(4-methylpiperazin-1-yl)phenyl]amino}-1,2-dihydro-3H-pyrazolo[3,4-d]pyrimidin-3-one 1) Production of 3-(1-hydroxy-1-methylethyl)phenylboronic acid In a nitrogen atmosphere with cooling with ice, 5.29 mL of 3'-bromoacetophenone was added to 25 mL of 2 M methylmagnesium iodide/diethyl ether solution and 100 mL of diethyl ether, and stirred for 20 minutes. Water and 2 N hydrochloric acid were added to the reaction liquid, extracted with ethyl acetate, washed with aqueous saturated sodium hydrogencarbonate solution and saturated saline water, and dried with anhydrous magnesium sulfate. The solvent was evaporated away under reduced pressure to obtain crude 2-(3-bromophenyl)propan-2-ol.

In a nitrogen atmosphere, 33 mL of 1.66 M n-butyllithium/hexane solution was dropwise added to tetrahydrofuran (200 mL) solution of the obtained compound at −60° C. or lower, and stirred for 20 minutes. 11.08 mL of triisopropoxyborane was added to the reaction liquid, and stirred for 30 minutes. Water was added to the reaction liquid, washed with diethyl ether, and the resulting aqueous layer was made acidic with aqueous 10% phosphoric acid solution. This was extracted with ethyl acetate, washed with aqueous saturated sodium hydrogencarbonate solution and saturated saline water, and dried with anhydrous magnesium sulfate. The solvent was evaporated away under reduced pressure, and the resulting crystal was collected to obtain 3.13 g of the entitled compound as a white solid.

$^1$H-NMR (400 MHz, CDCl$_3$) δ: 7.96 (2H, s), 7.88 (1H, brs), 7.60 (1H, d, J=7.3 Hz), 7.50 (1H, d, J=8.3 Hz), 7.24 (1H, t, J=7.6 Hz), 4.93 (1H, s), 1.43 (6H, d, J=13.7 Hz).

2) Production of 2-allyl-1-[3-(1-hydroxy-1-methyl-ethyl)phenyl]-6-{[4-(4-methylpiperazin-1-yl)phenyl]amino}-1,2-dihydro-3H-pyrazolo[3,4-d]pyrimidin-3-one 35.2 mg of the entitled compound was obtained as a yellow solid in the same manner as in Example 1-1 to 1-3, for which, however, the above boronic acid was used in place of [3-(methoxycarbonyl)]phenylboronic acid used in Example 1-1.

$^1$H-NMR (400 MHz, CDCl$_3$) δ: 8.80 (1H, s), 7.57 (1H, s), 7.47 (2H, d, J=4.9 Hz), 7.43 (2H, d, J=8.8 Hz), 7.31-7.28 (1H, m), 6.88 (2H, d, J=8.8 Hz), 5.70 (1H, ddt, J=17.1, 10.0, 6.3 Hz), 5.10 (1H, dd, J=10.0, 1.2 Hz), 4.98 (1H, dd, J=17.1, 1.5 Hz), 4.38 (2H, d, J=6.3 Hz), 3.21 (4H, t, J=4.1 Hz), 2.66 (4H, s), 2.41 (3H, s), 1.62 (6H, s).

ESI-MS Found: m/z[M+H]+ 500.

Example 20

Production of 2-allyl-6-{[3-methyl-4-(4-methylpiperazin-1-yl)phenyl]amino}-1-pyridin-4-yl-1,2-dihydro-3H-pyrazolo[3,4-d]pyrimidin-3-one 5.4 mg of the entitled compound was obtained as a white solid in the same manner as in Example 1-1 to 1-3, for which, however, pyridin-4-ylboronic acid was used in place of [3-(methoxycarbonyl)]phenylboronic acid used in Example 1-1, and 3-methyl-4-(4-methylpiperazin-1-yl)aniline was used in place of 4-(4-methylpiperazin-1-yl)aniline used in Example 1-3.

$^1$H-NMR (400 MHz, CDCl$_3$) δ: 8.82 (1H, s), 8.72 (2H, dd, J=4.9, 1.5 Hz), 7.48 (2H, d, J=5.9 Hz), 7.03 (1H, d, J=8.8 Hz), 5.67 (1H, ddt, J=17.1, 10.2, 6.3 Hz), 5.12 (1H, dd, J=10.2, 1.2 Hz), 5.03 (1H, dd, J=17.1, 1.2 Hz), 4.44 (2H, d, J=6.3 Hz), 2.97 (4H, t, J=4.4 Hz), 2.64 (4H, s), 2.41 (3H, s), 2.34 (3H, s).

ESI-MS Found: m/z[M+H]+ 457.

Example 21

Production of 2-allyl-6-{[3-methyl-4-(4-methylpiperazin-1-yl)phenyl]amino}-1-pyridin-3-yl-1,2-dihydro-3H-pyrazolo[3,4-d]pyrimidin-3-one 26.5 mg of the entitled compound was obtained as a white solid in the same manner as in Example 1-1 to 1-3, for which, however, pyridin-3-ylboronic acid was used in place of [3-(methoxycarbonyl)]phenylboronic acid used in Example 1-1, and 3-methyl-4-(4-methylpiperazin-1-yl)aniline was used in place of 4-(4-methylpiperazin-1-yl)aniline used in Example 1-3.

$^1$H-NMR (400 MHz, CDCl$_3$) δ: 8.83 (1H, s), 8.80 (1H, d, J=2.4 Hz), 8.63 (1H, dd, J=4.4, 1.5 Hz), 7.79 (1H, d, J=7.8 Hz), 7.46 (2H, dd, J=8.0, 4.6 Hz), 6.99 (1H, d, J=8.8 Hz), 5.69 (1H, ddt, J=17.1, 10.2, 6.3 Hz), 5.12 (1H, dd, J=10.2, 1.0 Hz), 4.99 (1H, dd, J=17.1, 1.0 Hz), 4.40 (2H, d, J=6.3 Hz), 2.93 (4H, t, J=4.6 Hz), 2.61 (4H, s), 2.39 (3H, s), 2.30 (3H, s).

ESI-MS Found: m/z[M+H]+ 457.

Example 22

Production of 2-allyl-1-[3-(2-hydroxy-2-methylpropyl)phenyl]-6-{[4-(4-methylpiperazin-1-yl)phenyl]amino}-1,2-dihydro-3H-pyrazolo[3,4-d]pyrimidin-3-one 1) Production of 1-(3-bromophenyl)-2-methylpropan-1-ol With cooling with ice, 150 mL of 1.0 M isopropylmagnesium chloride/tetrahydrofuran solution was added to tetrahydrofuran (200 mL) solution of 21.9 g of 3-bromobenzaldehyde. 4 N hydrochloric acid was added to the reaction liquid, extracted with diethyl ether, and washed with saturated sodium hydrogencarbonate solution and saturated saline water in that order. This was dried with anhydrous magnesium sulfate, the solvent was evaporated away under reduced pressure, and the resulting residue was purified through silica gel column chromatography (hexane/ethyl acetate=19/1 to 4/1) to obtain 4.20 g of the entitled compound as an oily substance.

$^1$H-NMR (400 MHz, CDCl$_3$) δ: 7.48 (1H, s), 7.40 (1H, td, J=2.0, 7.3 Hz), 7.25-7.18 (2H, m), 4.36 (1H, d, J=6.8 Hz), 1.94 (1H, qq, J=6.8, 6.8 Hz), 0.98 (3H, d, J=6.8 Hz), 0.83 (3H, d, J=6.8 Hz).

2) Production of 1-bromo-3-(2-methyl-1-propylene-1-yl)benzene 2.4 g of p-toluenesulfonic acid monohydrate was added to toluene (70 mL) solution of 4 g of the alcohol obtained in the above 1, and heated under reflux for 2 hours. With cooling with ice, saturated sodium hydrogencarbonate solution was added to it and diluted with ethyl acetate. The organic layer was washed with saturated sodium hydrogencarbonate solution and saturated saline water in that order, and dried with anhydrous sodium sulfate. The solvent was evaporated away under reduced pressure, and the resulting residue was separated and purified through silica gel column chromatography (hexane) to obtain 1.9 g of the entitled compound as an oily substance.

$^1$H-NMR (400 MHz, CDCl$_3$) δ: 7.38-7.35 (1H, m), 7.32-7.29 (1H, m), 7.21-7.11 (2H, m), 6.19 (1H, s), 1.90 (3H, d, J=1.5 Hz), 1.85 (3H, d, J=1.5 Hz).

3) Production of 3-(3-bromophenyl)-2,2-dimethyloxirane

With cooling with ice, 3.4 g of m-chloroperbenzoic acid was gradually added to chloroform (40 mL) solution of 1.9 g of the alkene obtained in the above 2, and stirred at room temperature for 2 hours. Sodium sulfite solution was added to the reaction solution, and stirred at room temperature for 1 hour. Water was added to it, and washed with 0.1 N sodium hydroxide solution, saturated sodium hydrogencarbonate solution and saturated saline water in that order, and dried with anhydrous sodium sulfate. The solvent was evaporated away under reduced pressure to obtain 2.0 g of the entitled compound as an oily substance.
¹H-NMR (400 MHz, CDCl₃) δ: 7.46-7.44 (1H, m), 7.43-7.38 (1H, m), 7.24-7.20 (2H, m), 3.82 (1H, s), 1.48 (3H, s), 1.08 (3H, s).

4) Production of
1-(3-bromophenyl)-2-methyl-2-propanol

In a nitrogen atmosphere at −78° C., 16 mL of 1.0 M diisobutylaluminium hydride/toluene solution was dropwise added to dichloromethane (100 mL) solution of 1.8 g of the oxirane obtained in the above 3, and stirred for 20 minutes. 20 mL of aqueous 30% Rochelle salt solution was added to the reaction solution, stirred at 0° C. for 2 hours, and then the insoluble matter was removed through filtration through Celite. The filtrate was washed with aqueous 30% Rochelle salt solution, saturated sodium hydrogencarbonate solution and saturate saline water in that order, and dried with anhydrous sodium sulfate. The solvent was evaporated away under reduced pressure, and the resulting residue was separated and purified through silica gel column chromatography (hexane/ethyl acetate=4/1) to obtain 870 mg of the entitled compound as an oily substance.
¹H-NMR (400 MHz, CDCl₃) δ: 7.41-7.36 (2H, m), 7.21-7.12 (2H, m), 2.73 (2H, s), 1.23 (6H, s).

5) Production of
[3-(2-hydroxy-2-methylpropyl)phenyl]boronic acid

In a nitrogen atmosphere at −78° C., 5.5 mL of 1.58 M n-butyllithium/hexane solution was dropwise added to tetrahydrofuran (50 mL) solution of 870 mg of the alcohol obtained in the above 4, then 925 mg of triisopropylboronic acid was dropwise added thereto, and stirred for 20 minutes. Water was added to the reaction solution, and washed with diethyl ether. The aqueous layer was made weakly acidic with 10% phosphoric acid, and then extracted with ethyl acetate. The organic layer was washed with water and saturated saline water in that order, and dried with anhydrous sodium sulfate. The solvent was evaporated away under reduced pressure to obtain 274 mg of the entitled compound. Not purified, this was used in the next reaction.

6) Production of 2-allyl-1-[3-(2-hydroxy-2-methyl-propyl)phenyl]-6-{[4-(4-methylpiperazin-1-yl)phenyl]amino}-1,2-dihydro-3H-pyrazolo[3,4-d]pyrimidin-3-one In the same manner as in Example 1-1 to 1-3, 48 mg of the entitled compound was obtained as a yellow solid, for which, however, the boronic acid obtained in the above 5 was used in place of [3-(methoxycarbonyl)]phenylboronic acid used in Example 1-1.
¹H-NMR (400 MHz, CDCl₃) δ: 8.81 (1H, s), 7.55-7.20 (7H, m), 6.88 (2H, d, J=9.0 Hz), 5.70 (1H, ddt, J=17.2, 10.2, 5.9 Hz), 5.10 (1H, d, J=10.2 Hz), 4.98 (1H, d, J=17.2 Hz), 4.39 (2H, d, J=5.9 Hz), 3.28-3.18 (4H, m), 2.84 (2H, s), 2.75-2.60 (4H, m), 2.43 (3H, s), 1.25 (6H, s).
ESI-MS Found: m/z[M+H]+: 514.

Example 23

Production of N-[3-(2-allyl-6-{[4-(4-methylpiperazin-1-yl)phenyl]amino}-3-oxo-1,2-dihydro-3H-pyrazolo[3,4-d]pyrimidin-1-yl)phenyl]acetamide 42 mg of the entitled compound was obtained as a yellow solid in the same manner as in Example 1-1 to 1-3, for which, however, [3-(acetylamino)phenyl]boronic acid was used in place of [3-(methoxycarbonyl)]phenylboronic acid used in Example 1-1.
¹H-NMR (400 MHz, CDCl₃) δ: 8.78 (1H, s), 7.65-7.55 (3H, m), 7.49-7.37 (4H, m), 7.22-7.14 (1H, m), 6.90-6.81 (2H, m), 5.68 (1H, ddt, J=17.1, 10.2, 5.4 Hz), 5.09 (1H, d, J=10.2 Hz), 5.00 (1H, d, J=17.1 Hz), 4.41 (2H, d, J=5.4 Hz), 3.25-3.13 (4H, m), 2.69-2.55 (4H, m), 2.38 (3H, s), 2.22 (3H, s).
ESI-MS Found: m/z[M+H]+ 499.

Example 24

Production of 2-allyl-6-{[4-(4-methylpiperazin-1-yl)phenyl]amino}-1-[3-(methylsulfonyl)phenyl]-1,2-dihydro-3H-pyrazolo[3,4-d]pyrimidin-3-one 75 mg of the entitled compound was obtained as a yellow solid in the same manner as in Example 1-1 to 1-3, for which, however, [3-(methylsulfonyl)phenyl]boronic acid was used in place of [3-(methoxycarbonyl)]phenylboronic acid used in Example 1-1.
¹H-NMR (400 MHz, CDCl₃) δ: 8.81 (1H, s), 8.17 (1H, s), 7.93-7.81 (1H, m), 7.76-7.60 (2H, m), 7.60-7.48 (1H, m), 7.44 (2H, d, J=8.3 Hz), 6.97 (2H, d, J=8.3 Hz), 5.69 (1H, ddt, J=17.1, 10.2, 5.9 Hz), 5.13 (1H, d, J=10.2 Hz), 5.01 (1H, d, J=17.1 Hz), 4.40 (2H, d, J=5.9 Hz), 3.30-3.19 (4H, m), 2.98 (3H, s), 2.74-2.59 (4H, m), 2.41 (3H, s).
ESI-MS Found: m/z[M+H]+ 520.

Example 25

Production of 2-allyl-1-[3-(1-hydroxy-1-methyl-ethyl)phenyl]-6-{[4-(1-methylpiperazin-4-yl)phenyl]amino}-1,2-dihydro-3H-pyrazolo[3,4-d]pyrimidin-3-one 26.3 mg of the entitled compound was obtained as a white solid in the same manner as in Example 1-1 to 1-3, for which, however, the boronic acid obtained in Example 19-1 was used in place of [3-(methoxycarbonyl)]phenylboronic acid used in Example 1-1, and 4-(1-methylpiperidin-4-yl)aniline was used in place of 4-(4-methylpiperazin-1-yl)aniline used in Example 1-3.
¹H-NMR (400 MHz, CDCl₃) δ: 8.83 (1H, s), 7.61 (1H, s), 7.52-7.46 (4H, m), 7.42 (1H, brs), 7.31-7.28 (1H, m), 7.17 (2H, d, J=8.3 Hz), 5.71 (1H, ddt, J=17.1, 10.2, 5.9 Hz), 5.11 (1H, d, J=10.2 Hz), 4.98 (1H, d, J=17.1 Hz), 4.39 (2H, d, J=5.9 Hz), 3.03 (2H, d, J=10.7 Hz), 2.51-2.41 (1H, m), 2.37 (3H, s), 2.18-2.07 (2H, m), 1.99-1.78 (4H, m), 1.63 (6H, s).
ESI-MS Found: m/z[M+H]+ 499.

Example 26

Production of 2-allyl-1-[3-(dimethylaminomethyl)phenyl]-6-{[4-(4-methylpiperazin-1-yl)phenyl]amino}-1,2-dihydro-3H-pyrazolo[3,4-d]pyrimidin-3-one 1) Production of 2-allyl-1-[3-(dimethylaminomethyl)phenyl]-6-(methylthio)-1,2-dihydro-3H-pyrazolo[3,4-d]pyrimidin-3-one 2.9 mL of methanesulfonyl chloride and 11 mL of N,N-diisopropylethylamine were added in that order to chloroform (50 mL) solution of 3.0 g of 2-allyl-1-[3-(hydroxymethyl)phenyl]-6-(methylthio)-1,2-dihydro-3H-pyrazolo[3,4-d]pyrimidin-3-one that had been obtained by the use of [3-(hydroxymethyl)phenyl]boronic acid in place of [3-

(methoxycarbonyl)]phenylboronic acid used in Example 1-1, and stirred at room temperature for 1 hour. The reaction liquid was washed with 0.5 N hydrochloric acid, and dried with anhydrous sodium sulfate. The solvent was evaporated away under reduced pressure to obtain crude 2-allyl-1-[3-(methylsulfonyloxymethyl)phenyl]-6-(methylthio)-1,2-dihydro-3H-pyrazolo[3,4-d]pyrimidin-3-one as a yellow oily substance.

20 mL of 2 M dimethylamine/tetrahydrofuran solution was added to tetrahydrofuran (100 mL) solution of 1.5 g of the above compound, and stirred at room temperature for 18 hours. The solvent was evaporated away under reduced pressure, and the residue was separated and purified through silica gel column chromatography (ethyl acetate) to obtain 2.5 g of the entitled compound as a yellow solid.

$^1$H-NMR (400 MHz, CDCl$_3$) δ: 8.90 (1H, s), 7.53-7.26 (4H, m), 5.73-5.62 (1H, m), 5.11 (1H, dd, J=10.2, 1.0 Hz), 4.95 (1H, dd, J=17.1, 1.0 Hz), 4.44 (2H, d, J=3.7 Hz), 3.49 (2H, s), 2.48 (3H, s), 2.27 (6H, s).

ESI-MS Found: m/z M+H]+356.1.

2) Production of 2-allyl-1-[3-(dimethylaminomethyl)phenyl]-6-{[4-(4-methylpiperazin-1-yl)phenyl]amino}-1,2-dihydro-3H-pyrazolo[3,4-d]pyrimidin-3-one 4 N hydrochloric acid/ethyl acetate solution was added to 100 mg of the compound obtained in the above 1, stirred at room temperature, and the solvent was evaporated away under reduced pressure to obtain 2-allyl-1-[3-(dimethylaminomethyl)phenyl]-6-(methylthio)-1,2-dihydro-3H-pyrazolo[3,4-d]pyrimidin-3-one hydrochloride.

70 mg of m-chloroperbenzoic acid was added to N,N-dimethylformamide (2 mL) solution of the above compound, and stirred at room temperature for 15 minutes. The reaction liquid was washed with aqueous saturated sodium hydrogencarbonate solution, and dried with anhydrous sodium sulfate. The solvent was evaporated away under reduced pressure to obtain crude 2-allyl-1-[3-(dimethylaminomethyl)phenyl]-6-(methylsulfinyl)-1,2-dihydro-3H-pyrazolo[3,4-d]pyrimidin-3-one as a white solid.

50 mg of 4-(4-methylpiperazin-1-yl)aniline and 0.1 μmL of N,N-diisopropylethylamine were added in that order to dimethylsulfoxide/toluene (1/10, 10 mL) solution of the above compound, and stirred at 120° C. for 15 hours. The solvent was evaporated away under reduced pressure, water was added thereto, and extracted with ethyl acetate and dried with anhydrous sodium sulfate. The solvent was evaporated away under reduced pressure, and the residue was separated and purified through basic silica gel column chromatography (entyl acetate) to obtain 11.4 mg f the entitled compound as a yellow solid.

$^1$H-NMR (400 MHz, CDCl$_3$) δ: 8.80 (1H, s), 7.48-7.33 (6H, m), 6.87 (2H, d, J=8.8 Hz), 5.80-5.60 (1H, m), 5.09 (1H, dd, J=10.2, 1.0 Hz), 4.97 (1H, dd, J=17.1, 1.5 Hz), 4.38 (1H, d, J=5.9 Hz), 3.51 (2H, s), 3.18 (4H, t, J=4.9 Hz), 2.60 (4H, t, J=4.9 Hz), 2.37 (3H, s), 2.28 (6H, s).

ESI-MS Found: m/z[M+H]+ 499.

Example 27

Production of 2-allyl-6-{[3-methyl-4-(4-methylpiperazin-1-yl)phenyl]amino}-1-[3-(pyrrolidin-1-ylmethyl)phenyl]-1,2-dihydro-3H-pyrazolo[3,4-d]pyrimidin-3-one 12 mg of the entitled compound was obtained as a yellow solid in the same manner as in Example 26-1 to 26-2, for which, however, pyrrolidine was used in place of N,N-dimethylamine used in Example 26-1, and 3-methyl-4-(4-methylpiperazin-1-yl)aniline was used in place of 4-(4-methylpiperazin-1-yl)aniline used in Example 26-2.

$^1$H-NMR (400 MHz, CDCl$_3$) δ: 8.80 (1H, s), 7.28-7.48 (6H, m), 6.95 (1H, d, J=8.5 Hz), 5.62-5.78 (1H, m), 5.09 (1H, d, J=10.3 Hz), 4.93 (1H, d, J=17.5 Hz), 4.37 (2H, d, J=6.1 Hz), 3.69 (2H, s), 2.90 (4H, t, J=4.7 Hz), 2.50-2.62 (8H, m), 2.36 (3H, s), 2.26 (3H, s), 1.72-1.90 (4H, m).

ESI-MS Found: m/z[M+H]+ 539.

Example 28

Production of 3-(2-ethyl-6-{[3-methyl-4-(4-methylpiperazin-1-yl)phenyl]amino}-3-oxo-1,2-dihydro-3H-pyrazolo[3,4-d]pyrimidin-1-yl)-N,N-dimethylbenzamide 1) Production of 2-ethyl-6-(methylthio)-1,2-dihydro-3H-pyrazolo[3,4-d]pyrimidin-3-one 5.8 g of the entitled compound was obtained as a yellow solid in the same manner as in Production example 1-2, for which, however, tert-butyl 1-ethylhydrazinecarboxylate was used in place of tert-butyl 1-allylhydrazinecarboxylate used in Production Example 1-2.

$^1$H-NMR (400 MHz, CDCl$_3$) δ: 9.10 (1H, s), 4.18 (2H, q, J=7.1 Hz), 2.67 (3H, s), 1.48 (3H, t, J=7.1 Hz).

ESI-MS Found: m/z[M+H]+ 211.

2) Production of 3-(2-ethyl-6-{[3-methyl-4-(4-methylpiperazin-1-yl)phenyl]amino}-3-oxo-1,2-dihydro-3H-pyrazolo[3,4-d]pyrimidin-1-yl)-N,N-dimethylbenzamide 24.8 mg of the entitled compound was obtained as a yellow solid in the same manner as in Example 1-1 to 1-4, for which, however, 2-ethyl-6-(methylthio)-1,2-dihydro-3H-pyrazolo[3,4-d]pyrimidin-3-one obtained in the above was used in place of 2-allyl-6-(methylthio)-1,2-dihydro-3H-pyrazolo[3,4-d]pyrimidin-3-one used in Example 1-1, and 3-methyl-4-(4-methylpiperazin-1-yl)aniline was used in place of 4-(4-methylpiperazin-1-yl)aniline used in Example 1-3.

$^1$H-NMR (400 MHz, CDCl$_3$) δ: 8.80 (1H, s), 7.60-7.48 (4H, m), 7.44-7.32 (3H, m), 6.98 (1H, d, J=8.3 Hz), 3.87 (2H, q, J=7.0 Hz), 3.14 (3H, s), 2.98 (3H, s), 2.95-2.91 (4H, m), 2.67-2.54 (4H, m), 2.38 (3H, s), 2.29 (3H, s), 1.07 (3H, t, J=7.0 Hz).

ESI-MS Found: m/z[M+H]+ 515.

Example 29

Production of 2-allyl-6-{[3-hydroxymethyl-4-(4-methylpiperazin-1-yl)phenyl]amino}-1-pyridin-2-yl-1,2-dihydro-3H-pyrazolo[3,4-d]pyrimidin-3-one 1) Production of 2-allyl-6-(methylthio)-1-pyridin-2-yl-3H-pyrazolo[3,4-d]pyrimidin-3-one 2.4 mL of N,N'-dimethylethylenediamine was added to 1,4-dioxane (50 mL) solution of 4.44 g of 2-allyl-6-(methylthio)-1,2-dihydro-3H-pyrazolo[3,4-d]pyrimidin-3-one, 3.80 g of copper(I) iodide, 5.33 g of 2-iodopyridine and 3.80 g of potassium carbonate, and stirred overnight at 95° C. The reaction liquid was cooled, aqueous ammonia was added thereto and extracted with ethyl acetate, washed with saturated saline water and dried with anhydrous magnesium sulfate. The solvent was evaporated away under reduced pressure, and crystallized with ethyl acetate to obtain 5.15 g of the entitled compound as a white solid.

$^1$H-NMR (400 MHz, CDCl$_3$) δ: 8.94 (1H, s), 8.52 (1H, d, J=5.1 Hz), 7.90 (2H, d, J=3.5 Hz), 7.29-7.25 (1H, m), 5.68 (1H, ddt, J=17.0, 10.2, 6.3 Hz), 5.05 (1H, d, J=10.2 Hz), 4.91 (1H, d, J=17.0 Hz), 4.85 (1H, d, J=6.3 Hz), 2.58 (3H, s).

ESI-MS Found: m/z[M+H]+ 300.

2) Production of 2-allyl-6-{[3-hydroxymethyl-4-(4-methylpiperazin-1-yl)phenyl]amino}-1-pyridin-2-yl-1,2-dihydro-3H-pyrazolo[3,4-d]pyrimidin-3-one 796 mg of m-chloroperbenzoic acid (>65%) was added to toluene (20 mL) solution of 898 mg of 2-allyl-6-(methylthio)-1-pyridin-2-yl-3H-pyrazolo[3,4-d]pyrimidin-3-one, and stirred for 30 minutes. 1.60 mL of N,N-diisopropylethylamine, 800 mg of [5-amino-2-(4-methylpiperazin-1-yl)phenyl]methanol and 10 mL of tetrahydrofuran were added to the reaction liquid, and stirred overnight. Aqueous saturated sodium hydrogencarbonate solution was added to the reaction liquid, and extracted with a mixed solution of chloroform/isopropanol (80/20). This was dried with anhydrous magnesium sulfate, the solvent was evaporated away, and the residue was purified through basic silica gel column chromatography (hexane/ethyl acetate=50/50 to 0/100). The resulting crystal was recrystallized from ethanol to obtain 941 mg of the entitled compound as a white crystal.

$^1$H-NMR (400 MHz, CDCl$_3$) δ: 8.84 (1H, s), 8.53 (1H, d, J=4.8 Hz), 7.91 (1H, dd, 7.88 (1H, dd, J=8.8, 7.6 Hz), 7.87 (1H, d, J=7.6 Hz), 7.64 (1H, s), 7.33 (1H, d, J=8.8 Hz), 7.26 (1H, dd, J=8.8, 4.8 Hz), 7.19 (1H, d, J=8.8 Hz), 5.68 (1H, ddd, J=17.2, 10.4, 5.6 Hz), 5.50 (1H, s), 5.01 (1H, d, 10.4 Hz), 4.91 (1H, d, J=17.2 Hz), 4.79 (2H, s), 4.79 (2H, d, J=5.6 Hz), 3.01 (4H, m), 2.62 (4H, m), 2.37 (3H, s).

ESI-MS Found: m/z[M+H]+ 472.

Example 30

Production of 2-allyl-6-{[3-methyl-4-(4-methylpiperazin-1-yl)phenyl]amino}-1-pyridin-2-yl-1,2-dihydro-3H-pyrazolo[3,4-d]pyrimidin-3-one 18.8 mg of the entitled compound was obtained as a yellow solid in the same manner as in Example 29-1 to 29-2, for which, however, 3-methyl-4-(4-methylpiperazin-1-yl)aniline was used in place of [5-amino-2-(4-methylpiperazin-1-yl)phenyl]methanol used in Example 29-2.

$^1$H-NMR (400 MHz, CDCl$_3$) δ: 8.83 (1H, s), 7.88 (1H, dd, J=8.0, 8.0 Hz), 7.86 (1H, d, J=8.0 Hz), 7.52 (1H, s), 7.26 (1H, d, J=8.0, 4.8 Hz), 7.25 (1H, J=8.4 Hz), 7.01 (1H, d, J=4.8 Hz), 5.68 (1H, ddd, J=17.2, 10.0, 6.0 Hz), 5.01 (1H, d, J=10.0 Hz), 4.91 (1H, J=17.2 Hz), 4.79 (1H, J=6.0 Hz), 2.94 (4H, m), 2.61 (4H, m), 2.37 (3H, s), 2.32 (3H, s).

ESI-MS Found: m/z[M+H]+ 457.

Example 31

Production of 2-allyl-6-({4-[4-(2-hydroxyethyl)piperazin-1-yl]-3-methylphenyl}amino)-1-pyridin-2-yl-1,2-dihydro-3H-pyrazolo[3,4-d]pyrimidin-3-one 95 mg of the entitled compound was obtained as a yellow solid in the same manner as in Example 29-1 to 29-2, for which, however, 4-[4-(hydroxyethyl)piperazin-1-yl]aniline was used in place of [5-amino-2-(4-methylpiperazin-1-yl)phenyl]methanol used in Example 29-2.

$^1$H-NMR (400 MHz, CDCl$_3$) δ: 8.81 (1H, s), 8.49 (1H, dd, J=5.0, 1.1 Hz), 7.88-7.80 (2H, m), 7.51-7.45 (1H, m), 7.29 (1H, dd, J=8.5, 2.6 Hz), 7.22-7.19 (1H, m), 6.97 (1H, d, J=8.5 Hz), 5.65 (1H, ddt, J=17.0, 10.2, 6.3 Hz), 4.98 (1H, dd, J=10.2, 1.4 Hz), 4.88 (1H, dd, J=17.0, 1.4 Hz), 4.75 (2H, d, J=6.3 Hz), 3.65 (2H, t, J=5.5 Hz), 2.93-2.88 (4H, m), 2.71-2.64 (4H, m), 2.61 (2H, t, J=5.5 Hz), 2.29 (3H, s).

ESI-MS Found: m/z[M+H]+ 487.

Example 32

Production of 2-allyl-6-{[4-(4-methylpiperazin-1-yl)phenyl]amino}-1-pyridin-2-yl-1,2-dihydro-3H-pyrazolo[3,4-d]pyrimidin-3-one 2.28 g of the entitled compound was obtained as a yellow solid in the same manner as in Example 29-1 to 29-2, for which, however, 4-(4-methylpiperazin-1-yl)aniline was used in place of [5-amino-2-(4-methylpiperazin-1-yl)phenyl]methanol used in Example 29-2.

$^1$H-NMR (400 MHz, CDCl$_3$) δ: 8.82 (1H, s), 8.52 (1H, d, J=5.1 Hz), 7.87-7.84 (2H, m), 7.46 (2H, d, J=8.6 Hz), 7.46 (1H, brs), 7.26-7.21 (1H, m), 6.92 (2H, d, J=8.6 Hz), 5.71 (1H, ddt, J=17.2, 10.2, 5.9 Hz), 5.02 (1H, d, J=10.2 Hz), 4.92 (1H, d, J=17.2 Hz), 4.78 (2H, d, J=5.9 Hz), 3.23-3.20 (4H, m), 2.63-2.61 (4H, m), 2.38 (3H, s).

ESI-MS Found: m/z[M+H]+ 443.

Example 33

Production of 2-allyl-6-{[3-(hydroxymethyl)-4-(4-methylpiperazin-1-yl)phenyl]amino}-1-(6-methylpyridin-2-yl)-1,2-dihydro-3H-pyrazolo[3,4-d]pyrimidin-3-one 11.6 mg of the entitled compound was obtained as a white solid in the same manner as in Example 29-1 to 29-2, for which, however, 2-bromo-6-methylpyridine was used in place of 2-iodopyridine used in Example 29-1.

$^1$H-NMR (400 MHz, CDCl$_3$) δ: 8.84 (1H, s), 7.79 (1H, dd, J=7.8, 7.4 Hz), 7.64 (1H, d, J=8.2 Hz), 7.59 (1H, brs), 7.44 (1H, brs), 7.38 (1H, d, J=6.9 Hz), 7.20 (1H, d, J=8.2 Hz), 7.12 (1H, d, J=7.2 Hz), 5.96-5.66 (1H, m), 5.02 (1H, d, J=10.4 Hz), 4.92 (1H, d, J=17.0 Hz), 4.78 (4H, brs), 3.03 (4H, brs), 2.65 (4H, brs), 2.60 (3H, s), 2.39 (3H, s).

ESI-MS Found: m/z[M+H]+ 487.

Example 34

Production of 6-(2-allyl-6-{[3-methyl-4-(4-methylpiperazin-1-yl)phenyl]amino}-3-oxo-1,2-dihydro-3H-pyrazolo[3,4-d]pyrimidin-1-yl)-N,N-dimethylpyridine-2-carboxamide 1.21 g of the entitled compound was obtained as a white solid in the same manner as in Example 29-1 to 29-2, for which, however, 6-bromo-N,N-dimethyl-2-pyridinecarboxamide was used in place of 2-iodopyridine used in Example 29-1, and 3-methyl-4-(4-methylpiperazin-1-yl)aniline was used in place of [5-amino-2-(4-methylpiperazin-1-yl)phenyl]methanol used in Example 29-2.

$^1$H-NMR (400 MHz, CDCl$_3$) δ: 8.83 (1H, s), 8.01 (1H, d, J=9.0 Hz), 7.94 (1H, dd, J=7.8, 7.6 Hz), 7.56 (1H, d, J=7.3 Hz), 7.47 (2H, brs), 7.31 (1H, d, J=8.0 Hz), 7.03 (1H, d, J=8.6 Hz), 5.67 (1H, ddt, J=17.2, 9.6, 6.3 Hz), 5.02 (1H, d, J=9.6

Hz), 4.94 (1H, d, J=17.2 Hz), 4.77 (2H, d, J=6.3 Hz), 3.16 (3H, s), 3.09 (3H, s), 2.96 (4H, t, J=4.6 Hz), 2.62 (4H, brs), 2.39 (3H, s), 2.33 (3H, s).
ESI-MS Found: m/z[M+H]+ 528.

Example 35

Production of 2-allyl-6-{[4-(4-hydroxypiperidin-1-yl)-3-methylphenyl]amino}-1-pyridin-2-yl-1,2-dihydro-3H-pyrazolo[3,4-d]pyrimidin-3-one 19.2 mg of the entitled compound was obtained as a yellow solid in the same manner as in Example 29-1 to 29-2, for which, however, [4-(4-hydroxypiperidin-1-yl)-3-methylphenyl]aniline was used in place of [5-amino-2-(4-methylpiperazin-1-yl)phenyl]methanol used in Example 29-2.
$^1$H-NMR (400 MHz, CDCl$_3$) δ: 8.83 (1H, s), 8.53 (1H, d, J=3.2 Hz), 7.83-7.91 (2H, m), 7.21-7.79 (3H, m), 7.00 (1H, d, J=7.3 Hz), 5.64-5.76 (1H, m), 5.02 (1H, d, J=10.3 Hz), 4.92 (1H, d, J=17.1 Hz), 4.79 (2H, d, J=6.0 Hz), 3.81-3.91 (1H, m), 3.06-3.13 (2H, m), 2.68-2.79 (2H, m), 2.33 (3H, s), 1.99-2.08 (2H, m), 1.70-1.80 (2H, m).
ESI-MS Found: m/z[M+H]+ 452.

Example 36

Production of 2-allyl-6-{[3-methyl-4-(4-methylpiperazin-1-yl)phenyl]amino}-1-5-(trifluoromethyl) pyridin-2-yl-1,2-dihydro-3H-pyrazolo[3,4-d]pyrimidin-3-one 41.7 mg of the entitled compound was obtained as a yellow solid in the same manner as in Example 29-1 to 29-2, for which, however, 2-bromo-5-(trifluoromethyl)pyridine was used in place of 2-iodopyridine used in Example 29-1, and 3-methyl-4-(4-methylpiperazin-1-yl)aniline was used in place of [5-amino-2-(4-methylpiperazin-1-yl)phenyl]methanol used in Example 29-2.
$^1$H-NMR (400 MHz, CDCl$_3$) δ: 8.85 (1H, s), 8.77-8.75 (1H, m), 8.17 (1H, d, J=8.8 Hz), 8.01 (1H, dd, J=8.8, 1.8 Hz), 7.58-7.40 (2H, m), 7.31-7.25 (1H, m), 7.05 (1H, d, J=8.5 Hz), 5.67 (1H, ddt, J=16.8, 10.2, 6.5 Hz), 5.03 (1H, dd, J=10.2, 1.3 Hz), 4.95 (1H, dd, J=16.8, 1.3 Hz), 4.84 (2H, d, J=6.5 Hz), 3.00-2.94 (4H, m), 2.72-2.53 (4H, m), 2.40 (3H, s), 2.34 (3H, s).
ESI-MS Found: m/z[M+H]+ 525.

Example 37

Production of 2-allyl-6-{[3-methyl-4-(1-methylpiperidin-4-yl)phenyl]amino}-1-pyridin-2-yl-1,2-dihydro-3H-pyrazolo[3,4-d]pyrimidin-3-one 1) Production of 1-(4-bromo-3-methylphenyl)-2,5-dimethyl-1H-pyrrole Acetic acid (30 mL) solution of 9.30 g of 4-bromo-3-methylaniline and 6.85 g of 2,5-hexanedione was stirred at 80° C. for 5 hours. The reaction liquid was concentrated, aqueous saturated sodium hydrogencarbonate solution was added thereto, extracted with ethyl acetate, washed with saturated saline water, and dried with anhydrous magnesium sulfate. This was filtered through silica gel column chromatography (ethyl acetate), the solvent was concentrated, hexane was added to it, and the formed solid was collected to obtain 10.90 g of the entitled compound as a white solid.

$^1$H-NMR (400 MHz, CDCl$_3$) δ: 7.60 (1H, d, J=8.2 Hz), 7.08 (1H, d, J=2.5 Hz), 6.91 (1H, dd, J=8.3, 2.4 Hz), 5.89 (2H, s), 2.44 (3H, s), 2.02 (6H, s).
ESI-MS Found: m/z[M+H]+ 264, 266.

2) Production of tert-butyl 4-[4-(2,5-dimethyl-1H-pyrrol-1-yl)-2-methylphenyl]-4-hydroxypiperidine-1-carboxylate Tetrahydrofuran (52 mL) solution of 2.64 g of the compound obtained in the above 1 was cooled in a dry ice/acetone bath, and at −65° C. or lower, 4.14 mL of 2.66 M n-butyllithium/hexane solution was added thereto. After this was stirred for 15 minutes, tetrahydrofuran (10 mL) solution of 2.0 g of 1-tert-butoxycarbonylpiperidin-4-one was added thereto at −65° C. or lower. After this was stirred for 10 minutes, water was added thereto and heated up to room temperature, extracted with ethyl acetate, washed with saturated saline water, and dried with anhydrous magnesium sulfate. The solvent was evaporated away, the residue was purified through silica gel column chromatography (hexane/ethyl acetate) to obtain 3.19 g of the entitled compound.
$^1$H-NMR (400 MHz, CDCl$_3$) δ: 7.42 (1H, d, J=8.4 Hz), 7.01 (1H, s), 7.00 (1H, d, J=8.4 Hz), 5.88 (2H, s), 4.05 (2H, brs), 3.31 (2H, brs), 2.64 (3H, s), 2.18-1.96 (4H, m), 2.03 (6H, s), 1.48 (9H, s).
ESI-MS Found: m/z[M+H]+ 385.

3) Production of tert-butyl 4-(4-amino-2-methylphenyl)-3,6-dihydropyridin-1(2H)-carboxylate 4.5 mL of aqueous 50% hydroxylamine solution and 10 mL of 4 N hydrochloric acid were added to ethanol (26 mL) solution of 2.64 g of the compound obtained in the above 2, and stirred at 90° C. for 2 days. The reaction liquid was concentrated, aqueous sodium hydrogencarbonate solution was added thereto, and extracted with ethyl acetate. This was washed with saturated saline water, dried with anhydrous magnesium sulfate, the solvent was evaporated away, and the residue was purified through silica gel column chromatography (hexane/ethyl acetate) and through basic silica gel column chromatography (hexane/ethyl acetate) to obtain 401 mg of the entitled compound as an amorphous substance.
$^1$H-NMR (400 MHz, CDCl$_3$) δ: 6.87 (1H, d, J=7.8 Hz), 6.51 (1H, s), 6.48 (1H, dd, J=8.0, 2.4 Hz), 5.49 (1H, brs), 4.00 (2H, brs), 3.59 (4H, t, J=5.4 Hz), 3.52 (2H, brs), 2.30 (2H, brs), 2.19 (3H, s), 1.50 (9H, s).
ESI-MS Found: m/z[M+H]+ 275.

4) Production of tert-butyl 4-(4-amino-2-methylphenyl)piperidine-1-carboxylate

In a nitrogen atmosphere, 100 mg of 10% palladium-carbon was added to tetrahydrofuran (2 mL)-methanol (2 mL) solution of 400 mg of the compound obtained in the above 3, and stirred in a hydrogen atmosphere for 4 hours. The reaction system was purged with nitrogen, the catalyst was removed through filtration, and the filtrate was concentrated to obtain 219 mg of the entitled compound as a white solid.
$^1$H-NMR (400 MHz, CDCl$_3$) δ: 7.00 (1H, d, J=7.8 Hz), 6.68-6.64 (2H, m), 4.24 (2H, brs), 2.79-2.75 (3H, m), 2.28 (3H, s), 1.72-1.54 (4H, m), 1.48 (9H, s).
ESI-MS Found: m/z[M+H]+ 277.

5) Production of 2-allyl-6-{[3-methyl-4-(1-methylpiperidin-4-yl)phenyl]amino}-1-pyridin-2-yl-1,2-dihydro-3H-pyrazolo[3,4-d]pyrimidin-3-one With cooling with ice, tetrahydrofuran (1 mL) solution of 60 mg of the compound obtained in the above 4 was added to tetrahydrofuran (2 mL) solution of 20 mg of lithiumaluminium hydride. The reaction liquid was heated at 60° C., and stirred for 1 hour and 40 minutes. The reaction liquid was restored to room temperature, and 0.05 mL of 4 N sodium hydroxide solution and 0.1 mL of water were added thereto, and the precipitated solid was taken out through filtration. The solvent was concentrated, and crude 3-methyl-4-(1-methylpiperidin-4-yl)aniline was obtained.

In the same manner as in Example 29-1 to 29-2, 32.7 mg of the entitled compound was obtained as a white solid, for which, however, the crude 3-methyl-4-(1-methylpiperidin-4-yl)aniline obtained in the above reaction was used in place of [5-amino-2-(4-methylpiperazin-1-yl)phenyl]methanol used in Example 29-2.

$^1$H-NMR (400 MHz, CDCl$_3$) δ: 8.84 (1H, s), 8.56-8.53 (1H, m), 7.91-7.85 (2H, m), 7.43-7.37 (3H, m), 7.22 (1H, d, J=8.2 Hz), 7.64 (1H, brs), 7.46-7.42 (2H, m), 7.19 (1H, d, J=8.2 Hz), 5.68 (1H, ddt, J=16.4, 10.4, 6.3 Hz), 5.02 (1H, d, J=10.4 Hz), 4.92 (1H, d, J=16.4 Hz), 4.79 (2H, d, J=6.3 Hz), 3.03 (2H, d, J=11.4 Hz), 2.74-2.62 (1H, m), 2.37 (3H, s), 2.35 (3H, s), 2.18-2.07 (2H, m), 1.94-1.73 (4H, m).

ESI-MS Found: m/z[M+H]+ 456.

Example 38

Production of 2-allyl-6-({4-[1-(2-hydroxyethyl)piperidin-4-yl]-3-methylphenyl}amino)-1-pyridin-2-yl-1,2-dihydro-3H-pyrazolo[3,4-d]pyrimidin-3-one 1) Production of tert-butyl 4-{4-[(2-allyl-3-oxo-1-pyridin-2-yl-2,3-dihydro-1H-pyrazolo[3,4-d]pyrimidin-6-yl)amino]-2-methylphenyl}piperidine-1-carboxylate 72 mg of the entitled compound was obtained as a white solid in the same manner as in Example 29-1 to 29-2, for which, however, tert-butyl 4-(4-amino-2-methylphenyl)piperidine-1-carboxylate obtained in Example 37-4 was used in place of [5-amino-2-(4-methylpiperazin-1-yl)phenyl]methanol used in Example 29-2.

$^1$H-NMR (400 MHz, CDCl$_3$) δ: 8.85 (1H, s), 8.54 (1H, dd, J=4.9, 1.5 Hz), 7.90-7.85 (2H, m), 7.46 (2H, brs), 7.37 (1H, d, J=9.2 Hz), 7.15 (1H, d, J=8.8 Hz), 5.69 (1H, ddt, J=16.4, 10.4, 6.3 Hz), 5.02 (1H, d, J=10.4 Hz), 4.92 (1H, d, J=16.4 Hz), 4.79 (2H, d, J=6.3 Hz), 4.34-4.22 (2H, m), 2.89-2.78 (3H, m), 2.37 (3H, s), 1.80-1.54 (4H, m), 1.50 (9H, s).

ESI-MS Found: m/z[M+H]+ 542.

2) Production of 2-allyl-6-[(3-methyl-4-piperidin-4-ylphenyl)amino]-1-pyridin-2-yl-1,2-dihydro-3H-pyrazolo[3,4-d]pyrimidin-3-one 1 mL of trifluoroacetic acid was added to the compound obtained in the above 1, stirred, and aqueous potassium carbonate solution was added to it, and extracted with a mixed solvent of chloroform and isopropanol. This was dried with anhydrous magnesium sulfate, and the solvent was evaporated away under reduced pressure to obtain 34 mg of the entitled compound as a white solid.

$^1$H-NMR (CD3OD) δ: 8.87 (1H, s), 8.57-8.56 (1H, m), 8.08-8.04 (1H, m), 7.95 (1H, d, J=8.2 Hz), 7.64 (1H, brs), 7.46-7.42 (2H, m), 7.19 (1H, d, J=8.2 Hz), 5.76 (1H, ddt, J=18.6, 10.2, 6.1 Hz), 5.08 (1H, d, J=10.2 Hz), 4.97 (1H, d, J=18.6 Hz), 4.75 (2H, d, J=6.1 Hz), 3.49-3.45 (2H, m), 3.17-3.10 (2H, m), 2.40 (3H, s), 2.01-1.85 (4H, m).

ESI-MS Found: m/z [M+H]+ 442.

3) Production of 2-allyl-6-({4-[1-(2-hydroxyethyl)piperidin-4-yl]-3-methylphenyl}amino)-1-pyridin-2-yl-1,2-dihydro-3H-pyrazolo[3,4-d]pyrimidin-3-one A mixed methanol solution (1 mL) of 0.3 M sodium borocyanohydride and 0.15 M zinc chloride was added to a tetrahydrofuran (1 mL) solution of 34 mg of the compound obtained in the above 2) and 20 mg of glycoaldehyde dimer. This was stirred at room temperature for 5 minutes, saturated sodium hydrogencarbonate was added thereto, and extracted with ethyl acetate. This was washed with saturated saline water, dried with anhydrous magnesium sulfate, the solvent was evaporated away, and the residue was purified through basic silica gel column chromatography (chloroform-methanol) to obtain the entitled compound (20.2 mg) as a white solid.

$^1$H-NMR (CDCl$_3$) δ: 8.85 (1H, s), 8.54 (1H, dt, J=4.9, 1.5 Hz), 7.90-7.87 (2H, m), 7.44 (2H, brs), 7.38 (1H, dd, J=8.8, 2.4 Hz), 7.20 (1H, d, J=8.3 Hz), 5.74-5.64 (1H, m), 5.02 (1H, dd, J=10.2, 1.5 Hz), 4.92 (1H, dd, J=17.1, 1.0 Hz), 4.79 (2H, d, J=6.3 Hz), 3.67 (2H, t, J=5.4 Hz), 3.09 (2H, d, J=11.2 Hz), 2.78-2.68 (1H, m), 2.62 (2H, dd, J=5.4, 4.9 Hz), 2.36 (3H, s), 2.30-2.20 (2H, m), 1.84-1.75 (4H, m).

ESI-MS Found: m/z[M+H]+486.

Example 39

Production of 2-allyl-6-{[4-(4-cyclopropylpiperazin-1-yl)-3-methylphenyl]amino}-1-pyridin-2-yl-1,2-dihydro-3H-pyrazolo[3,4-d]pyrimidin-3-one 33.2 mg of the entitled compound was obtained as a yellow solid in the same manner as in Example 29-1 to 29-2, for which, however, 4-(4-cyclopropyl-1-piperazinyl)-3-methylaniline was used in place of [5-amino-2-(4-methylpiperazin-1-yl)phenyl]methanol used in Example 29-2.

$^1$H-NMR (400 MHz, CDCl$_3$) δ: 8.83 (1H, s), 8.53 (1H, d, J=2.8 Hz), 7.82-7.93 (2H, m), 6.98-7.62 (4H, m), 5.64-5.75 (1H, m), 5.01 (1H, s, J=9.9 Hz), 4.92 (1H, d, J=17.0 Hz), 4.78 (2H, d, J=5.8 Hz), 2.90 (4H, bs), 2.80 (4H, bs), 2.34 (3H, s), 1.72 (1H, bs), 0.50 (4H, bs).

ESI-MS Found: m/z[M+H]+ 483.

Example 40

Production of 2-allyl-6-{[4-(4-cyclobutylpiperazin-1-yl)-3-methylphenyl]amino}-1-pyridin-2-yl-1,2-dihydro-3H-pyrazolo[3,4-d]pyrimidin-3-one 36.6 mg of the entitled compound was obtained as a yellow solid in the same manner as in Example 29-1 to 29-2, for which, however, 4-(4-cyclobutyl-1-piperazinyl)-3-methylaniline was used in place of [5-amino-2-(4-methylpiperazin-1-yl)phenyl]methanol used in Example 29-2.

$^1$H-NMR (400 MHz, CDCl$_3$) δ: 8.83 (1H, s), 8.52 (1H, d, J=3.2 Hz), 7.82-7.94 (2H, m), 7.01-7.62 (4H, m), 5.63-5.76 (1H, m), 5.01 (1H, d, J=10.1 Hz), 4.92 (1H, d, J=17.1 Hz), 4.78 (2H, d, J=5.9 Hz), 2.95 (4H, bs), 2.56 (4H, bs), 2.80-2.89 (1H, m), 2.32 (3H, s), 1.68-2.13 (6H, m).

ESI-MS Found: m/z[M+H]+ 497.

Example 41

Production of 2-allyl-6-{[4-(4-ethylpiperazin-1-yl)-3-methylphenyl]amino}-1-pyridin-2-yl-1,2-dihydro-3H-pyrazolo[3,4-d]pyrimidin-3-one 19 mg of the entitled compound was obtained as a yellow solid in the same manner as in Example 29-1 to 29-2, for which, however, 4-(4-ethyl-1-piperazinyl)-3-methylaniline was used in place of [5-amino-2-(4-methylpiperazin-1-yl)phenyl]methanol used in Example 29-2.

$^1$H-NMR (400 MHz, CDCl$_3$) δ: 8.83 (1H, s), 8.53 (1H, d, J=3.2 Hz), 7.83-7.92 (2H, m), 7.01-7.70 (4H, m), 5.63-5.76 (1H, m), 5.01 (1H, d, J=10.1 Hz), 4.91 (1H, d, J=16.9 Hz), 4.78 (2H, d, J=6.8 Hz), 2.96 (4H, bs), 2.63 (4H, bs), 2.52 (2H, q, J=7.5 Hz), 2.33 (3H, s), 1.15 (3H, t, J=4.5 Hz).

ESI-MS Found: m/z[M+H]+ 471.

Example 42

Production of 2-allyl-6-{[4-(4-isopropylpiperazin-1-yl)-3-methylphenyl]amino}-1-pyridin-2-yl-1,2-dihydro-3H-pyrazolo[3,4-d]pyrimidin-3-one 17.5 mg of the entitled compound was obtained as a yellow solid in the same manner as in Example 29-1 to 29-2, for which, however, 4-(4-isopropyl-1-piperazinyl)-3-methylaniline was used in place of [5-amino-2-(4-methylpiperazin-1-yl)phenyl]methanol used in Example 29-2.

$^1$H-NMR (400 MHz, CDCl3) δ: 8.83 (1H, s), 8.53 (1H, d, J=3.5 Hz), 7.82-7.91 (2H, m), 7.01-7.57 (4H, m), 5.64-5.73 (1H, m), 5.02 (1H, d, J=10.5 Hz), 4.91 (1H, d, J=17.5 Hz), 4.78 (2H, d, J=7.2 Hz), 2.97 (4H, bs), 2.73 (5H, m), 2.33 (3H, s), 1.13 (6H, d, J=5.2 Hz).

ESI-MS Found: m/z[M+H]+ 485.

Example 43

Production of 2-allyl-6-{[4-(4-methylpiperazin-1-yl)-phenyl]amino}-1-(6-methylpyridin-2-yl)-1,2-dihydro-3H-pyrazolo[3,4-d]pyrimidin-3-one 15.8 mg of the entitled compound was obtained as a yellow solid in the same manner as in Example 29-1 to 29-2, for which, however, 2-bromo-6-methylpyridine was used in place of 2-iodopyridine used in Example 29-1, and 4-(4-methyl-1-piperazinyl)aniline was used in place of [5-amino-2-(4-methylpiperazin-1-yl)phenyl]methanol used in Example 29-2.

$^1$H-NMR (400 MHz, CDCl$_3$) δ: 8.85 (1H, s), 7.76 (1H, dd, J=8.0, 7.6 Hz), 7.66 (1H, d, J=8.0 Hz), 7.51 (2H, d, J=8.8 Hz), 7.48 (1H, brs), 7.12 (1H, d, J=7.4 Hz), 6.95 (2H, d, J=8.8 Hz), 5.73 (1H, ddt, J=17.0, 10.2, 6.7 Hz), 5.05 (1H, d, J=10.2 Hz), 4.93 (1H, d, J=17.0 Hz), 4.80 (2H, d, J=6.7 Hz), 3.24 (4H, t, J=4.9 Hz), 2.66-2.62 (4H, m), 2.62 (3H, s), 2.42 (3H, s).

ESI-MS Found: m/z[M+H]+ 457.

Example 44

Production of 2-allyl-6-{[4-(1-methylpiperidin-4-yl)phenyl]amino}-1-pyridin-2-yl-1,2-dihydro-3H-pyrazolo[3,4-d]pyrimidin-3-one 10.2 mg of the entitled compound was obtained as a white solid in the same manner as in Example 29-1 to 29-2, for which, however, 4-(1'-methyl-4-piperidinyl)aniline was used in place of [5-amino-2-(4-methylpiperazin-1-yl)phenyl]methanol used in Example 29-2.

$^1$H-NMR (400 MHz, CDCl$_3$) δ: 8.85 (1H, s), 8.53 (1H, d, J=5.3 Hz), 7.87-7.83 (2H, m), 7.52 (2H, d, J=8.6 Hz), 7.52 (1H, brs), 7.21 (2H, d, J=8.6 Hz), 5.69 (1H, ddt, J=17.0, 10.4, 6.5 Hz), 5.02 (1H, d, J=10.4 Hz), 4.92 (1H, d, J=17.0 Hz), 4.79 (2H, d, J=6.5 Hz), 3.00 (2H, d, J=11.0 Hz), 2.50-2.44 (1H, m), 2.35 (1H, s), 2.11-2.04 (2H, m), 1.86-1.80 (4H, m).

ESI-MS Found: m/z[M+H]+ 442.

Example 45

Production of 2-allyl-6-{[4-(1'-ethylpiperidin-4-yl)phenyl]amino}-1-pyridin-2-yl-1,2-dihydro-3H-pyrazolo[3,4-d]pyrimidin-3-one 14.5 mg of the entitled compound was obtained as a white solid in the same manner as in Example 29-1 to 29-2, for which, however, 4-(1'-ethyl-4-piperidinyl)aniline was used in place of [5-amino-2-(4-methylpiperazin-1-yl)phenyl]methanol used in Example 29-2.

$^1$H-NMR (400 MHz, CDCl$_3$) δ: 8.86 (1H, s), 8.53 (1H, d, J=4.9 Hz), 7.87-7.83 (2H, m), 7.52 (2H, d, J=8.4 Hz), 7.50 (1H, brs), 7.22 (2H, d, J=8.4 Hz), 5.69 (1H, ddt, J=17.0, 10.2, 6.3 Hz), 5.02 (1H, d, J=10.2 Hz), 4.92 (1H, dd, J=17.0, 1.2 Hz), 4.79 (2H, d, J=6.3 Hz), 3.11 (2H, d, J=11.4 Hz), 2.49-2.47 (3H, m), 2.05-1.95 (2H, m), 1.90-1.80 (4H, m), 1.15 (3H, t, J=7.2 Hz).

ESI-MS Found: m/z[M+H]+ 456.

Example 46

Production of 2-allyl-6-{[4-[1-(2-hydroxyethyl)piperidin-4-yl]phenyl}amino)-1-pyridin-2-yl-1,2-dihydro-3H-pyrazolo[3,4-d]pyrimidin-3-one 16 mg of the entitled compound was obtained as a white solid in the same manner as in Example 29-1 to 29-2, for which, however, 2-[4-(4-aminophenyl)-1-piperidinyl]ethanol was used in place of [5-amino-2-(4-methylpiperazin-1-yl)phenyl]methanol used in Example 29-2.

$^1$H-NMR (400 MHz, CDCl$_3$) δ: 8.86 (1H, s), 8.54 (1H, t, J=4.7 Hz), 7.89-7.87 (2H, m), 7.53 (2H, d, J=8.6 Hz), 7.47 (1H, brs), 7.21 (2H, d, J=7.6 Hz), 5.69 (1H, ddt, J=17.0, 10.0, 6.5 Hz), 5.02 (1H, d, J=10.0 Hz), 4.92 (1H, dd, J=17.0, 1.3 Hz), 4.79 (2H, d, J=6.5 Hz), 3.67 (2H, t, J=5.1 Hz), 3.08 (2H, d, J=12.1 Hz), 2.62 (2H, t, J=5.5 Hz), 2.57-2.51 (1H, m), 2.23 (2H, t, J=10.9 Hz), 1.89-1.78 (2H, m).

ESI-MS Found: m/z[M+H]+ 472.

Example 47

Production of 2-allyl-6-({3-methyl-4-[(1-methylpiperidin-4-yl)amino]phenyl}amino)-1'-pyridin-2-yl-1,2-dihydro-3H-pyrazolo[3,4-d]pyrimidin-3-one 11 mg of the entitled compound was obtained as a yellow solid in the same manner as in Example 29-1 to 29-2, for which, however, 2-methyl-N$^1$-(1-methyl-4-piperidinyl)-1,4-benzenediamine was used in place of [5-amino-2-(4-methylpiperazin-1-yl)phenyl]methanol used in Example 29-2.

$^1$H-NMR (400 MHz, CD$_3$OD) δ: 8.78 (1H, s), 8.54 (1H, d, J=4.8 Hz), 8.01 (1H, dd, J=7.2, 7.2 Hz), 7.92 (1H, d, J=7.2 Hz), 7.43 (1H, s, J=2.0 Hz), 7.40 (1H, dd, J=4.8, 3.2 Hz), 7.27 (1H, dd, J=8.4, 2.0 Hz), 6.6 (1H, d, J=8.4 Hz), 5.74 (1H, ddd, J=18.4, 14.8, 10.0 Hz), 5.07 (1H, d, J=10.0 Hz), 4.95 (1H, d, J=18.4 Hz), 4.73 (2H, J=14.8 Hz), 4.37 (2H, d, J=4.7 Hz), 3.36-3.24 (1H, m), 2.89-2.75 (2H, m), 2.31 (3H, s), 2.23-2.12 (2H, m), 2.10-2.02 (5H, m), 1.60-1.45 (2H, m).
ESI-MS Found: m/z[M+H]+ 471.

Example 48

Production of 2-allyl-6-{[4-(4-ethylpiperazin-1-yl)-3-(hydroxymethyl)phenyl]amino}-1-pyridin-2-yl-1,2-dihydro-3H-pyrazolo[3,4-d]pyrimidin-3-one 57 mg of the entitled compound was obtained as a white solid in the same manner as in Example 29-1 to 29-2, for which, however, [5-amino-2-(4-ethylpiperazin-1-yl)phenyl]methanol was used in place of [5-amino-2-(4-methylpiperazin-1-yl)phenyl]methanol used in Example 29-2.

$^1$H-NMR (400 MHz, CDCl$_3$) δ: 8.85 (1H, s), 8.54 (1H, d, J=4.4 Hz), 7.93-7.83 (2H, m), 7.60 (1H, brs), 7.52 (1H, brs), 7.35 (1H, d, J=8.8 Hz), 7.26-7.20 (1H, m), 5.68 (1H, ddt, J=17.1, 10.2, 6.4 Hz), 5.02 (1H, dd, J=10.2, 1.0 Hz), 4.91 (1H, dd, J=17.1, 1.5 Hz), 4.82-4.77 (5H, m), 3.04 (4H, t, J=4.6 Hz), 2.67 (4H, brs), 2.52 (2H, d, J=6.8 Hz), 1.15 (3H, t, J=7.1 Hz).
ESI-MS Found: m/z[M+H]+ 487.

Example 49

Production of 2-allyl-1-(6-aminopyridin-2-yl)-6-{[3-methyl-4-(4-methylpiperazin-1-yl)phenyl]amino}-1,2-dihydro-3H-pyrazolo[3,4-d]pyrimidin-3-one 1) Production of di-tert-butyl{6-[2-allyl-6-(methylthio)-3-oxo-1,2-dihydro-3H-pyrazolo[3,4-d]pyrimidin-1-yl]-2-pyridinyl}imidedicarboxylate 2.00 g of the entitled compound was obtained as a white solid in the same manner as in Example 29-1, for which, however, di-tert-butyl (6-bromopyridin-2-yl)imidedicarboxylate was sued in place of 2-iodopyridine used in Example 29-1.

$^1$H-NMR (400 MHz, CDCl$_3$) δ: 8.92 (1H, s), 7.92 (1H, t, J=8.0 Hz), 7.80 (1H, d, J=8.8 Hz), 7.35 (1H, d, J=7.8 Hz), 5.63 (1H, ddt, J=17.1, 10.2, 6.3 Hz), 5.03 (1H, dd, J=10.2, 1.0 Hz), 5.00 (1H, dd, J=17.1, 1.2 Hz), 4.82 (2H, d, J=6.3 Hz), 2.58 (3H, s), 1.51 (18H, s).
ESI-MS Found: m/z[M+H]+ 515.

2) Production of 2-allyl-1-(6-aminopyridin-2-yl)-6-{[3-methyl-4-(4-methylpiperazin-1-yl)phenyl]amino}-1,2-dihydro-3H-pyrazolo[3,4-d]pyrimidin-3-one 53 mg of m-chloroperbenzoic acid (>65%) was added to toluene (2 mL) solution of 103 mg of di-tert-butyl {6-[2-allyl-6-(methylthio)-3-oxo-2,3-dihydro-1H-pyrazolo[3,4-d]pyrimidin-1-yl]-2-pyridinyl}imidedicarboxylate, and stirred for 30 minutes. 0.105 mL of N,N-diisopropylethylamine and 49 mg of 3-methyl-4-(4-methylpiperazin-1-yl)aniline were added to the reaction liquid, and stirred overnight. Aqueous saturated sodium hydrogencarbonate solution was added to the reaction liquid, ethyl acetate was added thereto for extraction, the resulting extract was washed with saturated saline water, and dried with anhydrous magnesium sulfate. The solvent was evaporated away, and the residue was purified through basic silica gel column chromatography (hexane/ethyl acetate=1/1 to 0/1). After concentrated, 93.2 mg of a white solid was obtained.
2 mL of trifluoroacetic acid was added to the obtained compound, stirred, and saturated sodium hydrogencarbonate was added thereto, extracted with ethyl acetate, washed with saline water, and dried with anhydrous magnesium sulfate. The solvent was evaporated away under reduced pressure to obtain 51.8 mg of the entitled compound as a white solid.

$^1$H-NMR (400 MHz, CDCl$_3$) δ: 8.81 (1H, s), 7.60 (1H, t, J=7.8 Hz), 7.52 (1H, s), 7.34 (1H, dd, J=8.8, 2.4 Hz), 7.00 (1H, d, J=8.3 Hz), 6.43 (1H, d, J=7.8 Hz), 5.71 (1H, ddt, J=16.8, 10.2, 5.9 Hz), 5.06 (1H, dd, J=10.2, 1.0 Hz), 5.00 (1H, dd, J=16.8, 1.2 Hz), 4.71 (2H, d, J=5.9 Hz), 4.58 (2H, s), 2.95 (4H, t, J=4.6 Hz), 2.66 (4H, s), 2.42 (3H, s), 2.31 (3H, s).
ESI-MS Found: m/z[M+H]+ 412.

Example 50

Production of 2-allyl-1-(6-aminopyridin-2-yl)-6-{[4-(4-methylpiperazin-1-yl)phenyl]amino}-1,2-dihydro-3H-pyrazolo[3,4-d]pyrimidin-3-one 966 mg of the entitled compound was obtained as a yellow solid in the same manner as in Example 49-1 to 49-2, for which, however, 4-(4-methylpiperazin-1-yl)aniline was used in place of 3-methyl-4-(4-methylpiperazin-1-yl)aniline used in Example 49-2.

$^1$H-NMR (400 MHz, CDCl$_3$) δ: 8.80 (1H, s), 7.59 (1H, t, J=7.8 Hz), 7.39 (1H, brs), 6.91 (2H, d, J=8.8 Hz), 6.42 (1H, d, J=8.3 Hz), 5.71 (1H, ddt, J=17.1, 10.2, 5.9 Hz), 5.06 (1H, dd, J=10.2, 1.0 Hz), 5.00 (1H, dd, J=17.1, 1.0 Hz), 4.70 (2H, d, J=5.9 Hz), 4.57 (2H, s), 3.20 (4H, t, J=5.1 Hz), 2.61 (4H, t, J=4.9 Hz), 2.38 (3H, s).
ESI-MS Found: m/z[M+H]+ 458.

Example 51

Production of 2-allyl-1-{6-[(dimethylamino)methyl]pyridin-2-yl}-6-{[4-(4-methylpiperazin-1-yl)phenyl]amino}-1,2-dihydro-3H-pyrazolo[3,4-d]pyrimidin-3-one 1) Production of 2-allyl-1-[6-(hydroxymethyl)-2-pyridinyl]-6-(methylthio)-1,2-dihydro-3H-pyrazolo[3,4-d]pyrimidin-3-one 3.40 g of the entitled compound was obtained as a white solid in the same manner as in Example 29-1, for which, however, (6-bromopyridin-2-yl)methanol was used in place of 2-iodopyridine used in Example 29-1.

$^1$H-NMR (400 MHz, CDCl$_3$) δ: 8.94 (1H, s), 7.91 (1H, t, J=7.8 Hz), 7.78 (1H, dd, J=8.0, 0.7 Hz), 7.27 (1H, d, J=7.8 Hz), 5.76-5.66 (1H, m), 5.07 (1H, dd, J=10.2, 1.0 Hz), 4.95 (1H, dd, J=17.1, 1.0 Hz), 4.84-4.77 (4H, m), 2.58 (3H, s).
ESI-MS Found: m/z[M+H]+ 330.

2) Production of 2-allyl-1-{6-[(dimethylamino)methyl]-2-pyridinyl}-6-(methylthio)-1,2-dihydro-3H-pyrazolo[3,4-d]pyrimidin-3-one hydrochloride 1.16 mL of triethylamine and 0.451 mL of methanesulfonyl chloride were added to tetrahydrofuran (20 mL) solution of 1.37 g of the compound obtained in the above 1, and stirred for 30 minutes, and then 6 mL of 2.0 M dimethylamine/tetrahydrofuran solution was added to the reaction liquid and stirred for 8 hours. Water was added to the reaction liquid, and extracted with ethyl acetate. This was washed with saturated saline water, dried with anhydrous magnesium sulfate, and concentrated under reduced pressure. 10 mL of ethyl acetate and 1.5 mL of 4 N hydrochloric acid-dioxane solution were added to the resulting residue, then the solvent was concentrated under reduced pressure, and the residue was crystallized with methanol/diethyl ether to obtain 1.50 g of the entitled compound as a white solid.

$^1$H-NMR (400 MHz, DMSO-d$_6$) δ: 8.17 (1H, s), 7.36 (1H, t, J=7.8 Hz), 7.21 (1H, d, J=7.8 Hz), 6.76 (1H, d, J=7.3 Hz), 4.92 (1H, ddt, J=17.1, 10.2, 6.0 Hz), 4.26 (1H, dd, J=10.2, 1.5 Hz), 4.14 (1H, dd, J=17.1, 1.5 Hz), 4.00 (2H, dt, J=6.0, 1.3 Hz), 3.75 (2H, s), 2.14 (6H, s), 1.78 (3H, s).

ESI-MS Found: m/z[M+H]+ 357.

3) Production of 2-allyl-1-{6-[(dimethylamino)methyl]pyridin-2-yl}-6-{[4-(4-methylpiperazin-1-yl)phenyl]amino}-1,2-dihydro-3H-pyrazolo[3,4-d]pyrimidin-3-one 65 mg of m-chloroperbenzoic acid was added to N,N-dimethylformamide (2 mL) solution of 100 mg of the compound obtained in the above 2, and stirred at room temperature for 15 minutes. The reaction liquid was washed with aqueous saturated sodium hydrogencarbonate solution, and dried with anhydrous sodium sulfate. The solvent was evaporated away under reduced pressure to obtain crude 2-allyl-1-{6-[(dimethylamino)methyl]pyridin-2-yl}-6-(methylsulfinyl)-1,2-dihydro-3H-pyrazolo[3,4-d]pyrimidin-3-one as a white solid.

40 mg of 4-(4-methylpiperazin-1-yl)aniline and 0.1 mL of N,N-diisopropylethylamine were added in that order to dimethylsulfoxide/toluene (1/10, 10 mL) solution of 40 mg of the above compound, and stirred at 120° C. for 15 hours. The solvent was evaporated away under reduced pressure, water was added thereto, extracted with ethyl acetate, and dried with anhydrous sodium sulfate. The solvent was evaporated away under reduced pressure, and the residue was separated and purified through basic silica gel column chromatography (ethyl acetate) to obtain 8.4 mg of the entitled compound as a yellow solid.

$^1$H-NMR (400 MHz, CDCl$_3$) δ: 8.82 (1H, s), 7.82 (1H, t, J=7.8 Hz), 7.74 (1H, d, J=7.8 Hz), 7.47 (2H, d, J=8.8 Hz), 7.39 (1H, d, J=7.3 Hz), 6.92 (2H, d, J=6.3 Hz), 5.74-5.63 (1H, m), 5.00 (1H, dd, J=10.2, 1.0 Hz), 4.89 (1H, dd, J=17.1, 1.0 Hz), 4.80 (2H, d, J=5.9 Hz), 3.64 (2H, s), 3.22 (4H, t, J=4.9 Hz), 2.64 (4H, d, J=4.4 Hz), 2.39 (3H, s), 2.34 (6H, s).

ESI-MS Found: m/z[M+H]+ 500.

Example 52

Production of 2-allyl-1-[6-[(dimethylamino)methyl]pyridin-2-yl]-6-{[3-methyl-4-(4-methylpiperazin-1-yl)phenyl]amino}-1,2-dihydro-3H-pyrazolo[3,4-d]pyrimidin-3-one 682 mg of the entitled compound was obtained as a white solid in the same manner as in Example 51-1 to 51-2, for which, however, 3-methyl-4-(4-methylpiperazin-1-yl)aniline was used in place of 4-(4-methylpiperazin-1-yl)aniline used in Example 51.

$^1$H-NMR (400 MHz, CDCl$_3$) δ: 8.83 (1H, s), 7.83 (1H, t, J=7.8 Hz), 7.77 (1H, d, J=7.8 Hz), 7.50 (1H, s), 7.39 (1H, brs), 7.38 (1H, d, J=7.8 Hz), 7.32 (1H, dd, J=8.5, 2.7 Hz), 7.02 (1H, d, J=8.8 Hz), 5.68 (1H, ddt, J=17.1, 10.2, 6.3 Hz), 5.00 (1H, dd, J=10.2, 1.0 Hz), 4.89 (1H, dd, J=17.1, 1.0 Hz), 4.81 (2H, d, J=6.3 Hz), 3.62 (2H, s), 2.95 (4H, t, J=4.6 Hz), 2.61 (4H, s), 2.39 (3H, s), 2.33 (6H, s), 2.32 (3H, s).

ESI-MS Found: m/z[M+H]+ 524.

Example 53

Production of 2-allyl-1-[6-(1-hydroxy-1-methylethyl)pyridin-2-yl]-6-{[4-(4-methylpiperazin-1-yl)phenyl]amino}-1,2-dihydro-3H-pyrazolo[3,4-d]pyrimidin-3-one 1) Production of 2-(6-bromo-2-pyridinyl)-2-propanol In a nitrogen atmosphere, 30 mL of 3 M methylmagnesium iodide/diethyl ether was added to 300 mL of diethyl ether solution of 8.72 g of methyl 6-bromopyridine-2-carboxylate. Water and 2 N hydrochloric acid were added to the reaction liquid, and extracted with ethyl acetate. This was washed with aqueous saturated sodium hydrogencarbonate solution and saturated saline water, and dried with anhydrous magnesium sulfate. The solvent was evaporated away under reduced pressure to obtain 8.51 g of crude 2-(6-bromo-2-pyridinyl)-2-propanol as a yellow oily substance.

$^1$H-NMR (400 MHz, CDCl$_3$) δ: 7.56 (1H, t, J=7.8 Hz), 7.38 (1H, dd, J=7.8, 1.0 Hz), 7.36 (1H, dd, J=7.8, 1.0 Hz), 1.55 (6H, s).

ESI-MS Found: m/z[M+H]+ 216, 218.

2) Production of 2-allyl-1-[6-(1-hydroxy-1-methylethyl)-2-pyridinyl]-6-(methylthio)-1,2-dihydro-3H-pyrazolo[3,4-d]pyrimidin-3-one 12.89 g of the entitled compound was obtained in the same manner as in Example 29-1, for which, however, the compound obtained in the above reaction was used in place of 2-iodopyridine used in Example 29-1.

$^1$H-NMR (400 MHz, CDCl$_3$) δ: 8.95 (1H, s), 7.91 (1H, t, J=8.0 Hz), 7.76 (1H, d, J=7.3 Hz), 7.40 (1H, dd, J=7.8, 1.0 Hz), 5.70 (1H, ddt, J=17.1, 10.2, 6.3 Hz), 5.06 (1H, dd, J=10.2, 1.0 Hz), 4.93 (1H, dd, J=17.1, 1.2 Hz), 4.81 (2H, d, J=6.3 Hz), 2.59 (4H, s), 1.59 (6H, s).

ESI-MS Found: m/z[M+H]+: 358.

3) Production of 2-allyl-1-[6-(1-hydroxy-1-methylethyl)pyridin-2-yl]-6-{[4-(4-methylpiperazin-1-yl)phenyl]amino}-1,2-dihydro-3H-pyrazolo[3,4-d]pyrimidin-3-one 817 mg of m-chloroperbenzoic acid (>65%) was added to toluene (20 mL) solution of 1.10 g of the above produce, and stirred for 20 minutes. 1.61 mL of N,N-diisopropylethylamine and 706 mg of 4-(4-methylpiperazin-1-yl)aniline were added to the reaction liquid, and stirred overnight. Aqueous saturated sodium hydrogencarbonate solution was added to the reaction liquid, extracted with ethyl acetate, washed with saturated saline water, and dried with anhydrous magnesium sulfate. The solvent was evaporated away, and the residue was purified through basic silica gel column chromatography (hexane/ethyl acetate=1/1 to 0/1, ethyl acetate/ethanol=98/2). After concentrated, this was recrystallized from ethyl acetate to obtain 1.20 g of the entitled compound as a yellow solid.

$^1$H-NMR (400 MHz, CDCl$_3$) δ: 8.83 (1H, s), 7.86 (1H, dd, J=8.0, 7.8 Hz), 7.75 (1H, d, J=7.3 Hz), 7.49 (1H, brs), 7.48 (2H, d, J=9.0 Hz), 7.34 (1H, d, J=7.4 Hz), 6.93 (2H, d, J=9.0 Hz), 5.70 (1H, ddt, J=17.2, 10.0, 6.5 Hz), 5.04 (1H, d, J=10.0 Hz), 4.94 (1H, d, J=17.2 Hz), 4.74 (2H, d, J=6.5 Hz), 3.26 (4H, t, J=4.8 Hz), 2.73 (4H, brs), 2.44 (3H, s), 1.59 (6H, s).

ESI-MS Found: m/z[M+H]+ 501.

Example 54

Production of 2-allyl-1-[6-(1-hydroxy-1-methyl-ethyl)pyridin-2-yl]-6-{[3-methyl-4-(4-methylpiperazin-1-yl)phenyl]amino}-1,2-dihydro-3H-pyrazolo[3,4-d]pyrimidin-3-one 56.8 mg of the entitled compound was obtained as a white solid in the same manner as in Example 53-1 to 53-3, for which, however, 3-methyl-4-(4-methylpiperazin-1-yl)aniline was used in place of 4-(4-methylpiperazin-1-yl)aniline used in Example 53-3.

$^1$H-NMR (DMSO-d$_6$) δ: 10.18 (1H, brs), 8.82 (1H, s), 8.02 (1H, t, J=7.8 Hz), 7.77 (1H, d, J=8.4 Hz), 7.67 (1H, brs), 7.62 (1H, d, J=8.2 Hz), 7.40 (1H, d, J=6.8 Hz), 6.99 (1H, d, J=8.6 Hz), 5.66 (1H, ddt, J=17.2, 10.4, 6.1 Hz), 5.33 (1H, s), 4.99 (1H, d, J=10.4 Hz), 4.81 (1H, d, J=17.2 Hz), 4.68 (2H, d, J=6.1 Hz), 2.82 (4H, brs), 2.50 (4H, brs), 2.25 (6H, s), 1.46 (6H, s).

ESI-MS Found: m/z[M+H]+ 525.

Example 55

Production of 2-allyl-1-[6-(1-hydroxy-1-methyl-ethyl)pyridin-2-yl]-6-{[3-(hydroxymethyl)-4-(4-methylpiperazin-1-yl)phenyl]amino}-1,2-dihydro-3H-pyrazolo[3,4-d]pyrimidin-3-one 48 mg of the entitled compound was obtained as a white solid in the same manner as in Example 53-1 to 53-3, for which, however, [5-amino-2-(4-methylpiperazin-1-yl)phenyl]methanol was used in place of 4-(4-methylpiperazin-1-yl)aniline used in Example 53-3.

$^1$H-NMR (400 MHz, CDCl$_3$) δ: 8.86 (1H, s), 7.92 (1H, t, J=8.0 Hz), 7.76 (1H, d, J=7.8 Hz), 7.60 (1H, s), 7.37 (2H, d, J=7.8 Hz), 7.22 (1H, d, J=8.8 Hz), 5.70 (1H, ddt, J=17.1, 10.2, 6.3 Hz), 5.04 (1H, d, J=10.2 Hz), 4.93 (1H, d, J=17.1 Hz), 4.79 (2H, s), 4.75 (2H, d, J=6.3 Hz), 3.03 (4H, t, J=5.0 Hz), 2.65 (4H, s), 2.40 (3H, s), 1.59 (6H, s).

ESI-MS Found: m/z[M+H]+ 531.

Example 56

Production of 2-allyl-1-[6-(1-hydroxy-1-methyl-ethyl)pyridin-2-yl]-6-{[4-(1-methylpiperidin-4-yl)phenyl]amino}-1,2-dihydro-3H-pyrazolo[3,4-d]pyrimidin-3-one 60.2 mg of the entitled compound was obtained as a white solid in the same manner as in Example 53-1 to 53-3, for which, however, 4-(1-methyl-4-piperidinyl)aniline was used in place of 4-(4-methylpiperazin-1-yl)aniline used in Example 53-3.

$^1$H-NMR (400 MHz, CDCl$_3$) δ: 8.86 (1H, s), 7.87 (1H, t, J=8.2 Hz), 7.76 (1H, d, J=8.2 Hz), 7.53 (2H, d, J=8.4 Hz), 7.52 (1H, brs), 7.36 (1H, d, J=7.6 Hz), 7.22 (1H, d, J=8.6 Hz), 5.70 (1H, ddt, J=16.8, 10.3, 6.3 Hz), 5.05 (1H, d, J=10.3 Hz), 4.94 (1H, d, J=16.8 Hz), 4.75 (2H, d, J=6.3 Hz), 3.94 (1H, brs), 3.01 (1H, d, J=11.5 Hz), 2.49-2.47 (1H, m), 2.35 (3H, s), 2.08-2.04 (2H, m), 1.86-1.80 (2H, m), 1.70-1.60 (2H, m), 1.59 (6H, s).

ESI-MS Found: m/z[M+H]+ 500.

Example 57

Production of 2-allyl-6-{[4-(4-tert-butylpiperazin-1-yl)phenyl]amino}-1-[6-(1-hydroxy-1-methylethyl)pyridin-2-yl]-1,2-dihydro-3H-pyrazolo[3,4-d]pyrimidin-3-one 43 mg of the entitled compound was obtained as a yellow solid in the same manner as in Example 53-1 to 53-3, for which, however, 4-(4-tert-butyl-1-piperazinyl)aniline was used in place of 4-(4-methylpiperazin-1-yl)aniline used in Example 53-3.

$^1$H-NMR (400 MHz, CDCl$_3$) δ: 8.83 (1H, s), 7.85 (1H, t, J=7.8 Hz), 7.76 (1H, d, J=7.3 Hz), 7.45 (2H, d, J=8.8 Hz), 7.33 (1H, d, J=8.3 Hz), 6.93 (2H, d, J=9.3 Hz), 5.76-5.65 (1H, m), 5.04 (1H, d, J=10.2 Hz), 4.94 (1H, dd, J=17.1, 1.5 Hz), 4.74 (2H, d, J=6.3 Hz), 3.21 (4H, brs), 2.78 (4H, brs), 1.58 (9H, s).

ESI-MS Found: m/z[M+H]+ 543.

Example 58

Production of 2-allyl-6-{[4-(4-ethylpiperazin-1-yl)phenyl]amino}-1-[6-(1-hydroxy-1-methylethyl)pyridin-2-yl]-1,2-dihydro-3H-pyrazolo[3,4-d]pyrimidin-3-one 50.3 mg of the entitled compound was obtained as a yellow solid in the same manner as in Example 53-1 to 53-3, for which, however, 4-(4-ethyl-1-piperazinyl)aniline was used in place of 4-(4-methylpiperazin-1-yl)aniline used in Example 53-3.

$^1$H-NMR (400 MHz, CDCl$_3$) δ: 8.83 (1H, s), 7.85 (1H, t, J=7.8 Hz), 7.76 (1H, d, J=7.8 Hz), 7.46 (2H, d, J=8.8 Hz), 7.34 (1H, d, J=8.3 Hz), 6.93 (2H, d, J=8.8 Hz), 5.76-5.64 (1H, m), 5.04 (1H, dd, J=10.2, 1.0 Hz), 4.94 (1H, dd, J=17.1, 1.0 Hz), 4.75 (2H, d, J=6.3 Hz), 4.00 (1H, brs), 3.23 (4H, t, J=4.9 Hz), 2.65 (4H, t, J=4.9 Hz), 2.51 (2H, q, J=7.3 Hz), 1.59 (6H, s), 1.16 (3H, t, J=7.3 Hz).

ESI-MS Found: m/z[M+H]+ 515.

Example 59

Production of 2-allyl-6-{[4-(4-isopropylpiperazin-1-yl)phenyl]amino}-1-[6-(1-hydroxy-1-methylethyl)pyridin-2-yl]-1,2-dihydro-3H-pyrazolo[3,4-d]pyrimidin-3-one 32.1 mg of the entitled compound was obtained as a yellow solid in the same manner as in Example 53-1 to 53-3, for which, however, 4-(4-isopropyl-1-piperazinyl)aniline was used in place of 4-(4-methylpiperazin-1-yl)aniline used in Example 53-3.

$^1$H-NMR (400 MHz, CDCl$_3$) δ: 8.83 (1H, s), 7.85 (1H, t, J=8.0 Hz), 7.75 (1H, d, J=8.3 Hz), 7.46 (2H, d, J=8.8 Hz), 7.33 (1H, d, J=7.8 Hz), 6.93 (2H, d, J=9.3 Hz), 5.76-5.64 (1H, m), 5.04 (1H, d, J=10.2 Hz), 4.93 (1H, dd, J=17.1, 1.5 Hz), 4.74 (2H, d, J=5.9 Hz), 3.97 (1H, s), 3.25-3.15 (4H, m), 2.82-2.70 (4H, m), 1.76-1.65 (1H, m), 1.58 (6H, s), 1.13 (6H, d, J=6.0 Hz).

ESI-MS Found: m/z[M+H]+ 529.

Example 60

Production of 2-allyl-6-{[4-(4-cyclopropylpiperazin-1-yl)phenyl]amino}-1-[6-(1-hydroxy-1-methylethyl)pyridin-2-yl]-1,2-dihydro-3H-pyrazolo[3,4-d]pyrimidin-3-one 76.6 mg of the entitled compound was obtained as a yellow solid in the same manner as in Example 53-1 to 53-3, for which, however, 4-(4-cyclopropylpiperazin-1-yl)aniline was used in place of 4-(4-methylpiperazin-1-yl)aniline used in Example 53-3.

¹H-NMR (400 MHz, CDCl₃) δ: 8.83 (1H, s), 7.85 (1H, t, J=8.0 Hz), 7.76 (1H, d, J=8.3 Hz), 7.46 (2H, d, J=8.8 Hz), 7.34 (1H, d, J=7.8 Hz), 6.93 (2H, d, J=9.3 Hz), 5.76-5.64 (1H, m), 5.04 (1H, d, J=10.2 Hz), 4.94 (1H, dd, J=17.1, 1.5 Hz), 4.74 (2H, d, J=5.9 Hz), 3.98 (1H, s), 3.20-3.15 (4H, m), 2.85-2.79 (4H, m), 1.76-1.65 (1H, m), 1.58 (6H, s), 0.54-0.44 (4H, m).

ESI-MS Found: m/z[M+H]+ 527.

Example 61

Production of 2-allyl-1-[6-(1-hydroxy-1-methylethyl)pyridin-2-yl]-6-{[4-[4-(2-methoxyethyl)piperazin-1-yl]phenyl}amino]-1,2-dihydro-3H-pyrazolo[3,4-d]pyrimidin-3-one 46.7 mg of the entitled compound was obtained as a yellow solid in the same manner as in Example 53-1 to 53-3, for which, however, 4-[4-(2-methoxyethyl)-1-piperazinyl]aniline was used in place of 4-(4-methylpiperazin-1-yl)aniline used in Example 53-3.

¹H-NMR (400 MHz, CDCl₃) δ: 8.83 (1H, s), 7.85 (1H, t, J=7.8 Hz), 7.75 (1H, d, J=7.8 Hz), 7.46 (2H, d, J=8.8 Hz), 7.34 (1H, d, J=7.3 Hz), 6.92 (2H, d, J=9.3 Hz), 5.75-5.65 (1H, m), 5.04 (1H, d, J=10.2 Hz), 4.94 (1H, d, J=17.1 Hz), 4.74 (2H, d, J=6.3 Hz), 3.99-3.96 (1H, m), 3.58 (2H, t, J=5.4 Hz), 3.39 (3H, s), 3.25-3.21 (4H, m), 2.73-2.63 (6H, m), 1.59 (6H, s).

ESI-MS Found: m/z[M+H]+ 545.

Example 62

Production of 2-allyl-6-({4-[4-(2-ethoxyethyl)-1-piperazinyl]phenyl}amino)-1-[6-(1-hydroxy-1-methylethyl)pyridin-2-yl]-1,2-dihydro-3H-pyrazolo[3,4-d]pyrimidin-3-one 48.6 mg of the entitled compound was obtained as a yellow solid in the same manner as in Example 53-1 to 53-3, for which, however, 4-[4-(2-ethoxyethyl)-1-piperazinyl]aniline was used in place of 4-(4-methylpiperazin-1-yl)aniline used in Example 53-3.

¹H-NMR (400 MHz, CDCl₃) δ: 8.82 (1H, s), 7.85 (1H, t, J=7.8 Hz), 7.75 (1H, d, J=7.8 Hz), 7.46 (2H, d, J=8.3 Hz), 7.34 (1H, d, J=7.3 Hz), 6.92 (2H, d, J=8.8 Hz), 5.76-5.64 (1H, m), 5.04 (1H, d, J=10.2 Hz), 4.93 (1H, d, J=17.1 Hz), 4.74 (2H, d, J=6.3 Hz), 4.02-3.96 (1H, m), 3.62 (2H, t, J=5.6 Hz), 3.53 (2H, q, J=7.0 Hz), 3.25-3.18 (4H, m), 2.75-2.63 (6H, m), 1.58 (6H, s), 1.22 (3H, t, J=7.0 Hz).

ESI-MS Found: m/z[M+H]+ 559.

Example 63

Production of 6-{[4-(4-acetylpiperazin-1-yl)phenyl]amino}-2-allyl-1-[6-(1-hydroxy-1-methylethyl)pyridin-2-yl]-1,2-dihydro-3H-pyrazolo[3,4-d]pyrimidin-3-one 66.4 mg of the entitled compound was obtained as a yellow solid in the same manner as in Example 53-1 to 53-3, for which, however, 4-(4-acetyl-1-piperazinyl)aniline was used in place of 4-(4-methylpiperazin-1-yl)aniline used in Example 53-3.

¹H-NMR (400 MHz, CDCl₃) δ: 8.84 (1H, s), 7.87 (1H, t, J=7.8 Hz), 7.74 (1H, d, J=8.8 Hz), 7.50 (2H, d, J=8.8 Hz), 7.36 (1H, d, J=8.3 Hz), 6.94 (2H, d, J=8.8 Hz), 5.76-5.65 (1H, m), 5.04 (1H, d, J=10.2 Hz), 4.94 (1H, d, J=17.1 Hz), 4.74 (2H, d, J=5.9 Hz), 4.03-3.95 (1H, m), 3.80 (2H, t, J=4.9 Hz), 3.65 (2H, t, J=5.1 Hz), 3.17 (2H, t, J=4.9 Hz), 3.14 (2H, t, J=5.1 Hz), 2.16 (3H, s), 1.59 (6H, s).

ESI-MS Found: m/z[M+H]+ 529.

Example 64

Production of 2-allyl-6-({4-[4-(2-hydroxyethyl)piperazin-1-yl]phenyl}amino)-1-[6-(1-hydroxy-1-methylethyl)pyridin-2-yl]-1,2-dihydro-3H-pyrazolo[3,4-d]pyrimidin-3-one 40 mg of the entitled compound was obtained as a yellow solid in the same manner as in Example 53-1 to 53-3, for which, however, 2-[4-(4-aminophenyl)-1-piperazinyl]ethanol was used in place of 4-(4-methylpiperazin-1-yl)aniline used in Example 53-3.

¹H-NMR (400 MHz, CDCl₃) δ: 8.83 (1H, s), 7.86 (1H, t, J=7.8 Hz), 7.75 (1H, d, J=7.8 Hz), 7.47 (2H, d, J=8.8 Hz), 7.34 (1H, d, J=8.3 Hz), 6.93 (2H, d, J=8.8 Hz), 5.76-5.65 (1H, m), 5.04 (1H, d, J=10.2 Hz), 4.94 (1H, d, J=17.1 Hz), 4.74 (2H, d, J=6.3 Hz), 4.03-3.95 (1H, m), 3.69 (2H, t, J=5.1 Hz), 3.22 (4H, t, J=4.9 Hz), 2.73 (4H, t, J=4.6 Hz), 2.65 (2H, t, J=5.4 Hz), 1.59 (6H, s).

ESI-MS Found: m/z[M+H]+ 531.

Example 65

Production of 2-allyl-6-({4-[(diethylamino)methyl]phenyl}amino)-1-[6-(1-hydroxy-1-methylethyl)pyridin-2-yl]-1,2-dihydro-3H-pyrazolo[3,4-d]pyrimidin-3-one 46 mg of the entitled compound was obtained as a white solid in the same manner as in Example 53-1 to 53-3, for which, however, 4-[(diethylamino)methyl]aniline was used in place of 4-(4-methylpiperazin-1-yl)aniline used in Example 53-3.

¹H-NMR (400 MHz, CDCl₃) δ: 8.87 (1.0H, s), 7.89 (1.0H, d, J=7.8 Hz), 7.78 (1.0H, d, J=7.8 Hz), 7.55 (2.0H, d, J=8.3 Hz), 7.36 (2.0H, d, J=7.8 Hz), 7.33 (1.0H, brs), 5.71 (1.0H, ddt, J=17.1, 10.2, 6.3 Hz), 5.05 (1.0H, d, J=10.2 Hz), 4.94 (1.0H, dd, J=17.1, 1.0 Hz), 4.76 (2.4H, d, J=6.3 Hz), 3.93 (1.0H, brs), 3.57 (2.0H, brs), 2.54 (4.0H, brs), 1.59 (6.0H, s), 1.07 (5.9H, t, J=5.9 Hz).

ESI-MS Found: m/z[M+H]+ 488.

Example 66

Production of 2-allyl-1-[6-(1-hydroxy-1-methylethyl)pyridin-2-yl]-6-[(1-methyl-1H-pyrazol-3-yl)amino]-1,2-dihydro-3H-pyrazolo[3,4-d]pyrimidin-3-one 17.5 mg of the entitled compound was obtained as a white solid in the same manner as in Example 53-1 to 53-3, for which, however, 1-methyl-1H-pyrazole-3-amine was used in place of 4-(4-methylpiperazin-1-yl)aniline used in Example 53-3.

¹H-NMR (400 MHz, CDCl₃) δ: 8.93 (s, 1H), 7.91 (ddd, 1H, J=7.6, 8.2, 1.0 Hz), 7.75 (d, 1H, J=8.2 Hz), 7.37 (d, 1H, J=7.6 Hz), 7.27-7.29 (m, 1H), 6.67-6.70 (m, 1H), 5.71 (ddt, 1H, J=17.0, 10.2, 6.3 Hz), 5.04 (d, 1H, J=10.2 Hz), 4.93 (d, 1H, J=17.0 Hz), 4.73 (d, 2H, J=6.3 Hz), 3.94 (brs, 1H), 3.85 (s, 3H), 1.59 (s, 6H).
ESI-MS Found: m/z[M+H]+ 407.

Example 67

Production of 2-allyl-1-[6-(1-hydroxy-1-methylethyl)piperidin-2-yl]-6-{[5-methyl-6-(4-methyl-1-piperazinyl)-3-pyridinyl]amino}-1,2-dihydro-3H-pyrazolo[3,4-d]pyrimidin-3-one 17.7 mg of the entitled compound was obtained as a yellow solid in the same manner as in Example 53-1 to 53-3, for which, however, 5-methyl-6-(4-methyl-1-piperazinyl)-3-pyridinamine was used in place of 4-(4-methylpiperazin-1-yl)aniline used in Example 53-3.
$^1$H-NMR (400 MHz, CDCl$_3$) δ: 8.86 (s, 1H), 8.24-8.27 (m, 1H), 7.88 (dd, 2H, J=7.6, 8.0 Hz), 7.83-7.85 (m, 2H), 7.73 (d, 1H, J=8.0 Hz), 7.37 (d, 1H, J=7.6 Hz), 5.70 (ddt, 1H, J=17.0, 10.0, 6.1 Hz), 5.04 (d, 1H, J=10.0 Hz), 4.93 (d, 1H, J=17.0 Hz), 4.75 (d, 2H, J=6.1 Hz), 3.88 (brs, 1H), 3.17-3.33 (m, 4H), 2.60-2.83 (m, 2H), 2.39-2.51 (m, 2H), 2.31 (s, 3H), 1.59 (s, 9H).
ESI-MS Found: m/z[M+H]+ 516.

Example 68

Production of 2-allyl-6-anilino-1-[6-(1-hydroxy-1-methylethyl)pyridin-2-yl]-1,2-dihydro-3H-pyrazolo[3,4-d]pyrimidin-3-one 7.0 mg of the entitled compound was obtained as a white solid in the same manner as in Example 53-1 to 53-3, for which, however, aniline was used in place of 4-(4-methylpiperazin-1-yl)aniline used in Example 53-3.
$^1$H-NMR (400 MHz, CDCl$_3$) δ: 8.87 (1H, s), 7.88 (1H, dd, J=8.0, 7.6 Hz), 7.77 (1H, d, J=8.0 Hz), 7.61 (1H, d, J=8.6 Hz), 7.39-7.34 (2H, m), 7.13 (1H, dd, J=7.2, 7.2 Hz), 5.70 (1H, ddd, J=17.2, 10.4, 6.4 Hz), 4.03 (1H, s), 1.56 (6H, s).
ESI-MS Found: m/z[M+H]+ 403.

Example 69

Production of 2-allyl-1-[6-(1-hydroxycyclobutyl)pyridin-2-yl]-6-{[4-(4-methylpiperazin-1-yl)phenyl]amino}-1,2-dihydro-3H-pyrazolo[3,4-d]pyrimidin-3-one 1) Production of 1-(6-bromo-2-pyrimidinyl)cyclobutanol In a nitrogen atmosphere at −10° C., 10.8 mL of 2.66 M n-butyllithium/hexane solution was dropwise added to 16 mL of 0.9 M n-butylmagnesium chloride/tetrahydrofuran solution, and toluene (60 mL) solution of 9.48 g of 2,6-dibromopyridine was dropwise added thereto at 0° C. or lower. The reaction liquid was stirred for 1.5 hours, then cooled in a dry ice/acetone bath, and 5.0 g of cyclobutanone was added thereto at −50° C. or lower. After stirred for 10 minutes, water and 2 N hydrochloric acid were added to the reaction liquid, and the organic layer was separated, washed with aqueous saturated sodium hydrogencarbonate solution and saturated saline water, and then dried with anhydrous magnesium sulfate. After concentrated under reduced pressure, the residue was purified through silica gel column chromatography (hexane/ethyl acetate=20/1 to 4/1) to obtain 5.30 g of the entitled compound as a yellow oily substance.
$^1$H-NMR (400 MHz, CDCl$_3$) δ: 7.60 (1H, t, J=7.8 Hz), 7.52 (1H, dd, J=7.8, 1.0 Hz), 7.40 (1H, dd, J=7.8, 1.0 Hz), 2.53-2.48 (4H, m), 2.12-2.01 (1H, m), 1.91-1.82 (1H, m).
ESI-MS Found: m/z[M+H]+ 228, 230.

2) Production of 2-allyl-1-[6-(1-hydroxycyclobutyl)-2-pyridinyl]-6-(methylthio)-1,2-dihydro-3H-pyrazolo[3,4-d]pyrimidin-3-one 1.44 g of the entitled compound was obtained in the same manner as in Example 53-2, for which, however, the compound obtained in the above reaction was used in place of 2-(6-bromo-2-pyridinyl)-2-propanol used in Example 53-2.
$^1$H-NMR (400 MHz, CDCl$_3$) δ: 8.94 (1H, s), 7.95 (1H, t, J=8.0 Hz), 7.77 (1H, d, J=7.8 Hz), 7.54 (1H, d, J=7.8 Hz), 5.70 (1H, ddt, J=17.1, 10.2, 6.3 Hz), 5.07 (1H, d, J=10.2 Hz), 4.94 (1H, d, J=17.1 Hz), 4.80 (2H, d, J=6.3 Hz), 2.58 (3H, s), 2.56-2.50 (4H, m), 2.15-2.03 (1H, m), 1.97-1.84 (1H, m).
ESI-MS Found: m/z[M+H]+ 370.

3) Production of 2-allyl-1-[6-(1-hydroxycyclobutyl)pyridin-2-yl]-6-{[4-(4-methylpiperazin 1-yl)phenyl]amino}-1,2-dihydro-3H-pyrazolo[3,4-d]pyrimidin-3-one 80.8 mg of the entitled compound was obtained as a yellow solid in the same manner as in Example 53-3, for which, however, the compound obtained in the above reaction was used in place of 2-allyl-1-[6-(1-hydroxy-1-methylethyl)-2-pyridinyl]-6-(methylthio)-1,2-dihydro-3H-pyrazolo[3,4-d]pyrimidin-3-one used in Example 53-3.
$^1$H-NMR (400 MHz, CDCl$_3$) δ: 8.83 (1H, s), 7.90 (1H, t, J=7.8 Hz), 7.77 (1H, d, J=7.8 Hz), 7.48 (2H, dd, J=12.2, 8.3 Hz), 7.48 (1H, brs), 6.93 (2H, d, J=9.3 Hz), 5.70 (1H, tdd, J=5.9, 17.1, 10.0 Hz), 5.04 (1H, dd, J=10.0, 1.2 Hz), 4.94 (1H, dd, J=17.1, 1.0 Hz), 4.73 (2H, d, J=5.9 Hz), 4.20 (1H, s), 3.24 (4H, t, J=4.6 Hz), 2.65 (4H, brs), 2.53 (4H, t, J=8.0 Hz), 2.41 (3H, s), 2.14-2.06 (1H, m), 1.96-1.84 (1H, m).
ESI-MS Found: m/z[M+H]+ 513.

Example 70

Production of 2-allyl-6-{[4-(4-cyclopropyl-1-piperazinyl)phenyl]amino}-1-[6-(1-hydroxycyclobutyl)-2-pyridinyl]-1,2-dihydro-3H-pyrazolo[3,4-d]pyrimidin-3-one 65.9 mg of the entitled compound was obtained as a yellow solid in the same manner as in Example 69-1 to 69-3, for which, however, 4-(4-cyclopropylpiperazin-1-yl)aniline was used in place of 4-(4-methylpiperazin-1-yl)aniline used in Example 69-3.
$^1$H-NMR (400 MHz, CDCl$_3$) δ: 8.83 (1H, s), 7.90 (1H, t, J=8.0 Hz), 7.76 (1H, d, J=7.8 Hz), 7.47 (4H, dd, J=15.6, 8.3 Hz), 6.93 (2H, d, J=8.8 Hz), 5.70 (1H, ddt, J=17.1, 10.2, 6.3 Hz), 5.04 (1H, d, J=10.2 Hz), 4.94 (1H, d, J=17.1 Hz), 4.73 (2H, d, J=6.3 Hz), 4.18 (1H, s), 3.18 (4H, s), 2.82 (4H, s), 2.53 (4H, t, J=7.8 Hz), 2.15-2.04 (1H, m), 1.96-1.86 (1H, m), 1.59 (4H, s).
ESI-MS Found: m/z[M+H]+ 539.

Example 71

Production of 2-{4-[4-({2-allyl-1-[6-(1-hydroxy-1-methylethyl)pyridin-2-yl]-3-oxo-1,2-dihydro-3H-pyrazolo[3,4-d]pyrimidin-6-yl}amino)phenyl]piperidin-1-yl}-N,N-dimethylacetamide 12 mg of the entitled compound was obtained as a yellow solid in the same manner as in Example 53-1 to 53-3, for which, however, 2-[4-(4-aminophenyl)piperidin-1-yl]-N,N-dimethylacetamide was used in place of 4-(4-methylpiperazin-1-yl)aniline used in Example 53-3.

$^1$H-NMR (400 MHz, CDCl$_3$) δ: 8.85 (1H, s), 7.88 (1H, dd, J=8.0, 7.6 Hz), 7.76 (1H, d, J=8.0 Hz), 7.52 (2H, d, J=8.8 Hz), 7.36 (1H, d, J=7.6 Hz), 7.21 (1H, d, J=8.8 Hz), 5.69 (1H, ddt, J=17.2, 10.0, 6.0 Hz), 5.04 (1H, d, J=10.0 Hz), 4.93 (1H, d, J=17.2 Hz), 4.73 (2H, d, J=6.0 Hz), 3.11 (3H, s), 3.04-3.08 (1H, m), 2.97 (3H, s), 2.20-2.27 (1H, m), 1.80-1.86 (7H, m), 1.59 (6H, s).

ESI-MS Found: m/z[M+H]+ 571.

Example 72

Production of 2-allyl-1-[6-(1-hydroxy-1-methylethyl)pyridin-2-yl]-6-{[6-(4-methylpiperazin-1-yl)pyridin-3-yl]amino}-1,2-dihydro-3H-pyrazolo[3,4-d]pyrimidin-3-one 39 mg of the entitled compound was obtained as a white solid in the same manner as in Example 53-1 to 53-3, for which, however, 6-(4-methylpiperazin-1-yl)pyridine-3-amine was used in place of 4-(4-methylpiperazin-1-yl)aniline used in Example 53-3.

$^1$H-NMR (400 MHz, CD$_3$OD) δ: 8.83 (1H, s), 8.31 (1H, br), 7.85 (1H, dd, J=8.0, 7.6 Hz), 7.78 (1H, dd, J=8.0, 2.8 Hz), 7.69 (1H, d, J=8.0 Hz), 7.34 (1H, d, J=7.6 Hz), 6.67 (1H, d, J=8.8 Hz), 5.71 (1H, ddt, J=17.2, 10.0, 6.0 Hz), 5.04 (1H, d, J=10.0 Hz), 4.93 (1H, d, J=17.2 Hz), 4.73 (2H, d, J=6.0 Hz), 3.56 (4H, t, J=4.8 Hz), 2.54 (4H, t, J=4.8 Hz), 2.36 (3H, s), 1.59 (6H, s).

ESI-MS Found: m/z[M+H]+ 502.

Example 73

Production of 2-allyl-1-[6-(1-hydroxy-1-methylethyl)pyridin-2-yl]-6-{[4-(4-methyl-1,4-diazepan-1-yl)phenyl]amino}-1,2-dihydro-3H-pyrazolo[3,4-d]pyrimidin-3-one 48 mg of the entitled compound was obtained as a yellow solid in the same manner as in Example 53-1 to 53-3, for which, however, 4-(4-methyl-perhydro-1H-1,4-diazepin-1-yl)aniline was used in place of 4-(4-methylpiperazin-1-yl)aniline used in Example 53-3.

$^1$H-NMR (400 MHz, CDCl$_3$) δ: 8.81 (1H, s), 7.83 (1H, dd, J=8.0, 7.6 Hz), 7.77 (1H, d, J=8.0 Hz), 7.37 (2H, brs), 7.34 (1H, d, J=7.6 Hz), 6.67 (1H, d, J=8.8 Hz), 5.69 (1H, ddt, J=17.2, 10.0, 6.0 Hz), 5.04 (1H, d, J=10.0 Hz), 4.93 (1H, d, J=17.2 Hz), 4.74 (2H, d, J=6.0 Hz), 3.59 (2H, br), 3.51 (2H, br), 2.72 (2H, br), 2.58 (2H, br), 2.39 (3H, s), 2.04 (2H, br), 1.59 (6H, s).

ESI-MS Found: m/z[M+H]+ 515.

Example 74

Production of 2-allyl-1-[6-(1-hydroxy-1-methylethyl)pyridin-2-yl]-6-{[4-(4-propionylpiperazin-1-yl)phenyl]amino}-1,2-dihydro-3H-pyrazolo[3,4-d]pyrimidin-3-one 50 mg of the entitled compound was obtained as a yellow solid in the same manner as in Example 53-1 to 53-3, for which, however, 4-(4-propionylpiperazin-1-yl)aniline was used in place of 4-(4-methylpiperazin-1-yl)aniline used in Example 53-3.

$^1$H-NMR (400 MHz, CDCl$_3$) δ: 8.84 (1H, s), 7.86 (1H, dd, J=8.0, 7.6 Hz), 7.74 (1H, d, J=8.0 Hz), 7.50 (2H, d, J=8.8 Hz), 7.36 (1H, d, J=7.6 Hz), 6.93 (1H, d, J=8.8 Hz), 5.69 (1H, ddt, J=17.2, 10.0, 6.0 Hz), 5.04 (1H, d, J=10.0 Hz), 4.93 (1H, d, J=17.2 Hz), 4.74 (2H, d, J=6.0 Hz), 3.80 (2H, br), 3.65 (2H, br), 3.15 (4H, br), 2.41 (2H, q, J=7.6 Hz), 1.59 (6H, s), 1.19 (3H, t, J=7.6 Hz).

ESI-MS Found: m/z[M+H]+ 543.

Example 75

Production of 2-allyl-1-[6-(1-hydroxy-1-methylethyl)pyridin-2-yl]-6-({4-[4-((2RS)-3-fluoro-2-hydroxypropyl)piperazin-1-yl]phenyl}amino)-1,2-dihydro-3H-pyrazolo[3,4-d]pyrimidin-3-one 41 mg of the entitled compound was obtained as a yellow solid in the same manner as in Example 53-1 to 53-3, for which, however, (±)-1-[4-(4-aminophenyl)piperazin-1-yl]-3-fluoropropan-2-ol was used in place of 4-(4-methylpiperazin-1-yl)aniline used in Example 53-3.

$^1$H-NMR (400 MHz, CDCl$_3$) δ: 8.83 (1H, s), 7.86 (1H, dd, J=8.0, 7.6 Hz), 7.74 (1H, d, J=8.0 Hz), 7.50 (2H, d, J=8.8 Hz), 7.36 (1H, d, J=7.6 Hz), 6.93 (1H, d, J=8.8 Hz), 5.69 (1H, ddt, J=17.2, 10.0, 6.0 Hz), 5.04 (1H, d, J=10.0 Hz), 4.93 (1H, d, J=17.2 Hz), 4.74 (2H, d, J=6.0 Hz), 4.33-4.59 (2H, m), 3.99 (1H, br), 3.22 (4H, br), 2.89 (2H, br), 2.65-2.84 (3H, m), 2.49-2.53 (1H, m), 1.59 (6H, s).

ESI-MS Found: m/z[M+H]+ 563.

Example 76

Production of 2-allyl-1-[6-(1-hydroxy-1-methylethyl)pyridin-2-yl]-6-({4-[4-(2-hydroxy-2-methylpropyl)piperazin-1-yl]phenyl}amino)-1,2-dihydro-3H-pyrazolo[3,4-d]pyrimidin-3-one 49 mg of the entitled compound was obtained as a yellow solid in the same manner as in Example 53-1 to 53-3, for which, however, 1-[4-(4-aminophenyl)piperazin-1-yl]-2-methylpropan-2-ol was used in place of 4-(4-methylpiperazin-1-yl)aniline used in Example 53-3.

$^1$H-NMR (400 MHz, CDCl$_3$) δ: 8.83 (1H, s), 7.86 (1H, dd, J=8.0, 7.6 Hz), 7.74 (1H, d, J=8.0 Hz), 7.46 (2H, d, J=8.8 Hz), 7.34 (1H, d, J=7.6 Hz), 6.91 (1H, d, J=8.8 Hz), 5.69 (1H, ddt, J=17.2, 10.0, 6.0 Hz), 5.04 (1H, d, J=10.0 Hz), 4.93 (1H, d, J=17.2 Hz), 4.74 (2H, d, J=6.0 Hz), 3.19 (4H, br), 2.83 (4H, br), 2.41 (2H, s), 1.59 (6H, s), 1.21 (6H, s).

ESI-MS Found: m/z[M+H]+ 559.

Example 77

Production of 4-[4-({2-allyl-1-[6-(1-hydroxy-1-methylethyl)pyridin-2-yl]-3-oxo-1,2-dihydro-3H-pyrazolo[3,4-d]pyrimidin-6-yl}amino)phenyl]-N,N-dimethylpiperazine-1-carboxamide 33 mg of the entitled compound was obtained as a yellow solid in the same manner as in Example 53-1 to 53-3, for which, however, 4-(4-aminophenyl)-N,N-dimethylpiperazine-1-carboxamide was used in place of 4-(4-methylpiperazin-1-yl)aniline used in Example 53-3.

¹H-NMR (400 MHz, CDCl₃) δ: 8.83 (1H, s), 7.86 (1H, dd, J=8.0, 7.6 Hz), 7.75 (1H, d, J=8.0 Hz), 7.48 (2H, d, J=8.8 Hz), 7.34 (1H, d, J=7.6 Hz), 6.92 (1H, d, J=8.8 Hz), 5.69 (1H, ddt, J=17.2, 10.0, 6.0 Hz), 5.04 (1H, d, J=10.0 Hz), 4.93 (1H, d, J=17.2 Hz), 4.74 (2H, d, J=6.0 Hz), 3.41 (4H, br), 3.17 (4H, br), 2.88 (6H, s), 1.59 (6H, s).

ESI-MS Found: m/z[M+H]+ 558.

Example 78

Production of 2-allyl-1-[6-(1-hydroxy-1-methylethyl)pyridin-2-yl]-6-[(4-piperazin-1-ylphenyl)amino]-1,2-dihydro-3H-pyrazolo[3,4-d]pyrimidin-3-one 81 mg of 2-allyl-1-[6-(1-hydroxy-1-methylethyl)pyridin-2-yl]-6-({4-[4-(trifluoroacetyl)piperazin-1-yl]phenyl}amino)-1,2-dihydro-3H-pyrazolo[3,4-d]pyrimidin-3-one was obtained as a yellow solid in the same manner as in Example 53-1 to 53-3, for which, however, tert-butyl-4-[(4-trifluoroacetyl)piperazin-1-yl]aniline was used in place of 4-(4-methylpiperazin-1-yl)aniline used in Example 53-3.

1.0 mL of aqueous 4 N sodium hydroxide solution was added to 3.0 mL of methanol containing 81 mg of the compound obtained in the above, and stirred at room temperature for 1 hour. The reaction liquid was concentrated under reduced pressure, water was added thereto, and extracted with a mixed solvent of tetrahydrofuran/ethyl acetate. This was washed with saturated saline water, and dried with anhydrous magnesium sulfate. Concentrated under reduced pressure, 32.1 mg of the entitled compound was obtained as a yellow solid.

¹H-NMR (400 MHz, CDCl₃) δ: 8.85 (1H, s), 7.88 (1H, t, J=7.8 Hz), 7.73 (1H, d, J=8.3 Hz), 7.52 (2H, d, J=8.8 Hz), 7.36 (2H, d, J=7.3 Hz), 6.94 (2H, d, J=9.3 Hz), 5.71 (1H, ddt, J=17.1, 10.2, 5.9 Hz), 5.05 (1H, d, J=10.7 Hz), 4.94 (1H, d, J=17.1 Hz), 4.74 (2H, d, J=5.9 Hz), 3.93 (1H, brs), 3.39-3.30 (6H, m), 3.21 (1H, brs), 1.59 (6H, s).

ESI-MS Found: m/z[M+H]+ 489.

Example 79

Production of 2-allyl-1-[6-(1-hydroxy-1-methylethyl)pyridin-2-yl]-6-[{4-(1-methyl-1,2,3,6-tetrahydropyridin-4-yl)phenyl]amino}-1,2-dihydro-3H-pyrazolo[3,4-d]pyrimidin-3-one 12.1 mg of the entitled compound was obtained as a white solid in the same manner as in Example 53-1 to 53-3, for which, however, 4-(1-methyl-1,2,3,6-tetrahydropyridin-4-yl)aniline was used in place of 4-(4-methylpiperazin-1-yl)aniline used in Example 53-3.

¹H-NMR (400 MHz, CDCl₃) δ: 8.87 (1H, s), 7.90 (1H, t, J=7.8 Hz), 7.76 (1H, d, J=7.3 Hz), 7.57 (2H, d, J=8.8 Hz), 7.56 (1H, brs), 7.38 (2H, dd, J=8.5, 2.7 Hz), 6.05 (1H, brs), 5.71 (1H, ddt, J=17.1, 10.2, 5.9 Hz), 5.05 (1H, dd, J=10.2, 1.0 Hz), 4.94 (1H, dd, J=17.1, 1.5 Hz), 4.75 (2H, d, J=5.9 Hz), 3.94 (1H, s), 3.26 (2H, brs), 2.81 (2H, brs), 2.67 (2H, brs), 2.51 (3H, s), 1.59 (6H, s).

ESI-MS Found: m/z[M+H]+ 498.

Example 80

Production of (±)-2-allyl-1-[6-(1-hydroxy-1-methylethyl)pyridin-2-yl]-6-({4-[4-((2RS)-2-hydroxypropyl)piperazin-1-yl]phenyl}amino)-1,2-dihydro-3H-pyrazolo[3,4-d]pyrimidin-3-one 21 mg of the entitled compound was obtained as a yellow solid in the same manner as in Example 53-1 to 53-3, for which, however, 1-[4-(4-aminophenyl)piperazin-1-yl]propan-2-ol was used in place of 4-(4-methylpiperazin-1-yl)aniline used in Example 53-3.

¹H-NMR (400 MHz, CDCl₃) δ: 8.83 (1H, s), 7.86 (1H, dd, J=8.0, 7.6 Hz), 7.75 (1H, d, J=8.0 Hz), 7.47 (2H, d, J=8.8 Hz), 7.34 (1H, d, J=7.6 Hz), 6.92 (1H, d, J=8.8 Hz), 5.70 (1H, ddt, J=17.2, 10.0, 6.0 Hz), 5.04 (1H, d, J=10.0 Hz), 4.93 (1H, d, J=17.2 Hz), 4.74 (2H, d, J=6.0 Hz), 3.93 (1H, br), 3.21 (4H, br), 2.87 (2H, brs), 2.62 (2H, brs), 2.36-2.42 (2H, m), 1.59 (6H, s), 1.18 (3H, d, J=6.0 Hz).

ESI-MS Found: m/z[M+H]+ 545.

Example 81

Production of 2-allyl-1-[6-(2-hydroxy-2-methylpropyl)pyridin-2-yl]-6-{[4-(4-methylpiperazin-1-yl)phenyl]amino}-1,2-dihydro-3H-pyrazolo[3,4-d]pyrimidin-3-one 1) Production of 1-(6-bromopyridin-2-yl)-2-methylpropan-2-ol In a nitrogen atmosphere, 400 mL of tetrahydrofuran containing 31 mL of diisopropylamine was cooled in a dry ice/acetone bath, and 82.7 mL of 2.66 M n-butyllithium/hexane solution was added thereto, and 50 mL of tetrahydrofuran containing 34.4 g of 6-bromopicoline was dropwise added thereto at −70° C. or lower. After the addition, 29.4 mL of acetone was added thereto at −60° C. or lower. After stirred for 35 minutes, water was added to the reaction liquid, and the organic solvent was concentrated under reduced pressure. This was extracted with diethyl ether, washed with saturated saline water, and dried with anhydrous magnesium sulfate. After concentrated under reduced pressure, the residue was purified through distillation to obtain 27.60 g of the entitled compound as a colorless oily substance.

¹H-NMR (400 MHz, CDCl₃) δ: 7.50 (1H, t, J=7.6 Hz), 7.37 (1H, d, J=7.8 Hz), 7.12 (1H, d, J=7.8 Hz), 2.91 (2H, s), 1.23 (6H, s).

ESI-MS Found: m/z[M+H]+: 230, 232.

2) Production of 2-allyl-1-[6-(2-hydroxy-2-methylpropyl)pyridin-2-yl]-6-(methylthio)-1,2-dihydro-3H-pyrazolo[3,4-d]pyrimidin-3-one 20.70 g of the entitled compound was obtained in the same manner as in Example 53-2, for which, however, the compound obtained in the above reaction was used in place of 2-(6-bromo-2-pyridinyl)-2-propanol used in Example 53-2.

¹H-NMR (400 MHz, CDCl₃) δ: 8.93 (1H, s), 7.84 (1H, t, J=7.8 Hz), 7.71 (1H, d, J=8.3 Hz), 7.15 (1H, d, J=7.3 Hz), 5.67 (1H, ddt, J=16.8, 10.2, 6.3 Hz), 5.05 (1H, dd, J=10.2, 1.0 Hz), 4.93 (1H, dd, J=16.8, 1.2 Hz), 4.77 (2H, d, J=6.3 Hz), 2.97 (2H, s), 2.58 (3H, s), 1.25 (6H, s).

ESI-MS Found: m/z[M+H]+ 372.

3) Production of 2-allyl-1-[6-(2-hydroxy-2-methylpropyl)pyridin-2-yl]-6-{[4-(4-methylpiperazin-1-yl)phenyl]amino}-1,2-dihydro-3H-pyrazolo[3,4-d]pyrimidin-3-one 1.06 g of the entitled compound was obtained as a yellow solid in the same manner as in Example 53-3, for which, however, the compound obtained in the above reaction was used in place of 2-allyl-1-[6-(1-hydroxy-1-methylethyl)-2-pyridinyl]-6-(methylthio)-1,2-dihydro-3H-pyrazolo[3,4-d]pyrimidin-3-one used in Example 53-3.

$^1$H-NMR (400 MHz, CDCl$_3$) δ: 8.82 (1H, s), 7.79 (1H, t, J=7.8 Hz), 7.66 (1H, brs), 7.45 (2H, d, J=8.8 Hz), 7.08 (1H, d, J=7.8 Hz), 6.93 (2H, d, J=8.8 Hz), 5.78-5.62 (1H, m), 5.13-4.94 (2H, m), 4.63 (2H, s), 3.23 (4H, t, J=4.6 Hz), 2.98 (2H, s), 2.64 (4H, s), 2.40 (3H, s), 1.24 (6H, s).

ESI-MS Found: m/z[M+H]+ 515.

Example 82

Production of 2-allyl-1-[6-(2-hydroxy-2-methylpropyl)pyridin-2-yl]-6-{[4-(4-isopropylpiperazin-1-yl)phenyl]amino}-1,2-dihydro-3H-pyrazolo[3,4-d]pyrimidin-3-one 49.1 mg of the entitled compound was obtained as a yellow solid in the same manner as in Example 81-1 to 81-3, for which, however, 4-(4-isopropylpiperazin-1-yl)aniline was used in place of 4-(4-methylpiperazin-1-yl)aniline used in Example 81-3.

$^1$H-NMR (400 MHz, CDCl$_3$) δ: 8.82 (1H, s), 7.81-7.66 (1H, brm), 7.78 (2H, t, J=7.8 Hz), 7.44 (2H, d, J=8.8 Hz), 7.07 (1H, d, J=7.8 Hz), 6.93 (2H, d, J=8.8 Hz), 5.79-5.61 (1H, m), 5.15-4.91 (2H, m), 4.78-4.48 (2H, m), 3.26-3.15 (4H, m), 2.98 (2H, s), 2.74 (1H, septet, J=6.8 Hz), 2.73-2.69 (4H, m), 1.24 (6H, s), 1.11 (6H, d, J=6.8 Hz).

ESI-MS Found: m/z[M+H]+ 543.

Example 83

Production of 2-allyl-1-[6-(2-hydroxy-2-methylpropyl)pyridin-2-yl]-6-{[4-(1-methylpiperidin-4-yl)phenyl]amino}-1,2-dihydro-3H-pyrazolo[3,4-d]pyrimidin-3-one 36.8 mg of the entitled compound was obtained as a yellow solid in the same manner as in Example 81-1 to 81-3, for which, however, 4-(1-methylpiperidin-4-yl)aniline was used in place of 4-(4-methylpiperazin-1-yl)aniline used in Example 81-3.

$^1$H-NMR (400 MHz, CDCl$_3$) δ: 8.85 (1H, s), 7.89-7.76 (2H, brm), 7.80 (1H, t, J=7.8 Hz), 7.52 (2H, d, J=8.3 Hz), 7.22 (2H, d, J=8.3 Hz), 7.10 (1H, d, J=7.8 Hz), 5.77-5.64 (1H, brm), 5.08 (1H, d, J=9.8 Hz), 5.01 (1H, d, J=17.6 Hz), 4.71-4.58 (2H, brm), 3.05 (2H, d, J=11.2 Hz), 2.99 (2H, s), 2.56-2.45 (1H, m), 2.38 (3H, s), 2.21-2.07 (2H, m), 1.95-1.81 (4H, m), 1.24 (6H, s).

ESI-MS Found: m/z[M+H]+ 514.

Example 84

Production of 2-allyl-1-[6-(4-hydroxytetrahydro-2H-pyran-4-yl)pyridin-2-yl]-6-{[3-methyl-4-(4-methylpiperazin-1-yl)phenyl]amino}-1,2-dihydro-3H-pyrazolo[3,4-d]pyrimidin-3-one 49.4 mg of the entitled compound was obtained as a white solid in the same manner as in Example 69-1 to 69-3, for which, however, tetrahydro-4H-pyran-4-one was used in place of cyclobutanone used in Example 69-1, and 3-methyl-4-(4-methylpiperazin-1-yl)aniline was used in place of 4-(4-methylpiperazin-1-yl)aniline used in Example 69-3.

$^1$H-NMR (400 MHz, CDCl$_3$) δ: 8.84 (1H, s), 7.92 (1H, t, J=8.0 Hz), 7.84 (1H, d, J=8.3 Hz), 7.47 (1H, s), 7.35-7.32 (2H, m), 7.03 (1H, d, J=8.3 Hz), 5.70 (1H, ddt, J=17.1, 10.2, 6.3 Hz), 5.04 (1H, dd, J=10.2, 1.2 Hz), 4.92 (1H, dd, J=17.1, 1.0 Hz), 4.73 (2H, d, J=6.3 Hz), 4.02-3.93 (4H, m), 2.97 (4H, t, J=4.6 Hz), 2.65 (4H, s), 2.41 (3H, s), 2.33 (3H, s), 2.19 (2H, td, J=12.6, 5.4 Hz), 1.62 (2H, d, J=12.2 Hz).

ESI-MS Found: m/z[M+H]+ 557.

Example 85

Production of 2-allyl-1-[6-(4-hydroxytetrahydro-2H-pyran-4-yl)pyridin-2-yl]-6-{[4-(4-methylpiperazin-1-yl)phenyl]amino}-1,2-dihydro-3H-pyrazolo[3,4-d]pyrimidin-3-one 51.1 mg of the entitled compound was obtained as a yellow solid in the same manner as in Example 69-1 to 69-3, for which, however, tetrahydro-4H-pyran-4-one was used in place of cyclobutanone used in Example 69-1.

$^1$H-NMR (400 MHz, CDCl$_3$) δ: 8.83 (1H, s), 7.91 (1H, t, J=7.8 Hz), 7.79 (1H, d, J=7.8 Hz), 7.46 (3H, d, J=8.8 Hz), 7.33 (1H, d, J=7.8 Hz), 6.93 (2H, d, J=8.8 Hz), 5.69 (1H, ddt, J=17.1, 10.2, 6.3 Hz), 5.04 (1H, d, J=10.2 Hz), 4.93 (1H, d, J=17.1 Hz), 4.72 (2H, d, J=6.3 Hz), 4.17 (1H, s), 4.03-3.92 (4H, m), 3.26 (4H, s), 2.69 (4H, s), 2.43 (3H, s), 2.19 (2H, td, J=12.7, 5.7 Hz), 1.62 (2H, d, J=12.2 Hz).

ESI-MS Found: m/z[M+H]+ 543.

Examples 86 and 87

Production of 2-allyl-1-{6-[(1R*)-1-hydroxyethyl]pyridin-2-yl}-6-{[4-(4-methylpiperazin-1-yl)phenyl]amino}-1,2-dihydro-3H-pyrazolo[3,4-d]pyrimidin-3-one, and 2-allyl-1-{6-[(1S*) 1-hydroxyethyl]pyridin-2-yl}-6-{[4-(4-methylpiperazin-1-yl)phenyl]amino}-1,2-dihydro-3H-pyrazolo[3,4-d]pyrimidin-3-one

1) Production of 1-(6-bromopyridin-2-yl)ethanol

With cooling with ice, 426 mg of sodium borohydride was added to ethanol (50 mL) solution of 4.50 g of 2-acetyl-6-bromopyridine. After stirred for 1 hour, aqueous saturated ammonium chloride solution was added to the reaction liquid, extracted with ethyl acetate, washed with saturated saline water, and dried with anhydrous magnesium sulfate. After concentrated under reduced pressure, 4.58 g of the entitled compound was obtained as a colorless oily substance.

$^1$H-NMR (400 MHz, CDCl$_3$) δ: 7.56 (1H, t, J=7.8 Hz), 7.39 (1H, d, J=7.8 Hz), 7.29 (1H, d, J=7.8 Hz), 4.88 (1H, q, J=6.7 Hz), 1.51 (3H, d, J=6.3 Hz).

ESI-MS Found: m/z[M+H]+ 202, 204.

2) Production of 2-allyl-1-{6-[(1R*)-1-hydroxyethyl]pyridin-2-yl}-6-(methylthio)-1,2-dihydro-3H-pyrazolo[3,4-d]pyrimidin-3-one, and 2-allyl-1-{6-[(1S*)-1-hydroxyethyl]pyridin-2-yl}-6-(methylthio)-1,2-dihydro-3H-pyrazolo[3,4-d]pyrimidin-3-one 396 mg of a racemic mixture of the entitled compounds was obtained in the same manner as in Example 53-2, for which, however, the compound obtained in the above reaction was used in place of 2-(6-bromo-2-pyridinyl)-2-propanol used in Example 53-2.

6.52 g of the above racemate was optically resolved through an optically-active column (Daicel's CHIRAL PAK AD column, 5 cm×50 cm; 0.1% diethylamine, hexane/ethanol=60/40, flow rate 100 mL/min); and 3.08 g (99.5% ee) of 2-allyl-1-{6-[(1R*)-1-hydroxyethyl]pyridin-2-yl}-6-(methylthio)-2,3-dihydro-1H-pyrazolo[3,4-d]pyrimidin-3-one was obtained as a white solid from the former fraction, and 2.91 g (99.8% ee) of 2-allyl-1-{6-[(1S*)-1-hydroxyethyl]pyridin-2-yl}-6-(methylthio)-2,3-dihydro-1H-pyrazolo[3,4-d]pyrimidin-3-one was as a white solid from the latter fraction. (Since the two were not identified, one was referred to as 1R* form and the other was as 1S* form for convenience sake.)

(1R* Form) of the Former Fraction:

Retention time, 4.9 min (optically-active column; Daicel's CHIRAL PAK AD-H, 0.46 cm×15 cm; 0.1% diethylamine, hexane/ethanol=1/1; flow rate 1 mL/min).

$^1$H-NMR and APCI-MS were the same as those of the racemate.

(1S* Form) of the Latter Fraction:

Retention time, 6.7 min (optically-active column; Daicel's CHIRAL PAK AD-H, 0.46 cm×15 cm; 0.1% diethylamine, hexane/ethanol=1/1; flow rate 1 mL/min).

$^1$H-NMR (400 MHz, CDCl$_3$) δ: 8.94 (1H, s), 7.91 (1H, t, J=7.8 Hz), 7.77 (1H, d, J=8.3 Hz), 7.30 (1H, d, J=7.8 Hz), 5.70 (1H, ddt, J=17.2, 10.2, 6.3 Hz), 5.06 (1H, dd, J=10.2, 1.5 Hz), 4.96-4.92 (2H, m), 4.80 (2H, dd, J=6.1, 1.2 Hz), 2.58 (3H, s), 1.55 (3H, d, J=6.8 Hz).

ESI-MS Found: m/z[M+H]+ 344.

3) Production of 2-allyl-1-{6-[(1R*)-1-hydroxyethyl]pyridin-2-yl}-6-{[4-(4-methylpiperazin-1-yl)phenyl]amino}-1,2-dihydro-3H-pyrazolo[3,4-d]pyrimidin-3-one, and 2-allyl-1-{6-[(1S*)-1-hydroxyethyl]pyridin-2-yl}-6-{[4-(4-methylpiperazin-1-yl)phenyl]amino}-1,2-dihydro-3H-pyrazolo[3,4-d]pyrimidin-3-one 2-allyl-1-{6-[(1R*)-1-hydroxyethyl]pyridin-2-yl}-6-{[4-(4-methylpiperazin-1-yl)phenyl]amino}-1,2-dihydro-3H-pyrazolo[3,4-d]pyrimidin-3-one (compound of Example 86), and 2-allyl-1-{6-[(1S*)-1-hydroxyethyl]pyridin-2-yl}-6-{[4-(4-methylpiperazin-1-yl)phenyl]amino}-1,2-dihydro-3H-pyrazolo[3,4-d]pyrimidin-3-one (compound of Example 87) were obtained both as a yellow solid in an amount of 52.5 mg and 57.9 mg, respectively, in the same manner as in Example 53-3, for which, however, the compound obtained in the above reaction 2) was used in place of 2-allyl-1-[6-(1-hydroxy-1-methylethyl)-2-pyridinyl]-6-(methylthio)-1,2-dihydro-3H-pyrazolo[3,4-d]pyrimidin-3-one used in Example 53-3.

Compound of Example 86:

$^1$H-NMR (400 MHz, CDCl$_3$) δ: 8.83 (1H, s), 7.86 (1H, t, J=7.8 Hz), 7.75 (1H, d, J=7.8 Hz), 7.46 (3H, d, J=8.8 Hz), 7.24 (2H, d, J=7.8 Hz), 6.93 (2H, d, J=8.8 Hz), 5.74-5.66 (1H, m), 5.04 (1H, dd, J=8.8, 1.5 Hz), 4.98-4.91 (2H, m), 4.73 (2H, d, J=5.9 Hz), 3.47 (1H, d, J=5.4 Hz), 3.26 (4H, s), 2.70 (4H, s), 2.44 (3H, s), 1.55 (3H, d, J=6.8 Hz).

ESI-MS Found: m/z[M+H]+ 487.

Compound of Example 87:

$^1$H-NMR and ESI-MS were both the same as those of the compound of Example 86.

Example 88

Production of (±)-2-allyl-1-{6-[(1RS)-1-hydroxyethyl]pyridin-2-yl}-6-{[3-methyl-4-(4-methylpiperazin-1-yl)phenyl]amino}-1,2-dihydro-3H-pyrazolo[3,4-d]pyrimidin-3-one 83.2 mg of the entitled compound was obtained as a white solid in the same manner as in Example 86-1 to 86-3, for which, however, a racemic starting material thereof was used in place of the chiral starting material of 2-allyl-1-{6-[(1R*)-1-hydroxyethyl]pyridin-2-yl}-6-(methylthio)-1,2-dihydro-3H-pyrazolo[3,4-d]pyrimidin-3-one used in Example 86-2, and 3-methyl-4-(4-methylpiperazin-1-yl)aniline was used in place of 4-(4-methylpiperazin-1-yl)aniline used in Example 86-3.

$^1$H-NMR (400 MHz, CDCl$_3$) δ: 8.84 (1H, s), 7.87 (1H, t, J=7.8 Hz), 7.80 (1H, d, J=7.3 Hz), 7.47 (1H, s), 7.34 (1H, dd, J=8.5, 2.2 Hz), 7.25 (1H, d, J=3.9 Hz), 7.03 (1H, d, J=8.3 Hz), 5.71 (1H, ddt, J=17.1, 10.0, 6.2 Hz), 5.04 (1H, dd, J=10.0, 1.2 Hz), 4.94 (1H, d, J=6.3 Hz), 4.94 (1H, dd, J=17.1, 1.2 Hz), 4.74 (2H, d, J=6.2 Hz), 3.46 (1H, d, J=5.4 Hz), 2.99 (4H, s), 2.67 (4H, s), 2.44 (3H, s), 2.32 (3H, s), 1.55 (3H, d, J=6.3 Hz).

ESI-MS Found: m/z[M+H]+ 501.

Example 89

Production of 1-(6-acetylpridin-2-yl)-2-allyl-6-{[3-methyl-4-(4-methylpiperazin-1-yl)phenyl]amino}-1,2-dihydro-3H-pyrazolo[3,4-d]pyrimidin-3-one 33.3 mg of the entitled compound was obtained as a white solid in the same manner as in Example 29-1 to 29-2, for which, however, 2-acetyl-6-bromopyridine was used in place of 2-iodopyridine used in Example 29-1, and 3-methyl-4-(4-methylpiperazin-1-yl)aniline was used in place of [5-amino-2-(4-methylpiperazin-1-yl)phenyl]methanol used in Example 29-2.

$^1$H-NMR (400 MHz, DMSO-d$_6$) δ: 10.25 (1H, brs), 8.89 (1H, s), 8.27-8.22 (2H, m), 7.91 (1H, d, J=8.0 Hz), 7.63 (1H, brs), 7.40 (1H, d, J=7.4 Hz), 7.00 (1H, d, J=8.6 Hz), 5.69 (1H, ddt, J=16.8, 10.7, 6.5 Hz), 5.01 (1H, d, J=10.7 Hz), 4.92 (1H, d, J=16.8 Hz), 4.75 (2H, d, J=6.5 Hz), 2.82 (4H, t, J=4.9 Hz), 2.65 (3H, s), 2.49 (4H, brs), 2.24 (6H, s).

ESI-MS Found: m/z[M+H]+ 499.

Example 90

Production of 1-(6-acetylpyridin-2-yl)-2-allyl-6-{[4-(4-methylpiperazin-1-yl)phenyl]amino}-1,2-dihydro-3H-pyrazolo[3,4-d]pyrimidin-3-one 11.3 mg of the entitled compound was obtained as a yellow solid in the same manner as in Example 29-1 to 29-2, for which, however, 2-acetyl-6-bromopyridine was used in place of 2-iodopyridine used in Example 29-1, and 4-(4-methylpiperazin-1-yl)aniline was used in place of [5-amino-2-(4-methylpiperazin-1-yl)phenyl]methanol used in Example 29-2.

$^1$H-NMR (400 MHz, CDCl$_3$) δ: 8.85 (1H, s), 8.15 (1H, dd, J=7.0, 2.2 Hz), 8.00-7.94 (2H, m), 7.44 (2H, d, J=8.8 Hz), 7.44 (1H, brs), 6.93 (2H, d, J=8.8 Hz), 5.73-5.63 (1H, m), 5.02 (1H, dd, J=10.3, 1.1 Hz), 4.94-4.87 (3H, m), 3.23 (4H, t, J=5.0 Hz), 2.72 (3H, s), 2.63 (4H, brs), 2.39 (3H, s).
ESI-MS Found: m/z[M+H]+ 485.

Example 91

Production of 2-allyl-1-[6-(2-hydroxyethyl)pyridin-2-yl]-6-{[4-(4-methylpiperazin-1-yl)phenyl]amino}-1,2-dihydro-3H-pyrazolo[3,4-d]pyrimidin-3-one 1) Production of ethyl(6-bromopyridin-2-yl)acetate 412 mg of the entitled compound was obtained as a colorless oily substance in the same manner as in Example 81-1, for which, however, diethyl carbonate was used in place of acetone used in Example 81-1.
$^1$H-NMR (400 MHz, CDCl$_3$) δ: 7.53 (1H, t, J=7.8 Hz), 7.40 (1H, d, J=7.8 Hz), 7.29 (1H, d, J=7.8 Hz), 4.19 (2H, q, J=7.2 Hz), 3.83 (2H, s), 1.27 (3H, t, J=7.3 Hz).
ESI-MS Found: m/z[M+H]+ 244, 246.

2) Production of 2-(6-bromopyridin-2-yl)ethanol

In a dry ice/acetone bath, 5.76 mL of 1.01 M diisobutylaluminium hydride/toluene solution was added to toluene (10 mL) solution of 355 mg of the compound obtained in the above reaction, and stirred for 40 minutes. Aqueous saturated ammonium chloride solution was added to the reaction liquid, extracted with ethyl acetate, washed with aqueous saturated sodium hydrogencarbonate solution and saturated saline water, and dried with anhydrous magnesium sulfate. After concentrated under reduced pressure, the residue was purified through silica gel column chromatography (hexane/ethyl acetate=3/1 to 1/1) to obtain 123 mg of the entitled compound as a colorless oily substance.
ESI-MS Found: m/z[M+H]+ 202, 204.

3) Production of 2-allyl-1-[6-(2-hydroxyethyl)pyridin-2-yl]-6-(methylthio)-1,2-dihydro-3H-pyrazolo[3,4-d]pyrimidin-3-one 36.6 mg of the entitled compound was obtained as a colorless solid in the same manner as in Example 53-2, for which, however, 2-(6-bromopyridin-2-yl)ethanol obtained in the above reaction was used in place of 2-(6-bromo-2-pyridinyl)-2-propanol used in Example 53-2.
$^1$H-NMR (400 MHz, CDCl$_3$) δ: 8.94 (1H, s), 7.84 (1H, t, J=7.6 Hz), 7.66 (1H, d, J=7.6 Hz), 7.17 (1H, d, J=7.8 Hz), 5.69-5.64 (1H, m), 5.05 (1H, dd, J=10.4 Hz), 4.94 (1H, dd, J=18.0 Hz), 4.79 (2H, d, J=6.5 Hz), 4.06 (2H, t, J=5.5 Hz), 4.06 (2H, t, J=5.5 Hz), 2.58 (3H, s).
ESI-MS Found: m/z[M+H]+ 344.

4) Production of 2-allyl-1-[6-(2-hydroxyethyl)pyridin-2-yl]-6-{[4-(4-methylpiperazin 1-yl)phenyl]amino}-1,2-dihydro-3H-pyrazolo[3,4-d]pyrimidin-3-one 25.9 mg of the entitled compound was obtained as a yellow solid in the same manner as in Example 53-3, for which, however, the compound obtained in the above reaction was used in place of 2-allyl-1-[6-(1-hydroxy-1-methylethyl)-2-pyridinyl]-6-(methylthio)-1,2-dihydro-3H-pyrazolo[3,4-d]pyrimidin-3-one used in Example 53-3.
$^1$H-NMR (400 MHz, CDCl$_3$) δ: 8.83 (1H, s), 7.78 (1H, t, J=8.0 Hz), 7.50 (1H, s), 7.44 (2H, d, J=8.3 Hz), 7.11 (1H, d, J=7.8 Hz), 6.92 (2H, d, J=9.3 Hz), 5.77-5.65 (1H, brm), 5.13-4.93 (2H, brm), 4.67 (2H, brs), 4.07 (2H, q, J=5.5 Hz), 3.23 (4H, t, J=4.9 Hz), 3.09 (2H, t, J=5.4 Hz), 2.64 (4H, brs), 2.40 (3H, s).
ESI-MS Found: m/z[M+H]+ 487.

Example 92

Production of 2-{4-[4-({2-allyl-1-[6-(1-hydroxy-1-methylethyl)pyridin-2-yl]-3-oxo-1,2-dihydro-3H-pyrazolo[3,4-d]pyrimidin-6-yl}amino)phenyl]piperazin-1-yl}-N,N-dimethylacetamide 60 mg of the entitled compound was obtained as a yellow solid in the same manner as in Example 53-1 to 53-3, for which, however, 2-[4-(4-aminophenyl)piperazin-1-yl]-N,N-dimethylacetamide was used in place of 4-(4-methylpiperazin-1-yl)aniline used in Example 53-3.
$^1$H-NMR (400 MHz, CDCl$_3$) δ: 8.83 (1H, s), 7.87 (1H, dd, J=8.0, 7.6 Hz), 7.74 (1H, d, J=8.0 Hz), 7.46 (2H, d, J=8.8 Hz), 7.34 (1H, d, J=7.6 Hz), 6.92 (1H, d, J=8.8 Hz), 5.69 (1H, ddt, J=17.2, 10.0, 6.0 Hz), 5.04 (1H, d, J=10.0 Hz), 4.93 (1H, d, J=17.2 Hz), 4.73 (2H, d, J=6.0 Hz), 3.32 (2H, brs), 3.27 (4H, brs), 3.09 (2H, s), 2.98 (3H, s), 2.86 (4H, br), 1.59 (6H, s).
ESI-MS Found: m/z[M+H]+ 572.

Example 93

Production of 2-{4-[4-({2-allyl-1-[6-(1-fluoro-1-methylethyl)pyridin-2-yl]-3-oxo-1,2-dihydro-3H-pyrazolo[3,4-d]pyrimidin-6-yl}amino)phenyl]piperazin-1-yl}-N,N-dimethylacetamide 16 mg of the compound obtained in Example 92 was dissolved in 3 mL of chloroform, and 0.1 mL of bis(2-methoxyethyl)aminosulfur trifluoride was added thereto and stirred at room temperature for 1 hour. Aqueous saturated sodium hydrogencarbonate solution was added to it and extracted with chloroform. The chloroform layer was washed with saturated saline water, dried with anhydrous sodium sulfate, and the solvent was evaporated away under reduced pressure. This was purified through column chromatography (ethyl acetate/chloroform=3/1) and then solidified from ethyl acetate/hexane solution to obtain 8 mg of the entitled compound as a yellow solid.
$^1$H-NMR (400 MHz, CDCl$_3$) δ: 8.83 (1H, s), 7.80-7.90 (2H, m), 7.46 (2H, d, J=8.8 Hz), 7.45 (1H, overlapped), 6.92 (1H, d, J=8.8 Hz), 5.69 (1H, ddt, J=17.2, 10.0, 6.0 Hz), 5.00 (1H, d, J=10.0 Hz), 4.88 (1H, d, J=17.2 Hz), 4.81 (2H, J=6.0 Hz), 3.49 (2H, s), 3.22 (2H, J=4.8 Hz), 3.11 (3H, s), 2.98 (3H, s), 2.73 (4H, d, J=4.8 Hz), 1.75 (3H, s), 1.69 (3H, s).
ESI-MS Found: m/z[M+H]+=574.

Example 94

Production of 2-allyl-1-{6-[(2-hydroxyethyl)(methyl)amino]pyridin-2-yl}-6-{[4-(4-methylpiperazin-1-yl)phenyl]amino}-1,2-dihydro-3H-pyrazolo[3,4-d]pyrimidin-3-one 1) Production of 2-[(6-bromopyridin-2-yl)(methyl)amino]ethanol 7.45 g of 2,6-dibromopyridine and 12 mL of N-methylethanol were stirred overnight at 140° C. Water was added to the reaction liquid, extracted with ethyl acetate, washed with saturated saline water, and dried with anhydrous magnesium sulfate. After concentrated under reduced pressure, the residue was purified through silica gel column chromatography (hexane/ethyl acetate=1/1) to obtain 3.98 g of the entitled compound as a colorless oily substance.

$^1$H-NMR (400 MHz, CDCl$_3$) δ: 7.30 (1H, dd, J=8.3, 7.3 Hz), 6.73 (1H, d, J=7.8 Hz), 6.45 (1H, d, J=8.3 Hz), 3.87 (2H, t, J=4.9 Hz), 3.73 (2H, t, J=4.9 Hz), 3.07 (3H, s).

ESI-MS Found: m/z[M+H]+ 231, 233.

2) Production of 2-allyl-1-{6-[(2-hydroxyethyl)(methyl)amino]pyridin-2-yl}-6-{[4-(4-methylpiperazin-1-yl)phenyl]amino}-1,2-dihydro-3H-pyrazolo[3,4-d]pyrimidin-3-one 40.1 mg of the entitled compound was obtained as a yellow solid in the same manner as in Example 53-2 to 53-3, for which, however, the compound obtained in the above reaction was used in place of 2-(6-bromo-2-pyridyl)-2-propanol used in Example 53-2.

$^1$H-NMR (400 MHz, CDCl$_3$) δ: 8.81 (1H, s), 7.58 (1H, t, J=8.0 Hz), 7.44 (2H, d, J=8.3 Hz), 6.92 (2H, d, J=9.3 Hz), 6.43 (1H, d, J=8.8 Hz), 5.73 (1H, dd, J=17.1, 10.2 Hz), 5.11 (1H, d, J=10.7 Hz), 5.07 (1H, d, J=17.6 Hz), 4.52 (2H, brs), 3.93 (4H, brs), 3.24 (4H, brs), 3.12 (3H, s), 2.68 (4H, brs), 2.42 (3H, s).

ESI-MS Found: m/z[M+H]+ 516.

Example 95

Production of 2-allyl-1-[6-(2-hydroxy-1,1,2-trimethylpropyl)pyridin-2-yl]-6-{[4-(4-methylpiperazin-1-yl)phenyl]amino}-1,2-dihydro-3H-pyrazolo[3,4-d]pyrimidin-3-one 1) Production of ethyl 2-(6-bromopyridin-2-yl)-2-methylpropionate In a nitrogen atmosphere, 100 mL of tetrahydrofuran containing 14 mL of diisopropylamine was cooled in a dry ice-acetone bath, and 38 mL of 2.66 M n-butyllithium/hexane solution was added thereto to prepare lithium-diisopropylamide. This was dropwise added to 100 mL of tetrahydrofuran containing 4.55 mL of 6-bromopicoline and 6.06 mL of diethyl carbonate, at −60° C. or lower. After stirred for 20 minutes, 6.23 mL of methyl iodide was added thereto and heated up to room temperature. Water was added to the reaction liquid, extracted with diethyl ether, washed with saturated saline water, and dried with anhydrous magnesium sulfate. After concentrated under reduced pressure, the residue was purified through silica gel column chromatography (hexane/ethyl acetate=100/0 to 8/1) to obtain 10.72 g of the entitled compound as a colorless oily substance.

$^1$H-NMR (400 MHz, CDCl$_3$) δ: 7.49 (1H, t, J=7.8 Hz), 7.33 (1H, dd, J=7.8, 1.0 Hz), 7.22 (1H, dd, J=7.8, 1.0 Hz), 4.16 (2H, q, J=7.0 Hz), 1.59 (6H, s), 1.20 (3H, t, J=7.1 Hz), 0.00 (1H, d, J=3.4 Hz).

ESI-MS Found: m/z[M+H]+ 272, 274.

2) Production of 3-(6-bromopyridin-2-yl)-2,3-dimethylbutan-2-ol

In a nitrogen atmosphere, 13 mL of 2 M methylmagnesium iodide/diethyl ether solution was added to diethyl ether (20 mL) solution of 2.72 g of ethyl 2-(6-bromopyridin-2-yl)-2-methylpropionate with cooling in an ice bath. The reaction liquid was stirred at room temperature for 3 hours, and then water and aqueous 10% phosphoric acid solution were added thereto, extracted with diethyl ether, washed with aqueous saturated sodium hydrogencarbonate solution and saturated saline water, and then dried with anhydrous magnesium sulfate. After concentrated under reduced pressure, the residue was purified through silica gel column chromatography (hexane/ethyl acetate=9/1 to 8/1) to obtain 1.47 g of the entitled compound as a colorless oily substance.

$^1$H-NMR (400 MHz, CDCl$_3$) δ: 7.53 (1H, t, J=7.8 Hz), 7.35 (1H, d, J=7.3 Hz), 7.31 (1H, d, J=7.8 Hz), 1.38 (6H, s), 1.09 (6H, s).

ESI-MS Found: m/z[M+H]+ 258, 260.

3) Production of 2-allyl-1-[6-(2-hydroxy-1,1,2-trimethylpropyl)pyridin-2-yl]-6-{[4-(4-methylpiperazin-1-yl)phenyl]amino}-1,2-dihydro-3H-pyrazolo[3,4-d]pyrimidin-3-one 74.5 mg of the entitled compound was obtained as a yellow solid in the same manner as in Example 53-2 to 53-3, for which, however, the compound obtained in the above reaction was used in place of 2-(6-bromo-2-pyridyl)-2-propanol used in Example 53-2.

$^1$H-NMR (400 MHz, CDCl$_3$) δ: 8.82 (1H, s), 7.81 (1H, t, J=7.9 Hz), 7.81 (1H, brs), 7.45 (2H, d, J=8.4 Hz), 7.30 (1H, s), 6.93 (2H, d, J=9.2 Hz), 5.71 (1H, s), 5.08 (2H, s), 4.63 (2H, s), 3.24 (4H, s), 2.66 (4H, s), 2.41 (3H, s), 1.47 (6H, s), 1.09 (6H, s).

ESI-MS Found: m/z[M+H]+ 543.

Example 96

Production of N-[6-(2-allyl-6-{[4-(4-methylpiperazin-1-yl)phenyl]amino}-3-oxo-1,2-dihydro-3H-pyrazolo[3,4-d]pyrimidin-1-yl)pyridin-2-yl]acetamide 0.2 mL of acetic anhydride was added to pyridine (2 mL) solution of 50 mg of 2-allyl-1-(6-aminopyridin-2-yl)-6-{[4-(4-methylpiperazin-1-yl)phenyl]amino}-1,2-dihydro-3H-pyrazolo[3,4-d]pyrimidin-3-one obtained in Example 50, and stirred at 50° C. for 6 hours. After this was concentrated under reduced pressure, saturated sodium hydrogencarbonate solution was added thereto, extracted with chloroform, and the organic layer was washed with saturated saline water and dried with anhydrous sodium sulfate. The solvent was evaporated away under reduced pressure, and the resulting residue was purified through preparative basic thin-layer chromatography (chloroform/methanol=40/1) to obtain 47 mg of the entitled compound as a yellow solid.

$^1$H-NMR (400 MHz, CDCl$_3$, 2 drops of CD$_3$OD) δ: 8.81 (1H, brs), 8.14 (1H, d, J=8.3 Hz), 7.87 (1H, dd, J=8.3, 8.0 Hz), 7.47 (2H, d, J=8.5 Hz), 7.47 (1H, d, J=8.0 Hz), 6.91 (2H, d, J=8.5 Hz), 5.67 (1H, ddt, J=17.0, 10.2, 6.3 Hz), 5.06 (1H, dd, J=10.2, 1.1 Hz), 4.96 (1H, dd, J=17.0, 1.1 Hz), 4.67 (2H, d, J=6.3 Hz), 3.34-3.13 (4H, m), 2.87-2.55 (4H, m), 2.44 (3H, s), 2.24 (3H, s).

ESI-MS Found: m/z[M+H]+ 500.

Example 97

Production of 2-allyl-6-{[4-(4-methylpiperazin-1-yl)phenyl]amino}-1-[6-(2-oxopyrrolidin-1-yl)pyridin-2-yl]-1,2-dihydro-3H-pyrazolo[3,4-d]pyrimidin-3-one With cooling with ice, 0.012 mL of triethylamine and 12.4 mg of 4-chlorobutyric acid chloride were added to tetrahydrofuran (1 mL) solution of 20 mg of the compound obtained in Example 50, 2-allyl-1-(6-aminopyridin-2-yl)-6-{[4-(4- methylpiperazin-1-yl)phenyl]amino}-1,2-dihydro-3H-pyrazolo[3,4-d]pyrimidin-3-one, and stirred at room temperature for 1 hour. Water was added to the reaction mixture, extracted with chloroform, and the organic layer was washed with saturated saline water, and dried with anhydrous sodium sulfate. The solvent was evaporated away under reduced pressure, the resulting residue was dissolved in 1 mL of N,N-dimethylformamide, and 5 mg of potassium tert-butoxide was added thereto and stirred at room temperature for 30 minutes. Saturated ammonium chloride solution was added to the reaction mixture, extracted with ethyl acetate, and the organic layer was washed with saturated saline water and dried with anhydrous sodium sulfate. The solvent was evaporated away under reduced pressure, and the resulting residue was purified through preparative thin-layer chromatography (chloroform/methanol=10/1) to obtain 5 mg of the entitled compound as a yellow solid.

$^1$H-NMR (400 MHz, CDCl$_3$) δ: 8.82 (1H, s), 8.34 (1H, d, J=8.0 Hz), 7.85 (1H, t, J=8.0 Hz), 7.58 (1H, d, J=8.0 Hz), 7.49-7.34 (1H, brm), 7.46 (2H, d, J=8.8 Hz), 6.92 (2H, d, J=8.8 Hz), 5.68 (1H, ddt, J=17.1, 10.2, 5.9 Hz), 5.04 (1H, dd, J=10.2, 1.0 Hz), 4.94 (1H, dd, J=17.1, 1.0 Hz), 4.76 (2H, d, J=5.9 Hz), 4.13-4.04 (2H, m), 3.30-3.20 (4H, m), 2.76-2.61 (6H, m), 2.42 (3H, s), 2.21-2.09 (2H, m).

ESI-MS Found: m/z[M+H]+ 526.

Example 98

Production of 2-allyl-1-[6-(2-hydroxyethoxy)pyridin-2-yl]-6-{[3-methyl-4-(4-methylpiperazin-1-yl)phenyl]amino}-1,2-dihydro-3H-pyrazolo[3,4-d]pyrimidin-3-one 1) Production of 2-[(6-bromopyridin-2-yl)oxy]ethanol 8.81 g of ethylene glycol monovinyl ether was added to toluene (100 mL) suspension of 2.4 g of sodium hydride (55% to 72%), and 9.48 g of 2,6-dibromopyridine was added thereto and stirred overnight at 110° C. The reaction liquid was left cooled to room temperature, and water was added thereto to separate the organic layer. This was washed with saturated saline water, dried with anhydrous magnesium sulfate, and concentrated under reduced pressure. 100 mL of methanol and 576 mg of p-toluenesulfonic acid hydrate were added to the resulting residue, and stirred for 5 hours. After this was concentrated under reduced pressure, aqueous saturated sodium hydrogencarbonate solution was added to it, and extracted with ethyl acetate. This was washed with saturated saline water, dried with anhydrous magnesium sulfate, concentrated under reduced pressure, and the resulting residue was purified through silica gel column chromatography (hexane/ethyl acetate=9/1 to 2/1) to obtain 7.74 g of the entitled compound as a colorless oily substance.

$^1$H-NMR (400 MHz, CDCl$_3$) δ: 7.45 (1H, t, J=7.5 Hz), 7.09 (1H, d, J=7.4 Hz), 6.74 (1H, d, J=8.2 Hz), 4.46 (2H, t, J=4.4 Hz), 3.96 (2H, t, J=4.4 Hz).

ESI-MS Found: m/z[M+H]+ 218, 220.

2) Production of 2-allyl-1-[6-(2-hydroxyethoxy)pyridin-2-yl]-6-{[3-methyl-4-(4-methylpiperazin-1-yl)phenyl]amino}-1,2-dihydro-3H-pyrazolo[3,4-d]pyrimidin-3-one 870 mg of the entitled compound was obtained as a white solid in the same manner as in Example 53-2 to 53-3, for which, however, the compound obtained in the above reaction was used in place of 2-(6-bromo-2-pyridyl)-2-propanol used in Example 53-2, and 3-methyl-4-(4-methylpiperazin-1-yl)aniline was used in place of 4-(4-methylpiperazin-1-yl)aniline used in Example 53-3.

$^1$H-NMR (400 MHz, DMSO-d$_6$) δ: 10.19 (1H, brs), 8.86 (1H, s), 7.96 (1H, t, J=8.0 Hz), 7.68 (1H, brs), 7.46 (1H, d, J=7.6 Hz), 7.43 (1H, dd, J=8.8, 2.9 Hz), 7.00 (1H, d, J=8.6 Hz), 6.82 (1H, d, J=8.2 Hz), 5.70 (1H, ddt, J=18.6, 11.3, 5.5 Hz), 5.05 (1H, d, J=11.3 Hz), 4.93 (1H, d, J=18.6 Hz), 4.87 (1H, t, J=5.5 Hz), 4.65 (2H, d, J=4.9 Hz), 4.30 (2H, t, J=5.1 Hz), 3.73 (2H, dd, J=10.0, 5.3 Hz), 2.82 (4H, t, J=4.7 Hz), 2.47 (4H, brs), 2.25 (6H, s).

ESI-MS Found: m/z[M+H]+ 517.

Example 99

Production of N-{[6-(2-allyl-6-{[4-(4-methylpiperazin-1-yl)phenyl]amino}-3-oxo-1,2-dihydro-3H-pyrazolo[3,4-d]pyrimidin-1-yl)pyridin-2-yl]methyl}-N-methylmethanesulfonamide 1) Production of 2-allyl-1-[6-(hydroxymethyl)pyridin-2-yl]-6-{[4-(4-methylpiperazin-1-yl)phenyl]amino}-1,2-dihydro-3H-pyrazolo[3,4-d]pyrimidin-3-one 1.36 g of imidazole and 1.81 g of tert-butyl(chloro)dimethylsilane were added to N,N-dimethylformamide (30 mL) solution of 3.29 g of the compound obtained in Example 51-1, and stirred overnight. Water was added to the reaction liquid, and extracted with diethyl ether. This was washed with saturated saline water, and dried with anhydrous magnesium sulfate. After concentrated under reduced pressure, the resulting residue was purified through silica gel column chromatography (hexane/ethyl acetate=9/1 to 4/1), and the solvent was evaporated away under reduced pressure. 40 mL of toluene and 3.20 g of m-chloroperbenzoic acid (>65%) were added to the residue, and stirred for 30 minutes. 5.20 mL of N,N-diisopropylethylamine and 2.29 g of 4-(4-methylpiperazin-1-yl)aniline were added to the reaction liquid, and stirred overnight. Aqueous saturated sodium hydrogencarbonate solution was added to the reaction liquid, and extracted with ethyl acetate. This was dried with anhydrous magnesium sulfate, the solvent was evaporated away, the residue was purified through silica gel column chromatography (chloroform/ethanol=100/1 to 100/3), and the solvent was evaporated away under reduced pressure. 50 mL of 4 N hydrochloric acid was added to the residue, and stirred, and then the solution was made alkaline with aqueous 4 N sodium hydroxide solution. This was extracted with a mixed solution of chloroform/isopropanol (80/20), dried with anhydrous magnesium sulfate, the solvent was evaporated away, and the residue was crystallized in ethyl acetate to obtain 3.78 g of the entitled compound as a yellow crystal.

$^1$H-NMR (400 MHz, CDCl$_3$) δ: 8.83 (1H, s), 7.86 (1H, t, J=6.0 Hz), 7.75 (1H, d, J=8.2 Hz), 7.46 (2H, d, J=8.6 Hz), 7.40 (1H, brs), 7.22 (1H, d, J=7.6 Hz), 6.92 (2H, d, J=9.0 Hz), 5.71 (1H, ddt, J=16.8, 10.2, 5.9 Hz), 5.06 (1H, d, J=10.2 Hz), 4.96 (1H, d, J=16.8 Hz), 4.81 (2H, d, J=5.5 Hz), 4.71 (1H, d, J=5.9 Hz), 3.23 (4H, brs), 3.14 (1H, t, J=5.5 Hz), 2.64 (4H, brs), 2.40 (3H, s).

ESI-MS Found: m/z[M+H]+ 473.

2) Production of 2-allyl-1-{6-[(methylamino)methyl]pyridin-2-yl}-6-{[4-(4-methylpiperazin-1-yl)phenyl]amino}-1,2-dihydro-3H-pyrazolo[3,4-d]pyrimidin-3-one 4.46 mL of triethylamine and 1.0 mL of methanesulfonyl chloride were added to tetrahydrofuran (120 mL) solution of 3.78 g of the compound obtained in the above 1, and stirred. 20 mL of 2.0 M methylamine/tetrahydrofuran solution was added to the reaction liquid, and stirred overnight. Water was added to the reaction liquid, and extracted with ethyl acetate. This was washed with saturated saline water, dried with anhydrous magnesium sulfate, concentrated under reduced pressure, and the resulting residue was purified through basic silica gel column chromatography (hexane/ethyl acetate=50/50 to 0/100 to chloroform) to obtain 3.38 g of the entitled compound as a yellow solid.

$^1$H-NMR (400 MHz, CDCl$_3$) δ: 8.82 (1H, s), 7.81 (1H, t, J=7.8 Hz), 7.72 (1H, d, J=7.8 Hz), 7.46 (2H, d, J=8.8 Hz), 7.25 (1H, d, J=7.3 Hz), 6.92 (2H, d, J=9.3 Hz), 5.69 (1H, ddt, J=17.1, 10.2, 6.3 Hz), 5.02 (1H, dd, J=10.2, 1.5 Hz), 4.92 (1H, dd, J=17.1, 1.5 Hz), 4.75 (2H, d, J=6.3 Hz), 3.91 (2H, s), 3.21 (4H, t, J=4.9 Hz), 2.62 (4H, t, J=4.9 Hz), 2.51 (3H, s), 2.38 (3H, s).

ESI-MS Found: m/z[M+H]+ 486.

3) Production of N-{[6-(2-allyl-6-{[4-(4-methylpiperazin-1-yl)phenyl]amino}-3-oxo-1,2-dihydro-3H-pyrazolo[3,4-d]pyrimidin-1-yl)pyridin-2-yl]methyl}-N-methylmethanesulfonamide 1.50 mL of triethylamine and 0.4 mL of methanesulfonyl chloride were added to tetrahydrofuran (50 mL) solution of 1.70 g of the compound obtained in the above 2, and stirred. Water was added to the reaction liquid, and extracted with ethyl acetate. This was washed with saturated saline water, dried with anhydrous magnesium sulfate, concentrated under reduced pressure, and the resulting residue was crystallized from 15 mL of ethyl acetate and 10 mL of ethanol to obtain 849 mg of the entitled compound as a yellow solid.

$^1$H-NMR (400 MHz, CDCl$_3$) δ: 8.83 (1H, s), 7.89 (1H, t, J=7.8 Hz), 7.81 (1H, d, J=8.3 Hz), 7.48 (1H, d, J=9.3 Hz), 7.47 (1H, brs), 7.41 (2H, d, J=7.3 Hz), 6.93 (2H, d, J=8.8 Hz), 5.68 (1H, ddt, J=17.1, 10.2, 6.3 Hz), 5.03 (1H, d, J=10.2 Hz), 4.92 (1H, d, J=18.0 Hz), 4.75 (2H, d, J=6.3 Hz), 4.50 (2H, s), 3.38 (4H, brs), 2.95 (3H, s), 2.92 (4H, brs), 2.91 (3H, s), 2.58 (3H, s).

ESI-MS Found: m/z[M+H]+ 564.

Example 100

Production of N-{[6-(2-allyl-6-{[4-(4-methylpiperazin-1-yl)phenyl]amino}-3-oxo-1,2-dihydro-3H-pyrazolo[3,4-d]pyrimidin-1-yl)pyridin-2-yl]methyl}-N-methylacetamide 77.5 mg of the entitled compound was obtained as a yellow amorphous substance in the same manner as in Example 99-1 to 99-3, for which, however, acetic anhydride was used in place of methanesulfonyl chloride used in Example 99-3.

$^1$H-NMR (400 MHz, CDCl$_3$) δ: 8.83 (0.33H, s), 8.82 (0.67H, s), 7.87-7.64 (2.00H, m), 7.47 (2.00H, dd, J=8.8, 4.9 Hz), 7.17 (0.67H, d, J=8.3 Hz), 7.07 (0.33H, d, J=7.8 Hz), 6.93 (2.00H, dd, J=9.3, 3.4 Hz), 5.73-5.62 (1.00H, m), 5.05-4.99 (1.00H, m), 4.92 (1.00H, d, J=17.1 Hz), 4.78 (2H, d, J=6.3 Hz), 4.70 (1.33H, s), 4.62 (0.67H, s), 3.22 (4.00H, t, J=5.0 Hz), 3.12 (2.00H, s), 3.02 (1.00H, s), 2.63 (4.00H, t, J=5.0 Hz), 2.39 (3.00H, s), 2.19 (3.00H, s).

ESI-MS Found: m/z[M+H]+ 528.

Example 101

Production of N-{[6-(2-allyl-6-{[3-methyl-4-(4-methylpiperazin-1-yl)phenyl]amino}-3-oxo-1,2-dihydro-3H-pyrazolo[3,4-d]pyrimidin-1-yl)pyridin-2-yl]methyl}-N-methylacetamide 21.9 mg of the entitled compound was obtained as a white amorphous substance in the same manner as in Example 99-1 to 99-3, for which, however, 3-methyl-4-(4-methylpiperazin-1-yl)aniline was used in place of 4-(4-methylpiperazin-1-yl)aniline used in Example 99-1, and acetic anhydride was used in place of methanesulfonyl chloride used in Example 99-3.

$^1$H-NMR (400 MHz, CDCl$_3$) δ: 8.84 (0.33H, s), 8.83 (0.67H, s), 7.88-7.80 (2.00H, m), 7.58 (0.33H, s), 7.49 (0.67H, s), 7.34-7.30 (1.00H, m), 7.18 (0.67H, t, J=4.1 Hz), 7.09 (0.33H, t, J=4.1 Hz), 7.03 (1.00H, dd, J=8.5, 4.6 Hz), 5.73-5.61 (0.99H, m), 5.05-4.99 (1.00H, m), 4.94-4.88 (1.00H, m), 4.81-4.75 (2.00H, m), 4.70 (1.33H, s), 4.62 (0.67H, s), 3.12 (2.00H, s), 3.03 (1.00H, s), 2.97 (4.00H, t, J=5.1 Hz), 2.65 (4.00H, brs), 2.41 (3.00H, s), 2.33 (1.00H, s), 2.32 (2.00H, s), 2.19 (3.00H, s).

ESI-MS Found: m/z[M+H]+ 542.

Example 102

Production of N-{[6-(2-allyl-6-{[3-methyl-4-(4-methylpiperazin-1-yl)phenyl]amino}-3-oxo-1,2-dihydro-3H-pyrazolo[3,4-d]pyrimidin-1-yl)pyridin-2-yl]methyl}-N-methylmethanesulfonamide 10.4 mg of the entitled compound was obtained as a white solid in the same manner as in Example 99-1 to 99-3, for which, however, 3-methyl-4-(4-methylpiperazin-1-yl)aniline was used in place of 4-(4-methylpiperazin-1-yl)aniline used in Example 99-1.

$^1$H-NMR (400 MHz, CDCl$_3$) δ: 8.83 (1H, s), 7.89 (1H, t, J=7.8 Hz), 7.81 (1H, d, J=8.3 Hz), 7.49 (1H, s), 7.48 (1H, d, J=9.3 Hz), 7.41 (1H, d, J=7.3 Hz), 7.02 (1H, d, J=8.8 Hz), 5.68 (1H, ddt, J=17.1, 10.2, 6.3 Hz), 5.03 (1H, d, J=10.2 Hz), 4.92 (1H, dd, J=17.1, 1.0 Hz), 4.75 (2H, d, J=6.3 Hz), 4.50 (2H, s), 3.38 (4H, brs), 2.95 (3H, s), 2.92 (4H, brs), 2.91 (3H, s), 2.58 (3H, s), 2.32 (3H, s).

ESI-MS Found: m/z[M+H]+ 578.

Example 103

Production of 2-allyl-1-[6-(2-hydroxy-1,1-dimethylethyl)pyridin-2-yl]-6-{[4-(4-methylpiperazin-1-yl)phenyl]amino}-1,2-dihydro-3H-pyrazolo[3,4-d]pyrimidin-3-one

1) Production of 2-(6-bromopyridin-2-yl)-2-methyl-propan-1-ol

In a dry ice/acetone bath, 100 mL of a toluene solution of 1.01 M diisobutylaluminium hydride was added to toluene (50 mL) solution of 10.72 g of the compound obtained in Example 95-1, heated up to room temperature, and stirred for 40 minutes. With cooling with ice, aqueous saturated ammonium chloride solution was added to the reaction liquid, and the organic layer was separated. This was washed with aqueous saturated sodium hydrogencarbonate solution and saturated saline water, dried with anhydrous magnesium sulfate, concentrated under reduced pressure, and the residue was purified through silica gel column chromatography (ethyl acetate) to obtain 8.74 g of the entitled compound as a colorless oily substance.

$^1$H-NMR (400 MHz, CDCl$_3$) δ: 7.52 (1H, t, J=7.8 Hz), 7.33 (1H, dd, J=7.8, 1.0 Hz), 7.27 (1H, d, J=7.8 Hz), 3.74 (2H, s), 1.32 (6H, s).

ESI-MS Found: m/z[M+H]+ 230, 232.

2) Production of 2-allyl-1-[6-(2-hydroxy-1,1-dimethylethyl)pyridin-2-yl]-6-(methylthio)-1,2-dihydro-3H-pyrazolo[3,4-d]pyrimidin-3-one 7.45 g of the entitled compound was obtained in the same manner as in Example 53-2, for which, however, the compound obtained in the above reaction was used in place of 2-(6-bromo-2-pyridinyl)-2-propanol used in Example 53-2.

$^1$H-NMR (400 MHz, CDCl$_3$) δ: 8.93 (1H, s), 7.86 (1H, t, J=8.0 Hz), 7.60 (1H, d, J=8.8 Hz), 7.31 (1H, d, J=7.8 Hz), 5.67 (1H, ddt, J=17.1, 10.2, 6.3 Hz), 5.05 (1H, dd, J=10.2, 1.0 Hz), 4.92 (1H, dd, J=17.1, 1.5 Hz), 4.79 (2H, d, J=6.3 Hz), 3.78 (2H, s), 2.58 (3H, s), 1.37 (6H, s).

ESI-MS Found: m/z[M+H]+ 372.

3) Production of 2-allyl-1-[6-(2-hydroxy-1,1-dimethylethyl)pyridin-2-yl]-6-{[4-(4-methylpiperazin-1-yl)phenyl]amino}-1,2-dihydro-3H-pyrazolo[3,4-d]pyrimidin-3-one 1.4 g of the entitled compound was obtained as a yellow solid in the same manner as in Example 53-3, for which, however, the compound obtained in the above reaction was used in place of 2-allyl-1-[6-(1-hydroxy-1-methylethyl)-2-pyridinyl]-6-(methylthio)-1,2-dihydro-3H-pyrazolo[3,4-d]pyrimidin-3-one used in Example 53-3.

$^1$H-NMR (400 MHz, CDCl$_3$) δ: 8.83 (1H, s), 7.81 (1H, t, J=7.8 Hz), 7.52-7.41 (3H, m), 7.25 (1H, d, J=9.3 Hz), 6.92 (2H, dd, J=6.8, 2.4 Hz), 5.72 (1H, brs), 5.14-4.96 (2H, brm), 4.64 (2H, brs), 3.79 (2H, d, J=6.3 Hz), 3.24 (4H, t, J=5.0 Hz), 2.65 (4H, brs), 2.41 (3H, s), 1.38 (6H, s).

ESI-MS Found: m/z[M+H]+ 515.

Example 104

Production of 2-allyl-1-[6-(2-hydroxy-1,1-dimethylethyl)pyridin-2-yl]-6-({4-[4-(2-methoxyethyl)piperazin-1-yl]phenyl}amino)-1,2-dihydro-3H-pyrazolo[3,4-d]pyrimidin-3-one 72 mg of the entitled compound was obtained as a yellow solid in the same manner as in Example 103-1 to 103-3, for which, however, 4-[4-(2-methoxyethyl)piperazin-1-yl]aniline was used in place of 4-(4-methylpiperazin-1-yl)aniline used in Example 103-3.

$^1$H-NMR (400 MHz, CDCl$_3$) δ: 8.82 (1H, s), 7.81 (1H, t, J=7.8 Hz), 7.50 (1H, brs), 7.42 (2H, d, J=7.8 Hz), 7.25 (1H, d, J=8.3 Hz), 6.91 (2H, d, J=8.8 Hz), 5.71 (1H, brs), 5.07 (2H, brs), 4.61 (2H, brs), 3.79 (2H, d, J=6.3 Hz), 3.58 (2H, s), 3.38 (3H, s), 3.23 (4H, t, J=4.6 Hz), 2.69 (6H, brs), 1.38 (6H, s).

ESI-MS Found: m/z[M+H]+ 559.

Example 105

Production of 2-allyl-6-({4-[4-(2-ethoxyethyl)piperazin-1-yl]phenyl}amino)-1-[6-(2-hydroxy-1,1-dimethylethyl)pyridin-2-yl]-1,2-dihydro-3H-pyrazolo[3,4-d]pyrimidin-3-one 73.3 mg of the entitled compound was obtained as a yellow solid in the same manner as in Example 103-1 to 103-3, for which, however, 4-[4-(2-ethoxyethyl)piperazin-1-yl]aniline was used in place of 4-(4-methylpiperazin-1-yl)aniline used in Example 103-3.

$^1$H-NMR (400 MHz, CDCl$_3$) δ: 8.82 (1H, s), 7.81 (1H, t, J=8.0 Hz), 7.54 (1H, s), 7.43 (2H, d, J=7.8 Hz), 7.25 (2H, d, J=8.3 Hz), 6.91 (2H, d, J=9.3 Hz), 5.70 (1H, brs), 5.08 (2H, brs), 4.61 (2H, brs), 3.79 (2H, s), 3.64 (2H, t, J=5.6 Hz), 3.53 (2H, q, J=7.0 Hz), 3.23 (4H, t, J=4.4 Hz), 2.79-2.65 (6H, m), 1.38 (6H, s), 1.22 (3H, t, J=7.1 Hz).

ESI-MS Found: m/z[M+H]+ 573.

Example 106

Production of 2-allyl-1-[6-(2-hydroxy-1,1-dimethylethyl)pyridin-2-yl]-6-{[3-methyl-4-(4-methylpiperazin-1-yl)phenyl]amino}-1,2-dihydro-3H-pyrazolo[3,4-d]pyrimidin-3-one 83.6 mg of the entitled compound was obtained as a white solid in the same manner as in Example 103-1 to 103-3, for which, however, 3-methyl-4-(4-methylpiperazin-1-yl)aniline was used in place of 4-(4-methylpiperazin-1-yl)aniline used in Example 103-3.

$^1$H-NMR (400 MHz, CDCl$_3$) δ: 8.84 (1H, s), 7.83 (1H, t, J=7.8 Hz), 7.51 (1H, brs), 7.37 (2H, d, J=8.3 Hz), 7.26-7.25 (1H, m), 7.03 (1H, d, J=8.5 Hz), 5.78-5.65 (1H, brm), 5.14-4.94 (2H, brm), 4.66 (2H, brs), 3.79 (2H, d, J=6.3 Hz), 3.00 (4H, brs), 2.69 (4H, brs), 2.45 (3H, brs), 2.31 (3H, s), 1.39 (6H, s).

ESI-MS Found: m/z[M+H]+ 529.

Example 107

Production of 2-allyl-1-[6-(2-hydroxy-1,1-dimethylethyl)pyridin-2-yl]-6-{[4-(1-methylpiperidin-4-yl)phenyl]amino}-1,2-dihydro-3H-pyrazolo[3,4-d]pyrimidin-3-one 49.5 mg of the entitled compound was obtained as a white solid in the same manner as in Example 103-1 to 103-3, for which, however, 4-(1-methylpiperidin-4-yl)aniline was used in place of 4-(4-methylpiperazin-1-yl)aniline used in Example 103-3.

$^1$H-NMR (400 MHz, CDCl$_3$) δ: 8.86 (1H, s), 7.83 (1H, t, J=8.0 Hz), 7.59 (1H, brs), 7.51 (2H, d, J=8.3 Hz), 7.27 (2H, d, J=5.4 Hz), 7.21 (2H, d, J=8.8 Hz), 7.18 (1H, d, J=7.3 Hz), 5.78-3.66 (1H, m), 5.08 (1H, d, J=10.2 Hz), 5.00 (1H, d, J=15.6 Hz), 4.67 (2H, brs), 3.79 (2H, d, J=6.8 Hz), 3.07 (2H, brs), 2.51 (1H, brs), 2.41 (3H, s), 2.36 (1H, s), 2.17 (2H, brs), 1.95-1.82 (4H, brm), 1.39 (6H, s).

ESI-MS Found: m/z[M+H]+ 514.

Example 108

Production of 2-ethyl-1-[6-(2-hydroxy-1,1-dimethylethyl)pyridin-2-yl]-6-{[3-methyl-4-(4-methylpiperazin-1-yl)phenyl]amino}-1,2-dihydro-3H-pyrazolo[3,4-d]pyrimidin-3-one 27 mg of the entitled compound was obtained as a yellow solid in the same manner as in Example 103-1 to 103-3, for which, however, the compound obtained in Example 28-1 was used in place of 2-allyl-6-(methylthio)-1,2-dihydro-3H-pyrazolo[3,4-d]pyrimidin-3-one used in Example 103-2, and 3-methyl-4-(4-methylpiperazin-1-yl)aniline was used in place of 4-(4-methylpiperazin-1-yl)aniline used in Example 103-3.

¹H-NMR (400 MHz, CDCl₃) δ: 8.83 (1H, s), 7.83 (1H, dd, J=8.0, 7.2 Hz), 7.55 (1H, s), 7.38-7.35 (2H), 7.28-7.26 (2H), 7.02 (1H, d, J=8.8 Hz), 4.09 (2H, d, J=7.2 Hz), 3.79 (2H, s), 2.96 (4H, m), 2.63 (4H, m), 2.41 (3H, s), 2.31 (3H, s), 1.39 (6H, s), 1.21 (3H, t, J=7.2 Hz).

ESI-MS Found: m/z[M+H]+ 517.

Example 109

Production of 2-ethyl-1-[6-(2-hydroxy-1,1-dimethylethyl)pyridin-2-yl]-6-{[3-(hydroxymethyl)-4-(4-methylpiperazin-1-yl)phenyl]amino}-1,2-dihydro-3H-pyrazolo[3,4-d]pyrimidin-3-one 11 mg of the entitled compound was obtained as a yellow solid in the same manner as in Example 103-1 to 103-3, for which, however, the compound obtained in Example 28-1 was used in place of 2-allyl-6-(methylthio)-1,2-dihydro-3H-pyrazolo[3,4-d]pyrimidin-3-one used in Example 103-2, and [5-amino-2-(4-methylpiperazin-1-yl)phenyl]methanol was used in place of 4-(4-methylpiperazin-1-yl)aniline used in Example 103-3.

¹H-NMR (400 MHz, CD₃OD) δ: 8.83 (1H, s), 8.03 (1H, dd, J=8.0, 8.0 Hz), 7.91 (1H, s), 7.88 (1H, d, J=8.0 Hz), 7.55 (1H, d, J=8.0 Hz), 7.46 (1H, d, J=8.0 Hz), 7.16 (1H, d, J=8.0 Hz), 4.76 (2H, s), 4.26 (2H, q, J=7.2 Hz), 3.00 (4H, m), 2.67 (4H, m), 2.41 (3H, s), 1.38 (6H, s), 1.12 (3H, t, J=7.2 Hz).

ESI-MS Found: m/z[M+H]+ 533.

Example 110

Production of 2-ethyl-1-[6-(2-hydroxy-1,1-dimethylethyl)pyridin-2-yl]-6-{[4-(4-methylpiperazin-1-yl)phenyl]amino}-1,2-dihydro-3H-pyrazolo[3,4-d]pyrimidin-3-one 21 mg of the entitled compound was obtained as a yellow solid in the same manner as in Example 103-1 to 103-3, for which, however, the compound obtained in Example 28-1 was used in place of 2-allyl-6-(methylthio)-1,2-dihydro-3H-pyrazolo[3,4-d]pyrimidin-3-one used in Example 103-2.

¹H-NMR (400 MHz, CDCl₃) δ: 8.82 (1H, s), 7.82 (1H, dd, J=8.0, 8.0 Hz), 7.52 (1H), 7.43 (2H, d, J=9.2 Hz), 7.26-7.25 (1H), 6.92 (1H, d, J=9.2 Hz), 4.05 (1H, q, J=7.6 Hz), 3.80 (2H, s), 3.23 (4H, m), 2.64 (4H, m), 2.94 (3H, s), 1.39 (6H, s), 1.11 (3H, t, J=7.6 Hz).

ESI-MS Found: m/z[M+H]+ 503.

Example 111

Production of 2-benzyl-6-{[3-methyl-4-(4-methylpiperazin-1-yl)phenyl]amino}-1-phenyl-1,2-dihydro-3H-pyrazolo[3,4-d]pyrimidin-3-one 1) Production of 2-benzyl-6-(methylthio)-1-phenyl-1,2-dihydro-3H-pyrazolo[3,4-d]pyrimidin-3-one 33 mg of potassium hydroxide and 0.092 mL of benzyl bromide were added in that order to ethanol (10 mL) solution of 100 mg of the compound obtained in Production Example 4, and heated under reflux for 23 hours. The reaction liquid was concentrated under reduced pressure, and the residue was separated and purified through silica gel column chromatography (hexane/ethyl acetate=60/40) to obtain 74 mg of the entitled compound as a white solid.

¹H-NMR (400 MHz, CDCl₃) δ: 8.80 (1H, s), 7.53-7.20 (10H, m), 2.48 (3H, s).

ESI-MS Found: m/z[M+H]+ 349.

2) Production of 2-benzyl-6-{[3-methyl-4-(4-methylpiperazin-1-yl)phenyl]amino}-1-phenyl-1,2-dihydro-3H-pyrazolo[3,4-d]pyrimidin-3-one 46 mg of m-chloroperbenzoic acid was added to chloroform (2 mL) solution of 74 mg of the compound obtained in the above 1, and stirred at room temperature for 20 minutes. The reaction liquid was washed with aqueous saturated sodium hydrogencarbonate solution, and dried with anhydrous sodium sulfate. The solvent was evaporated away under reduced pressure to obtain crude 2-benzyl-6-(methylsulfinyl)-1-phenyl-1,2-dihydro-3H-pyrazolo[3,4-d]pyrimidin-3-one as a white solid.

25 mg of 4-[3-methyl-4-(4-methylpiperazin-1-yl)]aniline and 0.05 mL of N,N-diisopropylethylamine were added in that order to toluene (5 mL) solution of 25 mg of the above compound, and stirred at 120° C. for 15 hours. The solvent was evaporated away under reduced pressure, water was added thereto, extracted with ethyl acetate, and dried with anhydrous sodium sulfate. The solvent was evaporated away under reduced pressure, and the residue was separated and purified through basic silica gel column chromatography (ethyl acetate) to obtain 24.7 mg of the entitled compound as a yellow solid.

¹H-NMR (400 MHz, CDCl₃) δ: 8.80 (1H, s), 6.91-7.53 (13H, m), 4.97 (2H, s), 2.91 (4H, s), 2.55-2.69 (4H, bs), 2.38 (3H, s), 2.25 (3H, s).

ESI-MS Found: m/z[M+H]+ 506.

Example 112

Production of 6-{[3-(hydroxymethyl)-4-(4-methylpiperazin-1-yl)phenyl]amino}-1-phenyl-2-(2-propynyl)-1,2-dihydro-3H-pyrazolo[3,4-d]pyrimidin-3-one 65.3 mg of the entitled compound was obtained as a yellow solid in the same manner as in Example 111-1 to 111-2, for which, however, 3-bromo-1-propyne was used in place of benzyl bromide used in Example 111-1, and [5-amino-2-(4-methylpiperazin-1-yl)phenyl]methanol was used in place of 3-methyl-4-(4-methylpiperazin-1-yl)aniline used in Example 111-2.

¹H-NMR (400 MHz, CDCl₃) δ: 8.83 (1H, s), 7.62-7.18 (9H, m), 4.75 (2H, s), 4.51 (2H, d, J=2.1 Hz), 3.02-2.99 (4H, m), 2.74-2.63 (4H, m), 2.38 (3H, s), 2.16 (1H, d, J=2.1 Hz).

ESI-MS Found: m/z[M+H]+ 470.

Example 113

Production of 1-[6-(1-hydroxy-1-methylethyl)pyridin-2-yl]-6-{[4-(4-methylpiperazin-1-yl)phenyl]amino}-2-(2-propynyl)-1,2-dihydro-3H-pyrazolo[3,4-d]pyrimidin-3-one 1) Production of 1-[6-(1-hydroxy-1-methylethyl)pyridin-2-yl]-6-(methylthio)-2-(2-propynyl)-1,2-dihydro-3H-pyrazolo[3,4-d]pyrimidin-3-one 440 mg of ammonium formate and 230 mg of [1,1'-bis(diphenylphosphino)ferrocene]palladium(II) dichloride were added to tetrahydrofuran (13.6 mL) solution of 500 mg of 2-allyl-1-[6-(1-hydroxy-1-methylethyl)-2-pyridinyl]-6-(methylthio)-1,2-dihydro-3H-pyrazolo[3,4-d]pyrimidin-3-one produced in Example 53, and stirred at 90° C. for 3 hours.

The reaction liquid was cooled to room temperature, distilled water was added thereof, and extracted with a mixed solution of chloroform/isopropanol (80/20). This was dried with anhydrous sodium sulfate, and the solvent was evaporated away under reduced pressure to obtain 7.70 mg of a black amorphous substance. 61.0 mg of sodium hydride was added to N,N-dimethylformamide (14.0 mL) solution of the resulting compound, and stirred for 30 minutes. 0.316 mL of propargyl bromide was added to the reaction solution, and stirred for 3.5 hours. Aqueous saturated sodium hydrogencarbonate solution and saturated saline water were added to the reaction liquid, and extracted with a mixed solution of chloroform/isopropanol (80/20). This was dried with anhydrous sodium sulfate, and the solvent was evaporated away under reduced pressure to obtain a black amorphous substance. The resulting amorphous substance was purified through silica gel column chromatography (hexane/ethyl acetate) to obtain 254 mg of the entitled compound as a white compound.

$^1$H-NMR (400 MHz, CDCl$_3$) δ: 8.94 (1H, s), 7.94 (2H, d, J=3.6 Hz), 7.43 (1H, t, J=3.6 Hz), 4.97 (2H, d, J=2.4 Hz), 2.62 (3H, s), 2.16 (1H, t, J=2.4 Hz), 1.59 (6H, s).

ESI-MS Found: m/z[M+H]+ 357.

2) Production of 1-[6-(1-hydroxy-1-methylethyl) pyridin-2-yl]-6-{[4-(4-methylpiperazin-1-yl)phenyl] amino}-2-(2-propynyl)-1,2-dihydro-3H-pyrazolo[3, 4-d]pyrimidin-3-one 7.3 mg of the entitled compound was obtained as a yellow solid in the same manner as in Example 53-3, for which, however, the compound obtained in the above reaction was used in place of 2-allyl-1-[6-(1-hydroxy-1-methylethyl)-2-pyridinyl]-6-(methylthio)-1,2-dihydro-3H-pyrazolo[3,4-d]pyrimidin-3-one used in Example 53-3.

$^1$H-NMR (400 MHz, CDCl$_3$) δ: 8.83 (1H, s), 7.92 (1H, d, J=8.0 Hz), 7.87 (1H, dd, J=8.0, 8.0 Hz), 7.47 (2H, d, J=7.6 Hz), 7.35 (1H, d, J=8.0 Hz), 6.94 (2H, d, J=7.6 Hz), 4.89 (2H, d, J=2.0 Hz), 3.23 (4H, m), 2.63 (4H, m), 2.39 (3H, s), 2.13 (1H, t, J=2.0 Hz), 1.59 (6H, s).

ESI-MS Found: m/z[M+H]+ 499.

Example 114

Production of 6-{[3-methyl-4-(4-methylpiperazin-1-yl)phenyl]amino}-2-(2-propynyl)-1-pyridin-2-yl-1,2-dihydro-3H-pyrazolo[3,4-d]pyrimidin-3-one 17.0 mg of the entitled compound was obtained as a yellow solid in the same manner as in Example 113-1 to 113-2, for which, however, 2-allyl-6-(methylthio)-1-pyridin-2-yl-3H-pyrazolo[3,4-d]pyrimidin-3-one obtained in Example 29-1 was used in place of 2-allyl-1-[6-(1-hydroxy-1-methylethyl)-2-pyridinyl]-6-(methylthio)-1,2-dihydro-3H-pyrazolo[3,4-d]pyrimidin-3-one used in Example 113-1, and 3-methyl-4-(4-methylpiperazin-1-yl)aniline was used in place of 4-(4-methylpiperazin-1-yl)aniline used in Example 113-2.

$^1$H-NMR (400 MHz, CDCl$_3$) δ: 8.84 (1H, s), 8.49 (1H, d, J=4.0 Hz), 8.19 (1H, d, J=4.0 Hz), 7.87 (1H, dd, J=8.0, 8.0 Hz), 7.54 (1H, d, J=2.0 Hz), 7.32 (1H, dd, J=8.8, 2.0 Hz), 7.25 (1H, dd, J=8.0, 4.0 Hz), 7.04 (1H, d, J=8.8 Hz), 4.99 (2H, d, J=1.6 Hz), 2.96 (4H, m), 2.61 (4H, m), 2.39 (3H, s), 2.34 (3H, s), 2.07 (1H, d, J=1.6 Hz).

ESI-MS Found: m/z[M+H]+ 455.

Example 115

Production of 6-{[4-(4-methylpiperazin-1-yl)phenyl] amino}-2-(2-propynyl)-1-pyridin-2-yl-1,2-dihydro-3H-pyrazolo[3,4-d]pyrimidin-3-one 20 mg of the entitled compound was obtained as a yellow solid in the same manner as in Example 113-1 to 113-2, for which, however, 2-allyl-6-(methylthio)-1-pyridin-2-yl-3H-pyrazolo[3,4-d]pyrimidin-3-one obtained in Example 29-1 was used in place of 2-allyl-1-[6-(1-hydroxy-1-methylethyl)-2-pyridinyl]-6-(methylthio)-1,2-dihydro-3H-pyrazolo[3,4-d]pyrimidin-3-one used in Example 113-1.

$^1$H-NMR (400 MHz, CDCl$_3$) δ: 8.82 (1H, s), 8.07 (1H, d, J=7.6 Hz), 7.85, (1H, dd, J=8.4, 7.6 Hz), 7.47 (2H, d, J=9.2 Hz), 7.22 (1H, dd, J=7.6, 4.8 Hz), 6.96 (1H, d, J=9.2 Hz), 4.99 (2H, d, J=1.6 Hz), 3.23 (4H, m), 2.62 (4H, m), 2.39 (3H, s), 2.07 (1H, d, J=1.6 Hz).

ESI-MS Found: m/z[M+H]+ 441.

Example 116

Production of 6-{[3-hydroxymethyl-4-(4-methylpiperazin-1-yl)phenyl]amino}-2-(2-propynyl)-1-pyridin-2-yl-1,2-dihydro-3H-pyrazolo[3,4-d]pyrimidin-3-one 10 mg of the entitled compound was obtained as a yellow solid in the same manner as in Example 113-1 to 113-2, for which, however, 2-allyl-6-(methylthio)-1-pyridin-2-yl-3H-pyrazolo[3,4-d]pyrimidin-3-one obtained in Example 29-1 was used in place of 2-allyl-1-[6-(1-hydroxy-1-methylethyl)-2-pyridinyl]-6-(methylthio)-1,2-dihydro-3H-pyrazolo[3,4-d]pyrimidin-3-one used in Example 113-1, and [5-amino-2-(4-methylpiperazin-1-yl)phenyl]methanol was used in place of 4-(4-methylpiperazin-1-yl)aniline used in Example 113-2.

$^1$H-NMR (400 MHz, CD$_3$OD) δ: 8.84 (1H, s), 8.50 (1H, d, J=9.0 Hz), 8.16 (1H, d, J=8.4 Hz), 8.08 (1H, dd, J=8.8, 8.4 Hz), 7.94 (1H, d, J=2.0 Hz), 7.53 (1H, d, J=8.4, 2.0 Hz), 7.38 (1H, dd, J=8.8, 3.6 Hz), 7.18 (2H, d, J=8.4 Hz), 4.94 (2H, d, J=2.0 Hz), 4.78 (2H, s), 3.01 (4H, m), 2.68 (4H, m), 2.62 (1H, d, J=2.0 Hz), 2.41 (3H, s).

ESI-MS Found: m/z[M+H]+ 470.

Example 117

Production of 1-[6-(2-hydroxy-2-methylpropyl)pyridin-2-yl]-6-{[4-(4-methylpiperazin-1-yl)phenyl] amino}-2-(2-propynyl)-1,2-dihydro-3H-pyrazolo[3, 4-d]pyrimidin-3-one 76 mg of the entitled compound was obtained as a yellow solid in the same manner as in Example 113-1 to 113-2, for which, however, 2-allyl-1-[6-(2-hydroxy-2-methylpropyl) pyridin-2-yl]-6-(methylthio)-1,2-dihydro-3H-pyrazolo[3,4-d]pyrimidin-3-one obtained in Example 81-2 was used in place of 2-allyl-1-[6-(1-hydroxy-1-methylethyl)-2-pyridinyl]-6-(methylthio)-1,2-dihydro-3H-pyrazolo[3,4-d]pyrimidin-3-one used in Example 113-1.

$^1$H-NMR (400 MHz, CDCl$_3$) δ: 8.83 (1H, s), 7.98 (1H, dd, J=8.0, 8.0 Hz), 7.45 (2H, m), 7.85 (1H, d, J=8.0 Hz), 6.94 (1H, d, 8.8 Hz), 4.80 (1H, s), 3.22 (4H, m), 2.37 (2H, s), 2.33 (1H, s), 1.24 (6H, s).

ESI-MS Found: m/z[M+H]+ 513.

Example 118

Production of 6-{[4-(4-acetylpiperazin-1-yl)phenyl]amino}-1-[6-(1-hydroxy-1-methylethyl)pyridin-2-yl]-2-(2-propynyl)-1,2-dihydro-3H-pyrazolo[3,4-d]pyrimidin-3-one 7.4 mg of the entitled compound was obtained as a yellow solid in the same manner as in Example 113-1 to 113-2, for which, however, 4-(4-acetylpiperazin-1-yl)aniline was used in place of 4-(4-methylpiperazin-1-yl)aniline used in Example 113-2.

$^1$H-NMR (400 MHz, CDCl$_3$) δ: 8.84 (1H, s), 7.92-7.86 (2H, m), 7.51 (2H, d, J=9.2 Hz), 7.36 (1H, d, J=6.8 Hz), 6.95 (2H, d, J=9.2 Hz), 4.90 (2H, s), 3.81-3.65 (4H), 3.66 (4H, m), 3.17 (4H, m), 2.17 (3H, s), 2.13 (1H, s), 1.59 (6H, s).

ESI-MS Found: m/z[M+H]+ 527.

Example 119

Production of 2-{4-[4-(1-[6-(1-hydroxy-1-methylethyl)pyridin-2-yl]-3-oxo-2-(2-propynyl)-1,2-dihydro-3H-pyrazolo[3,4-d]pyrimidin-6-yl]amino)phenyl]piperazin-1-yl}-N,N-dimethylacetamide 14 mg of the entitled compound was obtained as a yellow solid in the same manner as in Example 113-1 to 113-2, for which, however, 2-[4-(4-aminophenyl)piperazin-1-yl]-N,N-dimethylacetamide was used in place of 4-(4-methylpiperazin-1-yl)aniline used in Example 113-2.

$^1$H-NMR (400 MHz, CDCl$_3$) δ: 8.83 (1H, s), 7.91 (1H, dd, J=8.0, 8.0 Hz), 7.86 (1H, d, J=8.0 Hz), 7.47 (2H, d, J=9.2 Hz), 7.35 (1H, d, J=8.0H), 6.94 (2H, d, J=9.2 Hz), 4.89 (2H, d, J=2.4 Hz), 3.27 (4H, m), 3.23 (3H, s), 2.98 (3H, s), 2.74 (4H, m), 2.13 (1H, t, J=2.4 Hz), 1.58 (6H, s).

ESI-MS Found: m/z[M+H]+ 570.

Example 120

Production of 1-[6-(1-hydroxy-1-methylethyl)pyridin-2-yl]-6-({4-[4-(2-methoxyethyl)piperazin-1-yl]phenyl}amino)-2-(2-propynyl)-1,2-dihydro-3H-pyrazolo[3,4-d]pyrimidin-3-one 14 mg of the entitled compound was obtained as a yellow solid in the same manner as in Example 113-1 to 113-2, for which, however, 4-[4-(2-methoxyethyl)piperazin-1-yl]aniline was used in place, of 4-(4-methylpiperazin-1-yl)aniline used in Example 113-2.

$^1$H-NMR (400 MHz, CDCl$_3$) δ: 8.83 (1H, s), 7.91 (1H, dd, J=8.0, 8.0 Hz), 7.85 (1H, d, J=8.0 Hz), 7.47 (1H, d, J=8.8 Hz), 7.34 (1H, d, J=8.0 Hz), 6.94 (2H, d, J=8.8 Hz), 4.89 (2H, d, J=2.8 Hz), 3.82-3.60 (4H), 3.27 (4H, m), 2.74 (4H, m), 2.13 (1H, t, J=2.8 Hz), 1.58 (6H, s).

ESI-MS Found: m/z[M+H]+ 543.

Example 121

Production of 6-({4-[4-(2-methoxyethyl)piperazin-1-yl]phenyl}amino)-1-[6-(1-hydroxy-1-methylethyl)pyridin-2-yl]-2-(2-propynyl)-1,2-dihydro-3H-pyrazolo[3,4-d]pyrimidin-3-one 14 mg of the entitled compound was obtained as a yellow solid in the same manner as in Example 113-1 to 113-2, for which, however, 4-[4-(2-ethoxyethyl)piperazin-1-yl]aniline was used in place of 4-(4-methylpiperazin-1-yl)aniline used in Example 113-2.

$^1$H-NMR (400 MHz, CDCl$_3$) δ: 8.83 (1H, s), 7.91 (1H, dd, J=8.0, 8.0 Hz), 7.85 (1H, d, J=8.0 Hz), 7.47 (2H, d, J=9.2 Hz), 6.94 (2H, d, J=9.2 Hz), 4.89 (2H, d, J=2.4 Hz), 3.82-3.64 (4H), 3.25 (4H, m), 2.75 (4H, m), 2.13 (1H, t, J=2.4 Hz), 1.58 (6H, s), 1.23 (3H, t, J=6.8 Hz).

ESI-MS Found: m/z[M+H]+ 557.

Example 122

Production of 6-({4-[4-(2-methoxyethyl)piperazin-1-yl]phenyl}amino)-1-(6-methylpyridin-2-yl)-2-(2-propynyl)-1,2-dihydro-3H-pyrazolo[3,4-d]pyrimidin-3-one 45.3 mg of the entitled compound was obtained as a yellow solid in the same manner as in Example 113-1 to 113-2, for which, however, 2-allyl-1-(6-methylpyridin-2-yl)-6-(methylthio)-1,2-dihydro-3H-pyrazolo[3,4-d]pyrimidin-3-one was used in place of 2-allyl-1-[6-(1-hydroxy-1-methylethyl)-2-pyridinyl]-6-(methylthio)-1,2-dihydro-3H-pyrazolo[3,4-d]pyrimidin-3-one used in Example 113-1, and 4-[4-(2-methoxyethyl)-piperazin-1-yl]aniline was used in place of 4-(4-methylpiperazin-1-yl)aniline used in Example 113-2.

$^1$H-NMR (400 MHz, CDCl$_3$) δ: 8.81 (1H, s), 7.83 (1H, d, J=8.0 Hz), 7.73 (1H, t, J=8.0 Hz), 7.48 (2H, d, J=9.0 Hz), 7.07 (1H, d, J=8.0 Hz), 6.93 (2H, d, J=9.0 Hz), 4.98 (2H, d, J=2.3 Hz), 3.62-3.55 (2H, brm), 3.39 (3H, s), 3.28-3.20 (4H, brm), 2.76-2.64 (6H, brm), 2.57 (3H, s), 2.07 (1H, t, J=2.3 Hz).

ESI-MS Found: m/z[M+H]+ 499.

Example 123

Production of 6-({4-[4-(2-ethoxyethyl)piperazin-1-yl]phenyl}amino)-1-(6-methylpyridin-2-yl)-2-(2-propynyl)-1,2-dihydro-3H-pyrazolo[3,4-d]pyrimidin-3-one 31.8 mg of the entitled compound was obtained as a yellow solid in the same manner as in Example 113-1 to 113-2, for which, however, 2-allyl-1-(6-methylpyridin-2-yl)-6-(methylthio)-1,2-dihydro-3H-pyrazolo[3,4-d]pyrimidin-3-one was used in place of 2-allyl-1-[6-(1-hydroxy-1-methylethyl)-2-pyridinyl]-6-(methylthio)-1,2-dihydro-3H-pyrazolo[3,4-d]pyrimidin-3-one used in Example 113-1, and 4-[4-(2-ethoxyethyl)-piperazin-1-yl]aniline was used in place of 4-(4-methylpiperazin-1-yl)aniline used in Example 113-2.

$^1$H-NMR (400 MHz, CDCl$_3$) δ: 8.81 (1H, s), 7.83 (1H, d, J=8.0 Hz), 7.73 (1H, t, J=8.0 Hz), 7.47 (2H, d, J=8.8 Hz), 7.07 (1H, d, J=8.0 Hz), 6.93 (2H, d, J=8.8 Hz), 4.98 (2H, d, J=2.0 Hz), 3.63 (2H, t, J=5.7 Hz), 3.53 (2H, q, J=7.0 Hz), 3.27-3.19 (4H, brm), 2.78-2.64 (6H, brm), 2.57 (3H, s), 2.07 (1H, t, J=2.0 Hz), 1.23 (3H, t, J=7.0 Hz).

ESI-MS Found: m/z[M+H]+ 513.

Example 124

Production of N,N-dimethyl-2-[4-(4-{[1-(6-methylpyridin-2-yl)-3-oxo-2-(2-propynyl)-1,2-dihydro-3H-pyrazolo[3,4-d]pyrimidin-6-yl]amino}phenyl)piperazin-1-yl]acetamide 34.3 mg of the entitled compound was obtained as a yellow solid in the same manner as in Example 113-1 to 113-2, for which, however, 2-allyl-1-(6-methylpyridin-2-yl)-6-(methylthio)-1,2-dihydro-3H-pyrazolo[3,4-d]pyrimidin-3-one was used in place of 2-allyl-1-[6-(1-hydroxy-1-methylethyl)-2-pyridinyl]-6-(methylthio)-1,2-dihydro-3H-pyrazolo[3,4-d]pyrimidin-3-one used in Example 113-1, and 2-[4-(4-aminophenyl)piperazin-1-yl]-N,N-dimethylacetamide was used in place of 4-(4-methylpiperazin-1-yl)aniline used in Example 113-2.

$^1$H-NMR (400 MHz, CDCl$_3$) δ: 8.81 (1H, s), 7.83 (1H, d, J=8.0 Hz), 7.74 (1H, t, J=8.0 Hz), 7.48 (2H, d, J=9.0 Hz), 7.07 (1H, d, J=8.0 Hz), 6.93 (2H, d, J=9.0 Hz), 4.98 (2H, d, J=2.3 Hz), 3.28 (2H, s), 3.27-3.21 (4H, brm), 3.11 (3H, s), 2.98 (3H, s), 2.82-2.71 (4H, brm), 2.57 (3H, s), 2.07 (1H, t, J=2.3 Hz).

ESI-MS Found: m/z[M+H]+ 526.

Example 125

Production of 6-{[4-(4-acetylpiperazin-1-yl)phenyl]amino}-1-[6-(2-hydroxy-2-methylpropyl)pyridin-2-yl]-2-(2-propynyl)-1,2-dihydro-3H-pyrazolo[3,4-d]pyrimidin-3-one 23 mg of the entitled compound was obtained as a yellow solid in the same manner as in Example 113-1 to 113-2, for which, however, 2-allyl-1-[6-(2-hydroxy-2-methylpropyl)pyridin-2-yl]-6-(methylthio)-1,2-dihydro-3H-pyrazolo[3,4-d]pyrimidin-3-one obtained in Example 81-2 was used in place of 2-allyl-1-[6-(1-hydroxy-1-methylethyl)-2-pyridinyl]-6-(methylthio)-1,2-dihydro-3H-pyrazolo[3,4-d]pyrimidin-3-one used in Example 113-1, and 4-(4-acetylpiperazin-1-yl)aniline was used in place of 4-(4-methylpiperazin-1-yl)aniline used in Example 113-2.

$^1$H-NMR (400 MHz, CDCl$_3$) δ: 8.84 (1H, s), 7.80 (1H, dd, J=8.0, 8.0 Hz), 7.75 (1H, d, J=8.0 Hz), 7.49 (2H, d, J=8.4 Hz), 7.08 (1H, d, J=8.0 Hz), 6.94 (2H, d, J=8.4 Hz), 4.80 (2H, s), 3.80 (2H, m), 3.65 (2H, m), 3.17 (4H, m), 2.98 (2H, s), 2.15 (3H, s), 2.12 (1H, s), 1.26 (6H, s).

ESI-MS Found: m/z[M+H]+ 541.

Example 126

Production of 2-{-4-[4-({1-[6-(2-hydroxy-2-methylpropyl)pyridin-2-yl]-3-oxo-2-(2-propynyl)-1,2-dihydro-3H-pyrazolo[3,4-d]pyrimidin-6-yl}amino)phenyl]piperazin-1-yl}-N,N-dimethylacetamide 27 mg of the entitled compound was obtained as a yellow solid in the same manner as in Example 113-1 to 113-2, for which, however, 2-allyl-1-[6-(2-hydroxy-2-methylpropyl)pyridin-2-yl]-6-(methylthio)-1,2-dihydro-3H-pyrazolo[3,4-d]pyrimidin-3-one obtained in Example 81-2 was used in place of 2-allyl-1-[6-(1-hydroxy-1-methylethyl)-2-pyridinyl]-6-(methylthio)-1,2-dihydro-3H-pyrazolo[3,4-d]pyrimidin-3-one used in Example 113-1, and 2-[4-(4-aminophenyl)piperazin-1-yl]-N,N-dimethylacetamide was used in place of 4-(4-methylpiperazin-1-yl)aniline used in Example 113-2.

$^1$H-NMR (400 MHz, CDCl$_3$) δ: 8.82 (1H, s), 7.80 (1H, dd, J=8.0, 7.2 Hz), 7.80-7.60 (1H), 7.45 (2H, d, J=9.6 Hz), 7.07 (2H, d, J=7.2 Hz), 6.93 (2H, d, J=9.6 Hz), 4.83 (1H, s), 3.26-3.23 (6H), 3.11 (3H, s), 2.98 (3H, s), 2.73 (4H, m), 2.11 (1H, s), 1.24 (6H, s).

ESI-MS Found: m/z[M+H]+ 541.

Example 127

Production of 1-[6-(2-hydroxy-2-methylpropyl)pyridin-2-yl]-6-({4-[4-(2-methoxyethyl)piperazin-1-yl]phenyl}amino)-2-(2-propynyl)-1,2-dihydro-3H-pyrazolo[3,4-d]pyrimidin-3-one 31 mg of the entitled compound was obtained as a yellow solid in the same manner as in Example 113-1 to 113-2, for which, however, 2-allyl-1-[6-(2-hydroxy-2-methylpropyl)pyridin-2-yl]-6-(methylthio)-1,2-dihydro-3H-pyrazolo[3,4-d]pyrimidin-3-one obtained in Example 81-2 was used in place of 2-allyl-1-[6-(1-hydroxy-1-methylethyl)-2-pyridinyl]-6-(methylthio)-1,2-dihydro-3H-pyrazolo[3,4-d]pyrimidin-3-one used in Example 113-1, and 4-[4-(2-methoxyethyl)piperazin-1-yl]aniline was used in place of 4-(4-methylpiperazin-1-yl)aniline used in Example 113-2.

$^1$H-NMR (400 MHz, CDCl$_3$) δ: 8.82 (1H, s), 7.79 (1H, d, J=7.6 Hz), 7.79 (1H, dd, J=7.6, 7.6 Hz), 7.45 (2H, d, J=8.8 Hz), 7.07 (1H, d, J=7.6 Hz), 6.93 (2H, d, J=8.8 Hz), 5.0-4.8 (2H, m), 3.57 (2H, d, J=5.6 Hz), 3.39 (3H, s), 3.23 (4H, m), 2.64-2.69 (6H, m), 2.11 (1H, s), 1.24 (6H, s).

ESI-MS Found: m/z[M+H]+ 557.

Example 128

Production of 6-{[4-(4-methylpiperazin-1-yl)phenyl]amino}-1-(6-methylpyridin-2-yl)-2-(2-propynyl)-1,2-dihydro-3H-pyrazolo[3,4-d]pyrimidin-3-one 51.4 mg of the entitled compound was obtained as a yellow solid in the same manner as in Example 113-1 to 113-2, for which, however, 2-allyl-1-(6-methylpyridin-2-yl)-6-(methylthio)-1,2-dihydro-3H-pyrazolo[3,4-d]pyrimidin-3-one was used in place of 2-allyl-1-[6-(1-hydroxy-1-methylethyl)-2-pyridinyl]-6-(methylthio)-1,2-dihydro-3H-pyrazolo[3,4-d]pyrimidin-3-one used in Example 113-1.

$^1$H-NMR (400 MHz, CDCl$_3$) δ: 8.81 (1H, s), 7.83 (1H, d, J=7.8 Hz), 7.74 (1H, t, J=7.8 Hz), 7.62-7.43 (1H, brm), 7.48 (2H, d, J=8.8 Hz), 7.07 (1H, d, J=7.8 Hz), 6.94 (2H, d, J=8.8 Hz), 4.98 (2H, d, J=2.4 Hz), 3.30-3.19 (4H, m), 2.71-2.61 (4H, m), 2.57 (3H, s), 2.40 (3H, s), 2.07 (1H, t, J=2.4 Hz).

ESI-MS Found: m/z[M+H]+ 455.

Example 129

Production of [6-{[4-(4-methylpiperazin-1-yl)phenyl]amino}-1-(6-methylpyridin-2-yl)-3-oxo-1,2-dihydro-3H-pyrazolo[3,4-d]pyrimidin-2-yl]acetonitrile 21 mg of the entitled compound was obtained as a yellow solid in the same manner as in Example 113-1 to 113-2, for which, however, 2-allyl-1-(6-methylpyridin-2-yl)-6-(methylthio)-1,2-dihydro-3H-pyrazolo[3,4-d]pyrimidin-3-one was used in place of 2-allyl-1-[6-(1-hydroxy-1-methylethyl)-2-pyridinyl]-6-(methylthio)-1,2-dihydro-3H-pyrazolo[3,4-d]pyrimidin-3-one used in Example 113-1, and iodoacetonitrile was used in place of 3-bromo-1-propyne used in Example 113-1.

$^1$H-NMR (400 MHz, CDCl$_3$) δ: 8.79 (1H), 7.87 (1H, d, J=8.0 Hz), 7.45 (1H, dd, J=8.0, 8.0 Hz), 7.70 (2H, d, J=8.8 Hz), 7.60 (1H, s), 7.10 (1H, d, J=8.0 Hz), 6.98 (2H, d, J=8.0 Hz), 5.23 (2H, s), 3.22 (4H, m), 2.72 (3H, s), 2.63 (4H, m), 2.39 (3H, s).

ESI-MS Found: m/z[M+H]+ 456.

Example 130

Production of 2-(2-methoxyphenyl)-1-methyl-6-{[3-methyl-4-(4-methylpiperazin-1-yl)phenyl]amino}-1,2-dihydro-3H-pyrazolo[3,4-d]pyrimidin-3-one monotrifluoroacetate 1) Production of 1-methyl-6-(methylthio)-1,2-dihydro-3H-pyrazolo[3,4-d]pyrimidin-3-one 2.3 g of the entitled compound was obtained as a pale yellow solid in the same manner as in Production Example 4, for which, however, methylhydrazine was used in place of phenylhydrazine used in Production Example 4.

2) Production of 2-(2-methoxyphenyl)-1-methyl-6-(methylthio)-1,2-dihydro-3H-pyrazolo[3,4-d]pyrimidin-3-one 280 mg of o-methoxyphenylboronic acid, 320 mg of copper(II) acetate and 0.15 mL of pyridine were added to a chloroform/N,N-dimethylformamide (1/1) solution of 90 mg of 1-methyl-6-(methylthio)-1,2-dihydro-3H-pyrazolo[3,4-d]pyrimidin-3-one, and stirred at room temperature. Aqueous 28% ammonia solution and saturated sodium hydrogencarbonate solution were added to the reaction liquid, and extracted with chloroform. The crude product was purified through a silica gel column (hexane/ethyl acetate) to obtain 68 mg of 2-(2-methoxyphenyl)-1-methyl-6-(methylthio)-1,2-dihydro-3H-pyrazolo[3,4-d]pyrimidin-3-one.

$^1$H-NMR (400 MHz, CDCl$_3$) δ: 8.88 (1H, s), 7.52-7.47 (1H, m), 7.38 (1H, dd, J=7.6, 1.7 Hz), 7.11 (1H, dd, J=7.6, 1.0 Hz), 7.07 (1H, dd, J=8.3, 1.0 Hz), 3.81 (3H, s), 3.33 (3H, s), 2.63 (3H, s).

3) Production of 2-(2-methoxyphenyl)-1-methyl-6-{[3-methyl-4-(4-methylpiperazin-1-yl)phenyl]amino}-1,2-dihydro-3H-pyrazolo[3,4-d]pyrimidin-3-one monotrifluoroacetate At 0° C., 68 mg of m-chloroperbenzoic acid was added to a chloroform solution of 91 mg of 2-(2-methoxyphenyl)-1-methyl-6-(methylthio)-1,2-dihydro-3H-pyrazolo[3,4-d]pyrimidin-3-one, and stirred for 1 hour. Aqueous saturated sodium hydrogencarbonate solution was added thereto, and extracted with chloroform to obtain crude 2-(2-methoxyphenyl)-1-methyl-6-(methylsulfinyl)-1,2-dihydro-3H-pyrazolo[3,4-d]pyrimidin-3-one.

58 mg of 3-methyl-4-(4-methylpiperazin-1-yl)aniline and 0.1 mL of N,N-diisopropylethylamine were added to a toluene solution of 30 mg of the compound obtained in the above, and stirred at 130° C. for 12 hours. The solvent was evaporated away, the residue was purified through reversed-phase chromatography to obtain 56 mg of yellow amorphous 2-(2-methoxyphenyl)-1-methyl-6-{[3-methyl-4-(4-methylpiperazin-1-yl)phenyl]amino}-1,2-dihydro-3H-pyrazolo[3,4-d]pyrimidin-3-one monotrifluoroacetate.

$^1$H-NMR (400 MHz, CD$_3$OD) δ: 8.74 (1H, s), 7.62-7.57 (2H, m), 7.55-7.52 (1H, m), 7.46 (1H, dd, J=7.8, 1.6 Hz), 7.24 (1H, d, J=8.4 Hz), 7.18-7.11 (2H, m), 3.83 (3H, s), 3.62-3.55 (2H, m), 3.37-3.24 (7H, m), 3.13-3.03 (2H, m), 2.97 (3H, s), 2.35 (3H, s).

ESI-MS Found: m/z[M+H]+ 460.

Example 131

Production of 2-(2-chlorophenyl)-6-{[3-(hydroxymethyl)-4-(4-methylpiperazin-1-yl)phenyl]amino}-1-methyl-1,2-dihydro-3H-pyrazolo[3,4-d]pyrimidin-3-one 1) Production of 2-(2-chlorophenyl)-1-methyl-6-(methylthio)-1,2-dihydro-3H-pyrazolo[3,4-d]pyrimidin-3-one 2 mL of methyl iodide and 2.2 g of sodium carbonate were added in that order to acetonitrile (50 mL) solution of 2 g of the compound obtained in Production Example 2, and heated under reflux for 1 hour. The reaction liquid was concentrated under reduced pressure, and the residue was separated and purified through silica gel column chromatography (hexane/ethyl acetate=60/40) to obtain 1.14 g of the entitled compound as a white solid.

$^1$H-NMR (400 MHz, CDCl$_3$) δ: 8.91 (1H, s), 7.42-7.63 (4H, m), 3.34 (3H, s), 2.64 (3H, s).

ESI-MS Found: m/z[M+H]+ 307.

2) Production of 2-(2-chlorophenyl)-6-{[3-(hydroxymethyl)-4-(4-methylpiperazin-1-yl)phenyl]amino}-1-methyl-1,2-dihydro-3H-pyrazolo[3,4-d]pyrimidin-3-one 916 mg of m-chloroperbenzoic acid was added to chloroform (10 mL) solution of 1.14 g of the compound obtained in the above 1, and stirred at room temperature for 20 minutes. The reaction liquid was washed with aqueous saturated sodium hydrogencarbonate solution, and dried with anhydrous sodium sulfate. The solvent was evaporated away under reduced pressure to obtain crude 2-(2-chlorophenyl)-1-methyl-6-(methylsulfinyl)-1,2-dihydro-3H-pyrazolo[3,4-d]pyrimidin-3-one as a white solid.

200 mg of 4-[3-(hydroxymethyl)-4-(4-methylpiperazin-1-yl)]aniline and 0.2 mL of N,N-diisopropylethylamine were added in that order to toluene (20 mL) solution of 200 mg of the above compound, and stirred at 120° C. for 15 hours. The solvent was evaporated away under reduced pressure, water was added to the residue, extracted with ethyl acetate, and dried with anhydrous sodium sulfate. The solvent was evaporated away under reduced pressure, and the residue was separated and purified through basic silica gel column chromatography (ethyl acetate) to obtain 161 mg of the entitled compound as a yellow solid.

$^1$H-NMR (400 MHz, CDCl$_3$) δ: 8.84 (1H, s), 7.43-7.58 (7H, m), 4.82 (2H, s), 3.28 (3H, s), 2.52-3.04 (8H, m), 2.38 (3H, s).

ESI-MS Found: m/z[M+H]+ 480.

Example 132

Production of 2-(2-chlorophenyl)-1-methyl-6-{[3-methyl-4-(4-methylpiperazin-1-yl)phenyl]amino}-1,2-dihydro-3H-pyrazolo[3,4-d]pyrimidin-3-one 10 mg of the entitled compound was obtained as a yellow solid in the same manner as in Example 131-1 to 131-2, for which, however, 3-methyl-4-(4-methylpiperazin-1-yl)aniline was used in place of [5-amino-2-(4-methylpiperazin-1-yl)phenyl]methanol used in Example 131-2.

¹H-NMR (400 MHz, CDCl₃) δ: 8.82 (1H, s), 7.37-7.61 (6H, m), 7.06 (1H, d, J=8.3 Hz), 3.27 (3H, s), 2.95 (4H, t, J=4.1 Hz), 2.53-2.75 (4H, m), 2.38 (3H, s), 2.23 (3H, s).

ESI-MS Found: m/z[M+H]+ 464.

Example 133

Production of 2-(2-chlorophenyl)-6-{[3-methyl-4-(4-methylpiperazin-1-yl)phenyl]amino}-1-(3-thienyl)-1,2-dihydro-3H-pyrazolo[3,4-d]pyrimidin-3-one 1) Production of 2-(2-chlorophenyl)-6-(methylthio)-1-(3-thienyl)-1,2-dihydro-3H-pyrazolo[3,4-d]pyrimidin-3-one 15 mg of the entitled compound was obtained as a white solid in the same manner as in Example 1-1, for which, however, 3-thienylboronic acid was used in place of [3-(methoxycarbonyl)]phenylboronic acid used in Example 1-1.

2) Production of 2-(2-chlorophenyl)-6-{[3-methyl-4-(4-methylpiperazin-1-yl)phenyl]amino}-1-(3-thienyl)-1,2-dihydro-3H-pyrazolo[3,4-d]pyrimidin-3-one 10.1 mg of the entitled compound was obtained as a yellow solid in the same manner as in Example 1-2 to 1-3, for which, however, the compound obtained in the above reaction was used in place of methyl 3-[2-allyl-6-(methylthio)-3-oxo-1,2-dihydro-3H-pyrazolo[3,4-d]pyrimidin-1-yl]benzoate used in Example 1-2, and 3-methyl-4-(4-methylpiperazin-1-yl)aniline was used in place of 4-(4-methylpiperazin-1-yl)aniline used in Example 1-3.

¹H-NMR (400 MHz, CDCl₃) δ: 8.88 (1H, s), 7.20-7.53 (9H, m), 7.01 (1H, d, J=7.6 Hz), 2.96 (4H, m), 2.64 (4H, brs), 2.39 (3H, s), 2.31 (3H, s).

ESI-MS Found: m/z[M+H]+ 533.

Example 134

Production of 2-(2-chlorophenyl)-6-{[3-(hydroxymethyl)-4-(4-methylpiperazin-1-yl)phenyl]amino}-1-pyridin-2-yl-1,2-dihydro-3H-pyrazolo[3,4-d]pyrimidin-3-one 1) Production of 2-(2-chlorophenyl)-6-(methylthio)-1-pyridin-2-yl-1,2-dihydro-3H-pyrazolo[3,4-d]pyrimidin-3-one 736 mg of (2-pyridyl)tributyltin, 362 mg of copper(II) acetate and 1.1 mL of pyridine were added in that order to N,N-dimethylformamide(50 mL) solution of 292 mg of the compound obtained in Production Example 2, and stirred at room temperature for 48 hours. Aqueous 28% ammonia was added to the reaction liquid, extracted with ethyl acetate, and dried with anhydrous sodium sulfate. The solvent was concentrated under reduced pressure, and the residue was separated and purified through silica gel column chromatography (hexane/ethyl acetate=80/20) to obtain 65.2 mg of the entitled compound as a white solid.

¹H-NMR (400 MHz, CDCl₃) δ: 9.02 (1H, s), 8.30 (1H, d, J=5.2 Hz), 7.76-7.84 (2H, m), 7.58-7.65 (1H, m), 7.42-7.47 (1H, m), 7.26-7.33 (2H, m), 7.12-7.16 (1H, m), 2.62 (3H, s).

ESI-MS Found: m/z[M+H]+ 370.

2) Production of 2-(2-chlorophenyl)-6-{[3-(hydroxymethyl)-4-(4-methylpiperazin-1-yl)phenyl]amino}-1-pyridin-2-yl-1,2-dihydro-3H-pyrazolo[3,4-d]pyrimidin-3-one 44.2 mg of m-chloroperbenzoic acid was added to chloroform (5 mL) solution of 65.2 mg of the compound obtained in the above 1, and stirred at room temperature for 30 minutes. The reaction liquid was washed with aqueous saturated sodium hydrogencarbonate solution, and dried with anhydrous sodium sulfate. The solvent was evaporated away under reduced pressure to obtain crude 2-(2-chlorophenyl)-6-(methylsulfinyl)-1-pyridin-2-yl-1,2-dihydro-3H-pyrazolo[3,4-d]pyrimidin-3-one as a white solid.

60 mg of 4-[3-(hydroxymethyl)-4-(4-methylpiperazin-1-yl)]aniline and 0.1 mL of N,N-diisopropylethylamine were added in that order to toluene (5 mL) solution of the above compound, and stirred at 120° C. for 15 hours. The solvent was evaporated away under reduced pressure, then water was added to it, extracted with ethyl acetate, and dried with anhydrous sodium sulfate. The solvent was evaporated away under reduced pressure, and the residue was separated and purified through basic silica gel column chromatography (ethyl acetate) to obtain 24.7 mg of the entitled compound as a yellow solid.

¹H-NMR (400 MHz, CDCl₃) δ: 8.93 (1H, s), 8.37 (1H, d, J=3.9 Hz), 7.79 (1H, t, J=6.8 Hz), 7.71 (1H, d, J=7.8 Hz), 7.68-7.57 (1H, m), 7.57 (1H, dd, J=6.1, 3.7 Hz), 7.44 (1H, dd, J=6.1, 3.7 Hz), 7.41-7.36 (1H, m), 7.30-7.24 (2H, m), 7.21 (1H, d, J=8.8 Hz), 7.15 (1H, dd, J=6.8, 5.4 Hz), 4.79 (2H, s), 3.03 (4H, t, J=4.6 Hz), 2.77-2.53 (4H, m), 2.39 (3H, s).

ESI-MS Found: m/z[M+H]+ 543.

Example 135

Production of 2-benzyl-6-{[3-methyl-4-(4-methylpiperazin-1-yl)phenyl]amino}-1-pyridin-2-yl-1,2-dihydro-3H-pyrazolo[3,4-d]pyrimidin-3-one 1) Production of 2-benzyl-6-(methylthio)-1,2-dihydro-3H-pyrazolo[3,4-d]pyrimidin-3-one 2.9 g of the entitled compound was obtained as a white solid in the same manner as in Production Example 1-2, for which, however, benzylhydrazine was used in place of tert-butyl 1-allylhydrazinecarboxylate used in Production Example 1-2.

¹H-NMR (400 MHz, DMSO-d₆) δ: 12.8 (1H, s), 8.63 (1H, s), 7.20-7.33 (5H, m), 4.94 (2H, s), 2.49 (3H, s).

ESI-MS Found: m/z[M+H]+ 273.

2) Production of 2-benzyl-6-(methylthio)-1-pyridin-2-yl-1,2-dihydro-3H-pyrazolo[3,4-d]pyrimidin-3-one 300 mg of (2-pyridyl)tributyltin, 267 mg of copper(II) acetate and 1.0 mL of pyridine were added in that order to N,N-dimethylformamide (10 mL) solution of 200 mg of the compound obtained in the above 1, and stirred at room temperature for 48 hours. Aqueous 28% ammonia was added to the reaction liquid, extracted with ethyl acetate, and dried with anhydrous sodium sulfate. The solvent was concentrated under reduced pressure, and the residue was separated and purified through silica gel column chromatography (hexane/ethyl acetate=80/20) to obtain 111.2 mg of the entitled compound as a white solid.

¹H-NMR (400 MHz, CDCl₃) δ: 8.94 (1H, s), 8.56 (1H, d, J=4.9 Hz), 7.83 (1H, t, J=8.5 Hz), 7.66 (1H, d, J=8.5 Hz), 7.12-7.31 (4H, m), 6.92 (1H, d, J=6.8 Hz), 5.44 (2H, s), 2.53 (3H, s).
ESI-MS Found: m/z[M+H]+ 350.

3) Production of 2-benzyl-6-{[3-methyl-4-(4-methylpiperazin-1-yl)phenyl]amino}-1-pyridin-2-yl-1,2-dihydro-3H-pyrazolo[3,4-d]pyrimidin-3-one 78.1 mg of m-chloroperbenzoic acid was added to chloroform (10 mL) solution of 111.2 mg of the compound obtained in the above 1, and stirred at room temperature for 15 minutes. The reaction liquid was washed with aqueous saturated sodium hydrogencarbonate solution, and dried with anhydrous sodium sulfate. The solvent was evaporated away under reduced pressure to obtain crude 2-benzyl-6-(methylsulfinyl)-1-pyridin-2-yl-1,2-dihydro-3H-pyrazolo[3,4-d]pyrimidin-3-one as a white solid.
30 mg of 4-[3-(hydroxymethyl)-4-(4-methylpiperazin-1-yl)]aniline and 0.05 mL of N,N-diisopropylethylamine were added to toluene (5 mL) solution of the above compound, and stirred at 120° C. for 15 hours. The solvent was evaporated away under reduced pressure, water was added to the residue, extracted with ethyl acetate and dried with anhydrous sodium sulfate. The solvent was evaporated away under reduced pressure, and the residue was separated and purified through basic silica gel column chromatography (ethyl acetate) to obtain 22.6 mg of the entitled compound as a yellow solid.
¹H-NMR (400 MHz, CDCl₃) δ: 8.84 (1H, s), 8.58 (1H, m), 7.81 (1H, t, J=3.8 Hz), 7.68 (1H, d, J=3.8 Hz), 7.43 (1H, bs), 6.92-7.40 (8H, m), 5.37 (2H, s), 2.92-2.99 (4H, bs), 2.57-2.77 (4H, bs), 2.42 (3H, s), 2.29 (3H, s).
ESI-MS Found: m/z[M+H]+ 507.

Example 136

Production of 2-(2-chlorophenyl)-1-[6-(1-hydroxycyclobutyl)pyridin-2-yl]-6-{[3-methyl-4-(4-methylpiperazin-1-yl)phenyl]amino}-1,2-dihydro-3H-pyrazolo[3,4-d]pyrimidin-3-one 1) Production of 1-[6-(tributylstannyl)pyridin-2-yl]cyclobutanol Tetrahydrofuran (10 mL) solution of 293.1 mg of 1-(6-bromo-2-pyridinyl)cyclobutanol obtained in Example 69-1 was cooled to −78° C. in an acetone/dry ice bath in a nitrogen atmosphere, and 1.8 mL of 1.58 M n-butyllithium/hexane solution was gradually added thereto, and stirred for 30 minutes. Subsequently, tetrahydrofuran (2.0 mL) solution of 0.36 mL of tri-n-butyltin chloride was added thereto at −78° C., and the reaction solution was stirred for 30 minutes. This was processed with aqueous saturated ammonium chloride solution, extracted with ethyl acetate, and the organic layer was washed with saturated saline water, and purified through silica gel column chromatography (hexane/ethyl acetate) to obtain 48.7 mg of the entitled compound as a pale yellow oily substance.
ESI-MS Found: m/z[M+H]+ 439.

2) Production of 2-(2-chlorophenyl)-1-[6-(1-hydroxycyclobutyl)pyridin-2-yl]-6-(methylthio)-1,2-dihydro-3H-pyrazolo[3,4-d]pyrimidin-3-one 6.7 mg of the entitled compound was obtained as a pale yellow solid in the same manner as in Example 135-2, for which, however, the compound obtained in the above reaction was used in place of 2-(tributylstannyl)pyridine used in Example 135-2.
ESI-MS Found: m/z[M+H]+ 440.

3) Production of 2-(2-chlorophenyl)-1-[6-(1-hydroxycyclobutyl)pyridin-2-yl]-6-{[3-methyl-4-(4-methylpiperazin-1-yl)phenyl]amino}-1,2-dihydro-3H-pyrazolo[3,4-d]pyrimidin-3-one 3.4 mg of the entitled compound was obtained as a yellow solid in the same manner as in Example 1-2 to 1-3, for which, however, the compound obtained in the above was used in place of the starting compound used in Example 1-2, and 3-methyl-4-(4-methylpiperazin-1-yl)aniline was used in place of 4-(4-methylpiperazin-1-yl)aniline used in Example 1-3.
¹H-NMR (400 MHz, CDCl₃) δ: 8.92 (1H, s), 7.99 (1H, d, J=8.3 Hz), 7.83 (1H, dd, J=7.8, 3.9 Hz), 7.62-7.45 (3H, m), 7.47-7.35 (2H, m), 7.34-7.20 (3H, m), 7.06 (1H, d, J=8.8 Hz), 3.07-2.93 (4H, m), 2.80-2.55 (3H, m), 2.43 (3H, s), 2.35 (3H, s), 2.33-2.08 (3H, m), 2.03-1.89 (1H, m), 1.75-1.58 (1H, m), 1.33-1.19 (2H, m).
ESI-MS Found: m/z[M+H]+ 598.

Example 137

Production of 1-[6-(1-hydroxy-1-methylethyl)pyridin-2-yl]-2-isopropyl-6-{[4-(4-methylpiperazin-1-yl)phenyl]amino}-1,2-dihydro-3H-pyrazolo[3,4-d]pyrimidin-3-one 35 mg of the entitled compound was obtained as a yellow solid in the same manner as in Example 53-2 to 53-3, for which, however, 2-isopropyl-6-(methylthio)-1,2-dihydro-3H-pyrazolo[3,4-d]pyrimidin-3-one obtained in Production Example 3 was used in place of 2-allyl-6-(methylthio)-1,2-dihydro-3H-pyrazolo[3,4-d]pyrimidin-3-one used in Example 53-2.
¹H-NMR (400 MHz, CDCl₃) δ: 8.77 (1H, s), 7.88 (1H, dd, J=8.0, 7.6 Hz), 7.67 (1H, d, J=7.6 Hz), 7.44 (2H, d, J=8.0 Hz), 7.35 (1H, d, J=8.0 Hz), 6.92 (2H, d, J=8.0 Hz), 4.24 (1H, septet, J=6.8 Hz), 3.21 (4H, m), 2.61 (4H, m), 2.38 (3H, s), 1.58 (6H, s), 1.48 (6H, s).
ESI-MS Found: m/z[M+H]+ 503.

Example 138

Production of 1-[6-(2-hydroxy-1,1-dimethylethyl)pyridin-2-yl]-2-isopropyl-6-{[3-methyl-4-(4-methylpiperazin-1-yl)phenyl]amino}-1,2-dihydro-3H-pyrazolo[3,4-d]pyrimidin-3-one 55 mg of the entitled compound was obtained as a yellow solid in the same manner as in Example 53-2 to 53-3, for which, however, 2-isopropyl-6-(methylthio)-1,2-dihydro-3H-pyrazolo[3,4-d]pyrimidin-3-one obtained in Production Example 3 was used in place of 2-allyl-6-(methylthio)-1,2-dihydro-3H-pyrazolo[3,4-d]pyrimidin-3-one used in Example 53-2, 2-(6-bromopyridin-2-yl)-2-methylpropan-1-ol obtained in Example 103-1 was used in place of 2-(6-bromo-2-pyridinyl)-2-propanol used in Example 53-2, and 3-methyl-4-(4-methylpiperazin-1-yl)aniline was used in place of 4-(4-methylpiperazin-1-yl)aniline used in Example 53-3.
¹H-NMR (400 MHz, CDCl₃) δ: 8.79 (1H, s), 7.82 (1H, dd, J=8.0, 8.0 Hz), 7.56 (1H), 7.37-7.32 (2H), 7.30-7.24 (1H), 7.01 (1H, d, J=8.8 Hz), 3.81 (1H, d, J=7.2 Hz), 2.94 (4H, m), 2.62 (4H, m), 2.39 (3H, s), 2.30 (3H, s), 1.52 (6H, d, J=7.2 Hz), 1.39 (6H, s).
ESI-MS Found: m/z[M+H]+ 531.

Example 139

Production of 1-[6-(2-hydroxy-1,1-dimethylethyl) pyridin-2-yl]-2-isopropyl-6-{[4-(4-methylpiperazin-1-yl)phenyl]amino}-1,2-dihydro-3H-pyrazolo[3,4-d] pyrimidin-3-one 43 mg of the entitled compound was obtained as a yellow solid in the same manner as in Example 53-2 to 53-3, for which, however, 2-isopropyl-6-(methylthio)-1,2-dihydro-3H-pyrazolo[3,4-d]pyrimidin-3-one obtained in Production Example 3 was used in place of 2-allyl-6-(methylthio)-1,2-dihydro-3H-pyrazolo[3,4-d]pyrimidin-3-one used in Example 53-2, and 2-(6-bromopyridin-2-yl)-2-methylpropan-1-ol obtained in Example 103-1 was used in place of 2-(6-bromo-2-pyridinyl)-2-propanol used in Example 53-2.
¹H-NMR (400 MHz, CDCl₃) δ: 8.78 (1H, s), 7.83 (1H, dd, J=8.0, 8.0 Hz), 7.58 (1H, d, J=2.0 Hz), 7.41 (1H, d, J=8.8 Hz), 7.25 (1H, d, J=8.0 Hz), 6.91 (2H, J=8.8 Hz), 4.12 (1H, septet, J=6.8 Hz), 3.82 (2H, s), 3.20 (4H, m), 2.61 (4H, m), 2.37 (3H, s), 1.52 (6H, d, J=6.8 Hz), 1.39 (6H, s).
ESI-MS Found: m/z[M+H]+ 517.

Example 140

Production of 2-isopropyl-6-{[3-methyl-4-(4-methylpiperazin-1-yl)phenyl]amino}-1-pyridin-2-yl-1,2-dihydro-3H-pyrazolo[3,4-d]pyrimidin-3-one 14.5 mg of the entitled compound was obtained as a yellow solid in the same manner as in Example 53-2 to 53-3, for which, however, 2-isopropyl-6-(methylthio)-1,2-dihydro-3H-pyrazolo[3,4-d]pyrimidin-3-one obtained in Production Example 3 was used in place of 2-allyl-6-(methylthio)-1,2-dihydro-3H-pyrazolo[3,4-d]pyrimidin-3-one used in Example 53-2, 2-bromopyridin was used in place of 2-(6-bromo-2-pyridinyl)-2-propanol used in Example 53-2, and 3-methyl-4-(4-methylpiperazin-1-yl)aniline was used in place of 4-(4-methylpiperazin-1-yl)aniline used in Example 53-3.
¹H-NMR (400 MHz, CDCl₃) δ: 8.78 (1H, s), 8.57 (1H, d, J=4.9 Hz), 7.88 (1H, td, J=7.8, 1.8 Hz), 7.73 (1H, d, J=8.3 Hz), 7.59-7.20 (2H, m), 7.00 (1H, d, J=8.8 Hz), 4.33-4.26 (1H, m), 2.95 (4H, t, J=4.6 Hz), 2.82-2.49 (4H, m), 2.40 (3H, s), 2.30 (3H, s), 1.44 (6H, d, J=6.8 Hz).
ESI-MS Found: m/z[M+H]+ 459.

Example 141

Production of 3-chloro-2-(1-(6-chloropyridin-2-yl)-6-{[3-methyl-4-(4-methylpiperazin-1-yl)phenyl] amino}-3-oxo-1,3-dihydro-2H-pyrazolo[3,4-d]pyrimidin-2-yl)benzonitrile 1) Production of acetone(6-chloropyridin-2-yl)hydrazone Acetone was added to 2-chloro-6-hydrazone and concentrated under reduced pressure to obtain 3.10 g of the entitled compound as a white solid.

¹H-NMR (400 MHz, CDCl₃) δ: 7.67 (1H, brs), 7.49 (1H, t, J=7.8 Hz), 7.10 (1H, d, J=8.2 Hz), 6.72 (1H, d, J=7.4 Hz), 2.05 (3H, s), 1.88 (3H, s).
ESI-MS Found: m/z[M+H]+ 184, 186.

2) Production of acetone(6-chloropyridin-2-yl)[5-iodo-2-(methylthio)pyrimidin-4-yl]hydrazone With cooling with ice, 48 mg of sodium hydride (55% to 72%) was added to N,N-dimethylformamide (5.0 mL) solution of 367 mg of the above compound and 287 mg of 4-chloro-5-iodo-2-(methylthio)pyrimidine. After stirred for 3 hours, water was added to the reaction liquid, and extracted with ethyl acetate. This was washed with water and saturated saline water, dried with anhydrous magnesium sulfate, and concentrated under reduced pressure. The residue was purified through silica gel column chromatography (hexane/ethyl acetate=9/1 to 4/1) to obtain 128 mg of the entitled compound as a white solid.
¹H-NMR (400 MHz, CDCl₃) δ: 8.67 (1H, s), 7.62 (1H, t, J=8.0 Hz), 7.02 (1H, d, J=7.8 Hz), 6.92 (1H, d, J=8.0 Hz), 2.40 (3H, s), 2.22 (3H, s), 1.72 (3H, s).
ESI-MS Found: m/z[M+H]+ 434, 436.

3) Production of 4-[1-(6-chloropyridin-2-yl)hydrazino]-5-iodo-2-(methylthio)pyrimidine One mL of 2 N hydrochloric acid was added to methanol (2 mL) solution of 200 mg of the above compound, and stirred overnight. 2 mL of 2 N hydrochloric acid was further added thereto, and stirred for 4 days. Then, aqueous sodium carbonate solution was added to the reaction liquid, and extracted with ethyl acetate. This was washed with saturated saline water, dried with anhydrous magnesium sulfate, and concentrated under reduced pressure. The residue was purified through silica gel column chromatography (hexane/ethyl acetate=6/1 to 5/1) to obtain 129 mg of the entitled compound as a white solid.
ESI-MASS(m/e): 392, 394(M+H).

4) Production of methyl 2-(6-chloropyridin-2-yl)-2-[5-iodo-2-(methylthio)pyrimidin-4-yl]hydrazinecarboxylate With cooling with ice, 0.1 mL of methyl chlorocarbonate was added to a solution of 129 mg of the above compound in 2.0 mL of chloroform and 1 mL of pyridine, and stirred for 50 minutes. Water was added to the reaction liquid, and extracted with ethyl acetate. This was washed with aqueous 10% phosphoric acid solution, saturated sodium hydrogencarbonate, and saturated saline water, dried with anhydrous magnesium sulfate, and concentrated under reduced pressure. 147 mg of the entitled compound was thus obtained as a white solid.

5) Production of methyl 1-(2-chloro-6-cyanophenyl)-2-(6-chloropyridin-2-yl)-2-[5-iodo-2-(methylthio) pyrimidin-4-yl]hydrazinecarboxylate N-methylpyrrolidone (2.5 mL) solution of 147 mg of the above compound, 90 mg of potassium carbonate and 67 mg of 3-chloro-2-fluorobenzonitrile was stirred at 90° C. for 3 hours. Water was added to the reaction liquid, and extracted with ethyl acetate. This was washed with water and saturated saline water, dried with anhydrous magnesium sulfate, and concentrated under reduced pressure. The residue was purified through silica gel column chromatography (hexane/ethyl acetate=80/20) to obtain 62.1 mg of the entitled compound as a white amorphous substance.
ESI-MS Found: m/z[M+H]+ 587, 589.

6) Production of 3-chloro-2-[1-(6-chloropyridin-2-yl)-6-(methylthio)-3-oxo-1,3-dihydro-2H-pyrazolo[3,4-d]pyrimidin-2-yl]benzonitrile With cooling with ice, 0.1 mL of 2.0 M isopropylmagnesium chloride/tetrahydrofuran solution was added to tetrahydrofuran (3.0 mL) solution of 62 mg of the above compound, and stirred for 15 minutes. Water was added to the reaction liquid, and extracted with ethyl acetate. This was washed with saturated saline water, dried with anhydrous magnesium sulfate, and concentrated under reduced pressure. The residue was purified through basic silica gel column chromatography (hexane/chloroform=90/10 to 2/1), and crystallized from diethyl ether to obtain 8.5 mg of the entitled compound as a white solid.

$^1$H-NMR (400 MHz, CDCl$_3$) δ: 9.04 (1H, s), 8.19 (1H, d, J=8.2 Hz), 7.77 (1H, t, J=8.0 Hz), 7.74 (1H, dd, J=7.8, 1.4 Hz), 7.48 (1H, d, J=8.0 Hz), 7.10 (1H, d, J=7.8 Hz), 2.68 (3H, s).

ESI-MS Found: m/z[M+H]+ 429, 431.

7) Production of 3-chloro-2-(1-(6-chloropyridin-2-yl)-6-{[3-methyl-4-(4-methylpiperazin-1-yl)phenyl]amino}-3-oxo-1,3-dihydro-2H-pyrazolo[3,4-d]pyrimidin-2-yl)benzonitrile 3 mL of toluene and 8.5 mg of m-chloroperbenzoic acid (>65%) were added to 8.5 mg of the compound obtained in the above, and stirred for 40 minutes. 0.05 mL of N,N-diisopropylethylamine and 5 mg of 3-methyl-4-(4-methylpiperazin-1-yl)aniline were added to the reaction liquid, and stirred overnight. Aqueous saturated sodium hydrogencarbonate solution was added to the reaction liquid, and extracted with ethyl acetate. This was dried with anhydrous magnesium sulfate, the solvent was evaporated away under reduced pressure, and the residue was purified through basic silica gel column chromatography (hexane/ethyl acetate=2/1 to 0/100) to obtain 7.06 mg of the entitled compound as a white solid.

$^1$H-NMR (400 MHz, CDCl$_3$) δ: 8.93 (1H, s), 8.17 (1H, d, J=6.2 Hz), 7.73-7.63 (4H, m), 7.50 (1H, brs), 7.44 (1H, dd, J=8.2, 7.8 Hz), 7.34 (1H, d, J=6.0 Hz), 7.08-7.04 (2H, m), 2.97 (4H, t, J=4.6 Hz), 2.62 (4H, brs), 2.39 (3H, s), 2.34 (3H, s).

ESI-MS Found: m/z[M+H]+ 586, 588.

Example 142

Production of 3-chloro-2-(1-methyl-6-{[3-methyl-4-(4-methylpiperazin-1-yl)phenyl]amino}-3-oxo-1,3-dihydro-2H-pyrazolo[3,4-d]pyrimidin-2-yl)benzonitrile

1) Production of 5-iodo-4-(1-methylhydrazino)-2-(methylthio)pyrimidine 603 mg of potassium carbonate was added to ethanol (15 mL) solution of 1.25 g of 4-chloro-5-iodo-2-(methylthio)pyrimidine, and with cooling with ice, 0.28 mL of methylhydrazine was dropwise added thereto. This was stirred overnight at room temperature, then water was added thereto, and the precipitated crystal was taken out through filtration and dried to obtain 851 mg of the entitled compound as a white solid.

$^1$H-NMR (400 MHz, CDCl$_3$) δ: 8.43 (1H, s), 4.16 (2H, brs), 3.37 (3H, s), 2.49 (3H, s).

ESI-MS Found: m/z[M+H]+ 297.

2) Production of methyl 2-[5-iodo 2-(methylthio)pyrimidin-4-yl]-2-methylhydrazinecarboxylate 0.05 mL of methyl chlorocarbonate was added to pyridine (2 mL) solution of 160 mg of the above compound, stirred overnight, and then 0.08 mL of methyl chlorocarbonate was further added thereto. The reaction liquid was concentrated under reduced pressure, water was added thereto, and extracted with ethyl acetate. This was washed with saturated saline water, dried with anhydrous magnesium sulfate, and concentrated under reduced pressure to obtain 132 mg of the entitled compound as a white solid.

$^1$H-NMR (400 MHz, CDCl$_3$) δ: 8.47 (1H, s), 6.95 (1H, brs), 3.78 (3H, s), 3.37 (3H, s), 2.50 (3H, s).

ESI-MS Found: m/z[M+H]+ 355.

3) Production of methyl 1-(2-chloro-6-cyanophenyl)-2-[5-iodo-2-(methylthio)pyrimidin-4-yl]-2-methylhydrazinecarboxylate N-methylpyrrolidone (1 mL) solution of 36 mg of the above compound, 26 mg of potassium carbonate and 20 mg of 3-chloro-2-fluorobenzonitrile was stirred overnight at 90° C. Water was added to the reaction liquid, and extracted with ethyl acetate. This was washed with water and saturated saline water, dried with anhydrous magnesium sulfate, and concentrated under reduced pressure. The residue was purified through silica gel column chromatography (hexane/ethyl acetate=10/1 to 6/1) to obtain 32 mg of the entitled compound as a white solid.

$^1$H-NMR (400 MHz, CDCl$_3$) δ: 8.57 (1H, s), 7.70 (1H, dd, J=8.2, 1.4 Hz), 7.65 (1H, dd, J=7.8, 1.4 Hz), 7.37 (1H, dd, J=8.2, 7.8 Hz), 3.89 (3H, s), 3.61 (3H, s), 2.47 (3H, s).

ESI-MS Found: m/z[M+H]+ 490, 492.

4) Production of 3-chloro-2-[1-methyl-6-(methylthio)-3-oxo-1,3-dihydro-2H-pyrazolo[3,4-d]pyrimidin-2-yl]benzonitrile With cooling with ice, 0.1 mL of 2.0 M isopropylmagnesium chloride/tetrahydrofuran solution was added to tetrahydrofuran (2.0 mL) solution of 56 mg of the above compound, and stirred for 1 hour. Water was added to the reaction liquid, and extracted with methyl acetate. This was washed with saturated saline water, dried with anhydrous magnesium sulfate, and concentrated under reduced pressure. The residue was purified through silica gel column chromatography (hexane/ethyl acetate=6/1 to 2/1) to obtain 12.2 mg of the entitled compound as a white solid.

$^1$H-NMR (400 MHz, CDCl$_3$) δ: 8.92 (1H, s), 7.84 (1H, dd, J=8.2, 1.4 Hz), 7.79 (1H, dd, J=7.8, 1.4 Hz), 7.62 (1H, dd, J=8.2, 7.8 Hz), 3.39 (3H, s), 2.64 (3H, s).

ESI-MS Found: m/z[M+H]+ 332, 334.

5) Production of 3-chloro-2-(1-methyl-6-{[3-methyl-4-(4-methylpiperazin-1-yl)phenyl]amino}-3-oxo-1,3-dihydro-2H-pyrazolo[3,4-d]pyrimidin-2-yl)benzonitrile 11.1 mg of the entitled compound was obtained as a white solid in the same manner as in Example 141-7, for which, however, 12.2 mg of the compound obtained in the above was used in place of 3-chloro-2-(1-(6-chloropyridin-2-yl)-6-(methylthio)-3-oxo-1,3-dihydro-2H-pyrazolo[3,4-d]pyrimidin-2-yl)benzonitrile used in Example 141-7.

$^1$H-NMR (400 MHz, CDCl$_3$) δ: 8.84 (1H, s), 7.80 (1H, d, J=8.2 Hz), 7.77 (1H, dd, J=7.8, 1.4 Hz), 7.58 (1H, dd, J=8.2, 7.8 Hz), 7.55 (1H, brs), 7.45 (1H, brs), 7.37 (1H, d, J=2.5 Hz), 7.07 (1H, d, J=8.8 Hz), 3.32 (3H, s), 2.96 (4H, t, J=4.7 Hz), 2.61 (4H, brs), 2.38 (3H, s), 2.33 (3H, s).

ESI-MS Found: m/z[M+H]+ 489, 491.

Example 143

Production of 2-(1-methyl-6-{[3-methyl-4-(4-methylpiperazin-1-yl)phenyl]amino}-3-oxo-1,3-dihydro-2H-pyrazolo[3,4-d]pyridin-2-yl)benzonitrile 1) Production of 2-{2-[5-iodo-2-(methylthio)pyrimidin-4-yl]-2-methylhydrazino}benzonitrile N-methylpyrrolidone (5 mL) solution of 443 mg of the compound obtained in Example 142-2, 519 mg of potassium carbonate and 0.679 mL of 2-fluorobenzonitrile was stirred overnight at 90° C. Water was added to the reaction liquid, and extracted with ethyl acetate. This was washed with water and saturated saline water, dried with anhydrous magnesium sulfate, and concentrated under reduced pressure. The residue was purified through silica gel column chromatography (hexane/ethyl acetate=19/1 to 2/1) to obtain 125 mg of the entitled compound as a white solid.

$^1$H-NMR (400 MHz, CDCl$_3$) δ: 8.50 (1H, s), 7.53 (1H, d, J=7.8 Hz), 7.48 (1H, dd, J=8.0, 7.8 Hz), 6.94 (1H, dd, J=7.8, 7.4 Hz), 6.81 (1H, d, J=8.6 Hz), 6.65 (1H, brs), 3.41 (3H, s), 2.53 (3H, s).

ESI-MS Found: m/z[M+H]+ 397.

2) Production of 2-[1-methyl-6-(methylthio)-3-oxo-1,3-dihydro-2H-pyrazolo[3,4-d]pyrimidin-2-yl]benzonitrile Dioxane (5 mL) solution of 125 mg of the compound obtained in the above reaction, 25 mg of dichloro[1,1'-bis(diphenylphosphino)ferrocene]palladium(II)-dichloromethane adduct and 50 mg of sodium hydrogencarbonate was stirred in a carbon monoxide atmosphere under a pressure of 4 atmospheres at 90° C. for 6 hours. The reaction liquid was filtered, the filtrate was concentrated and purified through silica gel column chromatography (hexane/ethyl acetate=4/1 to 1/1) to obtain 22.7 mg of the entitled compound as a white solid.

$^1$H-NMR (400 MHz, CDCl$_3$) δ: 8.92 (1H, s), 7.86 (1H, dd, J=7.8, 1.0 Hz), 7.76 (1H, td, J=8.0, 1.5 Hz), 7.54 (1H, td, J=7.8, 1.0 Hz), 7.44 (1H, dd, J=8.0, 0.7 Hz), 3.40 (3H, t, J=13.7 Hz), 2.65 (3H, t, J=13.7 Hz).

ESI-MS Found: m/z[M+H]+ 298.

3) Production of 2-(1-methyl-6-{[3-methyl-4-(4-methylpiperazin-1-yl)phenyl]amino}-3-oxo-1,3-dihydro-2H-pyrazolo[3,4-d]pyrimidin-2-yl)benzonitrile 12.1 mg of the entitled compound was obtained as a white solid in the same manner as in Example 141-7, for which, however, 16 mg of the compound obtained in the above reaction was used in place of 3-chloro-2-(1-(6-chloropyridin-2-yl)-6-(methylthio)-3-oxo-1,3-dihydro-2H-pyrazolo[3,4-d]pyrimidin-2-yl)benzonitrile used in Example 141-7.

$^1$H-NMR (400 MHz, CDCl$_3$) δ: 8.82 (1H, s), 7.83 (1H, dd, J=7.6, 1.2 Hz), 7.72 (1H, td, J=7.8, 1.5 Hz), 7.56-7.37 (4H, m), 7.07 (1H, d, J=8.3 Hz), 3.34 (3H, s), 2.96 (4H, t, J=4.6 Hz), 2.61 (4H, brs), 2.38 (3H, s), 2.34 (3H, s).

ESI-MS Found: m/z[M+H]+ 455.

Example 144

Production of 6-(2-chlorophenyl)-2-{[3-methyl-4-(4-methylpiperazin-1-yl)phenyl]amino}-6,7-dihydro-5H-pyrrolo[3,4-d]pyrimidin-5-one 1) Production of ethyl 4-(chloromethyl)-2-(methylthio)pyrimidine-5-carboxylate 60 mL of ethyl triethylorthoformate and 70 mL of acetic anhydride were added to 30.4 g of ethyl 4-chloro-3-oxobutanoate, and the resulting reaction solution was stirred under heat at 110° C. for 3 hours. The solvent was evaporated away under reduced pressure, 100 mL of n-hexane was added to the residue, and the formed, pale yellow needle-like crystal was taken out through filtration and dried to obtain 19.5 g of crude ethyl 4-chloro-2-(ethoxymethylene)-2-oxobutanoate.

A solution of 1.81 g of sodium hydroxide in 20 mL of water was added to tetrahydrofuran (100 mL) suspension of 6.31 g of methyl imidothiocarbamate 0.5-sulfate, and stirred at room temperature for 10 minutes. Tetrahydrofuran (100 mL) solution of 10.0 g of the crude product obtained in the above was added to the resulting solution, and stirred at room temperature for 10 minutes. The reaction solution was partitioned between ethyl acetate and water, the organic layer was washed with saturated saline water, dried with magnesium sulfate, and the solvent was evaporated away under reduced pressure. The residue was purified through silica gel column chromatography (hexane/ethyl acetate) to obtain 7.60 g of the entitled compound as a yellow amorphous substance.

$^1$H-NMR (400 MHz, CDCl$_3$) δ: 9.04 (1H, s), 4.97 (1H, s), 4.44 (2H, q, J=7.0 Hz), 2.63 (3H, s), 1.42 (3H, t, J=7.0 Hz).

ESI-MS Found: m/z[M+H]+ 389.

2) Production of ethyl 4-{[(2-chlorophenyl)amino]methyl}-2-(methylthio)pyrimidine-5-carboxylate 0.15 mL of 2,6-lutidine and 0.13 mL of 2-chloroaniline were added to 3.0 mL of an ethanol solution of 205 mg of the compound obtained in the above, and heated under reflux for 18 hours. The reaction solution was cooled to room temperature, and the resulting colorless solid was taken out through filtration and washed with ethanol to obtain 169 mg of the entitled compound.

$^1$H-NMR (400 MHz, CDCl$_3$) δ: 9.02 (1H, s), 7.28 (1H, dd, J=7.8, 1.5 Hz), 7.17 (1H, ddd, J=7.8, 7.3, 1.4 Hz), 6.79 (1H, dd, J=6.8, 1.4 Hz), 6.66 (1H, ddd, J=7.3, 6.8, 1.4 Hz), 4.84 (2H, s), 4.43 (2H, q, J=7.0 Hz), 2.66 (3H, s), 1.44 (3H, t, J=7.0 Hz).

ESI-MS Found: m/z[M+H]+ 338.

3) Production of 6-(2-chlorophenyl)-2-(methylthio)-6,7-dihydro-5H-pyrrolo[3,4-d]pyrimidin-5-one 3 mL of aqueous 2 N sodium hydroxide solution was added to methanol (3 mL) solution of 741 mg of the compound obtained in the above reaction, and stirred at room temperature for 18 hours. This was made acidic with 2 N hydrochloric acid added thereto, extracted with chloroform, then the organic layer was washed with saturated saline water and dried with magnesium sulfate, and the solvent was evaporated away under reduced pressure to obtain 684 mg of crude 4-{[(2-chlorophenyl)amino]methyl}-2-(methylthio)pyrimidine-5-carboxylic acid.

The crude product was dissolved in 3.0 mL of N,N-dimethylformamide, and 86 mg of 1-hydroxybenzotriazole and 108 mg of 1-(3-dimethylaminopropyl)-3-ethylcarbodiimide hydrochloride were added thereto and stirred at room temperature for 3 hours. Ethyl acetate and water were added to the reaction solution for partition, the organic layer was washed with water and then with saturated saline water, and dried with magnesium sulfate. The solvent was evaporated away under reduced pressure, and the residue was purified through silica gel column chromatography (hexane/ethyl acetate) to obtain 42.0 mg of the entitled compound as a colorless amorphous substance.

$^1$H-NMR (400 MHz, CDCl$_3$) δ: 9.00 (1H, s), 7.56-7.44 (1H, m), 7.42-7.31 (3H, m), 4.80 (2H, s), 2.66 (3H, s).
ESI-MS Found: m/z[M+H]+ 292.

4) Production of 6-(2-chlorophenyl)-2-{[3-methyl-4-(4-methylpiperazin-1-yl)phenyl]amino}-6,7-dihydro-5H-pyrrolo[3,4-d]pyrimidin-5-one 19.2 mg of the entitled compound was obtained as a pale yellow solid in the same manner as in Example 1-2 to 1-3, for which, however, the compound obtained in the above reaction was used in place of the starting compound in Example 1-2, and 3-methyl-4-(4-methylpiperazin-1-yl)aniline was used in place of 4-(4-methylpiperazin-1-yl)aniline used in Example 1-3.

$^1$H-NMR (400 MHz, CDCl$_3$) δ: 8.87 (1H, s), 7.55-7.34 (7H, m), 7.06 (1H, d, J=8.4 Hz), 4.71 (2H, s), 2.96-2.93 (4H, m), 2.60-2.47 (4H, m), 2.37 (3H, s), 2.33 (3H, s).
ESI-MS Found: m/z[M+H]+ 429.

Example 145

Production of 6-benzyl-2-{[3-methyl-4-(4-methylpiperazin-1-yl)phenyl]amino}-6,7-dihydro-5H-pyrrolo[3,4-d]pyrimidin-5-one 4.0 mg of the entitled compound was obtained as a pale yellow solid in the same manner as in Example 144-2 to 144-4, for which, however, benzylamine was used in place of 2-chloroaniline used in Example 144-2.

$^1$H-NMR (400 MHz, CDCl$_3$) δ: 8.79 (1H, s), 7.43-7.29 (8H, m), 7.03 (1H, d, J=8.4 Hz), 4.75 (2H, s), 4.17 (2H, s), 2.98-2.92 (4H, m), 2.75-2.57 (4H, m), 2.38 (3H, s), 2.30 (3H, s).
ESI-MS Found: m/z[M+H]+ 449.

Example 146

Production of 2-allyl-1-[6-(1-hydroxy-1-methylethyl)pyridin-2-yl]-6-{[4-(4-methylpiperazin-1-yl)phenyl]amino}-1,2-dihydro-3H-pyrazolo[4,3-c]pyridin-2-one 1) Production of ethyl 4-[2-allyl-2-(tert-butoxycarbonyl)hydrazino]-6-chloronicotinate 7.0 mL of N,N-diisopropylethylamine was added to tetrahydrofuran (70 mL) solution of 4.40 g of ethyl 4,6-dichloronicotinate and 3.44 g of tert-butyl 1-allylhydrazinecarboxylate obtained in Production Example 1-1, and stirred overnight at 70° C. 30 mL of toluene was added to the reaction liquid, and tetrahydrofuran was evaporated away. This was stirred at 120° C. for 6 hours, and then heated overnight under reflux. The reaction liquid was restored to room temperature, water was added thereto, and extracted with ethyl acetate. This was washed with saturated saline water, dried with anhydrous magnesium sulfate, and concentrated under reduced pressure. The residue was purified through silica gel column chromatography (hexane/ethyl acetate=16/1 to 12/1) to obtain 1.29 g of the entitled compound as a colorless oily substance.

$^1$H-NMR (400 MHz, CDCl$_3$) δ: 9.47 (1H, s), 8.74 (1H, s), 6.75 (1H, s), 5.93-5.78 (1H, m), 5.28-5.15 (2H, m), 4.37 (2H, q, J=7.2 Hz), 4.00 (2H, d, J=5.9 Hz), 1.43 (9H, s), 1.40 (3H, t, J=7.3 Hz).
ESI-MS Found: m/z[M+H]+ 356, 358.

2) Production of 2-allyl-6-chloro-1,2-dihydro-3H-pyrazolo[4,3-c]pyrimidin-3-one 739 mg of the entitled compound was obtained as a white solid in the same manner as in Production Example 1-2, for which, however, 1.29 g of the compound obtained in the above reaction was used in place of tert-butyl 1-allylhydrazinecarboxylate used in Production Example 1-2.

$^1$H-NMR (400 MHz, CDCl$_3$) δ: 9.20 (1H, s), 7.30 (1H, s), 5.97 (1H, ddt, J=17.1, 10.2, 6.3 Hz), 5.33 (1H, dd, J=10.2, 1.0 Hz), 5.31 (1H, dd, J=17.1, 1.0 Hz), 4.76 (2H, d, J=6.3 Hz).
ESI-MS Found: m/z[M+H]+ 210, 212.

3) Production of 2-allyl-6-chloro-1-[6-(1-hydroxy-1-methylethyl)-2-pyridinyl]-1,2-dihydro-3H-pyrazolo[3,4-d]pyridin-3-one 47 mg of the entitled compound was obtained in the same manner as in Example 29-1, for which, however, the compound obtained in the above reaction was used in place of 2-iodopyridine used in Example 29-1.

$^1$H-NMR (400 MHz, CDCl$_3$) δ: 8.91 (1H, d, J=1.0 Hz), 7.93 (1H, t, J=7.8 Hz), 7.54-7.52 (2H, m), 7.12 (1H, dd, J=7.8, 1.0 Hz), 5.72 (1H, ddt, J=17.1, 10.2, 6.2 Hz), 5.11 (1H, dd, J=10.2, 1.5 Hz), 4.98 (1H, dd, J=17.1, 1.0 Hz), 4.60 (2H, dt, J=6.2, 1.3 Hz), 3.69 (1H, s), 1.65 (6H, s).
ESI-MS Found: m/z[M+H]+ 345, 347.

4) Production of 2-allyl-1-[6-(1-hydroxy-1-methylethyl)pyridin-2-yl]-6-{[4-(4-methylpiperazin-1-yl)phenyl]amino}-1,2-dihydro-3H-pyrazolo[4,3-c]pyridin-2-one 0.07 mL of diisopropylethylamine was added to toluene (5.0 mL) solution of 46 mg of the compound obtained in the above reaction and 51 mg of 4-(4-methylpiperazin-1-yl)aniline, and stirred at 200° C. for 3 days in a pressure reactor tube. The reaction liquid was restored to room temperature, concentrated, and the residue was purified through basic silica gel chromatography (hexane/ethyl acetate=1/1 to ethyl acetate to ethyl acetate/ethanol=49/1) and through silica gel chromatography (chloroform/methanol=29/1) to obtain 6.2 mg of the entitled compound as a yellow solid.

$^1$H-NMR (400 MHz, CDCl$_3$) δ: 8.70 (1H, s), 7.78 (1H, t, J=7.8 Hz), 7.30 (1H, d, J=7.3 Hz), 7.17 (2H, d, J=8.8 Hz), 6.96-6.86 (5H, m), 5.73 (1H, ddt, J=17.1, 10.2, 6.3 Hz), 5.09 (1H, d, J=10.2 Hz), 5.02 (1H, dd, J=17.1, 1.0 Hz), 4.43 (2H, d, J=6.3 Hz), 3.25 (4H, t, J=4.9 Hz), 2.66 (4H, t, J=4.9 Hz), 2.41 (3H, s), 1.44 (6H, s).
ESI-MS Found: m/z[M+H]+ 500.

Example 147

Production of 1-[6-(1-hydroxy-1-methylethyl)pyridin-2-yl]-2-isopropyl-6-{[4-(1-methylpiperidin-4-yl)phenyl]amino}-1,2-dihydro-3H-pyrazolo[3,4-d]pyrimidin-3-one In the same manner as in Example 29-1 to 29-2, but using 2-isopropyl-6-(methylthio)-1,2-dihydro-3H-pyrazolo[3,4-d]pyrimidin-3-one synthesized in Production Example 3 in place of 2-allyl-6-(methylthio)-1,2-dihydro-3H-pyrazolo[3,4-d]pyrimidin-3-one used in Example 29-1, using 2-(6-bromo-2-pyridinyl)-2-propanol synthesized in Example 53-1 in place of 2-iodopyridine and using 4-(1-methylpiperazin-4-yl)aniline in place of [5-amino-2-(4-methylpiperazin-1-yl)phenyl]methanol used in Example 29-2, 39.9 mg of the entitled compound was obtained as a yellow solid.

$^1$H-NMR (400 MHz, CDCl$_3$) δ: 8.80 (1H, s), 7.88 (1H, t, J=7.8 Hz), 7.69 (1H, d, J=7.8 Hz), 7.50 (3H, d, J=8.3 Hz), 7.38 (1H, d, J=7.8 Hz), 7.20 (2H, d, J=8.3 Hz), 4.26 (1H, t, J=6.8 Hz), 4.18 (1H, s), 2.98 (2H, d, J=11.7 Hz), 2.52-2.43 (1H, m), 2.33 (3H, s), 2.09-2.02 (2H, m), 1.86-1.77 (4H, m), 1.58 (6H, s), 1.48 (6H, d, J=6.8 Hz).

ESI-MS Found: m/z[M+H]502.

Example 148

Production of 2-allyl-1-[6-(3-methyl-2-oxoimidazolidin-1-yl)pyridin-2-yl]-6-{[4-(4-methylpiperazin-1-yl)phenyl]amino}-1,2-dihydro-3H-pyrazolo[3,4-d]pyrimidin-3-one

1) Production of 2-allyl-1-(6-bromopyridin-2-yl)-6-(methylthio)-1,2-dihydro-3H-pyrazolo[3,4-d]pyrimidin-3-one In the same manner as in Example 29-1, but using 2,6-dibromopyridin in place of 2-iodopyridin used in Example 29-1, 2.94 g of the entitled compound was obtained as a white solid.

$^1$H-NMR (400 MHz, CDCl$_3$)

δ: 8.94(1H, s), 7.95(1H, d, J=7.8 Hz), 7.73(1H, t, J=8.0 Hz), 7.43(1H, d, J=7.8 Hz), 5.69(1H, ddt, J=17.1, 10.2, 6.3 Hz), 5.06(1H, dd, J=10.2, 1.2 Hz), 5.00(1H, d, J=17.1 Hz), 4.88(2H, d, J=6.3 Hz), 2.60(3H, s).

2) Production of 2-allyl-1-[6-(3-methyl-2-oxoimidazolidin-1-yl)pyridin-2-yl]-6-(methylthio)-1,2-dihydro-3H-pyrazolo[3,4-d]pyrimidin-3-one 1-methylimidazolidin-2-one (96 mg), copper iodide (76 mg), potassium carbonate (110 mg) and N,N'-dimethylethane-1,2-diamine (85 µL) were added to a dioxane solution (5 mL) of 2-allyl-1-(6-bromopyridin-2-yl)-6-(methylthio)-1,2-dihydro-3H-pyrazolo[3,4-d]pyrimidin-3-one (150 mg), and stirred overnight in a sealed tube under heat at 100° C.

The reaction liquid was cooled, aqueous ammonia solution was added to it, and extracted three times with chloroform. The organic layer was washed with saturated saline water, dried with anhydrous magnesium sulfate, filtered, and the solvent was evaporated away. The obtained crude product was purified through silica gel column chromatography to obtain 136.4 mg of the entitled compound as a white solid.

$^1$H-NMR (400 MHz, CDCl$_3$) δ: 8.92 (1H, s), 8.26 (1H, d, J=8.4 Hz), 7.81 (1H, dd, J=8.4, 7.6 Hz), 7.41 (1H, d, J=7.6 Hz), 5.66 (1H, ddd, J=16.8, 10.0, 6.4 Hz), 5.06 (1H, d, J=10.0 Hz), 4.95 (1H, d, J=16.8 Hz), 4.80 (2H, d, J=6.4 Hz), 4.01 (2H, t, J=8.0 Hz), 3.51 (1H, t, J=8.0 Hz), 2.94 (3H, s), 2.57 (3H, s).

ESI-MS Found: m/z[M+H]398.

3) Production of 2-allyl-1-[6-(3-methyl-2-oxoimidazolidin-1-yl)pyridin-2-yl]-6-{[4-(4-methylpiperazin-1-yl)phenyl]amino}-1,2-dihydro-3H-pyrazolo[3,4-d]pyrimidin-3-one In the same manner as in Example 29-2, but using 4-(4-methylpiperazin-1-yl)aniline in place of [5-amino-2-(4-methylpiperazin-1-yl)phenyl]methanol used in Example 29-2 and using 2-allyl-1-[6-(3-methyl-2-oxoimidazolidin-1-yl)pyridin-2-yl]-6-(methylthio)-1,2-dihydro-3H-pyrazolo[3,4-d]pyrimidin-3-one in place of 2-allyl-6-(methylthio)-1-pyridin-2-yl-3H-pyrazolo[3,4-d]pyrimidin-3-one, 115.6 mg of the entitled compound was obtained as a yellow solid.

$^1$H-NMR (400 MHz, CDCl$_3$) δ: 8.81 (1H, s), 8.22 (1H, d, J=8.4 Hz), 7.78 (1H, dd, J=8.4, 8.0 Hz), 7.46 (2H, d, J=8.0 Hz), 7.40 (1H, d, J=8.0 Hz), 6.90 (2H, d, J=8.0 Hz), 5.68 (1H, ddd, J=16.8, 10.4, 6.0 Hz), 5.04 (1H, d, J=10.4 Hz), 4.95 (1H, d, J=16.8 Hz), 4.74 (2H, d, J=6.0 Hz), 4.02 (2H, t, J=8.4 Hz), 3.49 (2H, t, J=8.4 Hz), 3.02 (4H, m), 2.94 (3H, S), 2.60 (4H, m), 2.37 (3H, s).

ESI-MS Found: m/z[M+H]541.

Similarly to the above-mentioned Examples and suitably using corresponding starting compounds, Compounds Nos. 1a to 187a shown in the following Tables were obtained.

| Compound No | Structure |
|---|---|
| 1a | 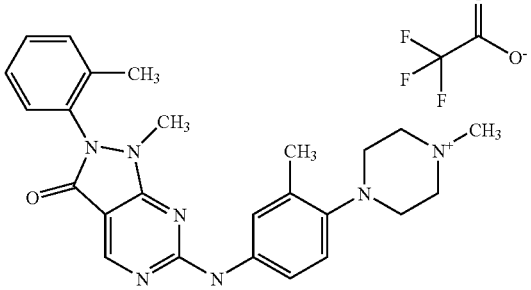 |

-continued

| Compound No | Structure |
|---|---|
| 2a | 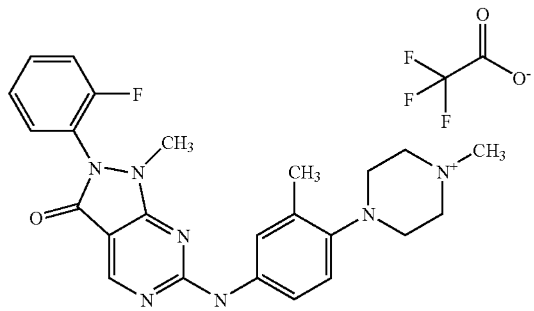 |
| 3a | 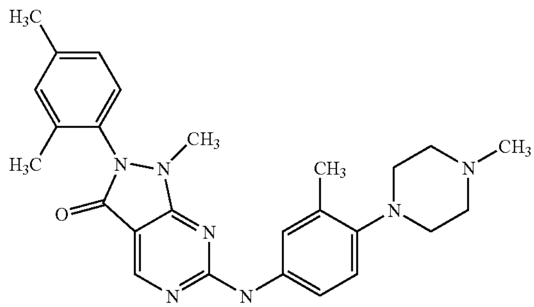 |
| 4a | 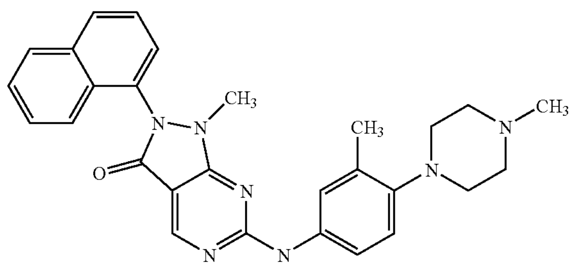 |
| 5a | 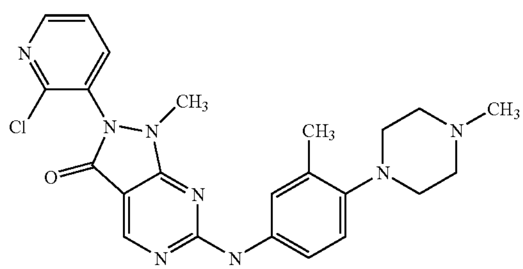 |
| 6a | 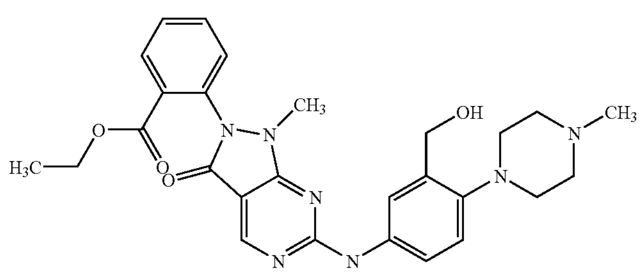 |

-continued

| Compound No | Structure |
|---|---|
| 7a | (structure) |
| 8a | (structure) |
| 9a | (structure) |
| 10a | (structure) |
| 11a | (structure) |

-continued

| Compound No | Structure |
|---|---|
| 12a | 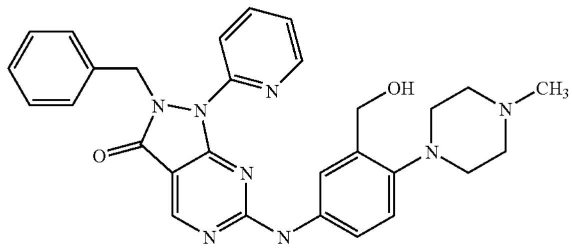 |
| 13a | 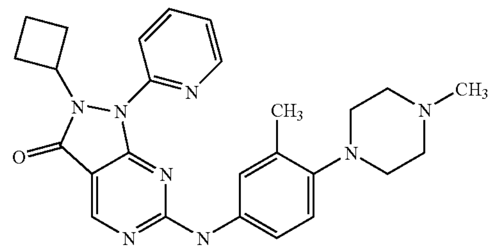 |
| 14a | 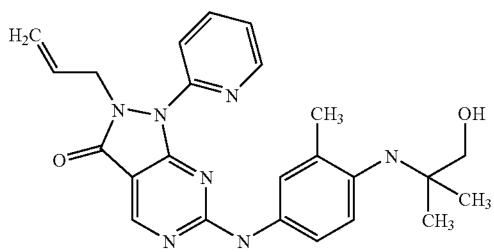 |
| 15a | 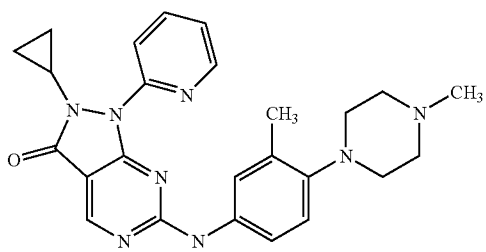 |
| 16a | 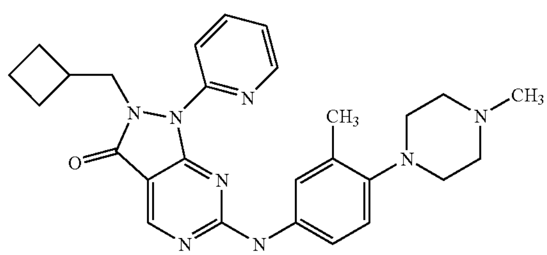 |
| 17a | 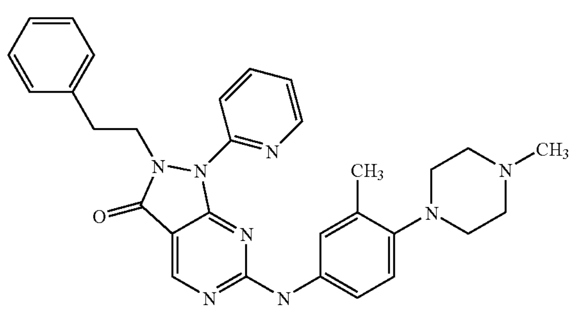 |

-continued
| Compound No | Structure |
|---|---|
| 18a | 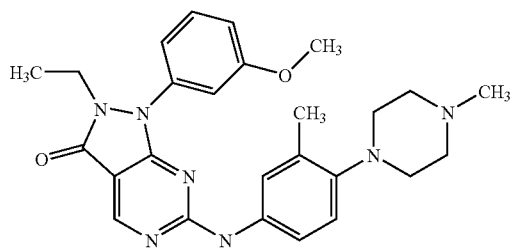 |
| 19a | 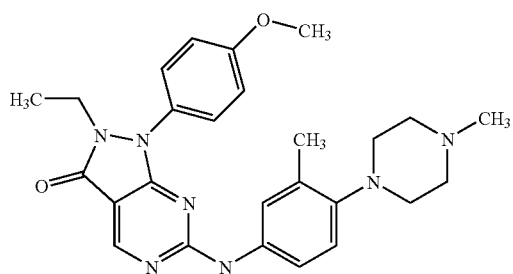 |
| 20a | 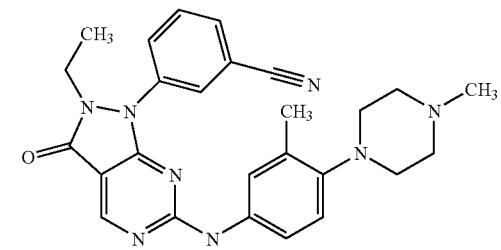 |
| 21a | 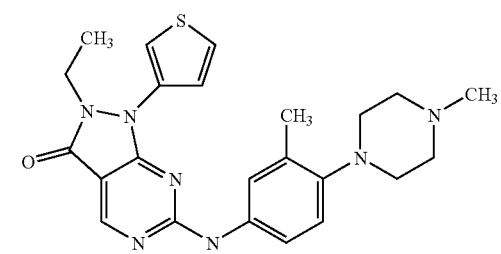 |
| 22a | 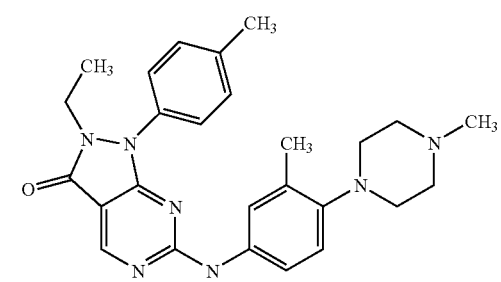 |

-continued

| Compound No | Structure |
| --- | --- |
| 23a | (structure) |
| 24a | (structure) |
| 25a | (structure) |
| 26a | (structure) |
| 27a | (structure) |

-continued

| Compound No | Structure |
|---|---|
| 28a | (structure) |
| 29a | (structure) |
| 30a | (structure) |
| 31a | (structure) |
| 32a | (structure) |
| 33a | (structure) |

| Compound No | Structure |
|---|---|
| 34a | (structure) |
| 35a | (structure) |
| 36a | (structure) |
| 37a | (structure) |
| 38a | (structure) |
| 39a | (structure) |

-continued
| Compound No | Structure |
|---|---|
| 40a | 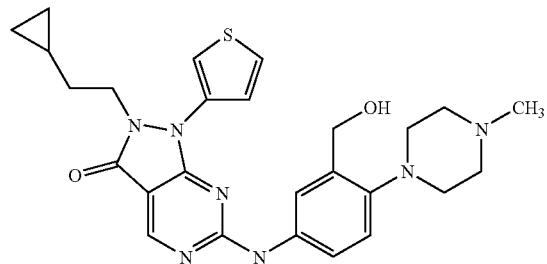 |
| 41a | 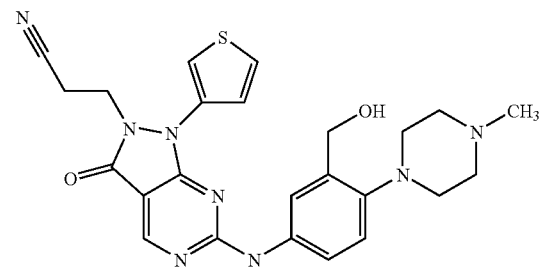 |
| 42a | 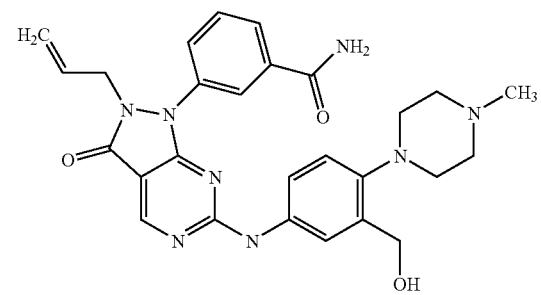 |
| 43a | 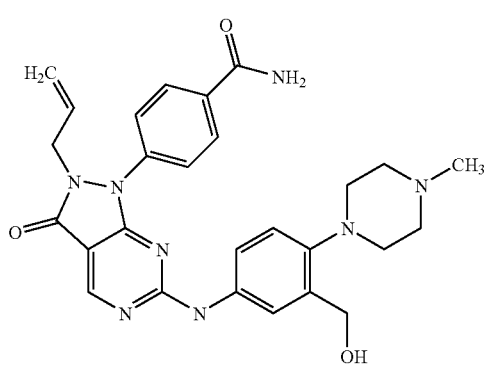 |
| 44a | 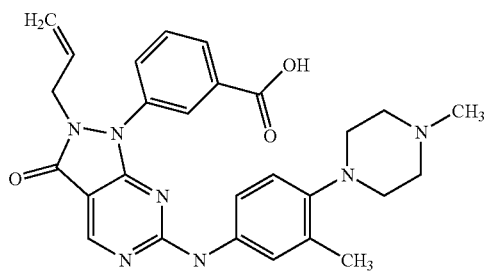 |

-continued

| Compound No | Structure |
|---|---|
| 45a | (structure) |
| 46a | (structure) |
| 47a | (structure) |
| 48a | (structure) |
| 49a | (structure) |
| 50a | (structure) |

-continued
| Compound No | Structure |
|---|---|
| 51a | 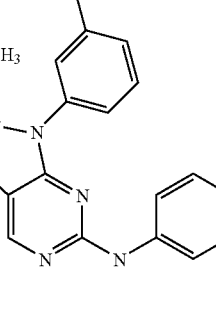 |
| 52a | 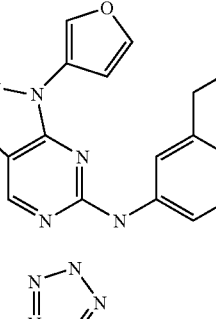 |
| 53a | 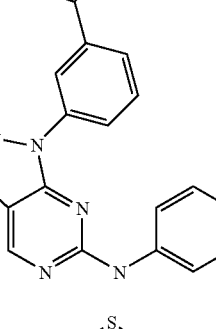 |
| 54a | 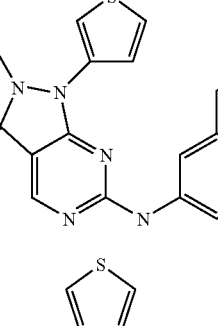 |
| 55a | 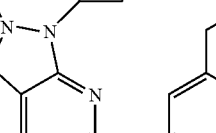 |

-continued

| Compound No | Structure |
|---|---|
| 56a | 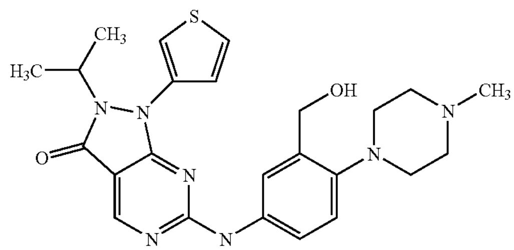 |
| 57a | 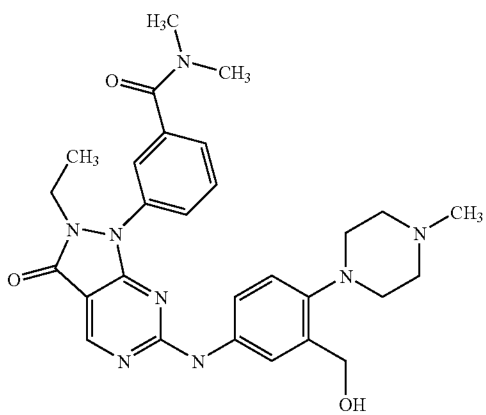 |
| 58a | 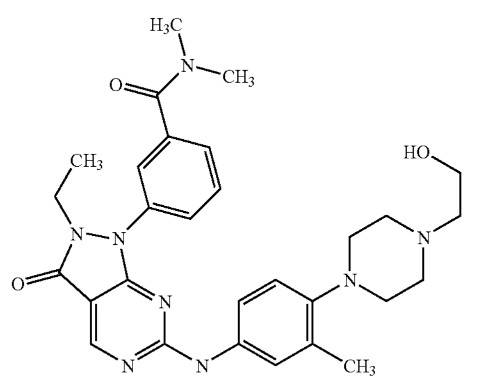 |
| 59a | 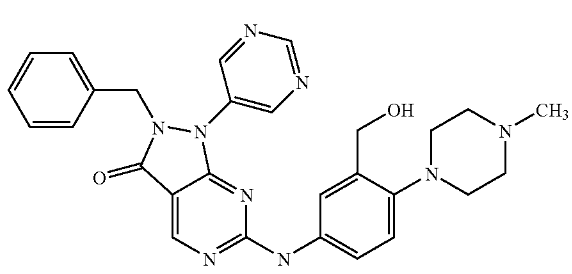 |

-continued
| Compound No | Structure |
|---|---|
| 60a | 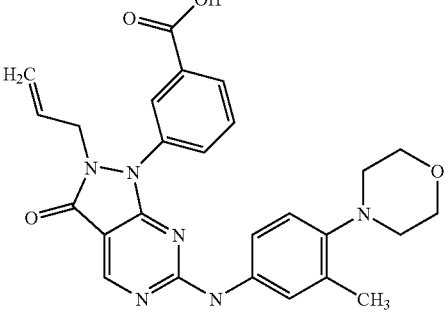 |
| 61a | 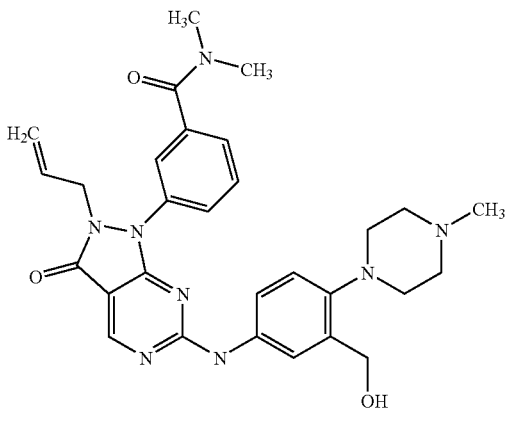 |
| 62a | 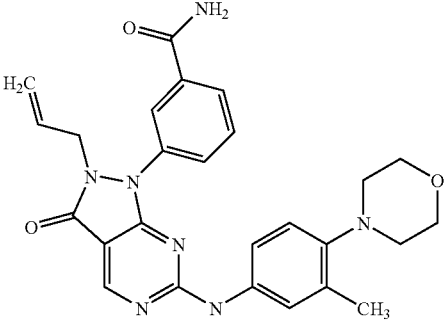 |
| 63a | 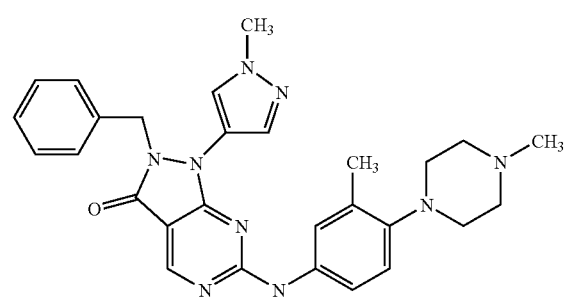 |

-continued

| Compound No | Structure |
|---|---|
| 64a | 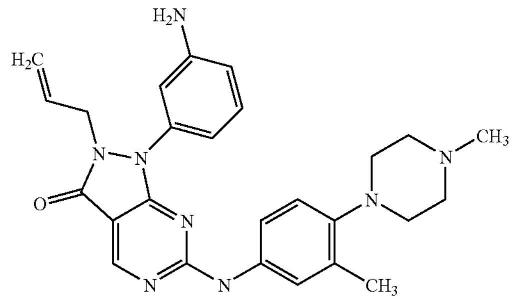 |
| 65a | 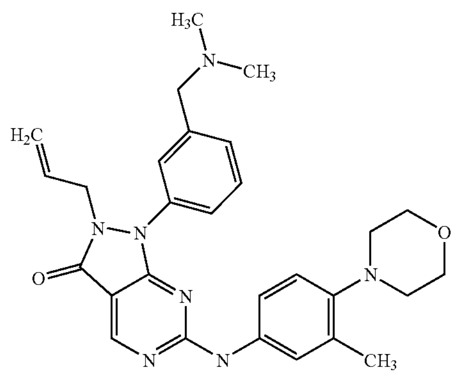 |
| 66a | 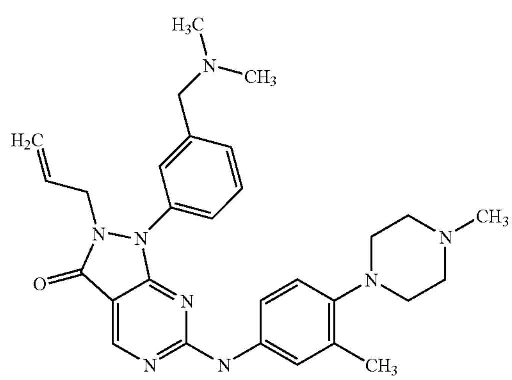 |
| 67a | 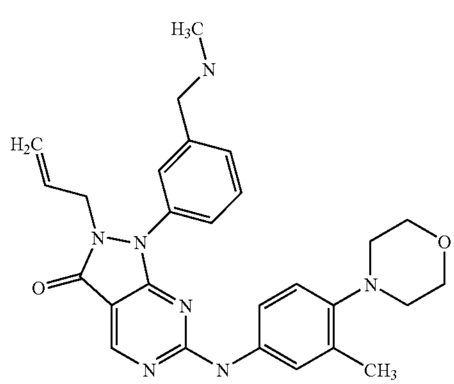 |

-continued
| Compound No | Structure |
|---|---|
| 68a | 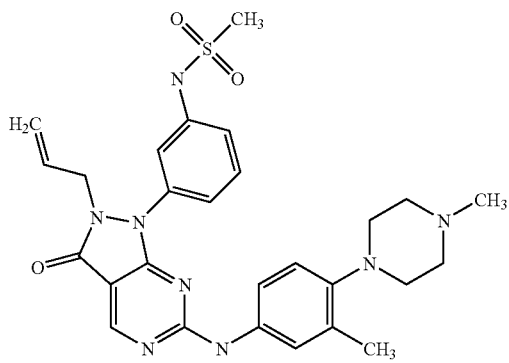 |
| 69a | 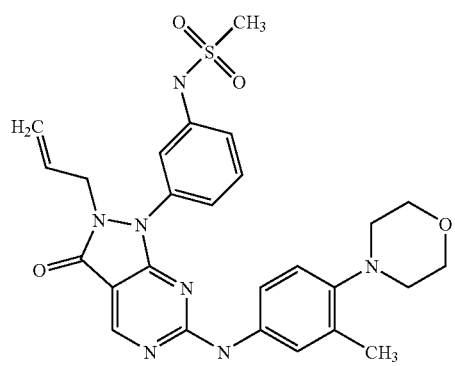 |
| 70a | 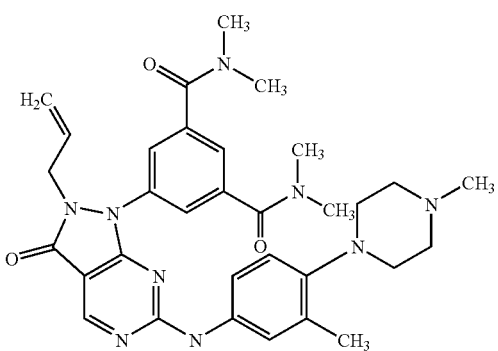 |
| 71a | 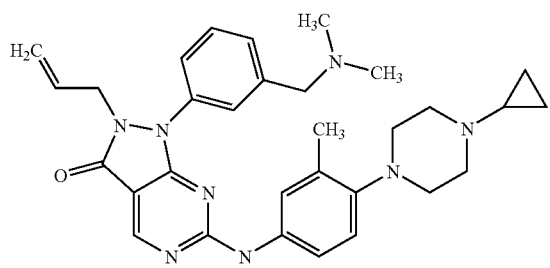 |

| Compound No | Structure |
|---|---|
| 72a | 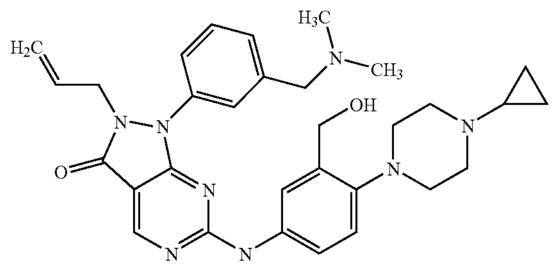 |
| 73a | 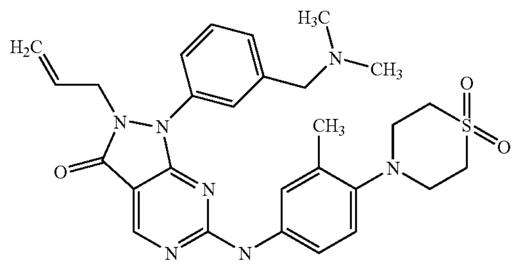 |
| 74a | 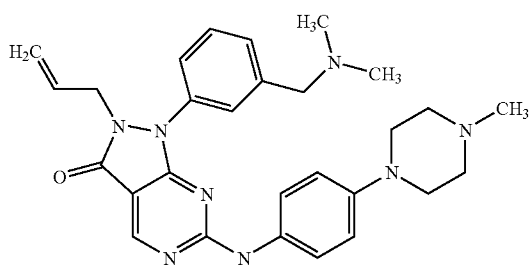 |
| 75a | 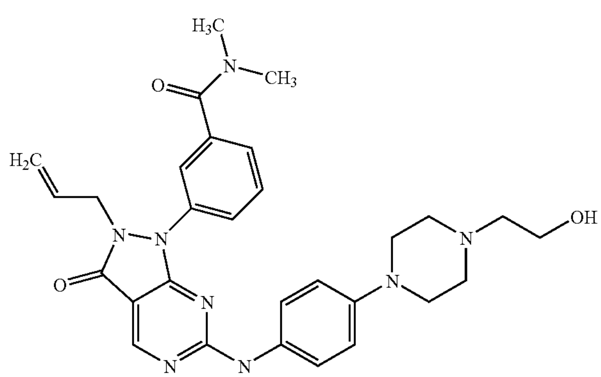 |
| 76a | 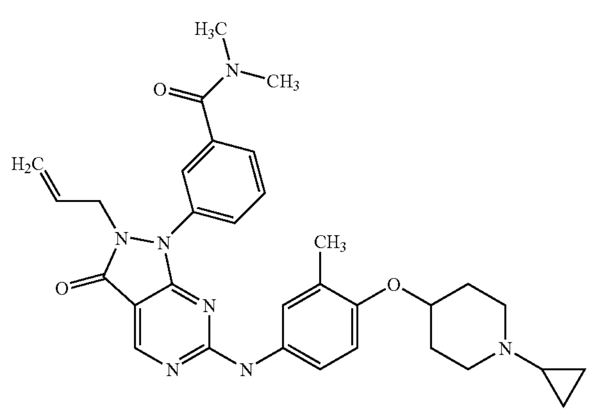 |

-continued
| Compound No | Structure |
|---|---|
| 77a | 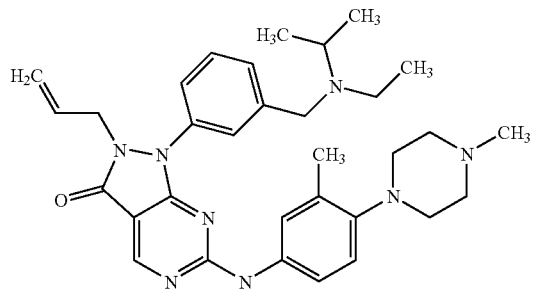 |
| 78a | 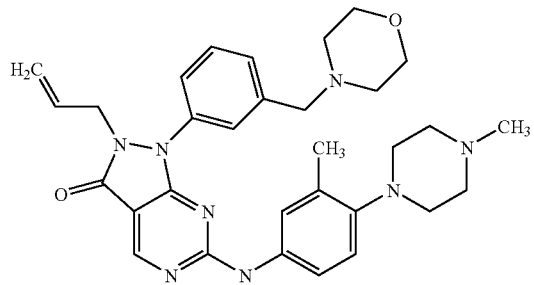 |
| 79a | 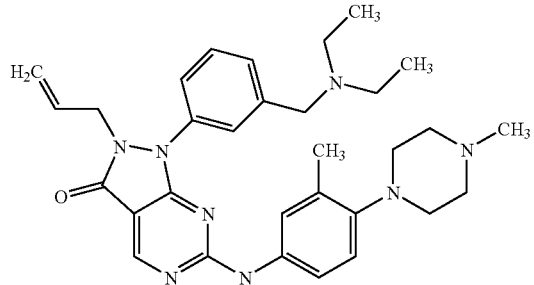 |
| 80a | 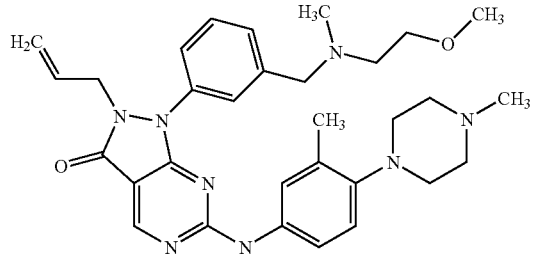 |
| 81a | 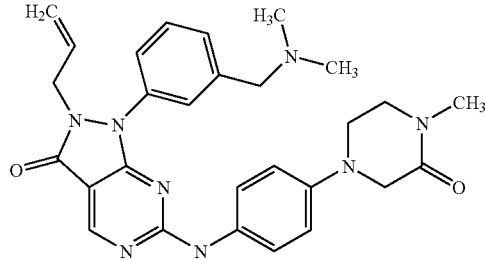 |

-continued
| Compound No | Structure |
|---|---|
| 82a | 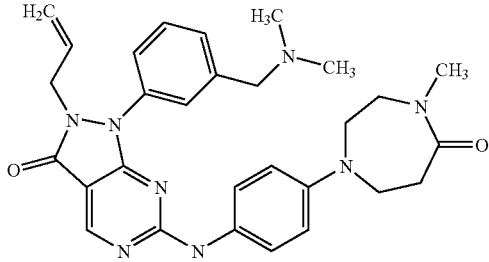 |
| 83a | 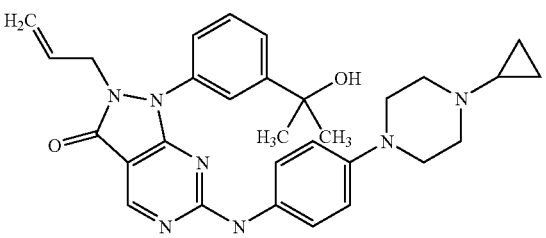 |
| 84a | 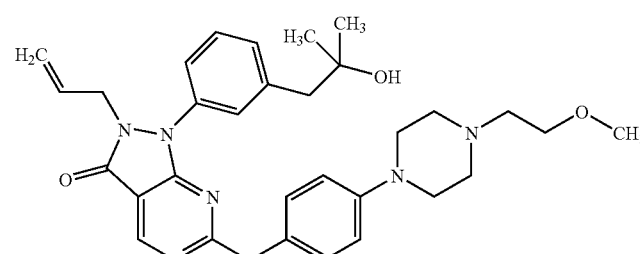 |
| 85a | 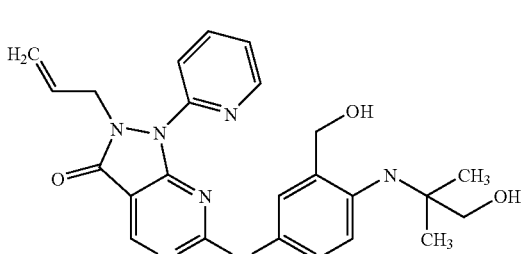 |
| 86a | 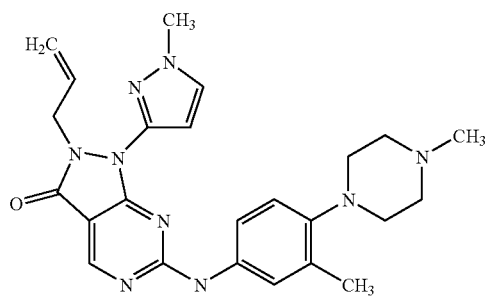 |

-continued

| Compound No | Structure |
|---|---|
| 87a | 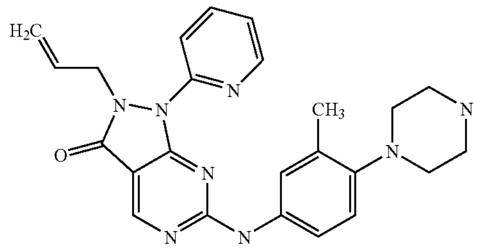 |
| 88a | 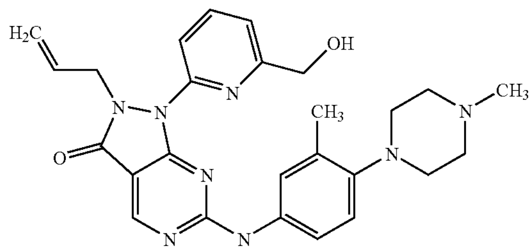 |
| 89a | 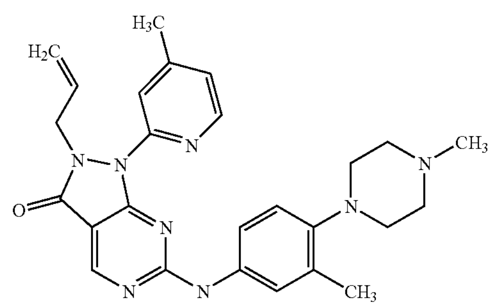 |
| 90a | 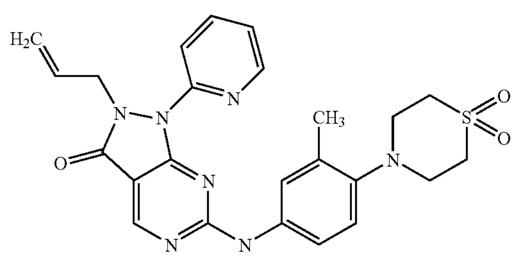 |
| 91a | 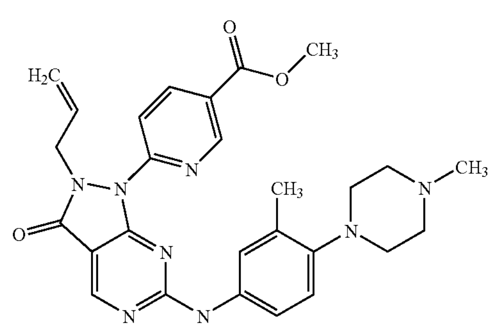 |

-continued
| Compound No | Structure |
|---|---|
| 92a | 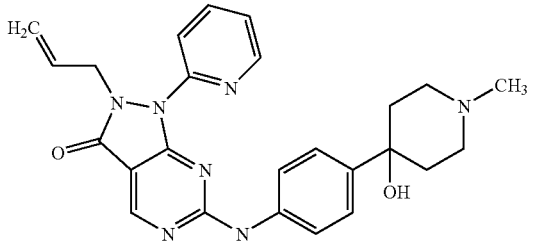 |
| 93a | 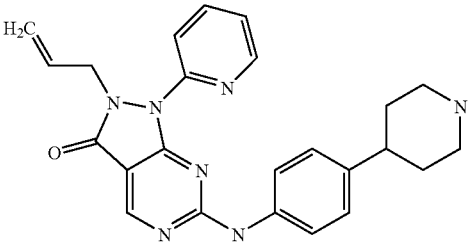 |
| 94a | 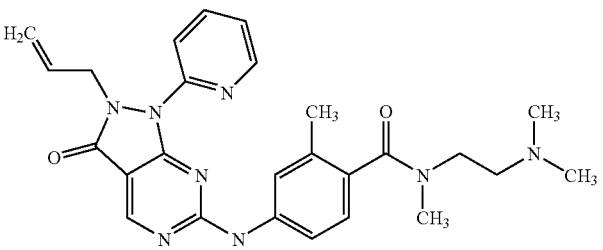 |
| 95a | 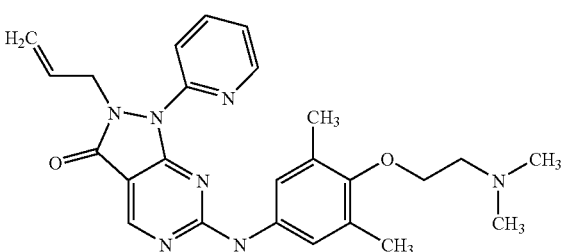 |
| 96a | 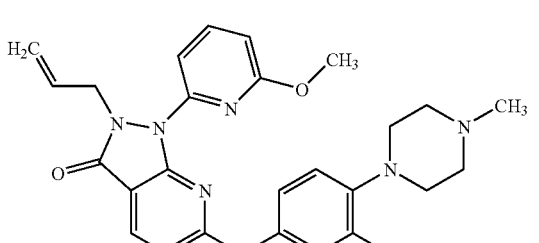 |
| 97a | 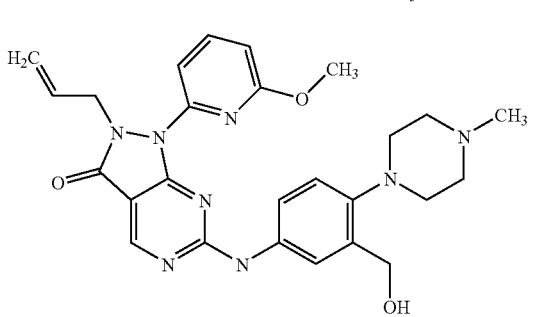 |

-continued

| Compound No | Structure |
| --- | --- |
| 98a | 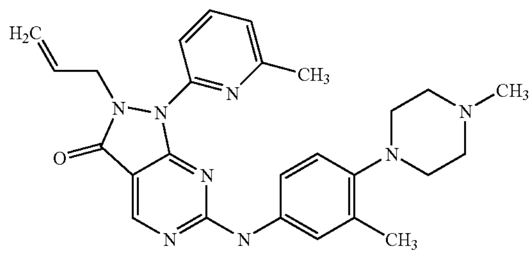 |
| 99a | 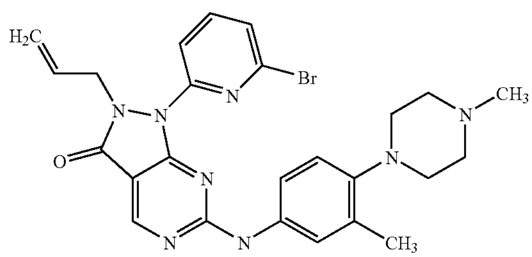 |
| 100a | 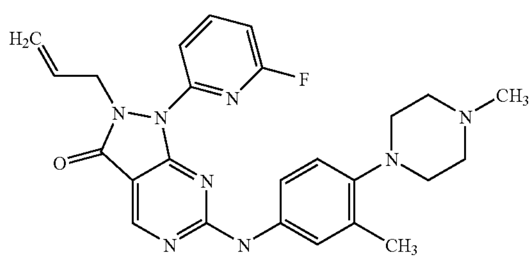 |
| 101a | 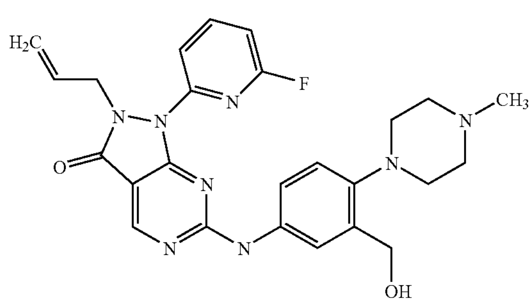 |
| 102a | 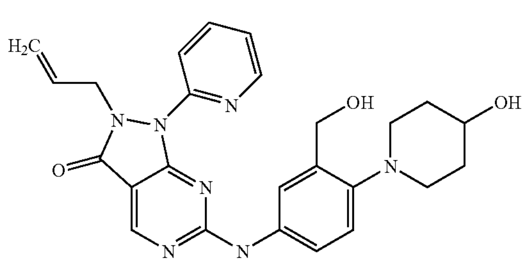 |

| Compound No | Structure |
|---|---|
| 103a | 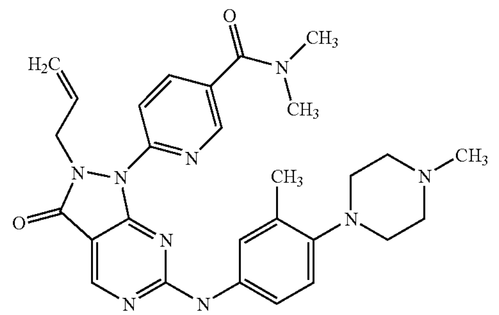 |
| 104a | 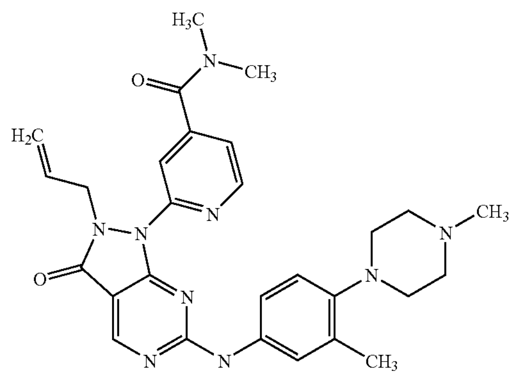 |
| 105a | 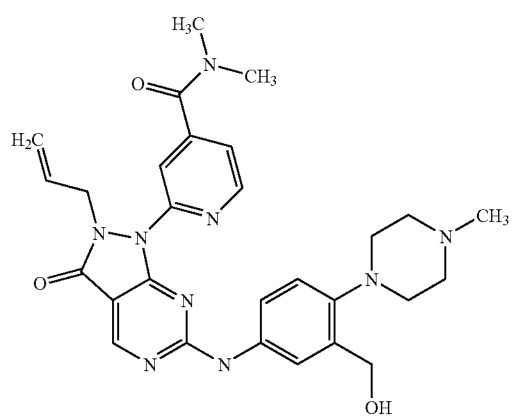 |
| 106a | 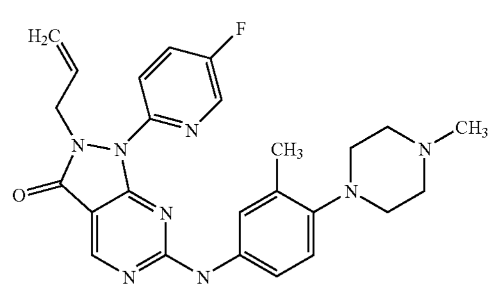 |

-continued
| Compound No | Structure |
|---|---|
| 107a | 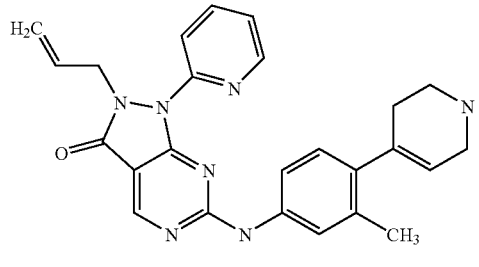 |
| 108a | 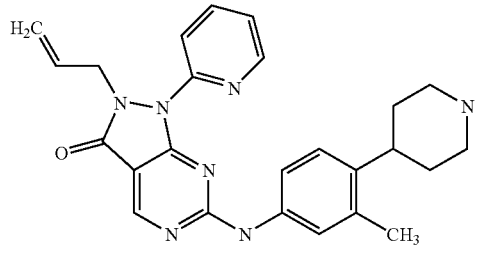 |
| 109a | 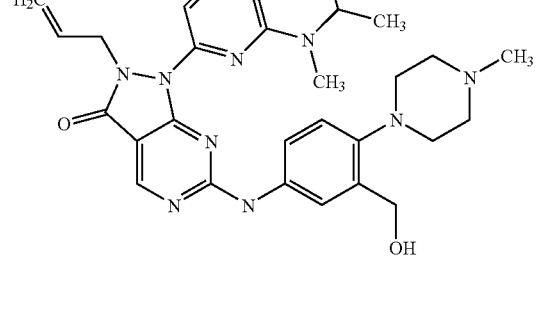 |
| 110a | 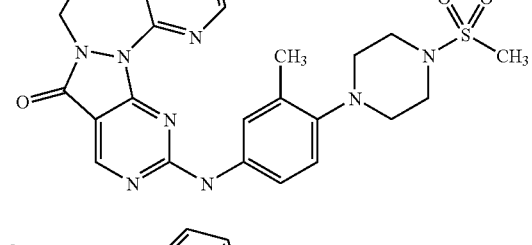 |
| 111a | 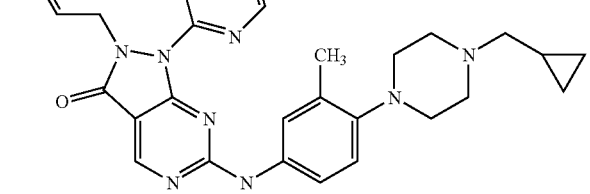 |

-continued

| Compound No | Structure |
|---|---|
| 112a | 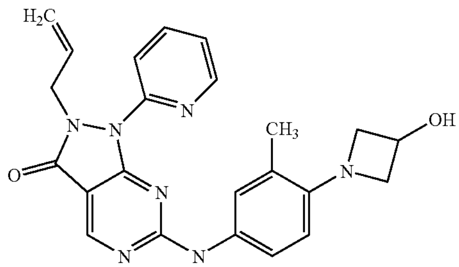 |
| 113a | 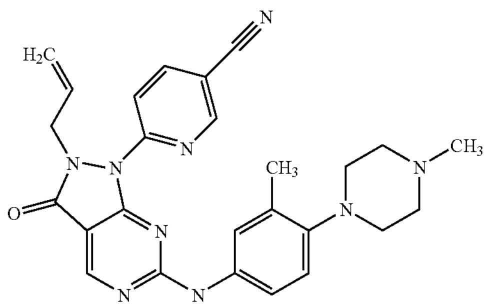 |
| 114a | 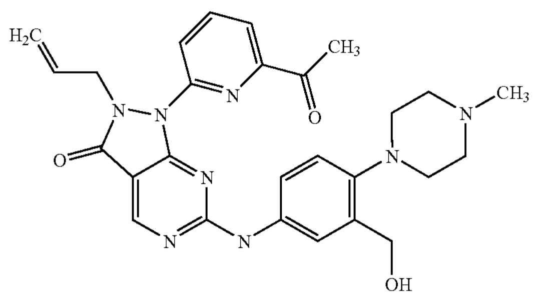 |
| 115a | 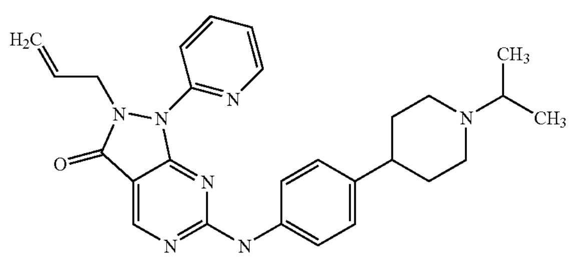 |
| 116a | 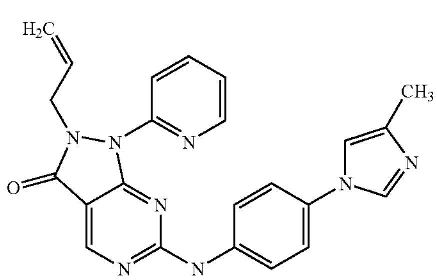 |

-continued

| Compound No | Structure |
|---|---|
| 117a | 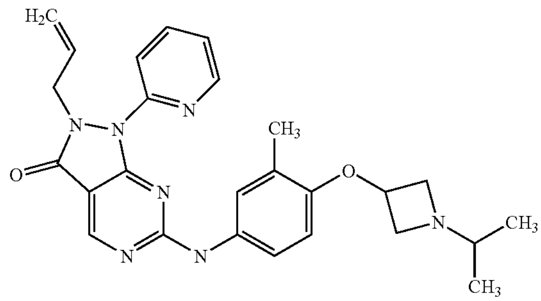 |
| 118a | 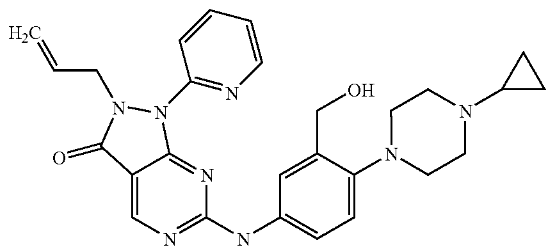 |
| 119a | 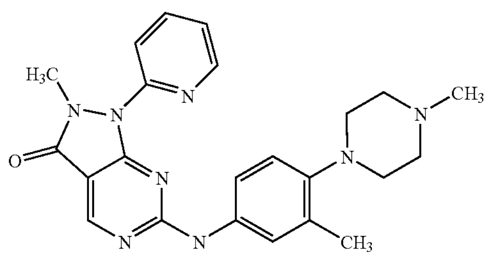 |
| 120a | 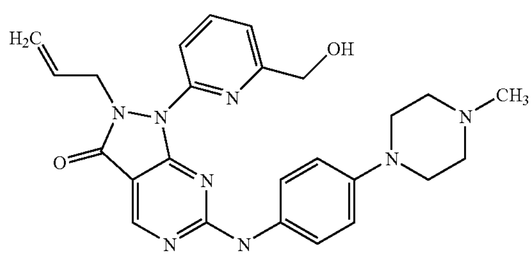 |
| 121a | 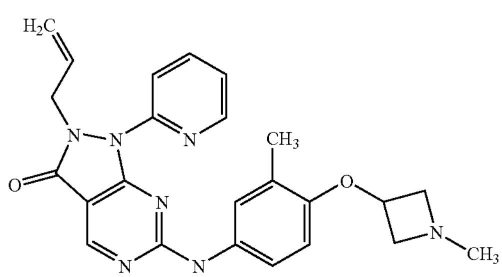 |

| Compound No | Structure |
|---|---|
| 122a | 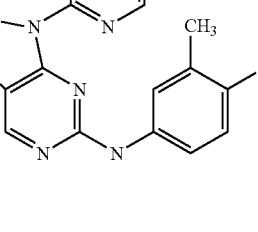 |
| 123a | 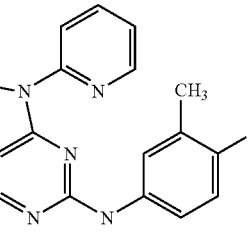 |
| 124a | 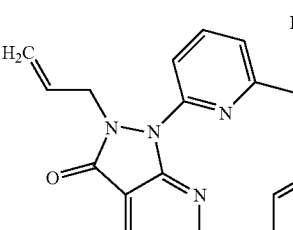 |
| 125a | 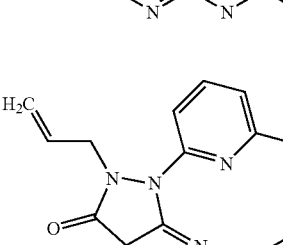 |
| 126a | 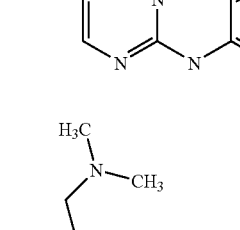 |

-continued

| Compound No | Structure |
| --- | --- |
| 127a | 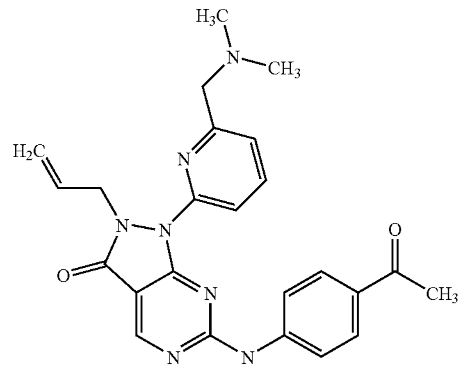 |
| 128a | 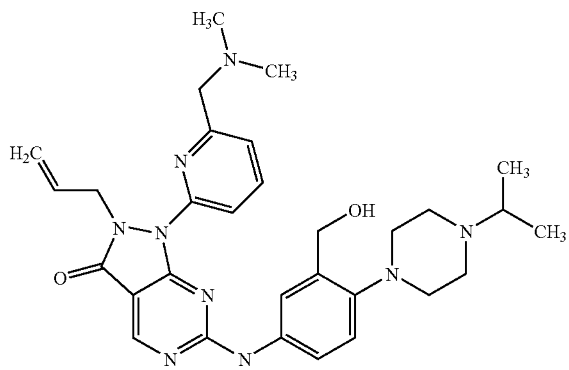 |
| 129a | 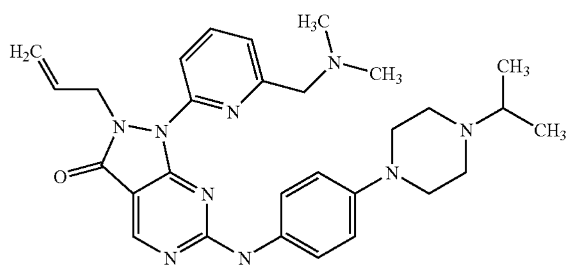 |
| 130a | 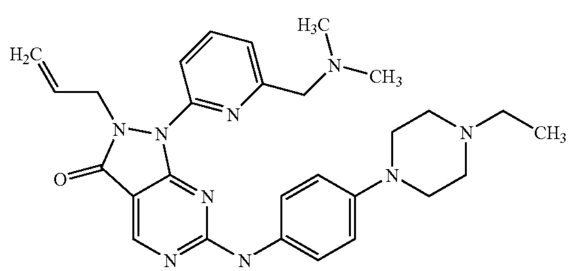 |
| 131a | 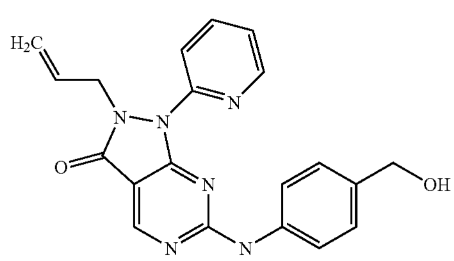 |

-continued

| Compound No | Structure |
|---|---|
| 132a | 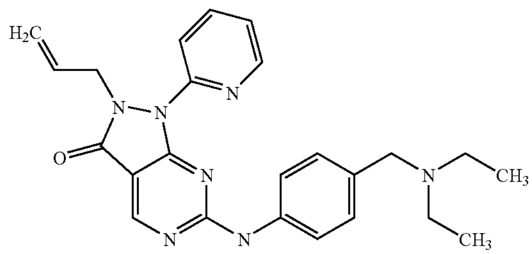 |
| 133a | 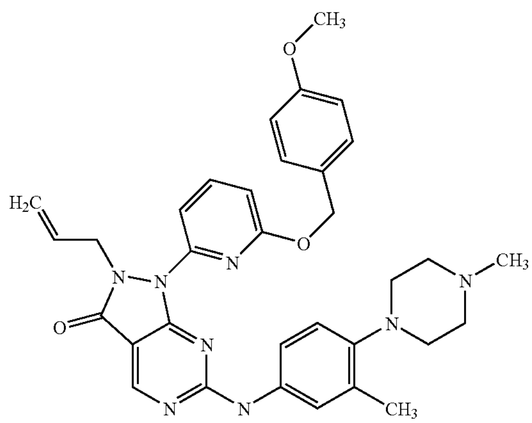 |
| 134a | 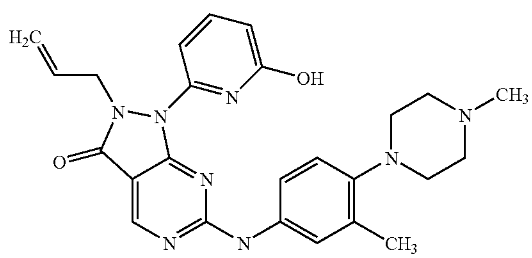 |
| 135a | 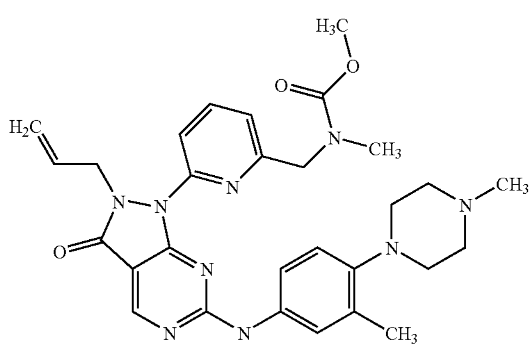 |
| 136a | 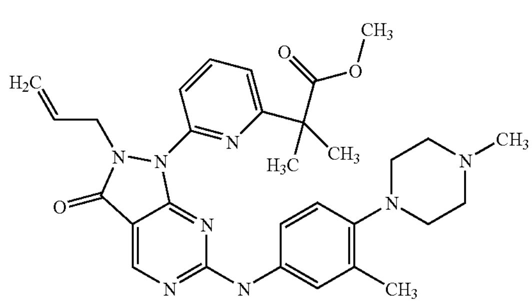 |

-continued

| Compound No | Structure |
|---|---|
| 137a | (structure) |
| 138a | (structure) |
| 139a | (structure) |
| 140a | (structure) |
| 141a | (structure) |
| 142a | (structure) |

-continued

| Compound No | Structure |
|---|---|
| 143a | 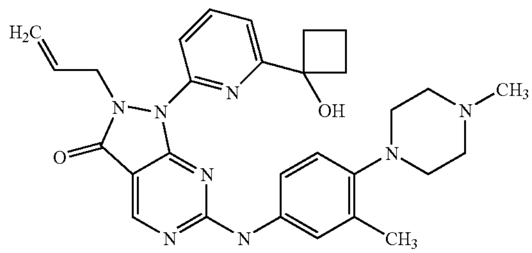 |
| 144a | 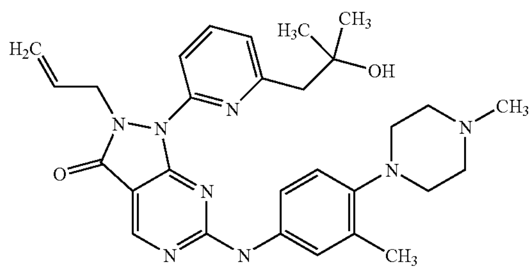 |
| 145a | 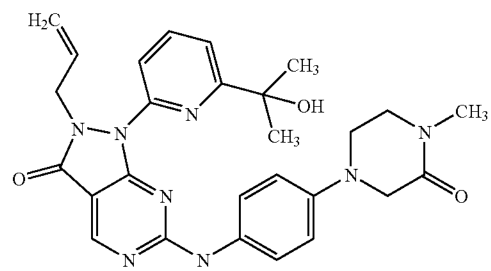 |
| 146a | 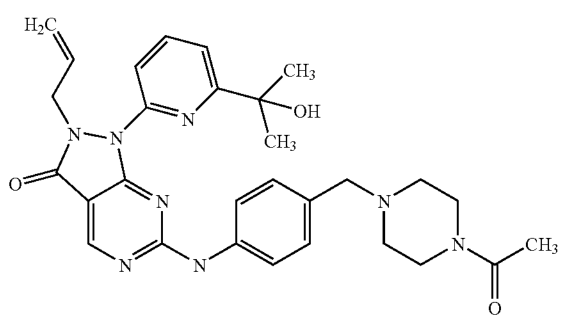 |
| 147a | 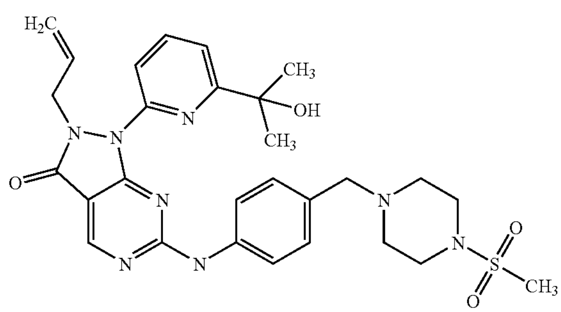 |

-continued
| Compound No | Structure |
|---|---|
| 148a | 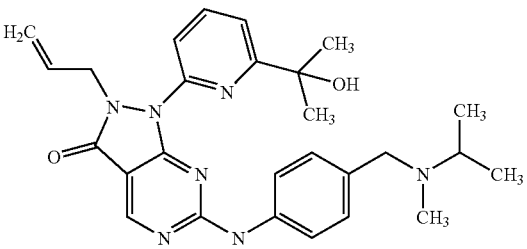 |
| 149a | 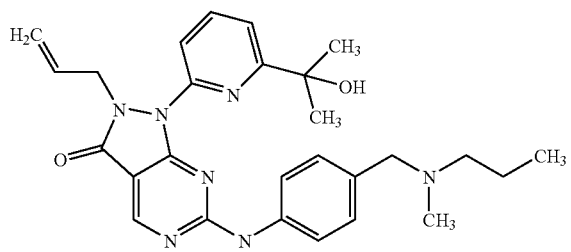 |
| 150a | 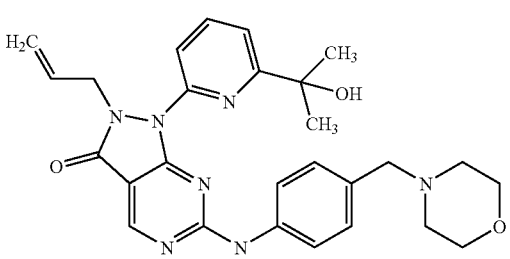 |
| 151a | 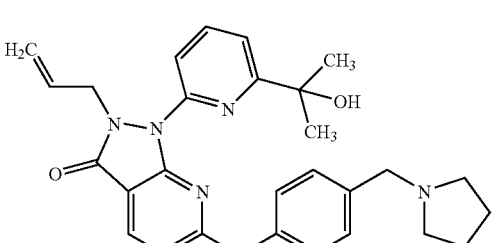 |
| 152a | 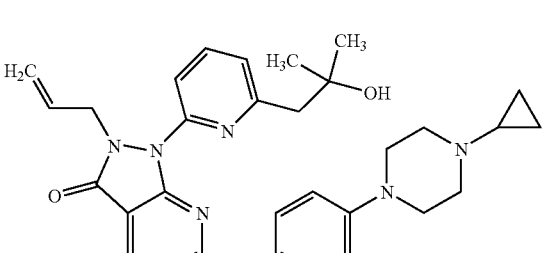 |
| 153a | 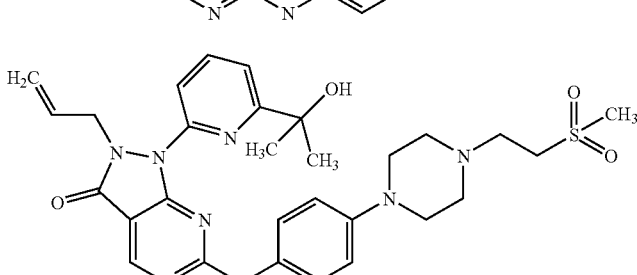 |

| Compound No | Structure |
|---|---|
| 154a | 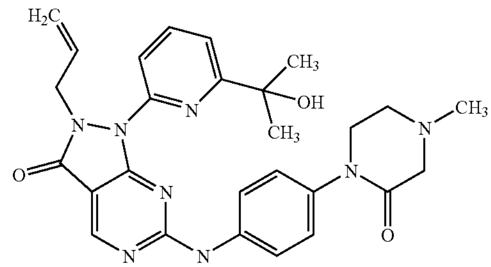 |
| 155a | 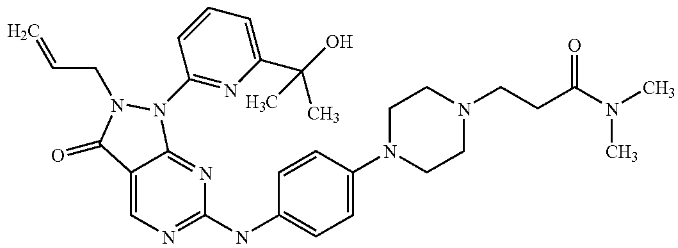 |
| 156a | 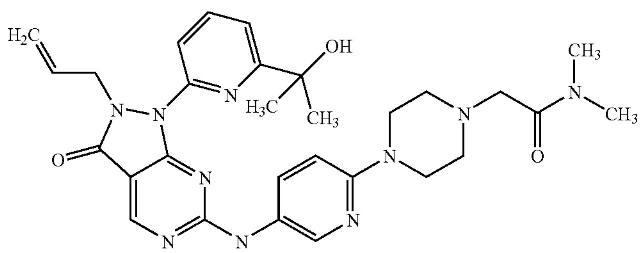 |
| 157a | 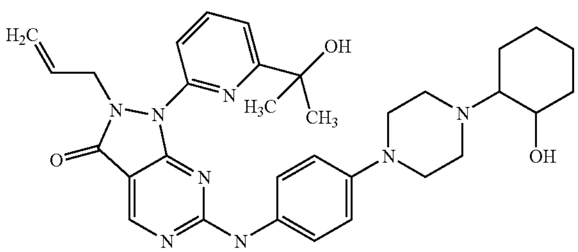 |
| 158a | 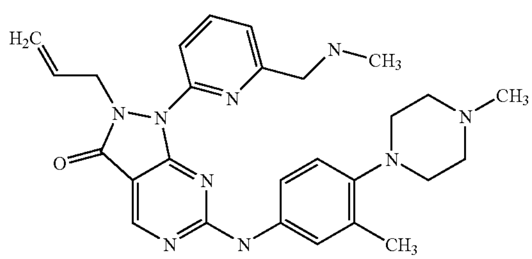 |
| 159a | 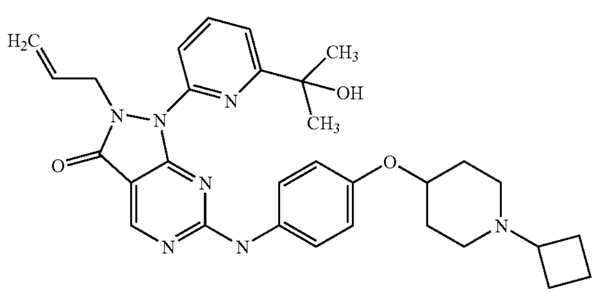 |

-continued
| Compound No | Structure |
|---|---|
| 160a | 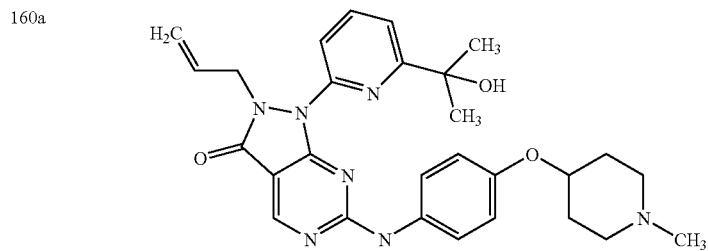 |
| 161a | 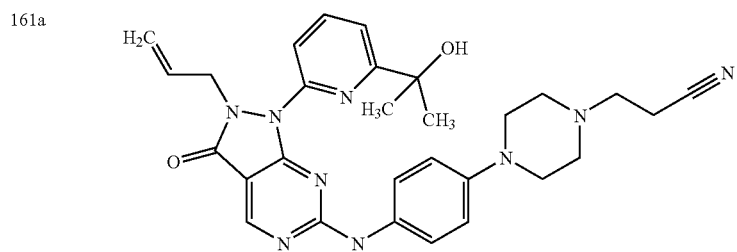 |
| 162a | 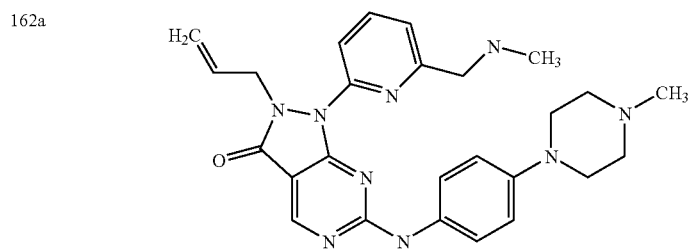 |
| 163a | 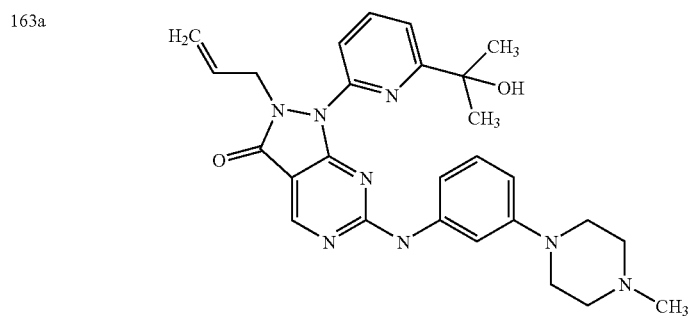 |
| 164a | 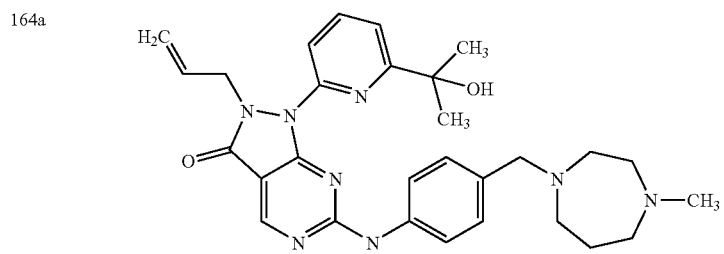 |

-continued

| Compound No | Structure |
|---|---|
| 165a | 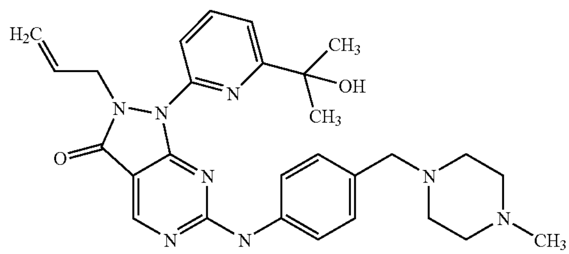 |
| 166a | 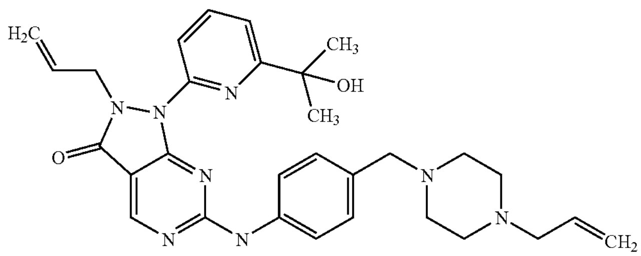 |
| 167a | 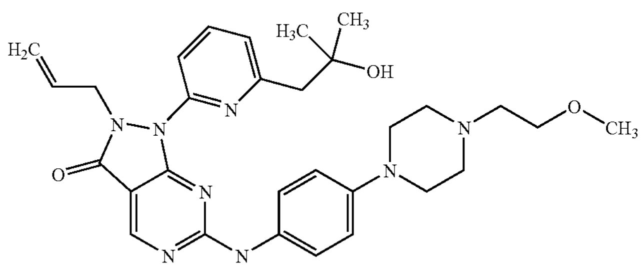 |
| 168a | 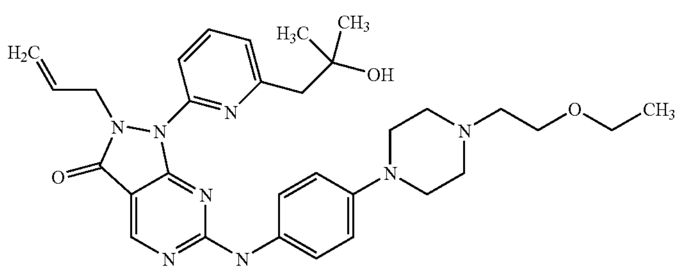 |
| 169a | 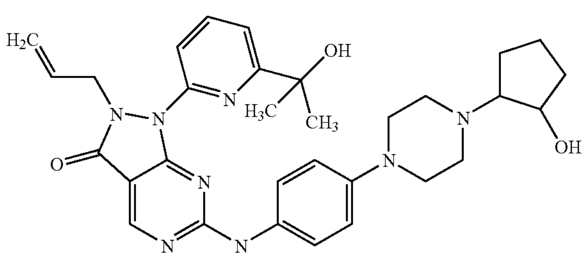 |
| 170a | 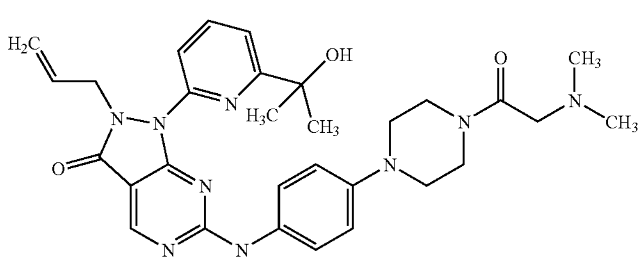 |

-continued

| Compound No | Structure |
|---|---|
| 171a | 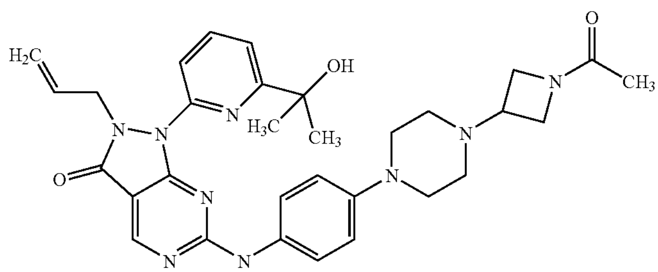 |
| 172a | 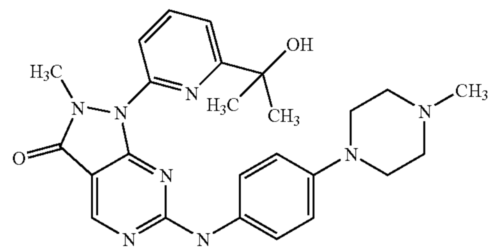 |
| 173a | 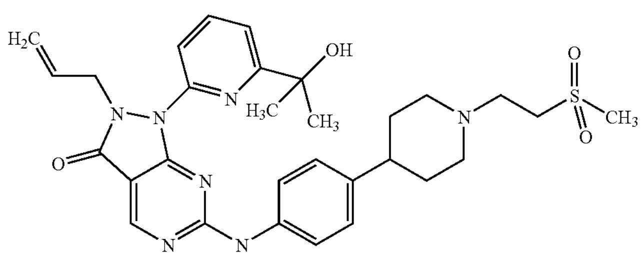 |
| 174a | 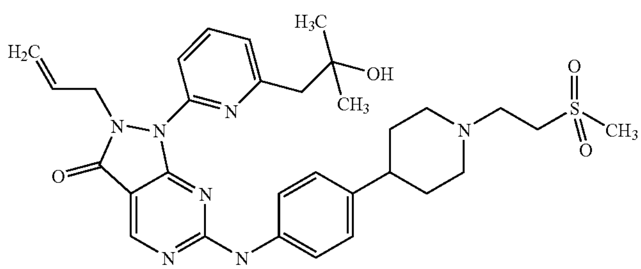 |
| 175a | 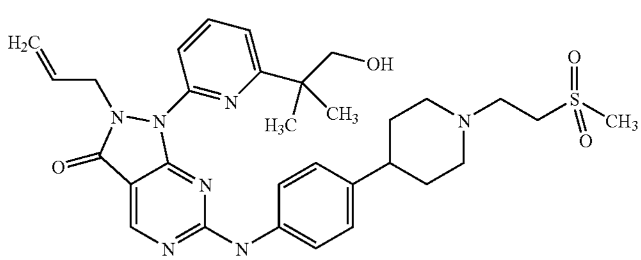 |
| 176a | 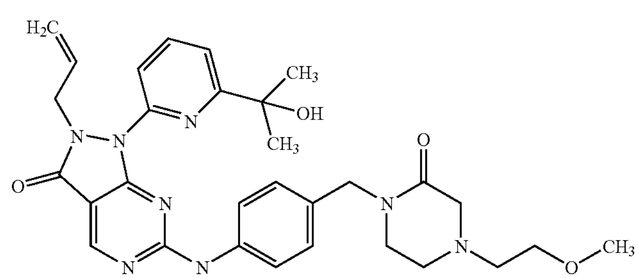 |

-continued
| Compound No | Structure |
|---|---|
| 177a | 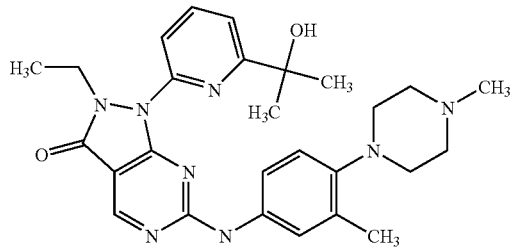 |
| 178a | 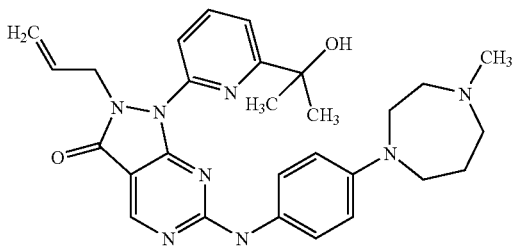 |
| 179a | 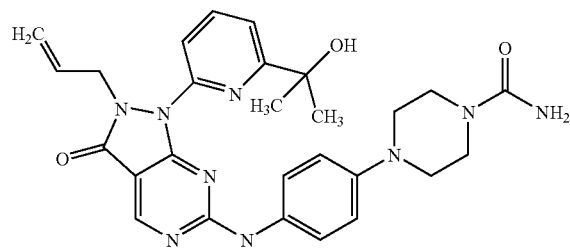 |
| 180a | 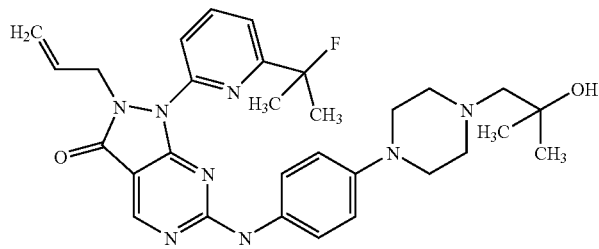 |
| 181a | 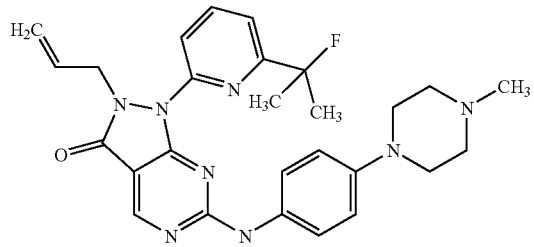 |
| 182a | 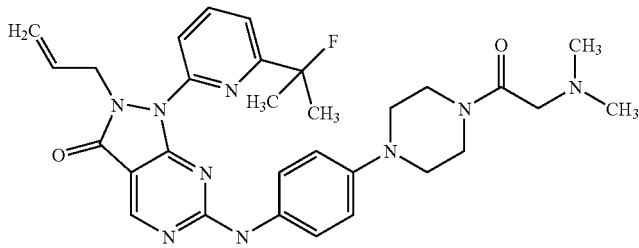 |

-continued

| Compound No | Structure |
|---|---|
| 183a | 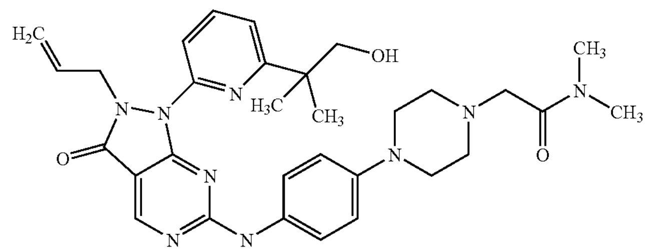 |
| 184a | 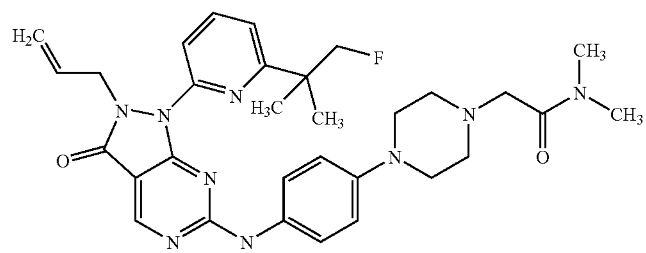 |
| 185a | 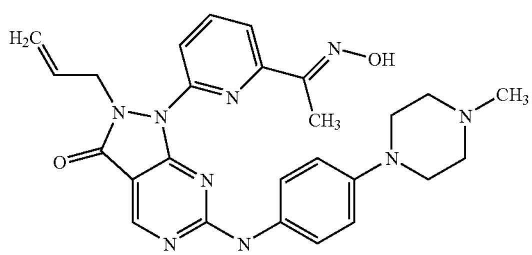 |
| 186a | 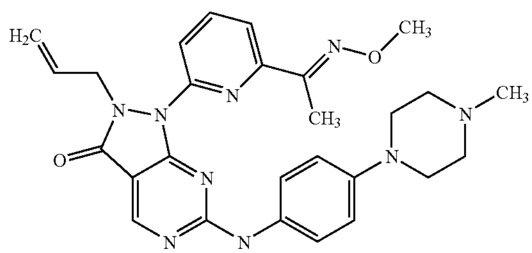 |
| 187a | 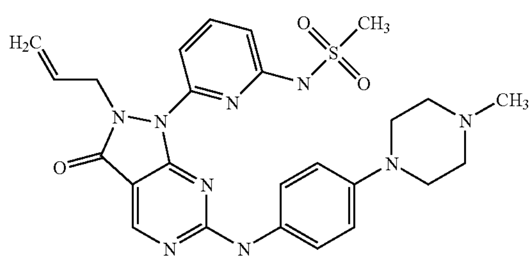 |
| 188a | 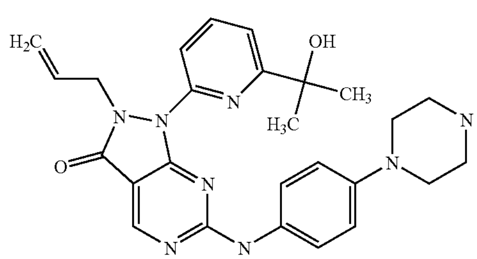 |

-continued

| Compound No | Structure |
|---|---|
| 189a | 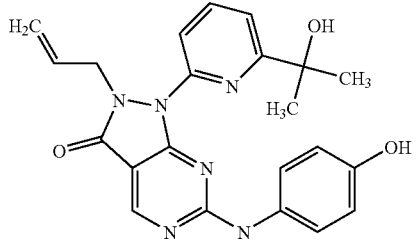 |

The data of ¹H-NMR and MS spectrum on the above compounds are shown in the below tables.

| Compound No | ¹H NMR(400MHz) | ESI-MS (M+H)+ |
|---|---|---|
| 1a | (CDCl3) δ: 8.80(1H, s), 7.45(1H, bs), 7.42(1H, t, J=8.3Hz), 7.30(1H, d, J=8.3Hz), 7.02(1H, d, J=8.3Hz), 6.99(1H, s), 6.95(1H, d, J=8.3Hz), 6.91(1H, d, J=8.3Hz), 3.89(2H, q, J=6.9Hz), 3.84(3H, s), 3.89-3.96(4H, m), 2.54-2.72(4H, m), 2.39(3H, s), 2.28(3H, s), 1.08(3H, t, J=6.9Hz). | 474 |
| 2a | (CDCl3) δ: 8.80(1H, s), 7.59(1H, bs), 7.37(1H, d, J=9.3Hz), 7.21-7.38(1H, m), 7.04(2H, d, J=9.3Hz), 6.97(1H, d, J=8.8Hz), 3.88(3H, s), 3.83(2H, q, J=6.8Hz), 3.88-3.99(4H, m), 3.52-3.77(4H, m), 2.40(3H, s), 2.27(3H, s), 1.09(3H, t, J=6.8Hz). | 474 |
| 3a | (CD3OD) δ: 8.79(1H, s), 7.65(1H, d, J=7.4Hz), 7.59-7.56(2H, m), 7.47-7.43(2H, m), 7.41-7.33(2H, m), 7.12(1H, d, J=8.8Hz), 3.62-3.55(2H, m), 3.39-3.24(7H, m), 3.11-3.01(2H, m), 2.98(3H, s), 2.36(3H, s), 2.26(3H, s). | 444 |
| 4a | (CD3OD) δ: 8.78(1H, s), 7.69-7.63(1H, m), 7.63-7.49(3H, m), 7.41-7.36(2H, m), 7.12(1H, d, J=8.6Hz), 3.62-3.56(2H, m), 3.38-3.24(7H, m), 3.10-3.02(2H, m), 2.99(3H, s), 2.36(3H, s). | 448 |
| 5a | (CD3OD) δ: 8.74(1H, s), 7.62-7.55(1H, m), 7.53-7.48(1H, m), 7.15(1H, d, J=8.6Hz), 7.04(1H, d, J=8.6Hz), 6.85-6.80(1H, m), 6.78-6.71(1H, m), 3.24(3H, s), 2.95-2.89(4H, m), 2.68-2.56(4H, m), 2.35(3H, s), 2.30(3H, s), 2.11(3H, s). | 460 |
| 6a | (CDCl3) δ: 8.79(1H, s), 7.24-7.57(6H, m), 6.99(1H, d, J=8.6Hz), 3.89(2H, t, J=7.8Hz), 2.94(4H, t, J=3.0Hz), 2.55-2.70(4H, m), 2.39(3H, s), 2.30(3H, s), 1.09(3H, t, J=7.8Hz). | 469 |
| 7a | (CDCl3) δ: 8.81(1H, s), 7.89(1H, s), 7.61-7.71(3H, m), 7.22-7.27(2H, m), 7.07(1H, d, J=8.9Hz), 3.86(2H, t, J=7.4Hz), 2.93-2.99(4H, m), 2.56-2.68(4H, m), 2.38(3H, s), 2.32(3H, s), 1.07(3H, t, J=7.4Hz). | 450 |
| 8a | (DMSO-d6) δ: 8.78(1H, s), 7.59-7.78(1H, m), 7.29-7.45(5H, m), 6.92(1H, d, J=8.3Hz), 3.64-3.72(2H, m), 2.77(4H, t, J=3.1Hz), 2.40-2.55(4H, m), 2.37(3H, s), 2.22(3H, s), 2.18(3H, s), 0.95(3H, t, J=6.9Hz). | 458 |
| 9a | (DMSO-d6) δ: 8.78(1H, s), 7.45-7.52(2H, m), 7.12(2H, s), 7.05(1H, s), 6.92(1H, d, J=8.7Hz), 3.66-3.75(2H, m), 2.77(4H, bs), 2.39-2.50(4h, m), 2.34(6H, s), 2.23(3H, s), 2.17(3H, s), 0.95(3H, t, J=7.4Hz). | 472 |
| 10a | (DMSO-d6) δ: 8.78(1H, s), 7.59(2H, d, J=8.8Hz), 7.45(2H, d, J=8.8Hz), 7.21-7.32(2H, m), 6.92(1H, d, J=8.7Hz), 3.65-3.77(2H, m), 2.73-2.81(4H, m), 2.38-2.55(4H, m), 2.21(3H, s), 2.17(3H, s), 0.96(3H, t, J=7.3Hz). | 500 |
| 11a | (CDCl3) δ: 8.78(1H, s), 7.31-7.55(6H, m), 6.97(1H, d, J=8.2Hz), 4.79(2H, s), 3.86(2H, q, J=7.2Hz), 2.87-2.94(4H, m), 2.51-2.70(4H, m), 2.36(3H, s), 2.27(3H, s), 1.07(3H, t, J=7.2Hz). | 474 |
| 12a | (CDCl3) δ: 8.80(1H, s), 7.53(2H, d, J=8.0Hz), 7.48(2H, d, J=8.0Hz), 6.97(1H, d, J=8.2Hz), 4.78(2H, s), 3.86(2H, q, J=7.2Hz), 2.89-2.95(4H, m), 2.56-2.71(4H, m), 2.39(3H, s), 2.29(3H, s), 1.07(3H, t, J=7.2Hz). | 474 |
| 13a | (CDCl3) δ: 8.80(1H, s), 7.23-7.58(7H, m), 6.98(1H, d, J=8.7Hz), 3.88(2H, q, J=7.4Hz), 2.90-2.98(4H, m), 2.52-2.73(4H, m), 2.40(3H, s), 2.29(3H, s), 1.08(3H, t, J=7.4Hz). | 444 |

-continued

| Compound No | $^1$H NMR(400MHz) | ESI-MS (M+H)+ |
|---|---|---|
| 14a | (CDCl3) δ: 8.81(1H, s), 7.20-7.58(5H, m), 6.99(1H, d, J=8.2Hz), 5.66-5.78(1H, m), 5.13(1H, d, J=9.3Hz), 5.04(1H, d, J=17.0Hz), 4.43(2H, d, J=7.6Hz), 2.89-2.96(4H, m), 2.53-2.73(4H, m), 2.38(3H, s), 2.29(3H, s). | 462 |
| 15a | (CDCl3) δ: 8.82(1H, s), 8.13(1H, s), 7.93(1H, bs), 7.19-7.44(3H, m), 5.67-5.77(1H, m9, 5.15(1H, d, J=10.3Hz), 5.06(1H, d, J=17.0Hz), 3.12-3.21(4H, m), 2.58-2.69(4H, m), 2.38(3H, s), 2.27(3H, s). | 463 |
| 16a | (DMSO-d6) δ: 8.79(1H, s), 8.31(1H, s), 7.28-7.80(2H, m), 7.28-7.38(2H, m), 6.92(1H, d, J=8.7Hz), 3.65-3.78(2H, m), 2.75-2.82(4H, m), 2.38-2.53(4H, m), 2.22(3H, s), 2.19(3H, s), 1.39-1.49(2H, m), 0.70(3H, t, J=7.3Hz). | 464 |
| 17a | (CDCl3) δ: 8.88(1H, s), 7.41-7.99(9H, m), 7.07(1H, d, J=8.8Hz), 3.25(3H, s), 2.95(4H, m), 2.64(4H, brs), 2.38(3H, s), 2.34(3H, s). | 480 |
| 18a | (CDCl3) δ: 8.81(1H, s), 7.21-7.57(5H, m), 6.98(1H, d, J=8.3Hz), 5.66-5.77(1H, m), 5.14(1H, d, J=9.3Hz), 5.04(1H, d, J=17.1Hz), 4.42(2H, d, J=5.9Hz), 3.82-3.89(4H, m), 2.86-2.93(4H,), 2.31(3H, s). | 449 |
| 19a | (CDCl3) δ: 8.84(1H, s), 8.22(1H, s), 7.62(1H, bs), 7.22-7.46(6H, m), 7.09(1H, s), 6.84(1H, d, J=8.8Hz), 5.68-5.78(1H, m), 5.14(1H, d, J=10.3Hz), 5.05(1H, d, J=17.1Hz), 4.43(2H, d<J=5.9Hz), 2.54(3H, s), 2.21(3H, s). | 471 |
| 20a | (CDCl3) δ: 8.80(1H, s), 7.30-8.45(5H, m), 7.08(1H, d, J=8.0Hz), 3.38(3H, s), 2.96(4H, m), 2.64(4H, brs), 2.38(3H, s), 2.34(3H, s). | 464 |
| 21a | (CDCl3) δ: 8.82(1H, s), 7.18-7.66(6H, m), 4.78(2H, s), 3.74(2H, d, J=6.9Hz), 3.02(4H, s), 2.50-78(4H, m), 2.39(3H, s), 0.89-0.97(1H, m), 0.38-0.44(2H, m), 0.17-0.21(2H, m). | 492 |
| 22a | (CDCl3) δ: 9.82(1H, bs), 8.84(1H, s), 8.42(1H, bs), 7.77(1H, b s), 7.64(1H, bs), 7.44(1H, s), 7.21-7.26(2H, m), 5.82(1H, b s), 5.67-5.77(1H, m), 5.14(1H, d, J=10.2Hz), 5.04(1H, d, J=17.1Hz), 4.44(2H, d, J=5.9Hz), 2.99-3.09(4H, bs), 2.51-2.79(4H, bs), 2.40(3H, s). | 491 |
| 23a | (CDCl3) δ: 8.83(1H, s), 7.21-7.78(6H, m), 5.68-5.77(1H, m), 5.01-5.17(2H, m), 5.43(2H, d, J=5.6Hz), 3.88(2H, t, J=3.9Hz), 3.67(2H, t, J=3.9Hz), 3.00-3.11(4H, m), 2.55-2.83(4H, m), 2.42(3H, s). | 535 |
| 24a | (CDCl3) δ: 8.83(1H, s), 8.24(1H, s), 7.10-7.93(8H, m), 6.80(1H, d, J=8.8Hz), 5.65-5.78(1H, m), 5.13(1H, d, J=10.2Hz), 5.04(1H, d, J=17.0Hz), 4.72(2H, s), 4.42(2H, d, J=5.8Hz), 2.54(3H, s). | 487 |
| 25a | (CDCl3) δ: 8.74(1H, s), 7.43-7.33(2H, m), 7.29-7.25(1H, m), 7.21-7.15(1H, m), 7.13-7.08(1H, m), 6.53(1H, d, J=8.6Hz), 5.73-5.62(1H, m), 5.09(1H, d, J=10.2Hz), 5.03-4.97(1H, m), 4.37(2H, d, J=4.7Hz), 3.36-3.24(1H, m), 2.89-2.75(2H, m), 2.31(3H, s), 2.23-2.12(2H, m), 2.10-2.02(5H, m), 1.60-1.45(2H, m). | 476 |
| 26a | (CDCl3) δ: 8.82(1H, s), 7.21-7.69(5H, m), 6.93(1H, d, J=7.8Hz), 5.66-5.77(1H, m), 5.13(1H, d, J=10.0Hz), 5.03(1H, d, J=16.9Hz), 4.42(2H, d, J=6.1Hz), 3.60(2H, s), 3.43(2H, t, J=6.2Hz), 3.16(2H, t, J=6.2Hz), 3.04(3H, s), 2.30(3H, s). | 476 |
| 27a | (CDCl3) δ: 8.83(1H, s), 7.03-7.78(6H, m), 5.66-5.77(1H, m), 5.13(1H, d, J=10.1Hz), 5.03(1H, d, J=17.0Hz), 4.74(2H, s), 4.42(2H, d, J=5.9Hz), 3.63(2H, s), 3.41-3.47(2H, m), 3.20-3.26(2H, m), 3.04(3H, s). | 492 |
| 28a | (CDCl3) δ: 8.92(1H, s), 7.28-7.71(6H, m), 4.88(2H, s), 4.06(2H, t, J=7.3Hz), 3.11-3.13(4H, m), 2.60-2.85(4H, m), 2.49(3H, s), 1.53(2H, q, J=7.3Hz), 1.60-1.70(1H, m), 1.45-1.49(2H, m), −0.5--0.4(2H, m). | 506 |
| 29a | (CDCl3) δ: 8.83(1H, s), 7.50-7.70(1H, m), 7.52(1H, t, J=8.4Hz), 7.44(1H, t, J=3.4Hz), 7.29-7.38(1H, m), 7.23(1H, d, J=4.5Hz), 7.18(1H, d, J=8.7Hz), 4.76(2H, s), 4.10(2H, t, J=6.6Hz), 3.00(4H, t, J=4.7Hz), 2.64(2H, t, J=6.6Hz), 2.55-2.74(4H, m), 2.38(3H, s). | 491 |
| 30a | (CDCl3) δ: 8.82(1H, s), 8.00(1H, dd, J=7.8, 1.5Hz), 7.67-7.59(2H, m), 7.52-7.47(2H, m), 7.41(1H, dd, J=7.8, 1.0Hz), 7.25(1H, d, J=8.8Hz), 4.82(2H, s), 4.30-4.18(2H, m), 3.33(3H, s), 3.07-2.99(4H, m), 2.78-2.51(4H, m), 2.39(3H, s), 1.21(3H, t, J=7.1Hz). | 518 |
| 31a | (CDCl3) δ: 5.70(1H, ddt, J=17.1, 10.2, 5.9Hz), 5.12(1H, dd, J=10.2, 1.5Hz), 4.99(1H, dd, J=17.1, 1.5Hz), 4.72(2H, s), 4.40(2H, d, J=5.9Hz), 4.33-4.26(1H, m), 3.02-2.96(4H, m), 2.72-2.51(4H, m), 2.38(3H, s). | 515 |

-continued

| Compound No | ¹H NMR(400MHz) | ESI-MS (M+H)+ |
|---|---|---|
| 32a | (CDCl3) δ: 8.83(1H, s), 8.02(2H, d, J=8.3Hz), 7.58-7.50(3H, m), 7.22-7.18(1H, m), 7.17-7.08(1H, m), 5.68(1H, ddt, J=17.1, 10.2, 5.9Hz), 5.10(1H, dd, J=10.2, 1.5Hz), 4.99(1H, dd, J=17.1, 1.5Hz), 4.62(2H, s), 4.45(2H, d, J=5.9Hz), 3.05-2.99(4H, m), 2.73-2.55(4H, m), 2.39(3H, s). | 515 |
| 33a | (CD3OD) δ: 8.79(1H, s), 7.99(1H, s), 7.71(1H, s), 7.56(1H, d, J=2.4Hz), 7.38(1H, dd, J=8.4, 2.4Hz), 6.99(1H, d, J=8.4Hz), 5.79(1H, ddd, J=17.2, 10.4, 5.6Hz), 5.20(1H, d, J=10.4Hz), 5.07(1H, d, J=17.2Hz), 4.43(2H, d, J=5.6Hz), 3.99(3H, s), 2.92(4H, m), 2.66(4H, m), 2.40(3H, s), 2.26(3H, s). | 460 |
| 34a | (CD3OD) δ: 8.81(1H, s), 8.02(1H, s), 7.83(1H, d, J=2.4Hz), 7.71(1H, s), 7.51(1H, dd, J=8.4, 2.4Hz), 7.10(1H, d, J=8.4Hz), 5.79(1H, ddd, J=17.2, 10.0, 5.2Hz), 5.20(1H, d, J=10.0Hz), 5.07(1H, d, J=17.2Hz), 4.71(2H, s), 4.44(2H, d, J=5.2Hz), 4.00(3H, s), 2.98(4H, m), 2.91(4H, m), 2.38(3H, s). | 476 |
| 35a | (CDCl3) δ: 8.79(1H, s), 8.12(1H, d, J=6.8Hz), 8.06(1H, brs), 7.63-7.50(3H, m), 7.22-7.09(1H, m), 6.96(1H, d, J=8.3Hz), 5.69(1H, ddt, J=17.1, 9.8, 5.9Hz), 5.08(1H, d, J=9.8Hz), 4.97(1H, d, J=17.1Hz), 4.41(2H, d, J=5.9Hz), 3.22-2.80(8H, m), 2.67(3H, s), 2.24(3H, s). | 500 |
| 36a | (CDCl3) δ: 8.81(1H, s), 7.86-7.85(1H, m), 7.80-7.76(1H, m), 7.61-7.56(2H, m), 7.47-7.38(1H, m), 7.36-7.30(2H, m), 6.97(1H, d, J=8.3Hz), 6.24-6.18(1H, m), 5.69(1H, ddt, J=17.1, 10.2, 5.9Hz), 5.10(1H, dd, J=10.2, 1.0Hz), 4.98(1H, dd, J=17.1, 1.0Hz), 4.39(2H, d, J=5.9Hz), 3.03(3H, d, J=4.9Hz), 2.94-2.89(4H, m), 2.64-2.53(4H, m), 2.37(3H, s), 2.25(3H, s). | 513 |
| 37a | (CDCl3) δ: 8.77(1H, s), 7.17-7.49(5H, m), 6.91(1H, d, J=8.1Hz), 5.65-5.71(1H, m), 5.12(1H, d, J=10.2Hz), 5.06(1H, d, J=17.0Hz), 4.63(2H, s), 4.40(2H, d, J=6.0Hz), 3.57(3H, s), 1.30(6H, s). | 467 |
| 38a | (CDCl3) δ: 8.84(1H, s), 7.20-7.60(7H, m), 5.65-5.80(1H, m), 5.14(1H, d, 10.3Hz), 5.04(1H, d, J=17.1Hz), 4.42(2H, d, J=5.8Hz), 3.67(2H, s), 3.38(2H, s), 1.17(6H, s). | 451 |
| 39a | (CDCl3) δ: 8.84(1H, s), 7.24-7.71(8H, m), 5.69-5.78(1H, m), 5.15(1H, d, J=10.1Hz), 5.04(1H, d, J=17.0Hz), 4.43(2H, d, J=6.1Hz), 3.96(3H, s), 2.38(3H, s). | 444 |
| 40a | (CDCl3) δ: 8.77(1H, s), 7.18-7.50(5H, m), 6.65(1H, d, J=7.5Hz), 5.65-5.78(1H, m), 5.12(1H, d, J=10.5Hz), 5.04(1H, d, J=16.8Hz), 4.63(2H, s), 4.38-3.43(2H, m), 3.27-3.30(2H, m), 2.61-2.67(2H, m), 2.31(6H, s). | 466 |
| 41a | (CDCl3) δ: 8.74(1H, s), 8.51(1H, d, J=4.4Hz), 7.79-7.89(2H, m), 7.19-7.70(3H, m), 6.92(1H, d, J=7.3Hz), 5.59-5.71(1H, m), 5.00(1H, d, J=10.2Hz), 4.91(1H, d, J=16.8Hz), 4.74(2H, d, J=6.5Hz), 4.64(2H, s), 3.60(2H, s), 1.32(6H, s). | 462 |
| 42a | (CDCl3) δ: 8.82(1H, s), 7.46-7.43(2H, m), 7.38-7.28(2H, m), 7.00(1H, d, J=8.8Hz), 6.48(1H, d, J=1.5Hz), 5.73(1H, ddt, J=17.0, 10.2, 4.4Hz), 5.10-5.06(2H, m), 4.60(2H, d, J=4.4Hz), 3.95(3H, s), 2.97-2.90(4H, m), 2.69-2.53(4H, m), 2.38(3H, s), 2.29(3H, s). | 460 |
| 43a | (CDCl3) δ: 8.80(1H, s), 7.72(1H, brs), 7.52-7.47(1H, m), 7.46-7.41(1H, m), 7.41-7.36(2H, m), 7.34-7.31(2H, m), 7.06(1H, d, J=8.8Hz), 3.87(2H, q, J=7.0Hz), 2.96-2.91(4H, m), 2.66-2.53(4H, m), 2.38(3H, s), 2.30(3H, s), 1.07(4H, t, J=7.0Hz). | 522 |
| 44a | (DMSO-d6) δ: 8.85(1H, s), 8.54(1H, d, J=2.5Hz), 8.05(1H, t, J=8.3Hz), 7.88(1H, d, J=8.3Hz), 7.59-7.77(1H, m), 7.38-7.43(2H, m), 6.97(1H, d, J=8.3Hz), 5.61-5.72(1H, m), 5.01(1H, d, J=10.2Hz), 4.85(1H, d, J=17.0Hz), 4.59(2H, m), 2.93-3.01(4H, m), 3.78-3.86(4H, m), 2.24(3H, s). | 443 |
| 45a | (CDCl3) δ: 8.81(1H, s), 7.80(1H, s), 7.66(1H, s), 7.56(1H, br s), 7.53-7.46(3H, m), 7.39-7.29(3H, m), 6.90-6.81(1H, m), 3.97(3H, s), 3.90(3H, q, J=7.0Hz), 2.92-2.84(4H, m), 2.66-2.50(4H, m), 2.38(3H, s), 2.19(3H, s), 1.10(4H, t, J=7.0Hz). | 524 |
| 46a | (DMSO-d6) δ: 10.15(1H, brs), 8.85(1H, s), 8.05(1H, dd, J=8.0, 7.8Hz), 7.76(1H, d, J=8.4Hz), 7.66(1H, brs), 7.45(1H, d, J=8.2Hz), 7.41(1H, d, J=9.0Hz), 6.99(1H, d, J=8.6Hz), 5.75-5.60(1H, m), 5.54(1H, t, J=5.7Hz), 5.01(1H, d, J=10.0Hz), 4.87(1H, d, J=17.2Hz), 4.60-4.58(4H, m), 2.81(4H, brs), 2.45(4H, brs), 2.24(6H, s). | 487 |
| 47a | (CDCl3) δ: 8.82(1H, s), 8.54(1H, d, J=4.9Hz), 7.93-7.84(2H, m), 7.55-7.48(1H, m), 7.33-7.24(2H, m), 7.02(1H, d, J=8.8Hz), 4.19(2H, q, J=7.2Hz), 2.97-2.91(4H, m), 2.66-2.54(4H, m), 2.38(3H, s), 2.33(3H, s), 1.07(3H, t, J=7.2Hz). | 461 |
| 48a | (CDCl3) δ: 8.84(1H, s), 8.55(1H, dd, J=4.4, 2.0Hz), 7.94(1H, d, J=7.8, 2.0Hz), 7.87(1H, d, J=8.8Hz), 7.66-7.58(1H, m), 7.38-7.32(1H, m), 7.31-7.27(1H, m), 7.20(1H, d, J=8.8Hz), | 445 |

-continued

| Compound No | ¹H NMR(400MHz) | ESI-MS (M+H)+ |
|---|---|---|
| | 4.80(2H, s), 4.19(2H, q, J=7.2Hz), 3.05-2.99(4H, m), 2.73-2.53(4H, m), 2.38(3H, s), 1.08(3H, t, J=7.2Hz). | |
| 49a | (CD3OD) δ: 8.80(1H, s), 7.99(1H, s), 7.82(1H, d, J=2.0Hz), 7.69(1H, s), 7.57(1H, dd, J=8.8, 2.0Hz), 7.11(1h, d, J=8.8Hz), 5.80(1H, ddd, J=17.2, 10.4, 5.2Hz), 5.19(1H, d, J=10.4Hz), 5.10(1H, d, J=17.2Hz), 4.72(2H, s), 4.60(2H, d, J=5.2Hz), 2.97(4H, m), 2.66(4H, m), 2.39(3H, s). | 462 |
| 50a | (CD3OD) δ: 9.38(1H, s), 8.85(1H, s), 8.56(1H, d, J=11.2Hz), 8.56(1H, d, J=11.2Hz), 8.56(1H, d, J=11.2Hz), 7.83(1H, J=2.0Hz), 7.53(1H, dd, J=8.8, 2.0Hz), 7.18(1H, d, J=8.8Hz), 5.78(1H, ddd, J=16.8, 10, 6.8Hz), 5.09(1H, d, J=10Hz), 5.00(1H, d, J=16.8Hz), 4.79(1H, d, J=6.8Hz), 4.78(2H, s), 3.02(4H, m), 2.69(4H, m), 2.41(3H, s). | 474 |
| 51a | (CD3OD) δ: 8.78(1H, s), 8.42(1H, brs), 8.04(1H, d, J=7.3Hz), 7.73-7.66(1H, m), 7.61(1H, t, J=7.8Hz), 7.31(1H, d, J=7.8Hz), 7.15-7.06(1H, m), 6.36-6.17(1H, m), 5.77(1H, ddt, J=17.1, 10.2, 5.4Hz), 5.14(1H, d, J=10.2Hz), 5.04(1H, d, J=17.1Hz), 4.52(2H, d, J=5.4Hz), 3.38-3.25(4H, m), 2.97(3H, s), 2.96-2.88(4H, m), 2.08(3H, s). | 524 |
| 52a | (CDCl3) δ: 8.85(1H, s), 7.81-7.53(1H, m), 7.50(1H, dd, J=5.1, 3.2Hz), 7.42(1H, dd, J=3.2, 1.2Hz), 7.37-7.28(1H, m), 7.17(1H, d, J=8.8Hz), 7.14(1H, d, J=5.4Hz), 4.74(2H, s), 4.40(2H, q, J=8.1Hz), 3.00(4H, t, J=4.6Hz), 2.86-2.44(4H, m), 2.38(3H, s). | 520 |
| 53a | (CDCl3) δ: 8.82(1H, s), 8.36(1H, d, J=4.9Hz), 7.68(1H, brs), 7.59-7.50(1H, m), 7.22(1H, brs), 7.06-7.03(1H, m), 7.03(1H, d, J=8.8Hz), 5.68(1H, ddt, J=17.1, 10.2, 6.3Hz), 5.02(1H, dd, J=10.2, 1.5Hz), 4.92(1H, dd, J=17.1, 1.5Hz), 4.77(2H, d, J=6.3Hz), 2.97-2.90(4H, m), 2.69-2.52(4H, m), 2.46(3H, s), 2.38(3H, s), 2.30(3H, s). | 471 |
| 54a | (CDCl3) δ: 8.84(1H, s), 7.64-7.53(1H, m), 7.51(1H, dd, J=5.1, 3.2Hz), 7.42(1H, d, J=2.0Hz), 7.37-7.28(1H, m), 7.22-7.14(2H, m), 6.01(1H, tt, J=55.6, 4.4Hz), 4.75(2H, s), 4.12(1H, td, J=13.0, 4.2Hz), 3.01(4H, t, J=4.6Hz), 2.80-2.46(4H, m), 2.39(3H, s). | 502 |
| 55a | (CDCl3) δ: 8.77(1H, s), 7.62-7.47(1H, m), 7.45(1H, dd, J=5.1, 3.2Hz), 7.39(1H, dd, J=3.4, 1.5Hz), 7.34-7.28(1H, m), 7.21-7.14(2H, m), 4.76(2H, s), 4.32-4.25(1H, m), 3.00(4H, t, J=4.9Hz), 2.78-2.47(4H, m), 2.38(3H, s), 1.39(6H, d, J=6.8Hz). | 480 |
| 56a | (DMSO-d6) δ: 10.22(1H, brs), 8.87(1H, s), 8.56(1H, dd, J=4.9, 1.0Hz), 8.10-8.06(1H, m), 7.89(1H, d, J=8.3Hz), 7.69(1H, brs), 7.49-7.37(2H, m), 7.10(1H, d, J=8.8Hz), 5.68(1H, ddt, J=17.1, 10.2, 5.9Hz), 5.02(1H, dd, J=10.2, 1.5Hz), 4.87(1H, dd, J=17.1, 1.5Hz), 4.60(2H, d, J=5.9Hz), 3.32(2H, s), 3.26(8H, s), 2.28(3H, s). | 492 |
| 57a | (CDCl3) δ: 9.10(1H, d, J=2.3Hz), 8.85(1H, s), 8.39(1H, dd, J=8.6, 2.3Hz), 8.11(1H, d, J=8.6Hz), 7.57-7.39(2H, m), 7.31(1H, dd, J=8.6, 2.3Hz), 7.05(1H, d, J=8.6Hz), 5.65(1H, ddt, J=17.0, 10.2, 6.3Hz), 5.01(1H, dd, J=10.2, 1.2Hz), 4.92(1H, dd, J=17.0, 1.2Hz), 4.86(2H, d, J=6.3Hz), 3.99(3H, s), 2.98-2.93(4H, m), 2.72-2.52(4H, m), 2.38(3H, s), 2.35(3H, s). | 515 |
| 58a | (CDCl3) δ: 8.83(1H, s), 8.54(1H, d, J=5.3Hz), 7.90-7.83(2H, m), 7.58(2H, d, J=8.8Hz), 7.56(1H, brs), 7.48(1H, d, J=8.2Hz), 5.69(1H, ddt, J=17.6, 10.4, 6.5Hz), 5.02(1H, d, J=10.4Hz), 4.92(1H, d, J=17.6Hz), 4.78(2H, d, J=6.5Hz), 2.84-2.80(2H, m), 2.55-2.49(2H, m), 2.41(3H, s), 2.25-2.22(2H, m), 1.81-1.77(2H, m). | 548 |
| 59a | (CD3OD) δ: 8.87(1H, s), 8.57(1H, d, J=8.3Hz), 8.06(1H, t, J=8.5Hz), 7.93(1H, d, J=7.6Hz), 7.68(2H, d, J=8.2Hz), 7.43(1H, dd, J=7.4, 4.9Hz), 7.26(2H, d, J=8.6Hz), 5.80-5.70(1H, m), 5.08(1H, d, J=9.6Hz), 4.96(1H, d, J=17.8Hz), 4.74(2H, d, J=5.9Hz), 3.52(2H, d, J=12.7Hz), 3.14(2H, dd, J=13.3, 10.2Hz), 2.93-2.88(1H, m), 2.10(2H, d, J=12.7Hz), 1.98-1.87(2H, m). | 428 |
| 60a | (CDCl3) δ: 8.81(1H, s), 7.63-7.53(5H, m), 7.43(1H, d, J=6.8Hz), 7.38-7.32(1H, m), 7.16(1H, d, J=8.8Hz), 4.75(2H, s), 3.87(2H, q, J=7.0Hz), 3.15(3H, s), 3.05-2.95(7H, m), 2.74-2.52(4H, m), 2.38(3H, s), 1.07(3H, t, J=7.0Hz). | 531 |
| 61a | (CDCl3) δ: 8.80(1H, s), 7.63-7.48(4H, m), 7.46-7.33(3H, m), 6.98(1H, d, J=8.3Hz), 3.87(2H, q, J=7.0Hz), 3.68(2H, t, J=5.4Hz), 3.14(3H, s), 2.98(3H, s), 2.96-2.91(4H, m), 2.76-2.67(4H, m), 2.65(2H, t, J=5.4Hz), 2.29(3H, s), 1.07(3H, t, J=7.0Hz). | 545 |
| 62a | (CDCl3) δ: 8.85(1H, s), 8.58(1H, d, J=1.5Hz), 7.86(1H, dt, J=4.5, 1.5Hz), 7.65(1H, d, J=4.5Hz), 6.92-7.29(8H, m), 5.36(2H, s), 4.75(2H, s), 3.00-3.03(4H, m), 2.52-2.79(4H, m), 2.40(3H, s). | 523 |

-continued

| Compound No | $^1$H NMR(400MHz) | ESI-MS (M+H)+ |
|---|---|---|
| 63a | (CDCl3) δ: 9.17(1H, s), 8.84-8.87(3H, m), 7.55-7.80(3H, bs), 7.00-7.26(5H, m), 4.99(2H, s), 4.77(2H, m), 2.98-3.01(4H, m), 2.63(4H, bs), 2.37(3H, s). | 524 |
| 64a | (CDCl3) δ: 8.89(1H, s), 8.55(1H, d, J=5.1Hz), 8.14-7.85(3H, m), 7.63-7.16(4H, m), 5.71(1H, ddt, J=17.1, 10.2, 5.9Hz), 5.03(1H, d, J=10.2Hz), 4.92(1H, d, J=17.1Hz), 4.72(2H, d, J=5.9Hz), 3.26(0.75H, t, J=7.0Hz), 3.13(1.25H, s), 2.87(1.75H, s), 2.62(1.25H, t, J=7.0Hz), 2.34(3H, s), 2.32(3H, s), 2.05(3H, s), 2.04-1.90(2H, m) | 487 |
| 65a | (CDCl3) δ: 8.83(1H, s), 8.53(1H, d, J=4.9Hz), 7.93-7.31(6H, m), 5.69(1H, ddt, J=17.1, 10.2, 5.9Hz), 5.02(1H, d, J=10.2Hz), 4.92(1H, d, J=17.1Hz), 4.80(2H, d, J=5.9Hz), 3.88(2H, t, J=6.0Hz), 2.76(2H, t, J=6.0Hz), 2.38(6H, s), 2.30(6H, s). | 460 |
| 66a | (CDCl3) δ: 8.83(1H, s), 7.74(1H, brs), 7.52(1H, brs), 7.44(2H, brs), 7.27(2H, brs), 7.01(1H, d, J=8.5Hz), 6.70(1H, brs), 5.78-5.65(1H, m), 5.06-4.90(2H, m), 4.81(2H, brs), 3.94(3H, s), 2.94(4H, brs), 2.61(4H, brs), 2.39(3H, s), 2.32(3H, s). | 487 |
| 67a | (CDCl3) δ: 8.88(1H, s), 7.82(1H, dd, J=8.2, 7.8Hz), 7.64(1H, brs), 7.47(1H, brs), 7.43(1H, d, J=7.4Hz), 7.41(1H, brs), 7.24(1H, d, J=8.2Hz), 5.80-5.70(1H, m), 5.08(1H, d, J=9.2Hz), 5.00(1H, d, J=18.0Hz), 4.85-4.81(4H, m), 3.97(3H, s), 3.00(3H, brs), 2.67(4H, brs), 2.43(3H, s). | 503 |
| 68a | (CD3OD) δ: 8.79(1H, s), 7.89(1H, t, J=7.8Hz), 7.66(1H, d, J=7.9Hz), 7.55(1H, brs), 7.39(1H, d, J=8.8Hz), 7.25(1H, d, J=7.8Hz), 7.00(1H, d, J=8.6Hz), 5.72(1H, ddt, J=17.2, 10.8, 6.1Hz), 5.04(1H, d, J=10.8Hz), 4.92(1H, d, J=17.2Hz), 4.69(2H, d, J=6.1Hz), 2.91(4H, brs), 2.62(4H, brs), 2.56(3H, s), 2.36(3H, s), 2.27(3H, s). | 471 |
| 69a | (CDCl3) δ: 8.84(1H, s), 7.92(1H, d, J=8.3Hz), 7.68(1H, t, J=7.8Hz), 7.43(1H, brs), 7.40(1H, d, J=6.8Hz), 7.36(1H, dd, J=8.0, 1.2Hz), 7.05(1H, d, J=8.8Hz), 5.69(1H, ddt, J=17.1, 10.2, 6.3Hz), 5.04(1H, dd, J=10.2, 1.5Hz), 4.99(1H, dd, J=17.1, 1.5Hz), 4.81(2H, d, J=6.3Hz), 3.01(4H, brs), 2.71(4H, br s), 2.46(3H, s), 2.32(3H, s), 1.13(1H, d, J=6.3Hz), 0.00(6H, t, J=3.4Hz). | 535 |
| 70a | (CD3OD) δ: 8.80(1H, s), 8.12(1H, dd, J=15.6, 7.6Hz), 7.87(1H, d, J=7.8Hz), 7.56(1H, brs), 7.40(1H, d, J=11.2Hz), 7.05-7.01(2H, m), 5.73(1H, ddt, J=16.2, 10.2, 6.3Hz), 5.06(1H, d, J=10.2Hz), 4.98(1H, d, J=16.2Hz), 4.74(2H, d, J=6.3Hz), 2.93(4H, brs), 2.63(4H, brs), 2.36(3H, s), 2.30(3H, s). | 475 |
| 71a | (CDCl3) δ: 8.85(1H, s), 7.99(1H, dd, J=15.9, 7.8Hz), 7.79(1H, d, J=7.6Hz), 7.59(1H, brs), 7.52(1H, brs), 7.37(1H, brs), 7.22(1H, d, J=8.2Hz), 6.87(1H, dd, J=5.7, 2.4Hz), 5.75-5.60(1H, m), 5.02(1H, d, J=10.2Hz), 4.98(1H, d, J=17.2Hz), 4.80(4H, brs), 3.04(4H, brs), 2.64(4H, brs), 2.40(3H, s). | 491 |
| 72a | (CDCl3) δ: 8.85(1H, s), 8.53(1H, d, J=3.1Hz), 7.83-7.95(2H, m), 7.17-7.80(4H,), 5.62-5.73(1H, m), 5.60(1H, bs), 5.02(1H, d, J=10.0Hz), 4.91(1H, d, J=17.2Hz), 4.76-4.81(4H, m), 3.91(1H, bs), 3.12-3.20(2H, m), 2.79-2.87(2H, m), 2.06-2.12(2H, m), 1.73-1.86(2H, m). | 474 |
| 73a | (DMSO-d6) δ: 8.83(1H, s), 8.03-7.99(1H, m), 7.96(1H, d, J=6.8Hz), 7.73-7.65(2H, m), 7.52-7.45(2H, m), 6.93(1H, d, J=9.3Hz), 5.66(1H, ddt, J=17.1, 10.2, 8.3Hz), 5.07(1H, dd, J=10.2, 1.5Hz), 4.92(1H, dd, J=17.1, 1.5Hz), 4.29(2H, brs), 3.73-3.69(4H, m), 2.79-2.74(4H, m), 2.16(3H, s). | 487 |
| 74a | (CDCl3) δ: 8.83(1H, s), 7.62-7.49(5H, m), 7.43(1H, dd, J=7.3, 1.0Hz), 7.36-7.29(1H, m), 7.15(1H, d, J=8.8Hz), 5.68(1H, ddt, J=17.1, 10.2, 6.3Hz), 5.10(1H, d, J=10.2Hz), 4.98(1H, d, J=17.1Hz), 4.73(2H, s), 4.40(2H, d, J=6.3Hz), 3.14(3H, s), 3.04-2.96(7H, m), 2.72-2.54(4H, m), 2.38(3H, s). | 543 |
| 75a | (CDCl3) δ: 8.84(1H, s), 8.58(1H, dd, J=2.3, 0.7Hz), 8.05(1H, d, J=8.5Hz), 7.94(1H, dd, J=8.5, 2.3Hz), 7.63-7.40(2H, m), 7.30(1H, dd, J=8.6, 2.3Hz), 7.03(1H, d, J=8.6Hz), 5.67(1H, ddt, J=16.8, 10.0, 6.6Hz), 5.03(1H, dd, J=10.2, 1.2Hz), 4.95(1H, dd, J=16.8, 1.2Hz), 4.82(2H, d, J=6.6Hz), 3.17(3H, br s), 3.08(3H, brs), 2.99-2.89(4H, m), 2.72-2.51(4H, m), 2.39(3H, s), 2.34(3H, s). | 528 |
| 76a | (CD3OD) δ: 8.78(1H, s), 8.07(1H, brs), 7.91(1H, brs), 7.88-7.83(1H, m), 7.61-7.56(2H, m), 7.52-7.43(2H, m), 7.42-7.36(1H, m), 6.88(1H, d, J=8.8Hz), 5.61(1H, ddt, J=17.3, 10.5, 6.3Hz), 5.02(1H, dd, J=10.5, 1.2Hz), 4.86(1H, dd, J=17.3, 1.2Hz), 4.24(2H, brs), 3.67-3.62(4H, m), 2.72-2.68(4H, m), 2.11(3H, s). | 486 |
| 77a | (CDCl3) δ: 8.84(1H, s), 8.55(1H, d, J=5.1Hz), 7.96-7.94(1H, m), 7.60-7.44(2H, m), 7.19(1H, dd, J=5.1, 1.2Hz), 7.05(1H, d, J=8.3Hz), 5.69(1H, ddt, J=17.1, 10.0, 6.3Hz), 5.04(1H, dd, | 528 |

-continued

| Compound No | ¹H NMR(400MHz) | ESI-MS (M+H)+ |
|---|---|---|
| | J=10.0, 1.2Hz), 4.96(1H, dd, J=17.1, 1.0Hz), 4.80(2H, d, J=6.3Hz), 3.15(3H, s), 2.99-2.95(4H, m), 2.81(3H, s), 2.68-2.57(4H, m), 2.39(3H, s), 2.31(3H, s). | |
| 78a | (CDCl3) δ: 8.85(1H, s), 8.56(1H, d, J=5.4Hz), 7.95(1H, s), 7.80-7.66(1H, m), 7.52-7.46(2H, m), 7.23-7.17(2H, m), 5.68(1H, ddt, J=17.1, 10.2, 6.3Hz), 5.03(1H, d, J=10.2Hz), 4.94(1H, d, J=17.1Hz), 4.79(2H, d, J=6.3Hz), 4.77(2H, s), 3.16(3H, s), 3.04-2.99(4H, m), 2.90(3H, s), 2.71-2.55(4H, m), 2.38(3H, s). | 544 |
| 79a | (CDCl3) δ: 8.79(1H, s), 8.56-8.54(1H, m), 7.87(1H, td, J=7.8, 2.0Hz), 7.74(1H, d, J=7.8Hz), 7.52-7.37(2H, m), 7.30-7.26(1H, m), 7.00(1H, d, J=8.8Hz), 4.71-4.69(1H, m), 2.94(4H, t, J=4.6Hz), 2.69-2.45(6H, m), 2.39(3H, s), 2.32(3H, s), 2.23-2.15(2H, m), 1.74-1.56(2H, m), 1.26(3H, ddd, J=36.2, 20.6, 16.5Hz). | 471 |
| 80a | (CDCl3) δ: 8.83(1H, s), 8.37(1H, d, J=2.7Hz), 7.91-7.85(1H, m), 7.64-7.35(3H, m), 7.33-7.22(1H, m), 7.02(1H, d, J=8.5Hz), 5.67(1H, ddt, J=16.8, 10.2, 6.5Hz), 5.03(1H, d, J=10.2Hz), 4.93(1H, d, J=16.8Hz), 4.73(2H, d, J=6.5Hz), 2.98-2.92(4H, m), 2.72-2.50(4H, m), 2.39(3H, s), 2.32(3H, s). | 475 |
| 81a | (CDCl3) δ: 8.81(1H, s), 8.51(1H, d, J=3.2Hz), 7.79-7.92(2H, m), 7.18-7.70(3H, m), 6.86(1H, d, J=8.5Hz), 5.63-5.75(1H, m), 5.01(1H, d, J=10.2Hz), 4.91(1H, d, J=17.1Hz), 4.78(2H, d, J=6.0Hz), 3.59(2H, s), 2.22(3H, s), 1.30(9H, s). | 446 |
| 82a | (CD3OD) δ: 8.88(1H, s), 8.59-8.57(1H, m), 8.06(1H, t, J=8.2Hz), 7.95(1H, s), 7.70(1H, brs), 7.50-7.42(2H, m), 7.10(1H, d, J=8.6Hz), 5.76(1H, ddt, J=16.8, 10.8, 6.3Hz), 5.09(1H, d, J=10.8Hz), 4.96(1H, d, J=16.8Hz), 4.75(2H, d, J=6.3Hz), 3.86(2H, brs), 3.49(2H, t, J=6.0Hz), 2.64(2H, brs), 2.36(3H, s). | 440 |
| 83a | (CD3OD) δ: 8.87(1H, s), 8.57-8.56(1H, m), 8.08-8.04(1H, m), 7.95(1H, d, J=8.2Hz), 7.64(1H, brs), 7.46-7.42(2H, m), 7.19(1H, d, J=8.2Hz), 5.76(1H, ddt, J=18.6, 10.2, 6.1Hz), 5.08(1H, d, J=10.2Hz), 4.97(1H, d, J=18.6Hz), 4.75(2H, d, J=6.1Hz), 3.49-3.45(2H, m), 3.17-3.10(2H, m), 2.40(3H, s), 2.01-1.85(4H, m). | 442 |
| 84a | (CDCl3) δ: 8.83(1H, s), 7.64(1H, brs), 7.61(1H, dd, J=8.2, 7.8Hz), 7.42-7.34(2H, m), 7.26(1H, d, J=9.0Hz), 6.98(1H, d, J=8.0Hz), 6.41(1H, d, J=8.8Hz), 5.77-5.63(1H, m), 5.04(1H, d, J=10.0Hz), 4.97(1H, d, J=15.3Hz), 4.86-4.70(5H, m), 3.10-2.91(4H, brs), 2.85(3H, s), 2.76-2.60(4H, brs), 2.40(3H, s), 1.16(6H, d, J=6.9Hz). | 544 |
| 85a | (CDCl3) δ: 8.85(1H, s), 8.54(1H, d, J=4.9Hz), 7.90-7.84(2H, m), 7.76-7.45(2H, m), 7.36(1H, dd, J=8.5, 2.4Hz), 7.30-7.24(1H, m), 7.00(1H, d, J=8.5Hz), 5.69(1H, ddt, J=16.8, 10.2, 6.5Hz), 5.02(1H, d, J=10.2Hz), 4.92(1H, d, J=16.8Hz), 4.78(2H, d, J=6.5Hz), 3.43-3.37(4H, m), 3.03-2.98(4H, m), 2.86(3H, s), 2.33(3H, s). | 521 |
| 86a | (CDCl3) δ: 8.83(1H, s), 8.52(1H, d, J=2.8Hz), 7.01-7.80(4H, m), 5.63-5.74(1H, m), 5.02(1H, d, J=9.9Hz), 4.91(1H, d, J=17.5Hz), 4.79(2H, d, J=6.0Hz), 2.96-2.98(4H, m), 2.63(4H, bs), 2.34(3H, s), 2.32-2.382H, m), 0.89-0.99(1H, m), 0.54-0.59(2H, m), 0.15-0.192H, m). | 497 |
| 87a | (CDCl3) δ: 8.78(1H, s), 8.55(1H, d, J=3.9Hz), 7.89(2H, dt, J=3.9, 8.3Hz), 7.81(2H, d, J=8.3Hz), 7.49(1H, brs), 7.30-7.25(3H, m), 7.00(1H, d, J=8.8Hz), 3.33(1H, s), 2.94(4H, t, J=4.9Hz), 2.62(4H, brs), 2.39(3H, s), 2.31(3H, s), 0.95-0.89(4H, m). | 457 |
| 88a | (CDCl3) δ: 8.80(1H, s), 8.52(1H, dt, J=4.8, 1.4Hz), 7.89(1H, d, J=7.6Hz), 7.84(1H, dt, J=1.7, 7.6Hz), 7.57-7.14(4H, m), 6.48(1H, d, J=8.5Hz), 5.68(1H, ddt, J=16.8, 10.2, 6.5Hz), 5.01(1H, dd, J=10.2, 1.2Hz), 4.92(1H, dd, J=16.8, 1.2Hz), 4.78(2H, d, J=6.5Hz), 4.76-4.68(1H, m), 4.24-4.19(2H, m), 3.71-3.65(2H, m), 2.30-2.18(1H, m), 2.22(3H, s). | 430 |
| 89a | (CDCl3) δ: 8.83(1H, s), 7.47(1H, s), 6.96-7.36(9H, m), 4.96(2H, s), 3.92(3H, s), 2.92(4H, s), 2.55-2.72(4H, bs), 2.39(3H, s), 2.26(3H, s). | 510 |
| 90a | (CDCl3) δ: 8.80(1H, s), 7.46(1H, brs), 7.32(1H, dd, J=8.8, 2.0Hz), 7.27(1H, t, J=8.0Hz), 6.98(1H, d, J=8.8Hz), 6.81(1H, d, J=8.0Hz), 6.74(1H, s), 6.68(1H, dd, J=8.3, 2.0Hz), 5.71(1H, ddt, J=17.1, 10.2, 6.3Hz), 5.11(1H, dd, J=10.2, 1.0Hz), 5.02(1H, d, J=17.1, 1.0Hz), 4.40(2H, d, J=6.3Hz), 3.84(2H, s), 2.95-2.89(4H, m), 2.66-2.52(4H, m), 2.37(3H, s), 2.28(3H, s). | 471 |
| 91a | (CDCl3) δ: 8.82(1H, s), 7.57-7.49(1H, m), 7.47(1H, t, J=7.8Hz), 7.43-7.32(5H, m), 6.95(1H, d, J=8.8Hz), 5.70(1H, ddt, J=17.1, | 500 |

-continued

| Compound No | ¹H NMR(400MHz) | ESI-MS (M+H)+ |
|---|---|---|
| | 10.0, 5.9Hz), 5.09(1H, dd, J=10.0, 1.5Hz), 4.97(1H, dd, J=17.1, 1.5Hz), 4.39(2H, d, J=5.9Hz), 3.87-3.82(4H, m), 3.51(2H, s), 2.89-2.85(4H, m), 2.28(9H, s). | |
| 92a | (CDCl3) δ: 8.85(1H, s), 8.76(1H, dd, J=2.2, 0.7Hz), 8.25(1H, dd, J=8.8, 0.7Hz), 8.00(1H, d, J=8.8Hz), 7.69-7.22(3H, m), 7.06(1H, d, J=8.5Hz), 5.64(1H, ddt, J=16.8, 10.2, 6.6Hz), 5.03(1H, dd, J=10.2, 1.0Hz), 4.95(1H, dd, J=16.8, 1.0Hz), 4.85(2H, d, J=6.6Hz), 3.00-2.94(4H, m), 2.75-2.50(4H, m), 2.40(3H, s), 2.35(3H, s). | 482 |
| 93a | (CDCl3) δ: 8.81(1H, s), 7.47(1H, t, J=8.0Hz), 7.43-7.32(6H, m), 6.96(1H, d, J=8.0Hz), 5.69(1H, ddt, J=17.1, 10.2, 5.9Hz), 5.09(1H, dd, J=10.2, 1.0Hz), 4.96(1H, dd, J=17.1, 1.0Hz), 4.39(2H, d, J=5.9Hz), 3.50(2H, s), 2.94-2.90(4H, m), 2.65-2.55(4H, m), 2.38(3H, s), 2.27(6H, s), 2.17(3H, s). | 513 |
| 94a | (CDCl3) δ: 8.81(1H, s), 7.73-7.62(1H, m), 7.50-7.34(6H, m), 6.95(1H, d, J=8.8Hz), 5.69(1H, ddt, J=17.1, 10.2, 5.9Hz), 5.09(1H, dd, J=10.2, 1.0Hz), 4.98(1H, dd, J=17.1, 1.0Hz), 4.39(2H, d, J=5.9Hz), 3.88(2H, s), 3.86-3.82(4H, m), 2.89-2.85(4H, m), 2.50(3H, s), 2.28(3H, s). | 486 |
| 95a | (CDCl3) δ: 8.81(1H, s), 7.49(1H, t, J=8.8Hz), 7.40-7.23(6H, m), 6.99(1H, d, J=8.8Hz), 5.69(1H, ddt, J=17.1, 10.2, 6.3Hz), 5.10(1H, dd, J=10.2, 1.0Hz), 5.00(1H, dd, J=17.1, 1.0Hz), 4.41(2H, d, J=6.3Hz), 3.04(3H, s), 2.94-2.89(4H, m), 2.66-2.55(4H, m), 2.37(3H, s), 2.27(3H, s). | 549 |
| 96a | (CDCl3) δ: 8.91(1H, s), 8.19(1H, d, J=8.0Hz), 8.09(1H, dd, J=8.0, 7.6Hz), 8.01(1H, d, J=7.5Hz), 7.61(1H, brs), 7.39(1H, brs), 7.25(1H, d, J=8.8Hz), 5.76-5.68(1H, m), 5.06(1H, d, J=10.4Hz), 4.94-4.82(3H, m), 4.82(2H, s), 3.07(4H, t, J=4.9Hz), 2.75(3H, s), 2.72(4H, brs), 2.43(3H, s). | 515 |
| 97a | (CDCl3) δ: 8.86(1H, s), 8.53(1H, d, J=4.7Hz), 7.86(1H, d, J=4.3Hz), 7.72(1H, brs), 7.51(2H, d, J=8.2Hz), 7.25(2H, dd, J=4.9, 4.4Hz), 7.19(2H, d, J=8.4Hz), 5.69(1H, ddt, J=16.8, 10.4, 5.8Hz), 5.02(1H, d, J=10.4Hz), 4.92(1H, d, J=16.8Hz), 4.79(2H, d, J=5.8Hz), 3.06(2H, d, J=11.6Hz), 2.82(1H, septet, J=6.5Hz), 2.50-2.26(1H, m), 1.85-1.81(4H, m), 1.12(6H, d, J=6.5Hz). | 470 |
| 98a | (CD3OD) δ: 8.91(1H, s), 8.57(1H, d, J=5.2Hz), 8.12(1H, dd, J=8.8, 8.4H), 8.01(1H, s), 7.94(1H, d, J=8.4Hz), 7.98(1H, d, J=8.4Hz), 7.88(2H, d, J=9.2Hz), 7.51(2H, d, J=9.2Hz), 7.44(1H, dd, J=8.8, 5.2Hz), 7.30(1H, s), 5.76(1H, ddd, J=17.2, 10.4, 6.0Hz), 5.09(1H, d, J=10.4Hz), 4.97(1H, d, J=17.2Hz), 4.76(2H, d, J=6.0Hz), 2.29(3H, s). | 439 |
| 99a | (CDCl3) δ: 8.82(1H, s), 8.52(1H, td, J=3.2, 1.7Hz), 7.89-7.81(2H, m), 7.72-7.32(2H, m), 7.28-7.17(2H, m), 6.55(1H, d, J=8.8Hz), 5.68(1H, ddt, J=17.0, 10.3, 6.3Hz), 5.01(1H, dd, J=10.3, 1.3Hz), 4.92(1H, dd, J=17.0, 1.3Hz), 4.81-4.71(3H, m), 3.89-3.83(2H, m), 3.12-3.06(2H, m), 2.42(1H, ttt, J=6.1, 6.1, 6.1Hz), 2.24(3H, s), 0.99(6H, d, J=6.1Hz). | 482 |
| 100a | (CDCl3) δ: 8.84(1H, s), 8.54(1H, d, J=4.6Hz), 7.82-7.92(2H, m), 7.18-7.78(4H, m), 5.63-5.72(1H, m), 5.02(1H, d, J=10.2Hz), 4.91(1H, d, J=17.3Hz), 4.77-4.80(4H, m), 2.98(4H, bs), 2.83(4H, bs), 1.62(1H, bs), 0.43-0.59(4H, m). | 499 |
| 101a | (CDCl3) δ: 8.82(1H, s), 7.50(1H, t, J=8.3Hz), 7.41(1H, s), 7.37(1H, dd, J=8.8, 2.4Hz), 7.34-7.28(3H, m), 7.00(1H, d, J=8.3Hz), 5.70(1H, ddt, J=17.1, 10.0, 6.3Hz), 5.11(1H, dd, J=10.0, 1.0Hz), 5.00(1H, dd, J=17.1, 1.0Hz), 4.42(2H, d, J=6.3Hz), 3.87-3.83(4H, m), 3.05(3H, s), 2.91-2.87(4H, m), 2.31(3H, s). | 536 |
| 102a | (CDCl3) δ: 8.84(1H, s), 8.54(1H, d, J=4.9Hz), 7.90-7.87(2H, m), 7.50(1H, brs), 7.40(1H, brs), 7.31(1H, d, J=9.0Hz), 7.03(1H, d, J=8.6Hz), 3.56(3H, s), 2.96(4H, t, J=4.5Hz), 2.62(4H, brs), 2.39(3H, s), 2.33(3H, s). | 431 |
| 103a | (CD3OD) δ: 8.80(1H, s), 7.69(1H, s), 7.53(2H, m), 7.32(1H, s), 7.01(1H, d, J=8.8Hz), 5.77(1H, ddd, J=16.8, 10.4, 10.0Hz), 5.16(1H, d, J=10.4Hz), 5.06(1H, d, J=16.8Hz), 4.48(2H, d, J=10.0Hz), 3.16(6H, s), 3.01(6H, s), 2.95(4H, m), 2.66(4H, m), 2.39(3H, s), 2.27(3H, s). | 598 |
| 104a | (CDCl3) δ: 8.81(1H, s), 7.47(2H, t, J=7.8Hz), 7.43-7.29(4H, m), 6.94(1H, d, J=8.8Hz), 5.75-5.64(1H, m), 5.09(1H, dd, J=10.2, 1.0Hz), 4.96(1H, dd, J=17.1, 1.0Hz), 4.39(2H, d, J=6.3Hz), 3.51(2H, s), 2.86(4H, t, J=4.4Hz), 2.82-2.74(4H, m), 2.28(6H, s), 1.74-1.66(1H, m), 0.52-0.43(4H, m). | 539 |
| 105a | (CDCl3) δ: 8.82(1H, s), 7.66-7.55(1H, m), 7.46(2H, t, J=7.8Hz), 7.45-7.40(1H, m), 7.32(2H, t, J=9.0Hz), 7.11(1H, d, J=8.3Hz), 5.75-5.64(1H, m), 5.10(1H, dd, J=10.2, 1.0Hz), 4.97(1H, dd, J=17.1, 1.5Hz), 4.74(2H, s), 4.39(2H, d, J=5.9Hz), | 555 |

-continued

| Compound No | ¹H NMR(400MHz) | ESI-MS (M+H)+ |
|---|---|---|
| | 3.51(2H, s), 2.93(4H, t, J=4.6Hz), 2.88-2.69(4H, m), 2.25(6H, s), 1.71-1.68(1H, m), 0.53-0.42(4H, m). | |
| 106a | (CDCl3) δ: 8.83(1H, s), 7.61-7.33(6H, m), 6.99(1H, d, J=8.3Hz), 5.75-5.64(1H, m), 5.10(1H, d, J=10.2Hz), 4.96(1H, d, J=17.1Hz), 4.39(2H, d, J=5.9Hz), 3.51(2H, s), 3.38(4H, t, J=5.1Hz), 3.20(4H, t, J=5.1Hz), 2.27(6H, s). | 548 |
| 107a | (CDCl3) δ: 8.80(1H, s), 7.48-7.33(6H, m), 6.87(2H, d, J=8.8Hz), 5.80-5.60(1H, m), 5.09(1H, dd, J=10.2, 1.0Hz), 4.97(1H, dd, J=17.1, 1.5Hz), 4.38(1H, d, J=5.9Hz), 3.51(2H, s), 3.18(4H, t, J=4.9Hz), 2.60(4H, t, J=4.9Hz), 2.37(3H, s), 2.28(6H, s). | 499 |
| 108a | (CDCl3) δ: 8.83(1H, s), 7.86(1H, t, J=6.0Hz), 7.75(1H, d, J=8.2Hz), 7.46(2H, d, J=8.6Hz), 7.40(1H, brs), 7.22(1H, d, J=7.6Hz), 6.92(2H, d, J=9.0Hz), 5.71(1H, ddt, J=16.8, 10.2, 5.9Hz), 5.06(1H, d, J=10.2Hz), 4.96(1H, d, J=16.8Hz), 4.81(2H, d, J=5.5Hz), 4.71(1H, d, J=5.9Hz), 3.23(4H, brs), 3.14(1H, t, J=5.5Hz), 2.64(4H, brs), 2.40(3H, s). | 473 |
| 109a | (CDCl3) δ: 8.80(1H, s), 7.39-7.58(6H, m), 6.89(2H, d, J=8.1Hz), 5.62-5.77(1H, m), 5.10(1H, d, J=9.9Hz), 4.99(1H, d, J=17.0Hz), 4.40(2H, d, J=5.8Hz), 3.69(2H, t, J=5.9Hz), 3.190-03.28(4H, m), 3.14(3H, s), 2.95(3H, s), 3.68-3.74(4H, m), 2.65(2H, t, J=5.9Hz). | 543 |
| 110a | (CDCl3) δ: 8.80(1H, s), 7.26-7.68(6H, m), 6.80(1H, d, J=8.2Hz), 5.65-5.75(1H, m), 5.09(1H, d, J=10.0Hz), 4.99(1H, d, J=17.2Hz), 4.39(2H, d, J=5.9Hz), 4.31(1H, bs), 3.12(3H, s), 2.85-2.99(5H, m), 2.51(2H, bs), 2.21(3H, s), 1.92-2.01(2H, m), 1.77-1.89(2H, m), 1.62-1.70(1H, m), 0.42-0.53(4H, m). | 568 |
| 111a | (CD3OD) δ: 8.81(1H, s), 8.55(1H, d, J=4.8Hz), 8.02(1H, dd, J=8.0, 8.0Hz), 7.91(1H, d, J=8.0Hz), 7.56(1H, s), 7.42(1H, dd, 8.0, 4.8Hz), 7.34(1H, d, J=8.8Hz), 6.60(1H, d, J=8.8Hz), 5.75(1H, ddd, J=16.8, 10.4, 6.0Hz), 5.07(1H, d, J=10.4Hz), 4.95(1H, d, J=16.8Hz), 4.81(1H, m), 4.74(2H, d, J=6.0Hz), 3.87(1H, m), 3.28(1H, m), 2.67(3H, s), 2.49(3H, s). | 444 |
| 112a | (CD3OD) δ: 8.80(1H, s), 8.55(1H, d, J=4.8Hz), 8.03(1H, dd, 8.0, 8.0Hz), 7.91(1H, d, J=8.0Hz), 7.56(1H, s), 7.41(1H, d, J=8.0Hz), 7.32(1H, d, J=8.4Hz), 7.60(1H, d, J=8.4Hz), 5.73(1H, ddd, J=17.2, 10.0, 6.4Hz), 5.65(1H, d, J=10.0Hz), 4.94(1H, d, J=17.2Hz), 4.83(1H, m), 4.73(2H, d, J=6.4Hz), 3.83(1H, m), 3.22(1H, m), 2.63(2H, q, J=7.2Hz), 2.39(3H, s), 1.05(3H, t, J=7.2Hz). | 458 |
| 113a | (CD3OD) δ: 8.80(1H, s), 8.50(1H, d, J=4.8Hz), 8.03(1H, dd, J=8.0, 8.0Hz), 7.91(1H, d, J=8.0Hz), 7.56(1H, s), 7.41(1H, dd, J=8.0, 4.8Hz), 7.33(1H, d, J=8.4Hz), 6.59(1H, d, J=8.4Hz), 5.74(1H, ddd, J=16.8, 10.0, 6.0Hz), 5.07(1H, d, J=10.0Hz), 4.95(1H, d, J=16.8Hz), 4.83(1H, m), 4.73(1H, d, J=6.0Hz), 3.91(1H, m), 3.63(1H, t, J=5.6Hz), 3.29(1H, m), 2.74(1H, t, J=5.6Hz), 2.04(3H, s). | 474 |
| 114a | (CDCl3) δ: 8.82(1H, s), 8.54(1H, dd, J=4.9, 1.5Hz), 7.91-7.84(2H, m), 7.67-7.44(1H, m), 7.33-7.23(2H, m), 7.02(1H, d, J=8.3Hz), 4.21(2H, d, J=7.3Hz), 2.95(4H, t, J=4.9Hz), 2.72-2.50(4H, m), 2.49-2.40(1H, m), 2.39(3H, s), 2.33(3H, s), 1.90-1.69(4H, m), 1.65-1.53(2H, m). | 485 |
| 115a | (CDCl3) δ: 8.78(1H, s), 8.54(1H, d, J=4.9Hz), 7.87-7.82(1H, m), 7.81-7.75(1H, m), 7.67-7.41(2H, m), 7.40-7.10(3H, m), 7.10-6.95(3H, m), 4.42(2H, t, J=7.3Hz), 2.96(4H, t, J=4.6Hz), 2.82(2H, t, J=7.6Hz), 2.75-2.50(4H, m), 2.40(3H, s), 2.33(3H, s) | 521 |
| 116a | (CDCl3) δ: 8.83(1H, s), 7.87-7.77(2H, m), 7.52(1H, s), 7.34(1H, dd, J=8.5, 2.7Hz), 7.00(1H, d, J=8.8Hz), 5.68(1H, ddt, J=16.8, 10.2, 6.3Hz), 5.01(1H, dd, J=10.2, 1.5Hz), 4.89(1H, dd, J=16.8, 1.2Hz), 4.81(2H, d, J=6.3Hz), 3.86(4H, t, J=4.4Hz), 3.65(2H, s), 2.90(4H, t, J=4.4Hz), 2.35(6H, s), 2.34(3H, s). | 501 |
| 117a | (CDCl3) δ: 8.82(1H, s), 7.81(1H, t, J=7.8Hz), 7.73(1H, d, J=7.8Hz), 7.46(2H, d, J=8.8Hz), 7.38(1H, d, J=7.8Hz), 6.88(2H, d, J=8.8Hz), 5.68(1H, ddt, J=17.1, 10.2, 6.3Hz), 5.00(1H, dd, J=10.2, 1.0Hz), 4.89(1H, dd, J=17.1, 1.0Hz), 4.80(2H, dd, J=6.3, 0.5Hz), 4.53(1H, septet, J=5.9Hz), 3.63(2H, s), 2.34(6H, s), 1.35(6H, d, J=5.9Hz). | 460 |
| 118a | (CDCl3) δ: 8.85(1H, s), 7.89(1H, t, J=7.8Hz), 7.75(1H, d, J=7.8Hz), 7.71-7.66(2H, m), 7.42(2H, d, J=7.3Hz), 7.11(2H, d, J=8.3Hz), 5.74-5.62(1H, m), 5.01(1H, d, J=10.2Hz), 4.89(1H, d, J=17.1Hz), 4.85-4.71(2H, m), 4.80(2H, s), 4.16(2H, s), 3.87-3.74(2H, m), 3.74-3.65(2H, m), 3.63(2H, s), 3.46(3H, s), 2.99-2.93(4H, m), 2.34(6H, s). | 588 |

-continued

| Compound No | ¹H NMR(400MHz) | ESI-MS (M+H)+ |
|---|---|---|
| 119a | (CDCl3) δ: 8.91(1H, s), 7.99-7.90(3H, m), 7.77-7.70(3H, m), 7.49(1H, d, J=7.8Hz), 5.80-5.60(1H, m), 5.03(1H, dd, J=10.0, 1.2Hz), 4.91(1H, dd, J=17.1, 1.5Hz), 4.80(2H, d, J=5.9Hz), 3.69(2H, s), 3.49(2H, s), 2.62(3H, s), 2.38(3H, s). | 444 |
| 120a | (CDCl3) δ: 8.84(1H, s), 7.87(1H, t, J=7.8Hz), 7.75(1H, d, J=7.8Hz), 7.61-7.55(1H, m), 7.39(1H, d, J=7.3Hz), 7.37-7.34(1H, m), 7.21(1H, d, J=8.8Hz), 5.71-5.63(1H, m), 5.00(1H, dd, J=10.2, 1.0Hz), 4.88(1H, dd, J=17.1, 1.5Hz), 4.84-4.77(4H, m), 3.61(2H, s), 3.02(4H, t, J=4.6Hz), 2.83-2.64(4H, m), 2.33(3H, s), 1.11(3H, d, J=6.3Hz). | 558 |
| 121a | (CDCl3) δ: 8.82(1H, s), 7.47-7.23(6H, m), 6.96(1H, d, J=8.3Hz), 5.75-5.64(1H, m), 5.09(1H, d, J=10.2Hz), 4.96(1H, d, J=16.6Hz), 4.39(2H, d, J=6.3Hz), 3.62(2H, s), 3.05-2.96(1H, m), 2.91(4H, t, J=4.6Hz), 2.67-2.43(6H, m), 2.38(3H, s), 2.26(3H, s), 1.03(6H, d, J=6.3Hz), 0.99(3H, t, J=7.3Hz). | 555 |
| 122a | (CDCl3) δ: 8.90-8.70(1H, m), 7.47(1H, t, J=7.8Hz), 7.43-7.29(5H, m), 6.96(1H, d, J=8.3Hz), 5.75-5.64(1H, m), 5.09(1H, dd, J=10.2, 1.0Hz), 4.96(1H, dd, J=17.1, 1.5Hz), 4.38(2H, d, J=6.3Hz), 3.70(4H, t, J=4.6Hz), 3.56(2H, s), 2.92(4H, t, J=4.9Hz), 2.71-2.52(4H, m), 2.51-2.43(4H, m), 2.38(3H, s), 2.26(3H, s). | 555 |
| 123a | (CDCl3) δ: 8.81(1H, s), 7.27-7.46(6H, m), 6.94(1H, d, J=8.5Hz), 5.62-5.75(1H, m), 5.07(1H, d, J=10.3Hz), 4.95(1H, d, J=17.1Hz), 4.37(2H, d, J=5.9Hz), 3.62(2H, s), 2.90(4H, t, J=4.5Hz), 2.50-2.63(4H, m), 2.54(4H, q, J=7.1Hz), 2.36(3H, s), 2.25(3H, s), 1.04(6H, t, J=7.1Hz). | 541 |
| 124a | (CDCl3) δ: 8.82(1H, s), 7.82(1H, t, J=7.8Hz), 7.74(1H, d, J=7.8Hz), 7.47(2H, d, J=8.8Hz), 7.38(1H, d, J=7.3Hz), 6.92(1H, d, J=9.3Hz), 5.73-5.63(1H, m), 5.00(1H, dd, J=10.0, 1.2Hz), 4.89(1H, dd, J=17.1, 1.5Hz), 4.80(2H, d, J=6.3Hz), 3.63(2H, s), 3.23(4H, t, J=4.9Hz), 2.72-2.63(4H, m), 2.52(2H, t, J=7.1Hz), 2.33(6H, s), 1.16(3H, t, J=7.3Hz). | 514 |
| 125a | (CDCl3) δ: 8.87-8.76(1H, m), 7.82(1H, t, J=7.8Hz), 7.74(1H, d, J=7.8Hz), 7.47(2H, d, J=8.8Hz), 7.38(1H, d, J=7.3Hz), 6.92(2H, d, J=8.8Hz), 5.74-5.62(1H, m), 5.00(1H, d, J=10.2Hz), 4.89(1H, dd, J=17.1, 1.5Hz), 4.80(2H, d, J=6.3Hz), 3.63(2H, s), 3.32-3.20(4H, m), 2.90-2.70(4H, m), 2.34(6H, s), 1.16(6H, d, J=5.9Hz). | 528 |
| 126a | (CDCl3) δ: 8.81(1H, s), 7.81-7.63(1H, m), 7.48-7.28(5H, m), 6.96(1H, d, J=8.3Hz), 5.75-5.64(1H, m), 5.09(1H, dd, J=10.7, 1.0Hz), 4.97(1H, dd, J=17.1, 1.0Hz), 4.40(2H, d, J=6.3Hz), 3.63(2H, s), 3.52(2H, t, J=5.9Hz), 3.33(3H, s), 2.91(4H, t, J=4.6Hz), 2.67-2.49(4H, m), 2.63(2H, t, J=5.9Hz), 2.37(3H, s), 2.29(3H, s), 2.26(3H, s). | 557 |
| 127a | (CDCl3) δ: 8.86(1H, s), 8.54(1H, d, J=4.9Hz), 7.90-7.85(2H, m), 7.61(2H, d, J=8.4Hz), 7.60(1H, brs), 7.35(2H, d, J=8.4Hz), 7.19-7.16(1H, m), 5.67(1H, ddt, J=17.2, 10.0, 6.4Hz), 5.03(1H, d, J=10.0Hz), 4.93(1H, d, J=17.2Hz), 4.79(2H, d, J=6.4Hz). E | 375 |
| 128a | (CDCl3) δ: 8.86(1H, s), 8.53(1H, td, J=1.5, 4.9Hz), 7.88(2H, d, J=2.9Hz), 7.71(1H, brs), 7.55(2H, d, J=8.3Hz), 7.31(2H, d, J=8.3Hz), 7.25(1H, t, J=4.4Hz), 5.69(1H, ddt, J=17.1, 10.0, 6.3Hz), 5.02(1H, dd, J=10.0, 1.2Hz), 4.92(1H, dd, J=17.1, 1.0Hz), 4.79(2H, d, J=6.3Hz), 3.56(2H, s), 2.54(4H, q, J=7.2Hz), 1.6(7H, t, J=7.1Hz). | 430 |
| 129a | (CDCl3) δ: 8.83(1H, s), 7.74(1H, t, J=8.0Hz), 7.52(1H, s), 7.41(2H, d, J=7.8Hz), 7.36(2H, d, J=8.8Hz), 7.30(1H, d, J=8.8Hz), 7.00(1H, d, J=8.8Hz), 6.90(2H, dd, J=6.6, 2.2Hz), 6.74(1H, d, J=7.8Hz), 5.65(1H, ddt, J=17.1, 10.2, 5.9Hz), 5.30(2H, s), 5.01(1H, dd, J=10.2, 1.5Hz), 4.89(1H, dd, J=17.1, 1.5Hz), 4.66(2H, d, J=5.9Hz), 3.80(3H, s), 2.93(4H, t, J=4.9Hz), 2.59(4H, s), 2.38(3H, s), 2.31(3H, s). | 593 |
| 130a | (DMSO-d6) δ: 8.83(1H, s), 7.85(1H, t, J=7.8Hz), 7.70(1H, br s), 7.41(1H, dd, J=9.0, 2.2Hz), 7.27(1H, d, J=6.8Hz), 6.98(1H, d, J=8.8Hz), 6.62(1H, d, J=7.8Hz), 5.67(1H, ddt, J=17.1, 10.2, 5.9Hz), 5.03(1H, dd, J=10.2, 1.0Hz), 4.90(1H, dd, J=17.1, 1.0Hz), 4.56(2H, s), 3.32(4H, s), 2.89(4H, brs), 2.49(3H, s), 2.22(3H, s). | 473 |
| 131a | (CDCl3) δ: 8.83(1H, s), 8.03-7.79(3H, m), 7.51(1H, s), 7.33(1H, d, J=8.4Hz), 7.18-6.98(2H, m), 5.71-5.66(1H, m), 5.01(1H, d, J=10.0Hz), 4.91(1H, d, J=17.6Hz), 4.80(1H, d, J=6.3Hz), 4.61, 4.57(2H, s), 3.76, 3.72(3H, s), 3.04-2.95(7H, m), 2.66(4H, brs), 2.41(3H, s), 2.32(3H, s). | 588 |
| 132a | (CDCl3) δ: 8.83(1H, s), 7.86(1H, d, J=7.8Hz), 7.80(1H, t, J=7.8Hz), 7.52(1H, s), 7.45(1H, s), 7.31(1H, d, J=8.3Hz), 7.20(1H, dd, J=7.3, 1.0Hz), 7.02(1H, d, J=8.3Hz), 5.69-5.59(1H, m), 4.98(1H, d, J=11.2Hz), 4.90-4.84(3H, m), 3.70(3H, | 557 |

| Compound No | ¹H NMR(400MHz) | ESI-MS (M+H)+ |
|---|---|---|
| | s), 2.95(4H, t, J=4.6Hz), 2.61(3H, s), 2.38(4H, s), 2.33(3H, s), 1.63(6H, s). | |
| 133a | (CDCl3) δ: 8.84(1H, s), 8.55(1H, td, J=3.2, 1.6Hz), 7.89(2H, dd, J=4.9, 1.5Hz), 7.52(2H, s), 7.38-7.27(3H, m), 5.69(1H, ddt, J=17.1, 10.1, 6.3Hz), 5.02(1H, dd, J=10.2, 1.0Hz), 4.92(1H, dd, J=17.1, 1.0Hz), 4.79(2H, d, J=6.3Hz), 4.69(2H, s), 2.39(3H, s), 1.27(0H, d, J=6.8Hz), 0.00(5H, t, J=3.2Hz). | 389 |
| 134a | (CDCl3) δ: 8.85(1H, s), 8.54-8.52(1H, m), 7.94-7.85(2H, m), 7.49(2H, s), 7.29(2H, s), 7.26-7.23(1H, m), 5.69(1H, ddt, J=17.1, 10.2, 6.3Hz), 5.02(4H, d, J=10.2Hz), 4.92(4H, d, J=17.1Hz), 4.79(4H, d, J=6.3Hz), 3.50(2H, s), 2.52(4H, q, J=7.0Hz), 2.38(3H, s), 1.04(7H, t, J=7.1Hz). | 444 |
| 135a | (CDCl3) δ: 8.84(1H, s), 7.82(1H, t, J=7.8Hz), 7.76(1H, d, J=8.3Hz), 7.50(1H, s), 7.40(2H, dd, J=7.3, 1.0Hz), 7.33(1H, dd, J=8.8, 2.9Hz), 7.02(1H, d, J=8.8Hz), 5.68(1H, ddt, J=17.1, 10.0, 6.3Hz), 5.01(1H, dd, J=10.0, 1.2Hz), 490(1H, dd, J=17.1, 1.5Hz), 4.83(2H, d, J=6.3Hz), 2.98(4H, t, J=4.4Hz), 2.67(4H, brs), 2.43(3H, s), 2.32(3H, s), 1.54(6H, s). | 514 |
| 136a | (CDCl3) δ: 8.81(1H, s), 7.59-7.31(6H, m), 6.83(2H, d, J=8.8Hz), 5.75-5.63(1H, m), 5.11(1H, d, J=1.0Hz), 5.09(2H, dd, J=10.2, 1.0Hz), 4.97(1H, dd, J=17.1, 1.0Hz), 4.39(2H, d, J=5.9Hz), 3.83(2H, s), 3.50-3.38(6H, m), 3.04(3H, s), 2.45-2.21(6H, m). | 513 |
| 137a | (CDCl3) δ: 8.82(1H, s), 7.84(1H, t, J=7.8Hz), 7.74(1H, d, J=7.8Hz), 7.52(2H, d, J=8.8Hz), 7.42(1H, d, J=7.3Hz), 6.88(2H, d, J=9.3Hz), 5.74-5.63(1H, m), 5.01(1H, d, J=10.2Hz), 4.89(1H, d, J=17.1Hz), 4.80(2H, d, J=6.3Hz), 3.87(2H, s), 3.66(2H, s), 3.52-3.45(4H, m), 3.05(3H, s), 2.36(6H, s). | 514 |
| 138a | (CDCl3) δ: 8.81(1H, s), 7.49-7.40(6H, m), 7.34(2H, d, J=7.8Hz), 6.82(2H, d, J=8.8Hz), 5.75-5.63(1H, m), 5.09(1H, dd, J=10.2, 1.0Hz), 4.97(1H, dd, J=17.1, 1.0Hz), 4.38(2H, d, J=5.9Hz), 3.59-3.51(4H, m), 3.44-3.38(4H, m), 3.04(3H, s), 2.82-2.78(2H, m), 2.30(6H, s). | 527 |
| 139a | (CDCl3) δ: 8.82(1H, s), 7.83(1H, t, J=7.8Hz), 7.74(1H, d, J=8.3Hz), 7.48(2H, d, J=8.8Hz), 7.40(1H, d, J=7.3Hz), 6.87(2H, d, J=8.8Hz), 5.74-5.62(1H, m), 5.01(1H, d, J=10.2Hz), 4.89(1H, d, J=17.1Hz), 4.79(2H, d, J=6.3Hz), 3.64(2H, s), 3.59-3.55(2H, m), 3.47-3.42(4H, m), 3.05(3H, s), 2.85-2.81(2H, m), 2.35(6H, s). | 528 |
| 140a | (CDCl3) δ: 8.85(1.0H, s), 7.82(1.0H, t, J=7.8Hz), 7.74(1.0H, d, J=7.8Hz), 7.59(1.0H, brs), 7.52(2.0H, d, J=8.8Hz), 7.37(2.0H, d, J=8.3Hz), 7.34(1.0H, d, J=7.3Hz), 5.70(1.0H, ddt, J=16.8, 10.5, 5.9Hz), 5.04(1.0H, dd, J=10.5, 0.7Hz), 4.93(1.0H, dd, J=16.8, 1.2Hz), 4.75(2.0H, d, J=5.9Hz), 3.92(1.0H, s), 3.57(2.0H, s), 2.99-2.93(1.0H, m), 1.13(3.0H, d, J=6.3Hz), 1.10(3.0H, d, J=6.8Hz). | 474 |
| 141a | (CDCl3) δ: 8.84(1H, s), 7.93(1H, t, J=7.8Hz), 7.80(1H, d, J=7.8Hz), 7.51(1H, d, J=7.8Hz), 7.46(1H, brs), 7.37(1H, brs), 7.04(1H, d, J=8.8Hz), 5.70(1H, tdd, J=6.3, 16.6, 10.0Hz), 5.05(1H, dd, J=10.0, 1.7Hz), 4.94(1H, dd, J=16.6, 1.5Hz), 4.74(2H, d, J=6.3Hz), 4.14(1H, brs), 3.01(4H, brs), 2.57-2.43(4H, m), 2.32(3H, s), 2.14-2.06(1H, m), 1.97-1.85(1H, m). | 527 |
| 142a | (CDCl3) δ: 8.84(1H, s), 7.80(1H, t, J=7.8Hz), 7.64(1H, brs), 7.42(1H, brs), 7.35(1H, dd, J=8.8, 2.4Hz), 7.09(1H, d, J=7.8Hz), 7.03(1H, d, J=8.3Hz), 5.77-5.64(1H, m), 5.11-4.95(2H, m), 4.65(2H, brs), 2.98(6H, brs), 2.67(4H, brs), 2.43(3H, brs), 2.32(3H, s), 1.24(6H, s). | 529 |
| 143a | (CDCl3) δ: 8.83(1H, s), 7.87(1H, t, J=8.0Hz), 7.74(1H, d, J=7.3Hz), 7.51(2H, d, J=8.8Hz), 7.36(1H, d, J=7.3Hz), 6.88(2H, d, J=9.3Hz), 5.76-5.65(1H, m), 5.05(1H, d, J=10.2Hz), 4.93(1H, d, J=17.1Hz), 4.74(2H, d, J=6.3Hz), 4.06-3.95(1H, m), 3.87(2H, s), 3.52-3.45(4H, m), 3.06(3H, s), 1.59(6H, s). | 515 |
| 144a | (CDCl3) δ: 8.87(1H, s), 7.89(1H, t, J=7.8Hz), 7.75(1H, d, J=7.3Hz), 7.58(2H, d, J=8.8Hz), 7.38(1H, d, J=6.8Hz), 7.30(2H, d, J=8.8Hz), 5.76-5.66(1H, m), 5.05(1H, dd, J=10.2, 1.0Hz), 4.94(1H, dd, J=17.1, 1.0Hz), 4.75(2H, d, J=6.3Hz), 3.95(1H, brs), 3.63(2H, t, J=4.9Hz), 3.52(2H, s), 3.47(2H, t, J=4.9Hz), 2.48-2.40(4H, m), 2.09(3H, s), 1.59(6H, s). | 543 |
| 145a | (CDCl3) δ: 8.87(1H, s), 7.90(1H, t, J=7.8Hz), 7.75(1H, d, J=7.3Hz), 7.58(2H, d, J=8.3Hz), 7.38(1H, d, J=7.8Hz), 7.29(2H, d, J=8.3Hz), 5.76-5.66(1H, m), 5.05(1H, dd, J=10.2, 1.0Hz), 4.94(1H, dd, J=17.1, 1.0Hz), 4.75(2H, d, J=5.9Hz), 3.93(1H, s), 3.54(2H, s), 3.29-3.22(4H, m), 2.79(3H, s), 2.60-2.54(4H, m), 1.59(6H, s). | 579 |
| 146a | (CDCl3) δ: 8.86(s, 1H), 7.90(t, 1H, J=7.8Hz), 7.78(d, 1H, J=7.8Hz), 7.55(d, 2H, J=8.3Hz), 7.36(d, 1H, J=7.8Hz), 7.32(d, | 488 |

| Compound No | ¹H NMR(400MHz) | ESI-MS (M+H)+ |
|---|---|---|
| | 2H, J=8.3Hz), 5.71(ddt, 1H, J=17.1, 10.2, 5.9Hz), 5.05(d, 1H, J=10.2Hz), 4.94(d, 1H, J=17.1Hz), 4.75(d, 2H, J=5.9Hz), 3.94(brs, 1H), 3.51(s, 2H), 2.91(t, 1H, J=6.3Hz), 2.17(s, 3H), 1.59(s, 6H), 1.08(d, 6H, J=6.3Hz). | |
| 147a | (CDCl3) δ: 8.87(s, 1H), 7.90(t, 1H, J=7.8Hz), 7.77(d, 1H, J=7.8Hz), 7.56(d, 2H, J=8.3Hz), 7.36(d, 1H, J=7.8Hz), 7.30(d, 2H, J=8.3Hz), 5.71(ddt, 1H, J=17.1, 10.2, 6.3Hz), 5.05(d, 1H, J=10.2Hz), 4.94(d, 1H, J=17.1Hz), 4.75(d, 2H, J=6.3Hz), 3.93(brs, 1H), 3.48(s, 2H), 2.34(t, 2H, J=7.3Hz), 2.21(s, 3H), 1.59(s, 6H), 1.49-1.59(m, 2H), 0.91(t, 3H, J=7.3Hz). | 488 |
| 148a | (CDCl3) δ: 8.87(s, 1H), 7.90(t, 1H, J=7.8Hz), 7.76(d, 1H, J=7.8Hz), 7.57(d, 2H, J=8.3Hz), 7.37(d, 1H, J=7.8Hz), 7.32(d, 2H, J=8.3Hz), 5.71(ddt, 1H, J=17.1, 10.2, 6.3Hz), 5.05(d, 1H, J=10.2Hz), 4.94(d, 1H, J=17.1Hz), 4.75(d, 2H, J=6.3Hz), 3.92(brs, 1H), 3.66-3.79(brm, 4H), 3.50(s, 2H), 2.38-2.54(brm, 4H), 1.59(s, 6H). | 502 |
| 149a | (CDCl3) δ: 8.86(s, 1H), 7.90(t, 1H, J=7.8Hz), 7.77(d, 1H, J=7.8Hz), 7.56(d, 2H, J=8.8Hz), 7.36(d, 3H, J=7.8Hz), 7.32(d, 3H, J=8.8Hz), 5.71(ddt, 1H, J=17.1, 10.2, 5.9Hz), 5.05(d, 1H, J=10.2Hz), 4.94(d, 1H, J=17.1Hz), 4.76(d, 2H, J=5.9Hz), 3.95(brs, 1H), 3.61(s, 2H), 2.48-2.56(brm, 4H), 1.76-1.84(brm, 5H), 1.59(s, 6H). | 486 |
| 150a | (CDCl3) δ: 8.82(1H, s), 7.78(1H, t, J=7.8Hz), 7.44(2H, d, J=8.3Hz), 7.07(1H, d, J=7.8Hz), 6.92(2H, d, J=9.3Hz), 5.77-5.64(1H, brm), 5.12-4.95(2H, brm), 4.63(2H, brs), 3.16(4H, s), 2.98(2H, s), 2.80(4H, s), 1.69(1H, brs), 1.24(6H, s), 0.50(4H, brs). | 541 |
| 151a | (CDCl3) δ: 8.84(1H, s), 7.87(1H, dd, J=8.3, 7.8Hz), 7.74(1H, d, J=7.3Hz), 7.48(2H, d, J=8.8Hz), 7.35(1H, d, J=8.3Hz), 6.92(2H, d, J=8.8Hz), 5.70(1H, ddt, J=17.1, 10.2, 5.9Hz), 5.05(1H, dd, J=10.2, 1.5Hz), 4.94(1H, dd, J=17.1, 1.0Hz), 4.74(2H, d, J=5.9Hz), 3.33-3.14(5H, m), 3.07(3H, s), 3.04-2.93(2H, m), 2.86-2.62(5H, m), 1.59(6H, s). | 593 |
| 152a | (CDCl3) δ: 8.86(1.0H, s), 7.89(1.0H, t, J=7.8Hz), 7.73(1.0H, d, J=8.8Hz), 7.63(2.0H, d, J=8.8Hz), 7.37(1.0H, d, J=8.3Hz), 7.26(2.0H, d, J=9.8Hz), 5.76-5.65(1.0H, m), 5.05(1.0H, dd, J=10.0, 1.2Hz), 4.93(1.0H, dd, J=17.1, 1.2Hz), 4.75(2.0H, d, J=6.3Hz), 4.06-3.95(1.0H, m), 3.72(2.0H, t, J=5.4Hz), 3.31(2.0H, s), 2.81(2.0H, t, J=5.4Hz), 2.43(3.0H, s), 1.59(6.0H, s). | 515 |
| 153a | (CDCl3) δ: 8.83(1H, s), 7.83(1H, dd, J=8.0, 7.6Hz), 7.74(1H, d, J=8.0Hz), 7.47(2H, d, J=8.8Hz), 7.33(1H, d, J=7.6Hz), 6.92(2H, d, J=8.8Hz), 5.69(1H, ddt, J=16.8, 10.4, 5.6Hz), 5.04(1H, d, J=10.4Hz), 4.92(1H, d, J=16.8Hz), 4.74(2H, d, J=5.6Hz), 3.22(4H, t, J=4.8Hz), 3.04(3H, s), 2.96(3H, s), 2.86(2H, t, J=7.6Hz), 2.74(2H, t, J=4.8Hz), 2.62(2H, t, J=7.6Hz), 1.59(6H, s). | 586 |
| 154a | (CDCl3) δ: 8.83(1H, s), 8.30(1H, br), 7.86(1H, dd, J=8.0, 7.6Hz), 7.78(1H, dd, J=8.0, 2.8Hz), 7.68(1H, d, J=8.8Hz), 6.66(1H, d, J=8.8Hz), 5.69(1H, ddt, J=16.8, 10.4, 5.6Hz), 5.04(1H, d, J=10.4Hz), 4.92(1H, d, J=16.8Hz), 4.73(2H, d, J=5.6Hz), 3.58(4H, t, J=4.8Hz), 3.26(2H, s), 3.11(3H, s), 2.98(3H, s), 2.70(4H, t, J=4.8Hz), 2.62(2H, t, J=7.6Hz), 1.58(6H, s). | 573 |
| 155a | (CDCl3) δ: 8.83(1H, s), 7.86(1H, dd, J=8.0, 7.6Hz), 7.74(1H, d, J=8.0Hz), 7.47(2H, d, J=8.8Hz), 7.31(1H, d, J=7.6Hz), 6.92(2H, d, J=8.8Hz), 5.69(1H, ddt, J=16.8, 10.4, 5.6Hz), 5.04(1H, d, J=10.4Hz), 4.92(1H, d, J=16.8Hz), 4.74(2H, d, J=5.6Hz), 3.99(1H, brs), 3.40-3.45(1H, m), 3.14-3.24(4H, m), 2.92(2H, br), 2.61(2H, br), 2.30(1H, br), 2.18(1H, br), 1.68-1.88(4H, m), 1.59(6H, s). | 585 |
| 156a | (CDCl3) δ: 8.83(1H, s), 7.89-7.75(2H, m), 7.49(1H, s), 7.42(1H, s), 7.32(1H, dd, J=8.8, 2.4Hz), 7.24(1H, d, J=6.3Hz), 7.02(1H, dd, J=8.5, 3.2Hz), 5.69(1H, ddt, J=17.1, 10.2, 6.3Hz), 5.02(1H, dd, J=10.2, 1.5Hz), 4.92(1H, dd, J=17.1, 1.5Hz), 4.77(2H, d, J=6.3Hz), 3.90(1H, s), 2.96(4H, t, J=4.6Hz), 2.63(3H, s), 2.51(2H, s), 2.40(3H, s), 2.32(3H, s). | 500 |
| 157a | (CDCl3) δ: 8.84(s, 1H), 7.85(dd, 1H, J=7.8, 8.0Hz), 7.74(d, 1H, J=8.0Hz), 7.46(d, 2H, J=8.8Hz), 7.34(d, 1H, J=7.8Hz), 6.90(d, 2H, J=8.8Hz), 5.70(ddt, 1H, J=17.1, 10.2, 6.3Hz), 5.04(dd, 1H, J=10.2, 1.0Hz), 4.94(dd, 1H, J=17.1, 1.0Hz), 4.74(d, 2H, J=6.3Hz), 4.36-4.26(brm, 1H), 3.96(s, 1H), 2.79-2.72(m, 1H), 2.70-2.58(brm, 2H), 2.25-2.11(brm, 2H), 2.10-1.63(m, 10H), 1.58(s, 6H). | 556 |
| 158a | (CDCl3) δ: 8.84(1H, s), 7.86(1H, t, J=7.8Hz), 7.73(1H, d, J=7.8Hz), 7.48(2H, d, J=8.8Hz), 7.35(1H, d, J=7.8Hz), 6.91(2H, d, J=8.8Hz), 5.70(1H, ddt, J=17.1, 10.2, 6.3Hz), 5.04(1H, | 516 |

-continued

| Compound No | ¹H NMR(400MHz) | ESI-MS (M+H)+ |
|---|---|---|
| | d, J=10.2Hz), 4.94(1H, dd, J=17.1, 1.0Hz), 4.74(2H, d, J=3Hz), 4.39-4.27(1H, brm), 4.01-3.88(1H, brm), 2.84-2.69(2H, brm), 2.49-2.29(2H, brm), 2.37(3H, s), 2.15-2.02(2H, brm), 1.97-1.83(2H, brm), 1.59(6H, s). | |
| 159a | (CD3OD) δ: 8.82(1H, s), 7.89(1H, dd, J=8.0, 7.6Hz), 7.75(1H, d, J=8.0Hz), 7.49(2H, d, J=8.8Hz), 7.47(1H, d, J=7.6Hz), 6.94(2H, d, J=8.8Hz), 5.69(1H, ddt, J=16.8, 10.4, 5.6Hz), 5.04(1H, d, J=10.4Hz), 4.92(1H, d, J=16.8Hz), 4.77(2H, d, J=5.6Hz), 3.21(4H, t, J=4.8Hz), 2.79(2H, t, J=6.8Hz), 2.72(4H, t, J=4.8Hz), 2.62(2H, t, J=6.8Hz), 1.59(6H, s). | 540 |
| 160a | (CDCl3) δ: 8.82(1H, s), 7.81(1H, t, J=7.8Hz), 7.72(1H, d, J=7.8Hz), 7.46(2H, d, J=8.8Hz), 7.25(1H, d, J=7.3Hz), 6.92(2H, d, J=9.3Hz), 5.69(1H, ddt, J=17.1, 10.2, 6.3Hz), 5.02(1H, dd, J=10.2, 1.5Hz), 4.92(1H, dd, J=17.1, 1.5Hz), 4.75(2H, d, J=6.3Hz), 3.91(2H, s), 3.21(4H, t, J=4.9Hz), 2.62(4H, t, J=4.9Hz), 2.51(3H, s), 2.38(3H, s). | 486 |
| 161a | (CDCl3) δ: 8.80(1H, s), 7.57(1H, s), 7.47-7.46(2H), 7.42(2H, d, J=8.8Hz), 7.29(1H, m), 6.87(2H, d, J=8.8Hz), 5.70(1H, ddd, J=17.2, 10.0, 6.4Hz), 5.10(1H, d, J=10.0Hz), 4.98(1H, d, J=17.2Hz), 4.37(2H, d, J=6.4Hz), 3.11(4H, m), 2.79(4H, m), 1.87-1.68(1H, m), 1.61(6H, s), 0.50-0.49(4H, m). | 526 |
| 162a | (CDCl3) δ: 8.86(1H, s), 7.87(1H, t, J=8.0Hz), 7.75(1H, dd, J=8.0, 1.0Hz), 7.58(1H, brs), 7.37(1H, dd, J=8.0, 1.0Hz), 7.23(1H, t, J=8.0Hz), 7.11(1H, d, J=8.0Hz), 7.11-7.07(1H, m), 6.71(1H, dd, J=8.0, 1.7Hz), 5.70(1H, ddt, J=17.3, 10.0, 5.9Hz), 5.04(1H, d, J=10.0, 1.5Hz), 4.93(1H, dd, J=17.3, 1.5Hz), 4.74(2H, d, J=5.9Hz), 3.97(1H, brs), 3.23-3.11(4H, m), 2.62-2.51(4H, m), 2.37(3H, s), 1.58(6H, s). | 501 |
| 163a | (CDCl3) δ: 8.87(1H, s), 7.90(1H, t, J=7.8Hz), 7.77(1H, d, J=7.8Hz), 7.60-7.47(1H, brm), 7.55(2H, d, J=8.3Hz), 7.37(1H, d, J=7.8Hz), 7.33(2H, d, J=8.3Hz), 5.71(1H, ddt, J=17.1, 10.2, 6.3Hz), 5.05(1H, dd, J=10.2, 1.0Hz), 4.94(1H, dd, J=17.1, 1.0Hz), 4.75(2H, d, J=6.3Hz), 3.94(1H, brs), 3.63(2H, s), 2.78-2.69(6H, m), 2.68-2.61(2H, m), 2.40(3H, s), 1.90-1.80(2H, m), 1.59(6H, s). | 529 |
| 164a | (CDCl3) δ: 8.87(1H, s), 7.90(1H, t, J=8.0Hz), 7.76(1H, d, J=8.0Hz), 7.60-7.50(1H, brm), 7.56(2H, d, J=8.4Hz), 7.37(1H, d, J=8.0Hz), 7.31(2H, d, J=8.4Hz), 5.71(1H, ddt, J=17.2, 10.4, 6.3Hz), 5.05(1H, d, J=10.4Hz), 4.94(1H, d, J=17.2Hz), 4.75(2H, d, J=6.3Hz), 3.51(2H, s), 2.61-2.40(4H, brm), 2.33(3H, s), 1.82-1.62(4H, brm), 1.59(6H, s). | 515 |
| 165a | (CDCl3) δ: 8.87(1H, s), 7.90(1H, t, J=8.0Hz), 7.77(1H, d, J=8.0Hz), 7.60(1H, brs), 7.56(3H, d, J=8.4Hz), 7.37(1H, d, J=8.0Hz), 7.30(2H, d, J=8.4Hz), 5.87(1H, ddt, J=18.4, 11.0, 6.7Hz), 5.71(1H, ddt, J=17.0, 10.2, 6.3Hz), 5.19(1H, d, J=18.4Hz), 5.15(1H, d, J=11.0Hz), 5.05(1H, d, J=10.2Hz), 4.94(1H, d, J=17.0Hz), 4.75(2H, d, J=6.3Hz), 3.94(1H, brs), 3.51(2H, s), 3.02(2H, d, J=6.7Hz), 2.68-2.36(8H, brm), 1.59(6H, s). | 541 |
| 166a | (CDCl3) δ: 8.82(1H, s), 7.82-7.61(1H, m), 7.78(1H, t, J=7.8Hz), 7.44(2H, d, J=8.8Hz), 7.08(1H, d, J=7.8Hz), 6.92(2H, d, J=8.8Hz), 5.81-5.61(1H, m), 5.16-4.91(2H, m), 4.78-4.48(2H, m), 3.57(2H, t, J=5.4Hz), 3.38(3H, s), 3.26-3.18(4H, m), 2.98(2H, s), 2.75-2.61(6H, m), 1.24(6H, s). | 559 |
| 167a | (CDCl3) δ: 8.82(1H, s), 7.82-7.62(1H, brm), 7.78(2H, t, J=7.8Hz), 7.44(2H, d, J=8.8Hz), 7.08(1H, d, J=7.8Hz), 6.92(2H, d, J=8.8Hz), 5.79-5.62(1H, m), 5.16-4.91(2H, m), 4.78-4.51(2H, m), 3.62(2H, t, J=5.9Hz), 3.53(2H, q, J=7.0Hz), 3.24-3.17(4H, m), 2.98(2H, s), 2.75-2.62(4H, m), 2.67(2H, t, J=5.9Hz), 1.24(6H, s), 1.22(3H, t, J=7.0Hz). | 573 |
| 168a | (CD3OD) δ: 8.82(1H, s), 7.91(1H, dd, J=8.0, 7.6Hz), 7.77(1H, d, J=8.0Hz), 7.54(2H, d, J=8.8Hz), 7.54(1H, overlapped), 6.95(2H, d, J=8.8Hz), 5.68(1H, ddt, J=17.2, 10.4, 6.4Hz), 5.04(1H, d, J=10.4Hz), 4.92(1H, d, J=17.2Hz), 4.80(2H, d, J=6.4Hz), 4.16-4.19(1H, m), 3.24(4H, t, J=4.8Hz), 2.78-2.93(4H, m), 2.57-2.61(1H, m), 1.96-2.03(2H, m), 1.58(6H, s), 1.50-1.75(5H, m). | 571 |
| 169a | (CD3OD) δ: 8.82(1H, s), 7.91(1H, dd, J=8.0, 7.6Hz), 7.75(1H, d, J=8.0Hz), 7.56(2H, d, J=8.8Hz), 7.52(1H, d, J=7.6Hz), 6.95(2H, d, J=8.8Hz), 5.68(1H, ddt, J=17.2, 10.0, 5.6Hz), 5.04(1H, d, J=10.0Hz), 4.92(1H, d, J=17.2Hz), 4.77(2H, d, J=5.6Hz), 3.78(4H, brs), 3.20(2H, s), 3.16(4H, t, J=4.8Hz), 2.33(6H, s), 1.59(6H, s). | 572 |
| 170a | (CD3OD) δ: 8.83(1H, s), 7.86(1H, dd, J=8.0, 7.6Hz), 7.75(1H, d, J=8.0Hz), 7.48(2H, d, J=8.8Hz), 7.34(1H, d, J=7.6Hz), 6.93(2H, d, J=8.8Hz), 5.70(1H, ddt, J=17.2, 10.0, 5.6Hz), 5.04(1H, d, J=10.0Hz), 4.92(1H, d, J=17.2Hz), 4.74(2H, d, J=5.6Hz), | 584 |

-continued

| Compound No | ¹H NMR(400MHz) | ESI-MS (M+H)+ |
|---|---|---|
| | 4.16-4.20(1H, m), 4.03-4.09(2H, m), 3.21-3.24(5H, brs), 2.56(4H, t, J=4.8Hz), 1.89(3H, s), 1.59(6H, s). | |
| 171a | (CDCl3) δ: 8.83(1H, s), 7.88(1H, t, J=7.8Hz), 7.77(1H, d, J=8.3Hz), 7.47(2H, d, J=8.8Hz), 7.36(1H, d, J=8.3Hz), 6.94(2H, d, J=8.8Hz), 3.93(1H, brs), 3.55(3H, s), 3.25(4H, t, J=4.6Hz), 2.67(4H, brs), 2.42(3H, s), 1.58(6H, s). | 475 |
| 172a | (CDCl3) δ: 8.87(1H, s), 7.89(1H, dd, J=8.0, 7.8Hz), 7.75(1H, d, J=8.3Hz), 7.54(2H, d, J=8.3Hz), 7.51-7.41(1H, m), 7.37(1H, d, J=7.8Hz), 7.20(2H, d, J=8.3Hz), 5.70(1H, ddt, J=17.1, 10.2, 6.3Hz), 5.05(1H, d, J=10.2Hz), 4.94(1H, dd, J=17.1, 1.0Hz), 4.74(2H, d, J=6.3Hz), 3.40-2.74(7H, m), 3.08(3H, s), 2.64-2.50(1H, m), 2.37-2.08(2H, m), 1.98-1.85(3H, m), 1.59(6H, s). | 606 |
| 173a | (CDCl3) δ: 8.87(1H, s), 7.84-7.77(2H, m), 7.54(2H, d, J=8.7Hz), 7.20(2H, d, J=8.7Hz), 7.13-7.09(1H, m), 5.74-5.70(1H, m), 5.10-5.02(2H, m), 4.73-4.60(2H, m), 3.30-2.89(6H, m) 3.09(3H, s), 3.00(2H, s) 2.61-2.10(3H, m) 1.98-1.40(4H, m), 1.25(6H, s). | 606 |
| 174a | (CDCl3) δ: 8.86(1H, s), 7.83(1H, t, J=8.3Hz), 7.61(1H, brs), 7.52(2H, d, J=8.8Hz), 7.19(2H, d, J=8.8Hz), 7.00(1H, d, J=8.3Hz), 6.64(1H, d, J=8.3Hz), 5.80-5.64(1H, m), 5.14-4.93(2H, m), 4.73-4.56(2H, m), 3.84-3.76(2H, m), 3.36-2.84(6H, m), 3.07(3H, s), 2.61-2.46(1H, m), 2.32-2.13(2H, m), 1.94-1.82(4H, m), 1.39(6H, s). | 606 |
| 175a | (CDCl3) δ: 8.87(1.0H, s), 7.92(1.0H, t, J=8.0Hz), 7.74(1.0H, d, J=8.0Hz), 7.55(2.0H, t, J=11.3Hz), 7.38(1.0H, d, J=7.4Hz), 7.28-7.24(2.0H, m), 5.76-5.65(1.0H, m), 5.05(1.0H, d, J=9.8Hz), 4.94(1.0H, d, J=17.0Hz), 4.75(2.0H, d, J=6.3Hz), 4.57(2.0H, s), 3.97-3.92(1.0H, m), 3.52(2.0H, t, J=5.5Hz), 3.35(3.0H, s), 3.31(2.0H, s), 3.27(2.0H, t, J=5.2Hz), 2.72(2.0H, t, J=5.1Hz), 2.64(2.0H, t, J=5.3Hz), 1.57(6.0H, s). | 528 |
| 176a | (CDCl3) δ: 8.80(1H, s), 7.48-7.28(6H, m), 7.24(1H, d, J=7.3Hz), 6.87(2H, d, J=8.8Hz), 5.69(1H, ddt, J=17.0, 10.2, 6.0Hz), 5.09(1H, dd, J=10.2, 1.0Hz), 4.97(1H, dd, J=17.0, 1.0Hz), 4.39(2H, d, J=5.9Hz), 3.61-3.54(2H, m), 3.38(3H, s), 3.24-3.16(4H, m), 2.83(2H, s), 2.74-2.62(7H, m), 1.25(6H, s). | 558 |
| 177a | (CDCl3) δ: 8.83(1H, s), 7.90(1H, dd, J=8.4, 7.6Hz), 7.82(1H, d, J=8.4Hz), 7.48(1H, s), 7.37(1H, d, J=7.6Hz), 7.34(1H, d, J=8.8Hz), 7.03(1H, d, J=8.8Hz), 4.19(2H, q, J=7.2Hz), 2.95(4H, m), 2.61(4H, m), 2.39(3H, s), 2.33(3H, s), 1.58(6H, s), 1.08(3H, s) | 503 |
| 178a | (CD3OD) δ: 8.81(1H, s), 7.82(2H, br), 7.37-7.47(3H, m), 6.67(2H, d, J=8.8Hz), 5.67(1H, ddt, J=16.8, 10.0, 6.4Hz), 5.00(1H, d, J=10.0Hz), 4.88(1H, d, J=16.8Hz), 4.80(2H, d, J=6.4Hz), 3.64(2H, brs), 3.50(2H, brs), 2.82(2H, brs), 2.69(2H, br s), 2.47(3H, s), 2.12(2H, brs), 1.75(3H, s), 1.69(3H, s). | 517 |
| 179a | (CD3OD) δ: 8.82(1H, s), 7.93(1H, dd, J=8.0, 7.6Hz), 7.77(1H, d, J=8.0Hz), 7.56(2H, d, J=8.8Hz), 7.56(1H, overlapped), 6.96(2H, d, J=8.8Hz), 5.68(1H, ddt, J=17.2, 10.0, 5.6Hz), 5.04(1H, d, J=10.0Hz), 4.92(1H, d, J=17.2Hz), 4.81(2H, d, J=5.6Hz), 3.62(4H, t, J=4.8Hz), 3.17(4H, t, J=4.8H), 1.59(6 | 530 |
| 180a | (CD3OD) δ: 8.83(1H, s), 7.81-7.90(2H, m), 7.47(2H, d, J=8.8Hz), 7.47(1H, overlapped), 6.92(2H, d, J=8.8Hz), 5.67(1H, ddt, J=17.2, 10.0, 5.6Hz), 5.00(1H, d, J=10.0Hz), 4.88(1H, d, J=17.2Hz), 4.81(2H, d, J=5.6Hz), 3.20(4H, brs), 2.84(4H, br s), 2.42(2H, s), 1.75(3H, s), 1.69(3H, s), 1.21(6H, s), ESI-MA | 561 |
| 181a | (CDCl3) δ: 8.83(1H, s), 7.80-7.90(2H, m), 7.47(2H, d, J=8.8Hz), 7.47(1H, overlapped), 6.93(2H, d, J=8.8Hz), 5.67(1H, ddt, J=17.2, 10.0, 5.6Hz), 5.00(1H, d, J=10.0Hz), 4.88(1H, d, J=17.2Hz), 4.80(2H, d, J=5.6Hz), 3.25(4H, brs), 2.67(4H, brs), 2.42(3H, s), 1.75(3H, s), 1.69(3H, s). | 503 |
| 182a | (CD3OD) δ: 8.82(1H, s), 7.97(1H, dd, J=8.0, 7.6Hz), 7.89(1H, d, J=8.0Hz), 7.58(2H, d, J=8.8Hz), 7.52(2H, d, J=7.6Hz), 6.98(2H, d, J=8.8Hz), 5.69(1H, ddt, J=17.2, 10.0, 5.6Hz), 5.04(1H, d, J=10.0Hz), 4.92(1H, d, J=17.2Hz), 4.81(2H, d, J=5.6Hz), 3.77(4H, brs), 3.29(2H, s), 3.18(4H, brs), 2.37(6H, s,) 1.75(3H, s), 1.70(3H, s). | 574 |
| 183a | (CD3OD) δ: 8.82(1H, s), 7.83(1H, dd, J=8.0, 7.6Hz), 7.63(1H, brs), 7.42(2H, br), 7.26(1H, d, J=7.6Hz), 6.91(2H, d, J=8.8Hz), 5.70(1H, br), 5.07(4H, br), 3.78(2H, s), 3.22(4H, brs), 3.10(3H, s), 2.97(3H, s), 2.72(4H, s), 1.38(6H, s). | 586 |
| 184a | (CD3OD) δ: 8.82(1H, s), 7.74-7.80(2H, m), 7.47(2H, d, J=8.8Hz), 7.27(1H, br), 6.91(2H, d, J=8.8Hz), 5.61-5.69(1H, m), | 588 |

-continued

| Compound No | ¹H NMR(400MHz) | ESI-MS (M+H)+ |
|---|---|---|
| | 4.83-4.99(4H, m), 4.60(2H, J=47.6Hz), 3.22(4H, brs), 3.11(3H, s), 2.98(3H, s), 2.73(4H, brs), 2.72(4H, s), 1.40(6H, s). | |
| 185a | (DMSO-d6) δ: 11.68(1H, s), 10.18(1H, s), 8.83(1H, s), 8.06(1H, t, J=7.8Hz), 7.91-7.75(2H, m), 7.56(2H, brs), 6.90(2H, d, J=8.8Hz), 5.68(1H, ddt, J=17.1, 10.2, 5.4Hz), 5.00(1H, dd, J=10.2, 1.5Hz), 4.87(1H, dd, J=17.1, 1.5Hz), 4.66(2H, d, J=5.4Hz), 3.08(4H, t, J=4.9Hz), 2.44(4H, t, J=4.9Hz), 2.21 | 500 |
| 186a | (CDCl3) δ: 8.83(1H, s), 7.86-7.81(3H, m), 7.46(2H, d, J=8.8Hz), 6.92(2H, d, J=8.8Hz), 5.67(1H, ddt, J=17.1, 10.2, 6.3Hz), 5.01(1H, dd, J=10.2, 1.0Hz), 4.90(1H, dd, J=17.1, 1.0Hz), 4.82(2H, d, J=6.3Hz), 4.05(3H, s), 3.28(4H, brs), 2.72(4H, brs), 2.45(3H, s), 2.30(3H, s). | 514 |
| 187a | (CDCl3, 2dropsofCD3OD) δ: 8.82(1H, brs), 7.80(1H, dd, J=8.3, 8.0Hz), 7.56(1H, d, J=8.3Hz), 7.50(2H, d, J=8.7Hz), 6.93(2H, d, J=8.7Hz), 6.90(1H, d, J=8.0Hz), 5.70-5.58(1H, m), 5.05-4.95(2H, m), 4.87(2H, d, J=6.3Hz), 3.30(3H, s), 3.29-3.20(4H, m), 2.87-2.57(4H, m), 2.44(3H, s). | 536 |
| 188a | (CDCl3) δ: 8.85(1H, s), 7.88(1H, t, J=7.8Hz), 7.73(2H, d, J=8.3Hz), 7.52(2H, d, J=8.8Hz), 7.36(2H, d, J=7.3Hz), 6.94(2H, d, J=9.3Hz), 5.71(1H, ddt, J=17.1, 10.2, 5.9Hz), 5.05(1H, d, J=10.7Hz), 4.94(1H, d, J=17.1Hz), 4.74(2H, d, J=5.9Hz), 3.93(1H, brs), 3.39-3.30(6H, m), 3.21(1H, brs), 1.59(6H, | 487 |
| 189a | (DMSO-d6) δ: 10.09(1H, s), 9.24(1H, s), 8.81(1H, s), 7.96(1H, t, J=8.0Hz), 7.71(1H, d, J=7.3Hz), 7.59(1H, d, J=7.8Hz), 7.47(2H, d, J=6.8Hz), 6.72(2H, d, J=8.8Hz), 5.64(1H, ddt, J=17.1, 10.2, 5.9Hz), 5.32(1H, s), 4.98(1H, dd, J=10.2, 1.0Hz), 4.80(1H, dd, J=17.1, 1.5Hz), 4.66(2H, d, J=5.9Hz), 1.45 | 419 |

INDUSTRIAL APPLICABILITY

The compounds of the invention have excellent Weel kinase-inhibitory effect and are therefore useful in the field of medicines, especially treatment of various cancers.

The invention claimed is:

1. A compound of formula (I):

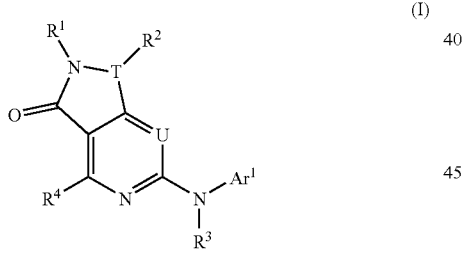

wherein;
Ar$^1$ is an aryl group or a heteroaromatic group, which is optionally substituted with a substituent selected from the group consisting of a halogen atom, a lower alkyl group, a halo-lower alkyl group, a hydroxy-lower alkyl group, a lower alkoxy group, a lower alkanoyl group, a hydroxy-lower alkylamino group, a carbamoyl group, a hydroxy-lower alkylcarbamoyl group, a heteroaromatic group optionally substituted by a lower alkyl group, and a group of -Q$^1$-A$^1$-Q$^2$-A$^2$(R$^{1a}$)R$^{1b}$;
A$^1$ is a single bond, an oxygen atom or a sulfur atom, or is an imino group optionally substituted by a lower alkyl group;
A$^2$ is a nitrogen atom, or is a methine or 1-vinyl-2-ylidene group optionally substituted by a hydroxyl group, a lower alkyl group or a hydroxy-lower alkyl group;
Q$^1$ is a single bond, a carbonyl group, or a methylene group optionally substituted by a lower alkyl group;
Q$^2$ is a single bond, or an ethylene group optionally substituted by a lower alkyl group;
R$^{1a}$ is a hydrogen atom, a lower alkyl group or a hydroxy-lower alkyl group,
R$^{1b}$ is a hydrogen atom, a lower alkyl group or a hydroxy-lower alkyl group, or
R$^{1a}$ and R$^{1b}$ together form a lower alkylene group wherein one or two or more methylene groups constituting the lower alkylene group may be independently replaced by an oxygen atom, a sulfur atom, a sulfinyl group, a sulfonyl group, a carbonyl group, a vinylene group or a group of —N(R$^{1c}$)—, or substituted by a hydroxyl group or a lower alkyl group;
R$^{1c}$ is a hydrogen atom, a lower alkenyl group or a group of -Q$^3$-A$^3$(R$^{1d}$)R$^{1e}$;
A$^3$ is a nitrogen atom, or is a methine or 1-vinyl-2-ylidene group optionally substituted by a hydroxyl group, a lower alkyl group or a hydroxy-lower alkyl group;
Q$^3$ is a single bond or a lower alkylene group, wherein one or two or more methylene groups constituting the lower alkylene group may be independently replaced by an oxygen atom, a sulfur atom, a carbonyl group, a sulfinyl group or a sulfonyl group, and/or substituted by a halogen atom, a cyano group, a hydroxyl group or a lower alkyl group;
R$^{1d}$ is a hydrogen atom, a halogen atom, a cyano group, a hydroxyl group, a lower alkyl group or a hydroxy-lower alkyl group,
R$^{1e}$ is a hydrogen atom, a halogen atom, a cyano group, a hydroxyl group, a lower alkyl group or a hydroxy-lower alkyl group, or
R$^{1d}$ and R$^{1e}$ together form a lower alkylene group wherein one or two or more methylene groups constituting the lower alkylene group may be independently replaced by an oxygen atom, a sulfur atom, a sulfinyl group, a sulfonyl group, a carbonyl group, a vinylene group or a group of —N(R$^{1f}$)—, and/or substituted by a hydroxyl group or a lower alkyl group;

R$^{1f}$ is a hydrogen atom, a lower alkyl group, a halo-lower alkyl group, a lower alkenyl group or a lower alkanoyl group;

R$^1$ is a lower alkenyl group, optionally substituted by a halogen atom;

R$^2$ is a hydrogen atom, a lower alkyl group, a lower alkenyl group or a lower alkynyl group, or is an aryl group, an aralkyl group or a heteroaromatic group optionally having a substituent selected from the group consisting of a halogen atom, a cyano group, a nitro group, a carboxyl group, a group of -Q$^4$-A$^4$(R$^{1g}$) R$^{1h}$ and a group of -Q$^5$-Ar$^a$, wherein one or two or more methylene groups constituting the lower alkyl group, the lower alkenyl group or the lower alkynyl group may be independently replaced by an oxygen atom, a sulfur atom, a sulfinyl group, a sulfonyl group, a carbonyl group or a group of —N(R$^{1j}$)—, or substituted by a halogen atom;

A$^4$ is a nitrogen atom, or is a methine group optionally substituted by a halogen atom, a hydroxyl group, a lower alkyl group or a hydroxy-lower alkyl group;

Ar$^a$ is an aryl group or a heteroaromatic group, which may have a substituent selected from a group consisting of a halogen atom, a lower alkyl group, a halo-lower alkyl group, a hydroxy-lower alkyl group and a lower alkoxy group;

Q$^4$ is a single bond or a lower alkylene group, wherein one or two or more methylene groups constituting the lower alkylene group may be independently replaced by an oxygen atom or a carbonyl group, or substituted by a lower alkyl group;

Q$^5$ is a single bond, an oxygen atom, a sulfur atom, a carbonyl group or a lower alkylene group, wherein one or two or more methylene groups constituting the lower alkylene group may be independently replaced by an oxygen atom, a sulfur atom or a carbonyl group, or substituted by a halogen atom or a lower alkyl group;

R$^{1g}$ is a hydrogen atom, a halogen atom, a cyano group, a hydroxyl group, a lower alkyl group, a lower alkoxy-lower alkyl group, a lower alkanoyl group, a lower alkoxycarbonyl group or a lower alkylsulfonyl group, R$^{1h}$ is a hydrogen atom, a halogen atom, a cyano group, a hydroxyl group, a lower alkyl group, a lower alkoxy-lower alkyl group, a lower alkanoyl group, a lower alkoxycarbonyl group or a lower alkylsulfonyl group, or R$^{1g}$ and R$^{1h}$ together form a lower alkylene group, wherein one or two or more methylene groups constituting the lower alkylene group may be independently replaced by an oxygen atom, a sulfur atom, a sulfinyl group, a sulfonyl group, a carbonyl group or a group of —N(R$^{1i}$)—, and/or substituted by a halogen atom or a lower alkyl group;

R$^{1i}$ is a hydrogen atom, a lower alkyl group or a halo-lower alkyl group;

R$^{1j}$ is a hydrogen atom or a lower alkyl group;

R$^3$ is a hydrogen atom or a lower alkyl group;

R$^4$ is a hydrogen atom, a halogen atom, a hydroxyl group, a lower alkyl group or a group of —N(R$^{1k}$)R$^{1m}$;

R$^{1k}$ is a hydrogen atom or a lower alkyl group;

R$^{1m}$ is a hydrogen atom or a lower alkyl group;

T is a nitrogen atom;

U is a nitrogen atom or a salt thereof.

2. The compound of formula (I-1) as claimed in claim 1, or a salt thereof:

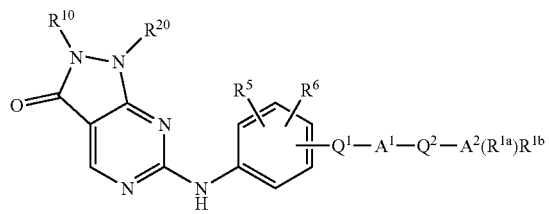

(I-1)

wherein,

A$^1$ is a single bond, an oxygen atom or a sulfur atom, or is an imino group optionally substituted by a lower alkyl group;

A$^2$ is a nitrogen atom, or is a methine or 1-vinyl-2-ylidene group optionally substituted by a hydroxyl group, a lower alkyl group or a hydroxy-lower alkyl group;

Q$^1$ is a single bond, a carbonyl group, or a methylene group optionally substituted by a lower alkyl group;

Q$^2$ is a single bond, or an ethylene group optionally substituted by a lower alkyl group;

R$^{1a}$ is a hydrogen atom, a lower alkyl group or a hydroxy-lower alkyl group, R$^{1b}$ is a hydrogen atom, a lower alkyl group or a hydroxy-lower alkyl group, or R$^{1a}$ and R$^{1b}$ together form a lower alkylene group wherein one or two or more methylene groups constituting the lower alkylene group may be independently replaced by an oxygen atom, a sulfur atom, a sulfinyl group, a sulfonyl group, a carbonyl group, a vinylene group or a group of —N(R$^{1c}$)—, and/or substituted by a hydroxyl group or a lower alkyl group;

R$^{1c}$ is a hydrogen atom, a lower alkenyl group or a group of -Q$^3$-A$^3$ (R$^{1d}$)R$^{1e}$;

A$^3$ is a nitrogen atom, or is a methine or 1-vinyl-2-ylidene group optionally substituted by a hydroxyl group, a lower alkyl group or a hydroxy-lower alkyl group;

Q$^3$ is a single bond or a lower alkylene group, wherein one or two or more methylene groups constituting the lower alkylene group may be independently replaced by an oxygen atom, a sulfur atom, a carbonyl group, a sulfinyl group or a sulfonyl group, and/or substituted by a halogen atom, a cyano group, a hydroxyl group or a lower alkyl group;

R$^{1d}$ is a hydrogen atom, a halogen atom, a cyano group, a hydroxyl group, a lower alkyl group or a hydroxy-lower alkyl group, R$^{1e}$ is a hydrogen atom, a halogen atom, a cyano group, a hydroxyl group, a lower alkyl group or a hydroxy-lower alkyl group, or R$^{1d}$ and R$^{1e}$ together form a lower alkylene group wherein one or two or more methylene groups constituting the lower alkylene group may be independently replaced by an oxygen atom, a sulfur atom, a sulfinyl group, a sulfonyl group, a carbonyl group, a vinylene group or a group of —N(R$^{1f}$)—, or substituted by a hydroxyl group or a lower alkyl group;

$R^{1f}$ is a hydrogen atom, a lower alkyl group, a halo-lower alkyl group, a lower alkenyl group or a lower alkanoyl group;

$R^5$ is a hydrogen atom, a halogen atom, a lower alkyl group, a halo-lower alkyl group, a hydroxy-lower alkyl group, a lower alkoxy group, a lower alkanoyl group, a hydroxy-lower alkylamino group, a carbamoyl group or a hydroxy-lower alkylcarbamoyl group;

$R^6$ is a hydrogen atom, a halogen atom, a lower alkyl group, a halo-lower alkyl group, a hydroxy-lower alkyl group, a lower alkoxy group, a lower alkanoyl group, a hydroxy-lower alkylamino group, a carbamoyl group or a hydroxy-lower alkylcarbamoyl group;

$R^{10}$ is a lower alkenyl group, which is optionally substituted with a halogen atom;

$R^{20}$ is an aryl group or a heteroaromatic group, which is optionally substituted with a substituent selected from the group consisting of a halogen atom, a cyano group, a nitro group, a carboxyl group, a group of $-Q^4-A^4(R^{1g})R^{1h}$ and a group of $-Q^5-Ar^a$;

$A^4$ is a nitrogen atom, or is a methine group optionally substituted by a halogen atom, a hydroxyl group, a lower alkyl group or a hydroxy-lower alkyl group;

$Ar^a$ is an aryl group or a heteroaromatic group, which is optionally substituted with a substituent selected from a group consisting of a halogen atom, a lower alkyl group, a halo-lower alkyl group, a hydroxy-lower alkyl group and a lower alkoxy group;

$Q^4$ is a single bond or a lower alkylene group, wherein one or two or more methylene groups constituting the lower alkylene group may be independently replaced by an oxygen atom or a carbonyl group, or substituted by a lower alkyl group;

$Q^5$ is a single bond, an oxygen atom, a sulfur atom, a carbonyl group or a lower alkylene group, wherein one or two or more methylene groups constituting the lower alkylene group may be independently replaced by an oxygen atom, a sulfur atom or a carbonyl group, or substituted by a halogen atom or a lower alkyl group;

$R^{1g}$ is a hydrogen atom, a halogen atom, a cyano group, a hydroxyl group, a lower alkyl group, a lower alkoxy-lower alkyl group, a lower alkanoyl group, a lower alkoxycarbonyl group or a lower alkylsulfonyl group;

$R^{1h}$ is a hydrogen atom, a halogen atom, a cyano group, a hydroxyl group, a lower alkyl group, a lower alkoxy-lower alkyl group, a lower alkanoyl group, a lower alkoxycarbonyl group or a lower alkylsulfonyl group, or $R^{1g}$ and $R^{1h}$ together form a lower alkylene group, wherein one or two or more methylene groups constituting the lower alkylene group may be independently replaced by an oxygen atom, a sulfur atom, a sulfinyl group, a sulfonyl group, a carbonyl group or a group of $-N(R^{1i})-$, or substituted by a halogen atom or a lower alkyl group;

$R^{1i}$ is a hydrogen atom, a lower alkyl group or a halo-lower alkyl group.

3. The compound as claimed in claim 2, or a salt thereof, wherein $R^{10}$ is an allyl group, a 2-methyl-2-propenyl group or a 3-methyl-2-butenyl group.

4. The compound as claimed in claim 2, or a salt thereof, wherein $R^{20}$ is a phenyl group, a thienyl group, a pyrazolyl group or a pyridyl group, which is optionally substituted with a substituent selected from a group consisting of a halogen atom, a cyano group, a nitro group, a carboxyl group, a group of $-Q^4-A^4(R^{1g})R^{1h}$ and a group of $-Q^5-Ar^a$.

5. The compound as claimed in claim 2, or a salt thereof, wherein $R^{20}$ is a phenyl or pyridyl group having a group of $-Q^4-A^4(R^{1g})R^{1h}$.

6. The compound as claimed in claim 2, or a salt thereof, wherein in the group of the formula $-Q^1-A^1-Q^2-A^2(R^{1a})R^{1b}$, (i) $A^1$, $Q^1$ and $Q^2$ are a single bond, $A^2$ is a nitrogen atom, and $R^{1a}$ and $R^{1b}$ together form a lower alkylene group wherein one or two methylene groups constituting the lower alkylene group may be independently replaced by an oxygen atom, a sulfonyl group, a carbonyl group or a group of $-N(R^{1c})-$, or substituted by a hydroxyl group;

(ii) $A^1$, $Q^1$ and $Q^2$ are a single bond, $A^2$ is a methine or 1-vinyl-2-ylidene group optionally substituted by a hydroxyl group, and $R^{1a}$ and $R^{1b}$ together form a lower alkylene group wherein one methylene group constituting the lower alkylene group is replaced by a group of $-N(R^{1c})-$;

(iii) $A^1$ is an oxygen atom, $A^2$ is a methine group, $Q^1$ and $Q^2$ are a single bond, and $R^{1a}$ and $R^{1b}$ together form a lower alkylene group wherein one methylene group constituting the lower alkylene group is replaced by a group of $-N(R^{1c})-$;

(iv) $A^1$ is an oxygen atom, $A^2$ is a nitrogen atom, $Q^1$ is a single bond, $Q^2$ is an ethylene group, $R^{1a}$ is a lower alkyl group, and $R^{1b}$ is a lower alkyl group; or (v) $A^1$ and $Q^2$ are a single bond, $A^2$ is a nitrogen atom, $Q^1$ is a methylene group, $R^{1a}$ is a lower alkyl group, and $R^{1b}$ is a lower alkyl group.

7. The compound as claimed in claim 2, or a salt thereof, wherein $R^{20}$ is a phenyl or pyridyl group having a group of $-Q^4-A^4(R^{1g})R^{1h}$, and the group of $-Q^1-A^1-Q^2-A^2(R^{1a})R^{1b}$ is selected from the formula (aa1'):

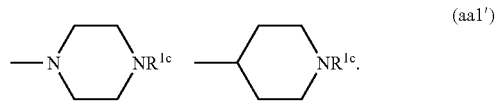

(aa1')

8. The compound as claimed in claim 6, or a salt thereof, wherein $R^{1c}$ is a hydrogen atom or a group of $-Q^3-A^3(R^{1d})R^{1e}$, and in the group of $-Q^3-A^3(R^{1d})R^{1e}$;

(i) $A^3$ is a methine group optionally substituted by a hydroxyl group or a lower alkyl group, $Q^3$ is a single bond, $R^{1d}$ is a hydrogen atom or a lower alkyl group, and $R^{1e}$ is a hydrogen atom or a lower alkyl group;

(ii) $A^3$ is a methine group, $Q^3$ is a single bond or a lower alkylene group, and $R^{1d}$ and $R^{1e}$ together form a lower alkylene group wherein one methylene group constituting the lower alkylene group may be replaced by a group of $-N(R^{1f})-$;

(iii) $A^3$ is a methine group optionally substituted with a hydroxyl group or a lower alkyl group, $Q^3$ is a lower alkylene group wherein one or two methylene groups constituting the lower alkylene group may be independently replaced by an oxygen atom, a carbonyl group or a sulfonyl group, and/or substituted by a hydroxyl group, $R^{1d}$ is a hydrogen atom, a halogen atom, a cyano group or a lower alkyl group, and $R^{1e}$ is a hydrogen atom, a halogen atom, a cyano group or a lower alkyl group; or (iv) $A^3$ is a nitrogen atom, $Q^3$ is a lower alkylene group wherein one methylene group constituting the lower alkylene group is replaced by a carbonyl group, $R^{1d}$— is a hydrogen atom or a lower alkyl group, and $R^{1e}$ is a hydrogen atom or a lower alkyl group.

9. The compound as claimed in claim 1, or a salt thereof, which is as follows:
   3-(2-allyl-6-{[4-(4-methylpiperazin-1-yl)phenyl]amino}-3-oxo-1,2-dihydro-3H-pyrazolo[3,4-d]pyrimidin-1-yl)-N,N-dimethylbenzamide,
   2-allyl-1-[3-(1-hydroxy-1-methylethyl)phenyl]-6-{[4-(4-methylpiperazin-1-yl)phenyl]amino}-1,2-dihydro-3H-pyrazolo[3,4-d]pyrimidin-3-one,
   2-allyl-1-[3-(dimethylaminomethyl)phenyl]-6-{[4-(4-methylpiperazin-1-yl)phenyl]amino}-1,2-dihydro-3H-pyrazolo[3,4-d]pyrimidin-3-one,
   2-allyl-6-{[3-hydroxymethyl-4-(4-methylpiperazin-1-yl)phenyl]amino}-1-pyridin-2-yl-1,2-dihydro-3H-pyrazolo[3,4-d]pyrimidin-3-one,
   2-allyl-1-(6-aminopyridin-2-yl)-6-{4-(4-methylpiperazin-1-yl)phenyl]amino}-1,2-dihydro-3H-pyrazolo[3,4-d]pyrimidin-3-one,
   2-allyl-1-[6-(1-hydroxy-1-methylethyl)pyridin-2-yl]-6-{[4-(4-methylpiperazin-1-yl)phenyl]amino}-1,2-dihydro-3H-pyrazolo[3,4-d]pyrimidin-3-one,
   2-allyl-6-{[4-(4-ethylpiperazin-1-yl)phenyl]amino}-1-[6-(1-hydroxy-1-methylethyl)pyridin-2-yl]-1,2-dihydro-3H-pyrazolo[3,4-d]pyrimidin-3-one,
   6-{[4-(4-acetylpiperazin-1-yl)phenyl]amino}-2-allyl-1-[6-(1-hydroxy-1-methylethyl)pyridin-2-yl]-1,2-dihydro-3H-pyrazolo[3,4-d]pyrimidin-3-one,
   2-allyl-6-({4-[4-(2-hydroxyethyl)piperazin-1-yl]phenyl}amino)-1-[6-(1-hydroxy-1-methylethyl)pyridin-2-yl]-1,2-dihydro-3H-pyrazolo[3,4-d]pyrimidin-3-one,
   2-allyl-1-[6-(2-hydroxy-2-methylpropyl)pyridin-2-yl]-6-{[4-(1-methylpiperidin-4-yl)phenyl]amino}-1,2-dihydro-3H-pyrazolo[3,4-d]pyrimidin-3-one,
   2-allyl-6-{[4-(4-methylpiperazin-1-yl)phenyl]amino}-1-[6-(2-oxopyrrolidin-1-yl)pyridin-2-yl]-1,2-dihydro-3H-pyrazolo[3,4-d]pyrimidin-3-one,
   N-{[6-(2-allyl-6-{[4-(4-methylpiperazin-1-yl)phenyl]amino}-3-oxo-1,2-dihydro-3H-pyrazolo[3,4-d]pyrimidin-1-yl)pyridin-2-yl]methyl}-N-methylmethanesulfonamide.

10. The compound as claimed in claim 1, or a salt thereof, which is 3-(2-allyl-6-{[4-(4-methylpiperazin-1-yl)phenyl]amino}-3-oxo-1,2-dihydro-3H-pyrazolo[3,4-d]pyrimidin-1-yl)-N,N-dimethylbenzamide.

11. The compound as claimed in claim 1, or a salt thereof, which is 2-allyl-6-{[3-(hydroxymethyl)-4-(4-methylpiperazin-1-yl)phenyl]amino}-1-(3-thienyl)-1,2-dihydro-3H-pyrazolo[3,4-d]pyrimidin-3-one.

12. The compound as claimed in claim 1, or a salt thereof, which is 2-allyl-1-[6-(1-hydroxy-1-methylethyl)pyridin-2-yl]-6-{[4-(4-methylpiperazin-1-yl)phenyl]amino}-1,2-dihydro-3H-pyrazolo[3,4-d]pyrimidin-3-one.

13. The compound as claimed in claim 1, or a salt thereof, which is 2-allyl-1-[6-(3-methyl-2-oxoimidazolidin-1-yl)pyridin-2-yl]-6-{[4-(4-methylpiperazin-1-yl)phenyl]amino}-1,2-dihydro-3H-pyrazolo[3,4-d]pyrimidin-3-one.

14. A pharmaceutical composition comprising a therapeutically-effective amount of the compound as claimed in claim 1, or a salt thereof, and a pharmaceutically acceptable carrier or diluent.

15. A pharmaceutical composition comprising:
   (a) a preparation comprising, together with a pharmaceutically acceptable carrier or diluent, the compound of above formula (I) or a pharmaceutically acceptable salt thereof; and
   (b) a preparation comprising, together with a pharmaceutically acceptable carrier or diluent, one anticancer agent selected from the group consisting of anticancer alkylating agents, anticancer antimetabolites, anticancer antibiotics, plant-derived anticancer agents, anticancer platinum-coordinated complex compounds, anticancer camptothecin derivatives, anticancer tyrosine kinase inhibitors, monoclonal antibodies, interferons, biological response modifiers, and other anticancer agents or a pharmaceutically acceptable salt thereof, wherein:
   the anticancer alkylating agents are selected from the group consisting of nitrogen mustard N-oxide, cyclophosphamide, ifosfamide, melphalan, busulfan, mitobronitol, carboquone, thiotepa, ranimustine, nimustine, temozolomide, and carmustine;
   the anticancer antimetabolites are selected from the group consisting of methotrexate, 6-mercaptopurine riboside, mercaptopurine, 5-fluorouracil, tegafur, doxifluridine, carmofur, cytarabine, cytarabine ocfosfate, enocitabine, S-1, gemcitabine, fludarabine, and pemetrexed disodium;
   the anticancer antibiotics are selected from the group consisting of actinomycin D, doxorubicin, daunorubicin, neocarzinostatin, bleomycin, peplomycin, mitomycin C, aclarubicin, pirarubicin, epirubicin, zinostatin stimalamer, idarubicin, sirolimus, and valrubicin;
   the plant-derived anticancer agents are selected from the group consisting of vincristine, vinblastine, vindeshine, etoposide, sobuzoxane, docetaxel, paclitaxel, and vinorelbine;
   the anticancer platinum-coordinated complex compounds are selected from the group consisting of cisplatin, carboplatin, nedaplatin, and oxaliplatin;
   the anticancer camptothecin derivatives are selected from the group consisting of irinotecan, topotecan, and camptothecin;
   the anticancer tyrosine kinase inhibitors are selected from the group consisting of gefitinib, imatinib, and erlotinib;
   the monoclonal antibodies are selected from the group consisting of cetuximab, bevacizumab, rituximab, bevacizumab, alemtuzumab, and trastuzumab;
   the interferons are selected from the group consisting of interferon α, interferon α-2a, interferon α-2b, interferon β, interferon γ-1a, and interferon α-n1,
   the biological response modifiers are selected from the group consisting of krestin, lentinan, sizofuran, picibanil, or ubenimex, and
   the other anticancer agents are selected from the group consisting of mitoxantrone, L-asparaginase, procarbazine, dacarbazine, hydroxycarbamide, pentostatin, tretinoin, alefacept, darbepoetin alfa, anastrozole, exemestane, bicalutamide, leuprorelin, flutamide, fulvestrant, pegaptanib octasodium, denileukin diftitox, aldesleukin, thyrotropin alfa, arsenic trioxide, bortezomib, capecitabine, and goserelin.

* * * * *